United States Patent
Hood et al.

(10) Patent No.: US 11,077,046 B2
(45) Date of Patent: Aug. 3, 2021

(54) GAMMA-DIKETONES FOR TREATMENT AND PREVENTION OF AGING SKIN AND WRINKLES

(71) Applicant: BioSplice Therapeutics, Inc., San Diego, CA (US)

(72) Inventors: John Hood, San Diego, CA (US); Sunil Kumar KC, San Diego, CA (US); Osman Kibar, La Jolla, CA (US); Charlene F. Barroga, San Diego, CA (US)

(73) Assignee: BioSplice Therapeutics, Inc., San Diego, CA (US)

(*) Notice: Subject to any disclaimer, the term of this patent is extended or adjusted under 35 U.S.C. 154(b) by 0 days.

(21) Appl. No.: 16/534,455

(22) Filed: Aug. 7, 2019

(65) Prior Publication Data

US 2020/0222295 A1    Jul. 16, 2020

Related U.S. Application Data

(60) Continuation of application No. 15/706,908, filed on Sep. 18, 2017, now Pat. No. 10,434,052, which is a division of application No. 14/831,456, filed on Aug. 20, 2015, now Pat. No. 9,795,550.

(60) Provisional application No. 62/039,786, filed on Aug. 20, 2014.

(51) Int. Cl.
| | |
|---|---|
| *A61K 31/137* | (2006.01) |
| *A61K 8/49* | (2006.01) |
| *A61K 8/35* | (2006.01) |
| *A61K 8/41* | (2006.01) |
| *A61K 8/69* | (2006.01) |
| *A61K 8/70* | (2006.01) |
| *A61Q 19/00* | (2006.01) |
| *A61Q 19/02* | (2006.01) |
| *A61Q 19/08* | (2006.01) |

(52) U.S. Cl.
CPC .......... *A61K 8/4986* (2013.01); *A61K 8/35* (2013.01); *A61K 8/41* (2013.01); *A61K 8/49* (2013.01); *A61K 8/492* (2013.01); *A61K 8/494* (2013.01); *A61K 8/498* (2013.01); *A61K 8/4913* (2013.01); *A61K 8/4926* (2013.01); *A61K 8/4946* (2013.01); *A61K 8/4953* (2013.01); *A61K 8/4973* (2013.01); *A61K 8/69* (2013.01); *A61K 8/70* (2013.01); *A61Q 19/007* (2013.01); *A61Q 19/02* (2013.01); *A61Q 19/08* (2013.01); *A61K 2800/10* (2013.01)

(58) Field of Classification Search
CPC .... A61K 31/137; A61K 31/121; C07C 49/84; C07C 49/82; C07C 49/80; C07C 49/76; C07C 211/04
USPC .......... 514/676, 685; 568/306, 311
See application file for complete search history.

(56) References Cited

U.S. PATENT DOCUMENTS

| | | |
|---|---|---|
| 3,040,054 A | 6/1962 | Bodanszky et al. |
| 3,855,675 A | 12/1974 | Denzel et al. |
| 4,014,889 A | 3/1977 | Stetter et al. |
| 4,032,526 A | 6/1977 | Cross et al. |
| 4,164,559 A | 8/1979 | Miyata et al. |
| 4,284,629 A | 8/1981 | Grohe et al. |
| 4,474,752 A | 10/1984 | Haslam et al. |
| 4,537,617 A | 8/1985 | Plath et al. |
| 4,761,471 A | 8/1988 | Urist |
| 5,068,393 A | 11/1991 | Maignan et al. |
| 5,194,619 A | 3/1993 | Reuschling et al. |
| 5,252,191 A | 10/1993 | Pauli et al. |
| 5,420,273 A | 5/1995 | Klaus et al. |
| 5,585,118 A | 12/1996 | Stoll |
| 5,977,108 A | 11/1999 | Kikuchi et al. |
| 6,020,488 A | 2/2000 | Wuonola et al. |
| 6,120,484 A | 9/2000 | Silverstein |
| 6,310,049 B1 | 10/2001 | Wada et al. |
| 6,346,260 B1 | 2/2002 | Hölzl et al. |
| 6,377,849 B1 | 4/2002 | Lenarz et al. |
| 6,440,102 B1 | 8/2002 | Arenberg et al. |
| 6,620,804 B2 | 9/2003 | Chang et al. |
| 6,624,184 B1 | 9/2003 | Gu et al. |
| 6,648,873 B2 | 11/2003 | Arenberg et al. |
| 6,911,211 B2 | 6/2005 | Eini et al. |
| 6,960,591 B2 | 11/2005 | Hirano et al. |

(Continued)

FOREIGN PATENT DOCUMENTS

| | | |
|---|---|---|
| CN | 1382688 | 12/2002 |
| CN | 1440391 | 9/2003 |

(Continued)

OTHER PUBLICATIONS

Adam et al., "The Importance of Spin Polarization in Electronic Substituent Effects of the Zero-Field EPR D Parameter in 1,3-Dialylcyclopentane-1,3-diyl Triplet Diradicals," *J. Am. Chem. Soc.*, 121(46): 10820-10827, Nov. 6, 1999.

Agathocleous et al., "A directional Wnt/β-catenin-Sox2-proneural pathway regulates the transition from proliferation to differentiation in the *Xenopus* retina," *Development* 2009, 136(19), 3289-3299.

Akin et al., "Wnt pathway aberrations including autocrine Wnt activation occur at high frequency in human non-small-cell lung carcinoma," *Oncogene* 2009, 28(21): 2163-2172.

Amit et al., "Axin-mediated CKI phosphorylation of β-catenin at Ser 45: a molecular switch for the Wnt pathway," *Genes & Development* 2002, 16(9): 1066-1076.

(Continued)

*Primary Examiner* — Jeffrey H Murray

(74) *Attorney, Agent, or Firm* — Fish & Richardson P.C.

(57) ABSTRACT

The present disclosure relates to compounds, cosmetic or dermopharmaceutical compositions comprising the same, and methods for using the compounds or compositions for treating, protecting, and/or improving the condition and/or aesthetic appearance of skin, for example, treating, preventing, ameliorating, reducing and/or eliminating fine lines and/or wrinkles of skin, or improving the appearance of fine lines and/or or wrinkles of skin comprising application of the compounds or compositions disclosed.

11 Claims, 2 Drawing Sheets

(56) References Cited

U.S. PATENT DOCUMENTS

Figure 1:
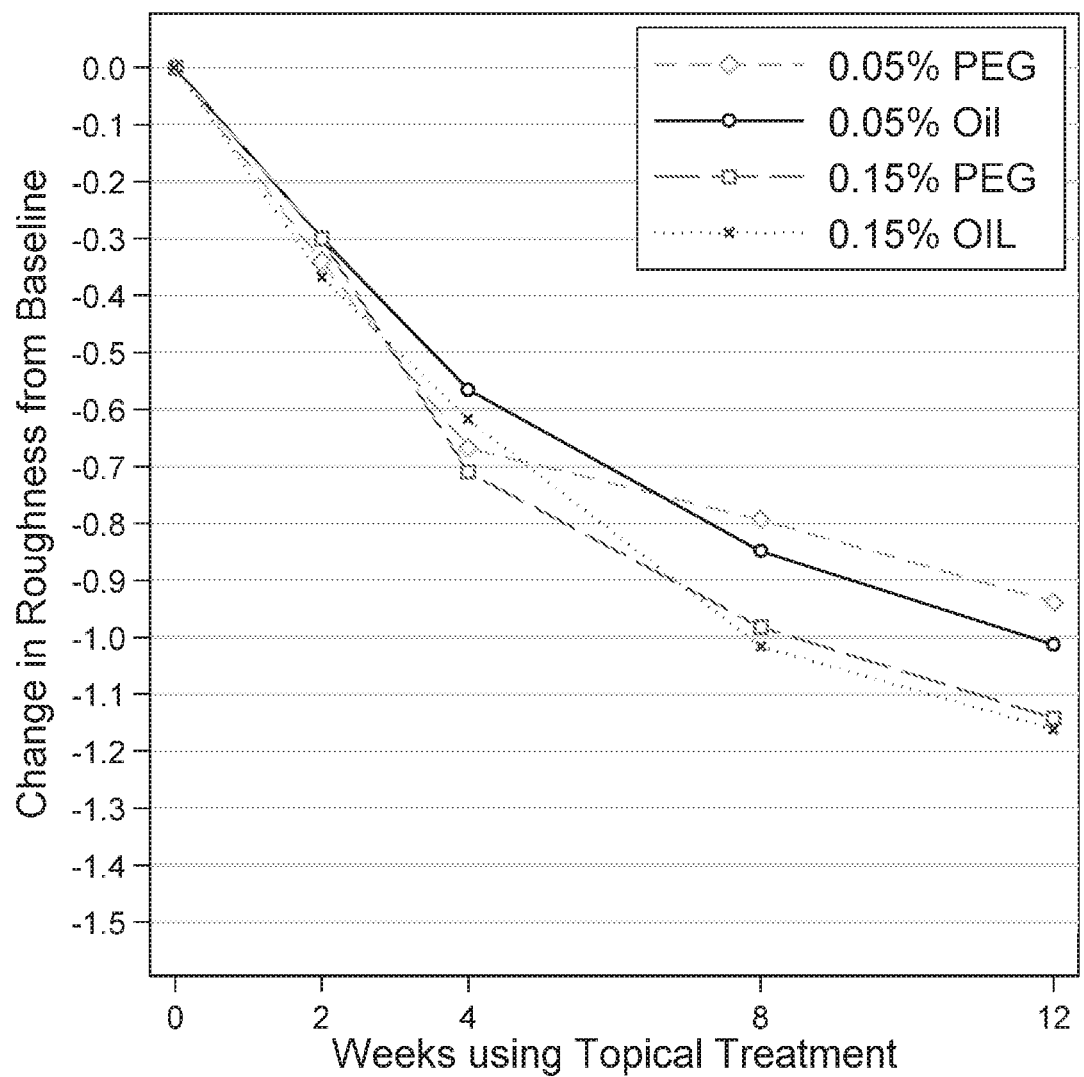

| | | |
|---|---|---|
| 7,012,075 B2 | 3/2006 | Prasit et al. |
| 7,041,837 B2 | 5/2006 | Lohray et al. |
| 7,053,111 B2 | 5/2006 | Gu et al. |
| 7,060,720 B2 | 6/2006 | Gu et al. |
| 7,205,324 B2 | 4/2007 | Gu et al. |
| 7,524,975 B2 | 4/2009 | Mae et al. |
| 7,709,519 B2 | 5/2010 | Hirano et al. |
| 7,960,562 B2 | 6/2011 | Hirano et al. |
| 8,088,369 B2 | 1/2012 | Izawa et al. |
| 8,124,760 B2 | 2/2012 | Haga et al. |
| 8,410,109 B2 | 4/2013 | Wong et al. |
| 8,609,717 B2 | 12/2013 | KC et al. |
| 8,629,176 B1 | 1/2014 | Kumar KC et al. |
| 8,741,357 B2 | 6/2014 | Linter et al. |
| 8,921,413 B2 | 12/2014 | Kumar KC et al. |
| 9,303,010 B2 | 4/2016 | Kumar KC et al. |
| 9,493,437 B2 | 11/2016 | Kumar KC et al. |
| 9,533,976 B2 | 1/2017 | Kumar KC et al. |
| 9,795,550 B2 | 10/2017 | Hood et al. |
| 9,884,053 B2 | 2/2018 | KC et al. |
| 10,314,832 B2 | 6/2019 | Kumar KC et al. |
| 10,457,672 B2 * | 10/2019 | KC ............... C07D 319/18 |
| 2003/0087922 A1 | 5/2003 | Bethiel et al. |
| 2004/0224003 A1 | 11/2004 | Schultz |
| 2004/0266732 A1 | 12/2004 | Galvez et al. |
| 2005/0054578 A1 | 3/2005 | Sandberg et al. |
| 2005/0267110 A1 | 12/2005 | Hirano et al. |
| 2005/0282707 A1 | 12/2005 | Almsick et al. |
| 2006/0134155 A1 | 6/2006 | Dryer et al. |
| 2006/0142358 A1 | 6/2006 | Autier et al. |
| 2006/0264897 A1 | 11/2006 | Lobl |
| 2006/0276536 A1 | 12/2006 | Vander Jagt et al. |
| 2007/0021606 A1 | 1/2007 | Egle et al. |
| 2007/0060644 A1 | 3/2007 | Vander Jagt et al. |
| 2007/0185152 A1 | 8/2007 | Yamashita et al. |
| 2007/0238733 A1 | 10/2007 | Joshi et al. |
| 2008/0139585 A1 | 6/2008 | Rathinavelu et al. |
| 2008/0146555 A1 | 6/2008 | Caligiuri et al. |
| 2008/0262205 A1 | 10/2008 | ter Harr et al. |
| 2009/0232754 A1 | 9/2009 | Meyer et al. |
| 2010/0152493 A1 | 6/2010 | Shibata et al. |
| 2010/0204245 A1 | 8/2010 | Malamas et al. |
| 2010/0204246 A1 | 8/2010 | Davies et al. |
| 2010/0210036 A1 | 8/2010 | Arnold et al. |
| 2012/0046320 A1 | 2/2012 | KC et al. |
| 2013/0079643 A1 | 3/2013 | Korichi et al. |
| 2013/0171274 A1 | 7/2013 | Son et al. |
| 2013/0172291 A1 | 7/2013 | Peter et al. |
| 2014/0005228 A1 | 1/2014 | Kumar KC et al. |
| 2014/0080902 A1 | 3/2014 | Kumar |
| 2014/0179642 A1 | 6/2014 | Santhanam et al. |
| 2014/0243349 A1 | 8/2014 | Kumar KC et al. |
| 2015/0299157 A1 | 10/2015 | Kumar KC et al. |
| 2015/0299174 A1 | 10/2015 | Kumar KC et al. |
| 2017/0260176 A1 | 9/2017 | Kumar KC et al. |
| 2018/0193244 A1 | 7/2018 | Hood et al. |

FOREIGN PATENT DOCUMENTS

| | | |
|---|---|---|
| CN | 1558758 | 12/2004 |
| CN | 103153053 | 2/2015 |
| EA | 201000673 | 4/2011 |
| EA | 201000718 | 6/2011 |
| EA | 201101244 | 4/2012 |
| EP | 0230110 | 7/1987 |
| EP | 0290442 | 11/1988 |
| EP | 0322033 | 6/1989 |
| EP | 0360701 | 3/1990 |
| EP | 0365089 | 4/1990 |
| EP | 0500005 | 8/1992 |
| EP | 0557089 | 8/1993 |
| EP | 0738705 | 10/1996 |
| EP | 0885869 | 12/1998 |
| EP | 1067195 | 1/2001 |
| EP | 2740741 | 9/2017 |
| JP | H05-170764 | 7/1993 |
| JP | 2001503381 | 3/2001 |
| JP | 2008106011 | 5/2008 |
| JP | 2008222606 | 9/2008 |
| JP | 2009-179619 | 8/2009 |
| JP | 2010195768 | 9/2010 |
| RU | 2003/128076 | 4/2005 |
| WO | WO1987005297 | 9/1987 |
| WO | WO1988003805 | 6/1988 |
| WO | WO1990011366 | 10/1990 |
| WO | WO1993022259 | 11/1993 |
| WO | WO1996021665 | 7/1996 |
| WO | WO1996032938 | 10/1996 |
| WO | WO1996040668 | 12/1996 |
| WO | WO9746225 | 12/1997 |
| WO | WO2000026197 | 5/2000 |
| WO | WO2001000578 | 1/2001 |
| WO | WO2001004100 | 1/2001 |
| WO | WO2001019822 | 3/2001 |
| WO | WO2001027116 | 4/2001 |
| WO | WO2001049291 | 7/2001 |
| WO | WO2001053268 | 7/2001 |
| WO | WO2001077090 | 10/2001 |
| WO | WO2002002533 | 1/2002 |
| WO | WO2002043675 | 6/2002 |
| WO | WO2003009841 | 2/2003 |
| WO | WO2003016266 | 2/2003 |
| WO | WO2003037316 | 5/2003 |
| WO | WO2004016592 | 2/2004 |
| WO | WO2005009997 | 2/2005 |
| WO | WO2005108347 | 11/2005 |
| WO | WO2005118556 | 12/2005 |
| WO | WO2006017896 | 1/2006 |
| WO | WO2006002119 | 2/2006 |
| WO | WO2006077851 | 7/2006 |
| WO | WO2006106812 | 10/2006 |
| WO | WO2007003389 | 1/2007 |
| WO | WO2007051314 | 5/2007 |
| WO | WO2007059108 | 5/2007 |
| WO | WO2007103584 | 9/2007 |
| WO | WO2008001921 | 1/2008 |
| WO | WO2008020625 | 2/2008 |
| WO | WO2008118626 | 10/2008 |
| WO | WO2008156345 | 12/2008 |
| WO | WO2009071997 | 6/2009 |
| WO | WO2009129267 | 10/2009 |
| WO | WO2009136889 | 11/2009 |
| WO | WO2010054126 | 5/2010 |
| WO | WO2010075551 | 7/2010 |
| WO | WO2011009826 | 1/2011 |
| WO | WO2012024404 | 2/2012 |
| WO | WO2012106343 | 8/2012 |
| WO | WO2013113722 | 8/2013 |
| WO | WO2013169724 | 11/2013 |
| WO | WO2014128207 | 8/2014 |
| WO | WO2014128591 | 8/2014 |
| WO | WO2014130869 | 8/2014 |
| WO | WO2014130879 | 8/2014 |

OTHER PUBLICATIONS

Baron and Rawadi, "Minireview: Targeting the Wnt/-Catenin Pathway to Regulate Bone Formation in the Adult Skeleton," *Endocrinology* Jun. 2007, 148(6): 2635-2643.

Belgodere et al., "Studies in isomeric pyridylisoxazoles," *Heterocycles*, 20(3): 501-504, 1983.

Benati et al., "Thermal reactions of aryl azides with trans-1,2-dibenzoyl- and trans-1,2-diacetyl-ethylene. Reactivity of 4,5-dibenzoyl- and 4,5-diacetyl-1-aryltriazoles" *J. Chem. Soc.*, Perkin Trans. 1, No. 12 (1989), pp. 2235-2243.

Bhattacharyya and Dayal, "Age-related cochlear hair cell loss in the chinchilla," *Ann Otol Rhinol Laryngol.*, 94(1 Pt 1):75-80, Jan.-Feb. 1985.

Bienz and Clevers, "Linking colorectal cancer to Wnt signaling," *Cell*, 103(2):311-320, Oct. 13, 2000.

Biftu et al., "Syntheses of lignans from 2,3-diaroylbutanes," J Chem Soc Perkin 1: Organic and Bio-Organic Chemistry (1972-1999), (1978), vol. 19, pp. 1147-1150.

(56) References Cited

OTHER PUBLICATIONS

Bodine et al., "A small molecule inhibitor of the Wnt antagonist secreted frizzled-related protein-1 stimulates bone formation," *Bone* 2009, 44(6): 1063-1068.
Bogdan Allemann et al., "Antioxidants used in skin care formulations," Skin Therapy Lett., 13(7):5-9, Sep. 2008.
Boger et al., "Non-Amide-Based Combinatorial Libraries Derived from N-Boc-Iminodiacetic Acid: Solution-Phase Synthesis of Piperazinone Libraries with Activity Against LEF-1/β-Catenin-Mediated Transcription," *Helvetica Chimica Acta*, 83(8): 1825-1845, Aug. 9, 2000.
Bruchhausen and Lingner, [A Synthesis of DL-Asarinin and DL-Sesamin] "Eine Synthese von DL-Asarinin und DL-Sesamin," *Archiv Der Pharmazie*, 290:1-16, Jan. 1957 [English translation. included], 38 pages.
Bylund et al., "Vertebrate neurogenesis is counteracted by Sox1-3 activity," *Nature Neuroscience* 2003, 6(11): 1162-1168.
Cairo et al., "Hepatic stem-like phenotype and interplay of Wnt/beta-catenin and Myc signaling in aggressive childhood liver cancer." *Cancer Cell* Dec. 2008, 14(6): 471-484.
Chai et al., "Wnt signaling induces proliferation of sensory precursors in the postnatal mouse cochlea," *Proc Natl Acad Sci U S A.*, 109(21):8167-72, Epub May 4, 2012.
Chemical Abstracts 154:83772 of Wang et al, Natural Product Communications (2009), 4(11), pp. 1571-1574. [Abstract].
Chen and Alman, "Wnt Pathway, an Essential Role in Bone Regeneration," 2009, *Journal of Cellular Biochemistry* 106:353-362.
Chilosi et al., "Aberrant Wnt/beta-catenin pathway activation in idiopathic pulmonary fibrosis," *Am J Pathol.*, 162(5):1495-1502, May 2003.
Chou and Talalay, "Quantitative analysis of dose-effect relationships: the combined effects of multiple drugs or enzyme inhibitors," *Adv Enzyme Regul.*, 22:27-55, 1984.
Clarke, A. R. "Wnt signalling in the mouse intestine," *Oncogene* 2006, 25(57): 7512-7521.
Cointet et al., "Synthèse et propriètès pharmacologiques des acètoacètyl-3 indoles et leurs dèrivès," [Synthesis and pharmacological properties of 3-acetoacetylindoles and their derivatives] *European Journal of Medicinal Chemistry*, 11(5):471-479, 1976 [English machine translation].
Constable et al., "Platinamacrocycles containing 2, 5-thiophenediyl and poly (2, 5-thiophenediyl)-linked azaaromatic ligands. New structural paradigms for metallosupramolecular chemistry," *Polyhedron* 25(8): 1844-1863, 2006.
Corr, "Wnt-β-catenin signaling in the pathogenesis of osteoarthritis" Nature Clinical Practice, Oct 2008, 4(10): 550-556.
Denayer et al., "Canonical Wnt signaling controls proliferation of retinal stem/progenitor cells in postembryonic Xenopus eyes," *Stem Cells* 2008, 26(8): 2063-2074.
Dulinska-Molak et al., "Age-related changes in the mechanical properties of human fibroblasts and its prospective reversal after anti-wrinkle tripeptide treatment," International journal of peptide research and therapeutics, 20(1): 77-85, 2014.
Extended European Search Report for Application No. 14753569.4, dated Jun. 8, 2016, 6 pages.
Extended European Search Report for Application No. 15833863.2, dated Mar. 12, 2018, 5 pages.
Extended European Search Report for Application No. 17193280.9, dated Mar. 6, 2018, 6 pages.
Farwick et al., "An ECM-derived Tetrapeptide to Counterbalance ECM Degeneration," Cosmetics & Toiletries, 124: 51-54, 2009.
Fernandez-Martos et al., "Differential expression of Wnts after spinal cord contusion injury in adult rats," *PLoS One*, 6(11):e27000, 12 pages, Epub Nov. 2011.
Fischer et al., "Direct and non-direct measurement techniques for analysis of skin surface topography," Skin Pharmacol Appl Skin Physiol., 12(1-2):1-11, Jan.-Apr. 1999.
Ford et al., "Anti-irritants: Myth or reality? an overview," Exogenous Dermatology., 3(3):154-160, 2004.

Gerbino, *Remington: The Science and Practice of Pharmacy*, 21st Edition. Philadelphia, PA: Lippincott Williams & Wilkins, 2005.
Glass et al., "Canonical Wnt Signaling in Differentiated Osteoblasts Controls Osteoclast Differentiation," *Developmental Cell* 2005, 8(5): 751-764.
González et al., "The latest on skin photoprotection," Clin Dermatol., 26(6):614-626, Nov.-Dec. 2008.
Graham et al., "SOX2 Functions to Maintain Neural Progenitor Identity," *Neuron* 2003, 39(5): 749-765.
Greene and Wuts, "The role of protective groups in organic synthesis," *Protective Groups in Organic Synthesis*, 4th Ed., John Wiley & Sons, 15 pages, 2007.
Harris, "Cellular diversification in the vertebrate retina," *Current Opinion in Genetics & Development* 1997, 7(5): 651-658.
Hollis and Zou, "Expression of the Wnt signaling system in central nervous system axon guidance and regeneration," *Front Mol Neurosci.*, 5:5, 5 pages, Feb. 2012.
Hollis and Zou, "Reinduced Wnt signaling limits regenerative potential of sensory axons in the spinal cord following conditioning lesion," *Proc Natl Acad Sci U S A.*, 109(36):14663-14668, Aug. 2012.
Huntzicker et al., "Controlling Hair Follicle Signaling Pathways through Polyubiquitination," *Investigative Dermatology* 2008, 128(5): 1081-1087.
Inestrosa and Arenas, "Emerging roles of Wnts in the adult nervous system" *Nature Reviews* 2010, 11: 77-86.
International Preliminary Report on Patentability for International App. No. PCT/US2015/046120, dated Mar. 2, 2017, 27 pages.
Invitation to Pay for International App. No. PCT/US2015/046120, dated Nov. 4, 2015, 2 pages.
Jaenisch and Young, "Stem cells, the molecular circuitry of pluripotency and nuclear reprogramming," *Cell*, 132(4):567-582, Feb. 22, 2008.
Japanese Office Action in Japanese Application No. 2017-529598, dated Jul. 29, 2019, 8 pages.
Jiang et al., "Pluripotency of mesenchymal stem cells derived from adult marrow," Nature 2002, 418(6893): 41-49.
Jończyk et al., "Reactions of carbanions from 2-(dialkylamino)-arylacetonitriles with acetylene—simple syntheses of 1,3-dienamines and 1,4-diketones[1]," *Tetrahedron*, vol. 46, No. 3 (1990), pp. 1025-1038.
Kale et al., "Synthesis and characterization of some important indazolyl derivatives," *Journal of Heterocyclic Chemistry*, 44(2): 289-301, Mar.-Apr. 2007.
Kel'in and Kulinkovich, "A New Simple Synthesis of Aryl-Substituted 1,4-Diketones," *Synthesis* 1996, pp. 330-332.
Kim et al., "Anti-wrinkle and anti-inflammatory effects of active garlic components and the inhibition of MMPs via NF-κB signaling," PLoS One., 8(9):e73877, Sep. 16, 2013.
Kim et al., "The mechanism of retinol-induced irritation and its application to anti-irritant development," Toxicol Lett., 146(1):65-73, Dec. 15, 2003.
Klopp et al., "Effect of four treatment variants on the functional and cosmetic state of mature scars," J Wound Care., 9(7):319-324, Jul. 2000.
Koenekoo et al., "Novel Rpgr mutations with distinct retinitis pigmentosa phenotypes in French-Canadian families," *Am J Ophthalmol.*, 136(4):678-687, Oct. 2003.
Kubo et al., "Wnt2b controls retinal cell differentiation at the ciliary marginal zone," *Development*, 130(3):587-598, Feb. 2003.
Kubo et al., "Wnt2b inhibits differentiation of retinal progenitor cells in the absence of Notch activity by downregulating the expression of proneural genes," *Development*, 132(12):2759-2770, Epub May 18, 2005.
Lee et al., "Canonical Wnt signaling through Lef1 is required for hypothalamic neurogenesis," *Development* 2006, 133(22): 4451-4461.
Li et al., "Ring-opening of tertiary cyclopropanols derived from β-diketones," *Tetrahedron*, 62(33):7762-7771, Aug. 14, 2006.
Lie et al., "Wnt signalling regulates adult hippocampal neurogenesis," *Nature* 2005, 437(7063): 1370-1375.
Lindsley et al., "Canonical Wnt signaling is required for development of embryonic stem cell-derived mesoderm," *Development*, 2006, 133(19): 3787-3796.

(56) References Cited

OTHER PUBLICATIONS

Livesey and Cepko, "Vertebrate Neural Cell-Fate Determination: Lessons from the Retina," *Nature Reviews Neuroscience* 2001, 2: 109-118

Logan and Nusse, "The Wnt signaling pathway in development and disease," *Annu Rev Cell Dev Biol.*, 20:781-810, 2004.

Lopes L M X et al: "Further lignoids from Virola Sebifera," Jan. 1, 1984 (Jan. 1, 1984), Phytochemistry, Pergamon Press, Gb pp. 2647-2652, XP02662136.

Mao et al., "Low-Density Lipoprotein Receptor-Related Protein-5 Binds to Axin and Regulates the Canonical Wnt Signaling Pathway," *Molecular Cell* 2001, 7(4): 801-809.

Maramaldi et al., "Anti-inflammaging and antiglycation activity of a novel botanical ingredient from African biodiversity (Centevita™)," Clin Cosmet Investig Dermatol., 7:1-9, Dec. 12, 2013.

Marson et al., "Wnt signaling promotes reprogramming of somatic cells to pluripotency," *Cell Stem Cell*, 3(2): 132-135, Aug. 7, 2008.

Marvin et al., "Inhibition of Wnt activity induces heart formation from posterior mesoderm," *Genes & Development* 2001, 15(3): 316-327.

McCormick et al., "Comparative ototoxicity of netilmicin, gentamicin, and tobramycin in cats," *Toxicol Appl Pharmacol.*, 77(3):479-489, Mar. 15, 1985.

McCrea et al., "A homolog of the armadillo protein in *Drosophila* (plakoglobin) associated with E-cadherin," *Science*, 1991, 254(5036): 1359-1361.

Merrill, "Develop-WNTs in Somatic Cell Reprogramming," *Cell Stem Cell* 2008, 3(5): 465-466.

Michaelidis and Lie, "Wnt signaling and neural stem cells: caught in the Wnt web," *Cell Tissue Res.*, 331(1):193-210, Epub Sep. 9, 2007.

Mitani et al., "Prevention of the photodamage in the hairless mouse dorsal skin by kojic acid as an iron chelator," Eur J Pharmacol., 411(1-2):169-174, Jan. 5, 2001.

Moon et al., "The Promise and Perils of Wnt Signaling Through β-Catenin," *Science*, 2002, 296(5573): 1644-1646.

More et al., "Synthesis antioxidant and antimicrobial activities of some 7-methoxy-3methyl benzofuran incorporated chromon-4-ones," *Indian Journal of Heterocyclic Chemistry*, 16(4): 379-382, Apr.-Jun. 2007.

Morin, "Beta-catenin signaling and cancer," *BioEssays*, Dec. 1999, 21(12): 1021-1030.

Morrison, Sean J. "Neuronal potential and lineage determination by neural stem cells," *Current Opinion in Cell Biology*, 2001, 13: 666-672.

Morvan et al., "Deletion of a single allele of the Dkk1 gene leads to an increase in bone formation and bone mass ," *Journal of Bone and Mineral Research*, 2009, 21(6): 934-945.

Naito et al., "Developmental stage-specific biphasic roles of Wnt/β-catenin signaling in cardiomyogenesis and hematopoiesis," *Proc Natl Acad Sci USA.* 2006, 103(52): 19812-19817.

Nevar et al., "One Step Preparation of 1,4-Diketones from Methyl Ketones and α-Bromomethyl Ketones in the Presence of ZnCl$_2$ • t-BuOH • Et$_2$NR as a Condensation Agent" *Synthesis*, No. 9 (2000), pp. 1259-1262.

Nishiyama and Kobayashi, "Synthesis of 1,4-Diketones: Reaction of α-Bromo Ketones with Tetrakis (dimethylamino)ethylene (TDAE)," *Tetrahedron Letters*, vol. 47, (2006) pp. 5565-5567.

Nuriev et al., "Synthetic pathways to a family of pyridine-containing azoles-promising ligands for coordination chemistry," Arkivoc 4: 208-224, 2005.

Okita et al., "Generation of germline-competent induced pluripotent stem cells," *Nature* (2007), 448(7151): 313-317.

Osakada et al., "Wnt Signaling Promotes Regeneration in the Retina of Adult Mammals," *Journal of Neuroscience* (2007), 27(15): 4210-4219.

Parker et al., "Polymers for drug eluting stents," *Curr Pharm Des.*, 16(36):3978-3988, 2010.

Passarotti et al., "Synthesis of some 5-azaflavones," *Bollettino Chimico Farmaceuitico*, 130(8):312-314, Sep. 1991.

Patani et al., "Bioisosterism: a rational approach in drug design," Chem. Rev. 96: 3147-3176, 1996.

Pelletier et al., "(1-(4-(Naphthalen-2-yl)pyrimidin-2-yl)piperidin-4-yl)methanamine: a wingless beta-catenin agonist that increases bone formation rate," *Journal of Medicinal Chemistry*, 2009, 52(22): 6962-6965.

Polakis, "Wnt signaling and cancer," *Genes Dev.*, 2000, 14(15): 1837-1851.

Rajesh et al., "Synthesis and in vitro short term cytotoxic studies of some novel β-di ketones," *Indian drugs*, 40(1): 37-40, Jan. 2003.

Robinson et al., "Wnt/-Catenin Signaling Is a Normal Physiological Response to Mechanical Loading in Bone," *The Journal of Biological Chemistry*, Oct. 2006, 281(42): 31720-31728.

Rosa et al., "N-and C-Acylation in β-Enamino Ketones: Structural Effects on Regiocontrol," *Synlett*, No. 20 (2007), pp. 3165-3717.

Rosenberg Zand et al., "Flavonoids can block PSA production by breast and prostate cancer cell lines," *Clinica Chimica Acta*, 317:17-26, 2002.

Sakanaka et al., "Casein kinase IE in the Wnt pathway: Regulation of β-catenin function," *Proceedings of the National Academy of Sciences of the USA* 1999, 96(22): 12548-12552.

Sampath, et al., "Isolation of osteogenin, an extracellular matrix-associated, bone-inductive protein, by heparin affinity chromatography," *Proc. Natl. Acad. Sci. USA* 1987, 84(20): 7109-7113.

Santini et al., "New molecular targets in bone metastases" *Cancer Treatment Reviews*, 36S3 (2010) S6-S10.

Sauthier et al., "Carbonylative 1,4-addition of potassium aryltrifluoroborates to vinyl ketones," *New J. Chem.*, vol. 33 (2009), pp. 969-971.

Schneider et al., "Wnt antagonism initiates cardiogenesis in *Xenopus laevis*," *Genes & Development*, 2001, 15(3): 304-315.

Selic et al., "A Simple Stereoselective One-Pot Conversion of Compounds with a Dimethylaminomethylene Group into Enol Esters," *Synthetic Communications*, vol. 31, No. 11 (2001) pp. 1743-1752.

Selvamurugan and Aidhen, "N-Methoxy-N-methyl-3-bromopropionamide: anew three carbon homologating agent for the synthesis of unsymmetrical 1,4-diketones," Tetrahedron vol. 57, No. 28 (Jul. 2001) pp. 6065-6069.

Sheikh et al., "Synthesis of heterocyclic beta-diketones," *Indian Journal of Heterocyclic Chemistry*, 18(4): 333-336, Jan.-Mar. 2009.

Shi et al., "Identification of a novel signal for activation of Ti plasmid-encoded vir genes from rice (*Oryza sativa* L.)," *Chinese Science Bulletin*, 40(21): 1824-1828, Nov. 1995.

Shi et al., "Wnt-responsive Lgr5-expressing stem cells are hair cell progenitors in the cochlea," *J Neurosci.*, 32(28):9639-9648, Jul. 11, 2012.

Silkstone et al., "β-Catenin in the race to fracture repair: in it to Wnt," *Nature Clinical Practice*, Aug. 2008, 4(8): 413-419.

Slepecky et al., "Correlation of audiometric data with changes in cochlear hair cell stereocilia resulting from impulse noise trauma," *Acta Otolaryngol.*, 93(5-6):329-340, May-Jun. 1982.

Sorsak et al., "The synthesis of ethyl 2[(2,2-dibenzoyl)ethenyl]amino-3-dimethyl-aminopropanoate and its application to the synthesis of fused 3-aminopyran-2-ones and 3-aminoazolo- and - aminopyridine-4(4H)-ones," *J. Heterocyclic Chem*, vol. 35, No. 6, pp. 1275-1279, 1998.

Sosnovskikh et al., "3-(Polyhaloacyl)chromones and Their Hetero Analogues: Synthesis and Reactions with Amines," Synthesis, No. 16 (2006) pp. 2707-2718.

Sosnovskikh et al., "Synthesis and some properties of 6-di(tri)fluoromethyl-and 5di(tri)fluoroacetyl-3-methyl-1-phenylpyrano[2,3-c]pyrazol-4(1H)-ones," *Russian Chemical Bulletin*, vol. 54, No. 12 (2005), pp. 2846-2850.

Soufyane et al., "Synthesis of some fluorinatednitrogen heterocycles from (diethylaminomethylene)hexafluoroacetylacetone (DAMFA)," Tetrahedron Letters, vol. 34, No. 48 (Nov. 1993), pp. 7737-7740.

Sperling, L. C.; "Hair anatomy for the clinician," *J. Amer. Acad. Dermatology* 1991, 25(1, Part 1): 1-17.

Suh et al., "Axonal regeneration effects of Wnt3a-secreting fibroblast transplantation in spinal cord-injured rats," *Acta Neurochir (Wien)*, 153(5):1003-1010, Epub Jan. 2011.

(56) References Cited

OTHER PUBLICATIONS

Tamura et al., "Role of the Wnt signaling pathway in bone and tooth," *Frontiers in Bioscience*, Jun. 2010, E2, 1405-1413.

Tashiro, et al., "A Synthetic Peptide Containing the IKVAV Sequence from the A Chain of Laminin Mediates Cell Attachment, Migration, and Neurite Outgrowth," *The Journal of Biological Chemistry* 1989, 264(27): 16174-16182.

Tencer, et al., "The effect of local controlled release of sodium fluoride on the stimulation of bone growth," *Journal of Biomedical Materials Research* 1989, 23(6): 571-589.

Trivedi et al., "Investigational anabolic therapies for osteoporosis" *Expert Opin. Investig. Drugs*, 2010, 19(8): 995-1005.

Tsukahara et al., "Inhibition of ultraviolet-B-induced wrinkle formation by an elastase-inhibiting herbal extract: implication for the mechanism underlying elastase-associated wrinkles," Int J Dermatol., 45(4):460-468, Apr. 2006.

Van Raay et al., "Frizzled 5 signaling governs the neural potential of progenitors in the developing Xenopus retina," *Neuron* 2005, 46(1): 23-36.

Van Uitert et al., "Coordination compounds. II. The dissociation constants of beta-diketones in water-dioxane solutions," Journal of the American Chemical Society, 75:455-457, Jan. 20, 1953.

Voituriez et al., "Preparation of a Storable Zinc Carbenoid Species and Its Application in Cyclopropanation, Chain Extension, and [2,3]-Sigmatropic Rearrangement Reactions," *J. Org. Chem*, vol. 75, No. 4 (2010), pp. 1244-1250.

Wagner et al., "The Therapeutic Potential of the Wnt Signaling Pathway in Bone Disorders" *Current Molecular Pharmacology*, 2011, 4:14-25.

Wang et al, "Evaluation of the influence of compound structure on stacked-dimer formation in the DNA minor groove," Biochemistry, 40(8): 2511-2521, Feb. 2001.

Wang et al., "Caspase inhibitors, but not c-Jun NH2-terminal kinase inhibitor treatment, prevent cisplatin-induced hearing loss," *Cancer Res.*, 64(24):9217-9224, Dec. 15, 2004.

Wang et al., "Two new lignans from the fruits of Schisandra sphenanthera," *Nat Prod Commun.*, 4(11):1571-1574, Nov. 2009.

Wernig et al., "Neurons derived from reprogrammed fibroblasts functionally integrate into the fetal brain and improve symptoms of rats with Parkinson's disease," *Proc. Natl. Acad. Sci. USA* 2008, 105(15): 5856-5861.

Wong et al., "Effects Effects of forced expression of an NH2-terminal truncated beta-Catenin on mouse intestinal epithelial homeostasis," *J Cell Biol.*, 141(3):765-777, May 4, 1998.

Wong et al., "Selection of multipotent stem cells during morphogenesis of small intestinal crypts of Lieberkuhn is perturbed by stimulation of Lef-1/beta-catenin signaling," *J Biol Chem.*, 277(18):15843-50. Epub Feb. 19, 2002.

Wu and Farrelly, "Regulatory perspectives of Type II prodrug development and time-dependent toxicity management: nonclinical Pharm/Tox analysis and the role of comparative toxicology," *Toxicology*, 236(1-2):1-6, Epub Apr. 2007.

Wu Anxin et al: "An Expeditious Synthetic Route to Furolignans having Two Different Aryl Groups+," J. of Chem. Res.—Synopses, No. 3, Jan. 1, 1998 (Jan. 1, 1997), pp. 136-137, XP055276538.

Xue et al., "Zinc-mediated chain extension reaction of 1,3-diketones to 1,4-diketones and diastereoselective synthesis of trans-1,2-disubstituted cyclopropanols," *Journal of Organic Chemistry* 2006, 71(1): 215-218.

Yamaguchi et al., "Histone deacetylase 1 regulates retinal neurogenesis in zebrafish by suppressing Wnt and Notch signaling pathways," *Development*, 132(13):3027-3043, Jul. 2005.

Yasuda et al., "Cross-coupling reaction of alpha-chloroketones and organotin enolates catalyzed by zinc halides for synthesis of gamma-diketones," *J Am Chem Soc.*, vol. 124, No. 25 (Jun. 2002), pp. 7440-7447.

Yavropoulou and Yovos, "The role of the wnt signaling pathway in osteoblast commitment and differentiation" *Hormones*, 2007, 6(4):279-294.

Yoon et al., "Anti-wrinkle effect of bone morphogenetic protein receptor 1a-extracellular domain (BMPR1a-ECD)," BMB Rep., 46(9):465-470, Sep. 2013.

Yoshimura et al., "Discovery of novel and potent retinoic acid receptor alpha agonists: syntheses and evaluation of benzofuranyl-pyrrole and benzothiophenyl-pyrrole derivatives," *J Med Chem.*, 43(15):2929-2937, Jul. 27, 2000.

Zaragosi et al., Effects of GSK3 inhibitors on in vitro expansion and differentiation of human adipose-derived stem cells into adipocytes. BMC Cell Biology 2008, 9(11), pp. 1-9, Published Feb. 13, 2006, Abstract; p. 2.

Zhang et al., "Role of the conserved aspartate and phenylalanine residues in prokaryotic and mitochondrial elongation factor Ts in guanine nucleotide exchange," *FEBS Lett.*, 391(3):330-332, Aug. 12, 1996.

Zhu and Zhang, "Synthesis and reaction of β,β-di(trifluoroacetyl) ethylenederivatives, $(CF_3CO)_2C=CR_1R_2$," *Journal of Fluorine Chemistry*, vol. 74, No. 2 (1995), pp. 167-170.

Australian Office Action in AU Appln. No. 2015305373, dated Nov. 22, 2019, 5 pages.

Yang et al., "Mixed-valence tetra- and hexanuclear manganese complexes from the flexibility of pyridine-containing beta-diketone ligands," Inorganic Chemistry, 2008, 47(6):1925-1939.

\* cited by examiner

GAMMA-DIKETONES FOR TREATMENT AND PREVENTION OF AGING SKIN AND WRINKLES

RELATED APPLICATIONS

This application is a continuation application of U.S. application Ser. No. 15/706,908, filed on Sep. 18, 2017, which is a divisional application of U.S. application Ser. No. 14/831,456, filed Aug. 20, 2015, which claims the benefit of U.S. Provisional Application No. 62/039,786, filed Aug. 20, 2014, both of which are incorporated herein by reference in its entirety.

BACKGROUND

Technical Field

The present disclosure relates to compounds, cosmetic or dermopharmaceutical compositions comprising the same, and methods for using the compounds or compositions for treating, protecting, and/or improving the condition and/or aesthetic appearance of skin, for example, treating, preventing, ameliorating, reducing and/or eliminating fine lines and/or wrinkles of skin, or improving the appearance of fine lines and/or wrinkles of skin, the methods comprising application of the disclosed compounds or compositions.

Background

Mammalian epidermis and its appendages (e.g., hair, nail, sebaceous and sweat glands) provide a barrier to keep harmful elements out of the body and essential body fluids in. As the first line of defense against the various physical traumas of the environment, the epidermis must protect itself as well as the underlying tissues. The epidermis is also exposed to mutagenic ultraviolet radiation. In nonhaired or sparsely haired regions such as most human skin, the epidermis is thicker than that of furred skin, and in these locations the skin functions primarily in a protective role. The constant assaults on the epidermis necessitate self-renewal, making the epidermis a prime example of an adult tissue that undergoes continual and rapid flux.

Aged skin differs from youthful skin both in appearance and in function. The aged epidermis lacks keratinocytes and is physically thinner, but mostly from effacement of the rete ridges. In addition to thinning, aging slows wound healing, prolongs epidermal turnover, and impairs barrier formation. The skin appears thin, wrinkled, bruised, and rough. Wrinkling and bruising can also result from aging-related changes in the dermis. The dermis, too, is characteristically thinner in aged persons. Aged fibroblasts are less likely to synthesize normal amounts of collagen, elastin, laminin glycosaminoglycans, and fibronectin. The dermis can, in such cases, lack elasticity, strength, vessel support, remodeling abilities, and ground substances. For example, rete ridges can be effaced, and basal cells can no longer display villous projections into the dermis. Epidermal cell turnover is reduced up to 50% in the aged as compared to youth. For example, melanocyte numbers can decrease 8-20% per decade. There are fewer Langerhans cells in the aged, and those present are often functionally impaired. Collagen synthesis decreases, for example, up to 30% within 4 years of menopause in women. The numbers of collagen and elastic fibers are also decreased. The dermis can also become less echogenic to ultrasounds, consistent with changes in collagen and elastic tissues.

SUMMARY

The present disclosure relates to compounds, compositions comprising the same, and methods of using the compounds or compositions for treating, protecting, and/or altering (e.g., improving) the condition and/or aesthetic appearance of skin, including, for example, treating, preventing, ameliorating, reducing and/or eliminating fine lines and/or wrinkles of skin and/or improving the aesthetic appearance of fine lines and/or wrinkles of skin, caused by, for example, cellular senescence, environmental damage or dermatoheliosis. The disclosure also relates to methods for stimulating skin cell renewal, promoting fibroblast proliferation, and/or synthesizing elastin, collagen, proteoglycans, or new connective tissue, thereby reducing wrinkles, restoring elasticity, resiliency, and/or suppleness to the skin.

Compounds and compositions described herein can be employed for cosmetic uses, dermopharmaceutical uses, or both cosmetic and dermopharmaceutical uses. A "cosmetic", as used herein, can be contacted with the skin, such as by being rubbed, poured, sprinkled, or sprayed on the skin or otherwise introduced into or onto the skin, and is intended to improve the aesthetic appearance of the skin, such as by cleansing, beautifying, promoting attractiveness, or altering, e.g., improving, the aesthetic appearance of the contacted skin. A cosmetic benefit is typically visual or aesthetic, and can be evaluated using subjective or objective assays.

A "dermopharmaceutical" as used herein, can similarly be contacted with the skin, and is intended to be used in the treatment, mitigation or prevention of a disease or disorder of the skin, and/or is intended to affect the structure or a function of the skin. A dermopharmaceutical typically has a physiological, pharmacological, and/or therapeutic effect on the skin. A dermopharmaceutical can result in an improved aesthetic appearance of the skin by virtue of its physiological, pharmacological, or therapeutic effects. A dermopharmaceutical benefit can be evaluated using subjective or objective assays.

In one embodiment, the present disclosure provides a cosmetic or dermopharmaceutical composition for improving the condition and/or aesthetic appearance of skin, wherein the composition comprises a compound according to Formula I, II, IIIa, IIIb, and/or IV.

In one embodiment, the present disclosure provides a cosmetic or dermopharmaceutical composition for altering the aesthetic appearance of skin associated with or affected by, or for preventing or reducing, wrinkles, dry skin, sensitive skin, or dermatological symptoms caused by ineffective homeostatic regulation of healthy skin, wherein the composition comprises a compound according to Formula I, II, IIIa, IIIb, and/or IV.

In one embodiment, the present disclosure provides a cosmetic or dermopharmaceutical composition for altering the aesthetic appearance of skin associated with or affected by wrinkling, sagging, and/or loss of skin elasticity, wherein the composition comprises a compound according to Formula I, II, IIIa, IIIb, and/or IV.

In another embodiment, the disclosure relates to the use of a compound according to Formula I, II, IIIa, IIIb, and/or IV for altering the aesthetic appearance of skin associated with or affected by wrinkles and/or fine lines, wizened skin, a lack of elasticity and/or tonus of the skin, thinning of the dermis, degradation of collagen fibers, flaccid skin, thinned skin, and/or the internal degradation of the skin following exposure to ultraviolet radiation.

In one embodiment, the present disclosure provides a cosmetic or dermopharmaceutical composition for altering the aesthetic appearance of skin associated with or affected by, or for treating or preventing, a skin condition/disorder accompanied by a loss of skin elasticity, wherein the composition comprises a compound according to Formula I, II, IIIa, IIIb, and/or IV.

In one embodiment, the present disclosure provides a cosmetic or dermopharmaceutical composition for altering the aesthetic appearance of skin associated with or affected by, or for treating or preventing, acne, wherein the composition comprises a compound according to Formula I, II, IIIa, IIIb, and/or IV.

In one embodiment, the present disclosure provides a cosmetic or dermopharmaceutical composition for treating or preventing deterioration in skin viscoelasticity, wherein the composition comprises a compound according to Formula I, II, IIIa, IIIb, and/or IV.

In one embodiment, the present disclosure provides a cosmetic or dermopharmaceutical composition for treating or preventing vitiligo (skin condition in which there is a loss of brown color (pigment) from areas of skin), wherein the composition comprises a compound according to Formula I, II, IIIa, IIIb, and/or IV.

In one embodiment, the disclosure provides methods for increasing cell or tissue regeneration. Such methods include administering to a vertebrate subject in need thereof a compound according to Formula I, II, IIIa, IIIb, and/or IV, or a dermatologically acceptable salt thereof.

In one embodiment, the present disclosure provides a cosmetic or dermopharmaceutical composition for activating or promoting proliferation and/or mobility of skin keratinocyte and/or dermis fibroblast, for example, to realize skin regeneration, wherein the composition comprises a compound according to Formula I, II, IIIa, IIIb, and/or IV.

In one embodiment, the present disclosure provides a cosmetic or dermopharmaceutical composition for increasing or improving epidermal cell repair activity, for example, in a human, wherein the composition comprises a compound according to Formula I, II, IIIa, IIIb, and/or IV.

In one embodiment, the present disclosure provides a cosmetic or dermopharmaceutical composition for increasing or improving the barrier function and/or viability of the skin, wherein the composition comprises a compound according to Formula I, II, IIIa, IIIb, and/or IV.

In one embodiment, the present disclosure provides a cosmetic or dermopharmaceutical composition for increasing fibroblast proliferation, keratinocyte proliferation, and/or expression of collagen, or reducing collagenase activity, wherein the composition comprises a compound according to Formula I, II, IIIa, IIIb, and/or IV.

In another embodiment, the disclosure relates to the use of a compound according to Formula I, II, IIIa, IIIb, and/or IV as a medicament for treating or preventing a wound healing disorder in a mammal.

In another embodiment, the disclosure relates to the use of a compound according to Formula I, II, IIIa, IIIb, and/or IV as a medicament for treating or preventing a wound such as a bedsore in a mammal.

Some embodiments provided herein include cosmetic or dermopharmaceutical compositions comprising one or more of the compounds provided herein and a dermatologically acceptable carrier.

One embodiment provided herein includes compounds of Formula I:

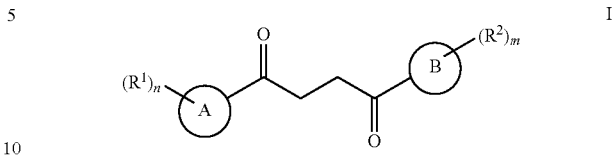

or a dermatologically acceptable salt thereof.

In some embodiments of Formula I:

Ring A is a 7-12 membered heteroaryl, with the proviso that a carbon atom on the ring is attached to the carbonyl carbon;

Ring B is selected from the group consisting of phenyl and a 5-6 membered heteroaryl, with the proviso that a carbon atom on the ring is attached to the carbonyl carbon;

$R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN;

$R^2$ is a substituent attached to Ring B and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN;

each $R^3$ is independently selected from the group consisting of H, unsubstituted —$C_{1-6}$ alkyl, and —$C_{1-3}$ haloalkyl;

each $R^{3b}$ is independently selected from the group consisting of H and unsubstituted —$C_{1-3}$ alkyl;

each n is 0 to 10; and each m is 0 to 5.

Another embodiment provided herein includes compounds of Formula II:

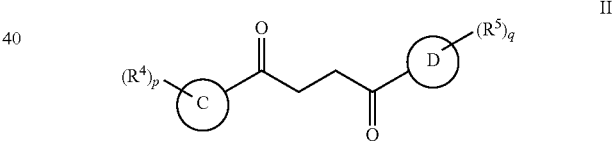

or a dermatologically acceptable salt thereof.

In some embodiments of Formula II:

Ring C is a 5-6 membered heteroaryl, with the proviso that a carbon atom on the ring is attached to the carbonyl carbon;

Ring D is selected from the group consisting of phenyl and a 5-6 membered heteroaryl, with the proviso that a carbon atom on the ring is attached to the carbonyl carbon;

$R^4$ is a substituent attached to Ring C and is independently selected at each occurrence from the group consisting of unsubstituted —$C_{1-6}$ alkyl, —$C_{1-3}$ haloalkyl, halide, —$OR^6$, and CN;

$R^5$ is a substituent attached to Ring D and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN;

each $R^6$ is independently selected from the group consisting of H, unsubstituted —$C_{1-6}$ alkyl, and —$C_{1-3}$ haloalkyl;

each $R^{6b}$ is independently selected from the group consisting of H and unsubstituted —$C_{1-3}$ alkyl;

each q is 0 to 4; and each p is 0 to 5.

Another embodiment provided herein includes compounds of Formula III:

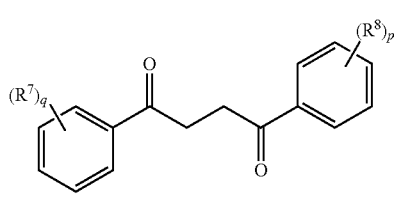

or a dermatologically acceptable salt thereof.

In some embodiments of Formula III:

$R^7$ is a substituent attached to the phenyl ring and is independently selected at each occurrence from the group consisting of unsubstituted —$C_{1-6}$ alkyl, —$CH_2OH$, —$CH_2N(R^{9a})_2$, —$C_{1-3}$ haloalkyl, halide, —$OR^9$, and CN;

$R^8$ is a substituent attached to the phenyl ring and is independently selected at each occurrence from the group consisting of unsubstituted —$C_{1-6}$ alkyl, —$CH_2OH$, —$CH_2N(R^{9a})_2$, —$C_{1-3}$ haloalkyl, halide, —$OR^9$, and CN;

each $R^9$ is independently selected from the group consisting of H, unsubstituted —$C_{1-6}$ alkyl, and —$C_{1-3}$ haloalkyl;

each $R^{9a}$ is independently selected from the group consisting of H and unsubstituted —$C_{1-3}$ alkyl; and each q is 1 to 5; and each p is 0 to 5.

Another embodiment provided herein includes compounds of Formula IIIa:

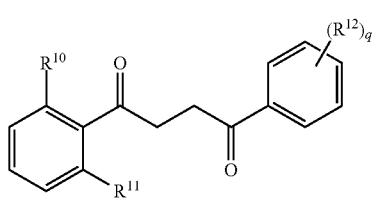

or a dermatologically acceptable salt thereof.

In some embodiments of Formula IIIa:

$R^{10}$ is selected from the group consisting of H, unsubstituted —$C_{1-6}$ alkyl, —$C_{1-3}$ haloalkyl, halide, —$OR^{13}$, and CN;

$R^{11}$ is selected from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN;

$R^{12}$ is a substituent attached to the phenyl ring and is independently selected at each occurrence from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN;

each $R^{13}$ is independently selected from the group consisting of unsubstituted —$C_{1-6}$ alkyl, and —$C_{1-3}$ haloalkyl;

each $R^{13b}$ is independently selected from the group consisting of H and unsubstituted —$C_{1-3}$ alkyl; and each q is 0 to 5.

Another embodiment provided herein includes compounds of Formula IIIb:

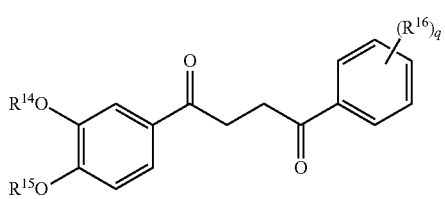

or a dermatologically acceptable salt thereof.

In some embodiments of Formula IIIb:

$R^{14}$ is selected from the group consisting of unsubstituted —$C_{1-6}$ alkyl and —$C_{1-3}$ haloalkyl;

$R^{15}$ is selected from the group consisting of unsubstituted —$C_{1-6}$ alkyl and —$C_{1-3}$ haloalkyl;

$R^{16}$ is a substituent attached to the phenyl ring and is independently selected at each occurrence from the group consisting of unsubstituted —$C_{1-6}$ alkyl, $CH_2OH$, —$CH_2N(R^{17b})_2$, —$C_{1-3}$ haloalkyl, halide, —$OR^{17}$, and CN;

each $R^{17}$ is independently selected from the group consisting of unsubstituted —$C_{1-6}$ alkyl and —$C_{1-3}$ haloalkyl;

each $R^{17b}$ is independently selected from the group consisting of H and unsubstituted —$C_{1-3}$ alkyl; and each q is 0 to 5.

Another embodiment provided herein includes compounds of Formula IV:

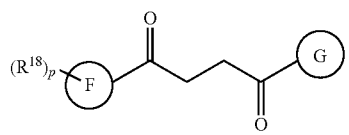

or a dermatologically acceptable salt thereof.

In some embodiments of Formula IV:

Ring F is

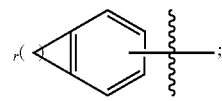

Ring G is selected from the group consisting of

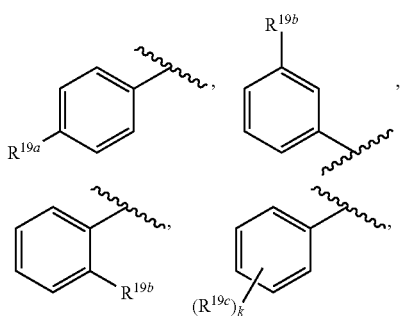

and a 5-6 membered heteroaryl($R^{19d}$)$_z$, with the proviso that a carbon atom on the heteroaryl ring is attached to the carbonyl carbon;

each $R^{18}$ is a substituent attached to Ring F and is independently selected at each occurrence from the group consisting of —$C_{1-3}$ haloalkyl, halide, —$OR^{20}$, and CN;

$R^{19a}$ is a substituent attached to the para position of phenyl and is selected from the group consisting of H, unsubstituted —$C_{2-6}$ alkyl, —$CH_2OH$, —$CH_2N(R^{21})_2$, —$C_{1-3}$ haloalkyl, F, Br, I, —$OR^{20}$, and CN;

$R^{19b}$ is a substituent attached to the meta or ortho position of phenyl and is selected from the group consisting of H, unsubstituted —$C_{2-6}$ alkyl, —$CH_2OH$, —$CH_2N(R^{21})_2$, —$C_{1-3}$ haloalkyl, halide, —$OR^{20}$, and CN;

$R^{19c}$ is a substituent attached to the phenyl and is independently selected at each occurrence from the group consisting of —$CH_2OH$, —$CH_2N(R^{21})_2$, —$C_{1-3}$ haloalkyl, halide, —$OR^{20}$, and CN;

$R^{19d}$ is a substituent attached to the heteroaryl ring and is independently selected at each occurrence from the group consisting of —$CH_2OH$, —$CH_2N(R^{21})_2$, —$C_{1-3}$ haloalkyl, halide, —$OR^{20}$, and CN;

each $R^{20}$ is independently selected from the group consisting of H, unsubstituted —$C_{3-6}$ alkyl and —$C_{1-3}$ haloalkyl;

each $R^{21}$ is independently selected from the group consisting of H and unsubstituted —$C_{1-3}$ alkyl;

k is 0 to 5;
p is 0 to 13;
r is 1 to 5;
z is 0 to 4.

Some embodiments include stereoisomers of a compound of Formula I, II, IIIa, IIIb, and/or IV.

Some embodiments include prodrugs of a compound of Formula I, II, IIIa, IIIb, and/or IV. For example, prodrugs of a compound of Formula I, II, IIIa, IIIb, and/or IV can be prodrug polymer conjugates for delayed release or extended release.

Also provided herein are cosmetic or dermopharmaceutical compositions comprising a compound of Formula I, II, IIIa, IIIb, and/or IV and a dermatologically acceptable carrier, diluent, or excipient.

It is to be understood that both the foregoing general description and the following detailed description are exemplary and explanatory only and are not restrictive of the disclosure, as claimed.

DETAILED DESCRIPTION OF THE DRAWINGS

FIG. 1 is a line graph showing the average change in roughness from baseline of test subjects skin after topical treatment of the periorbital areas by compound #222 (0.05% in oil, 0.05% in PEG, 0.15% in oil, and 0.15% in PEG). Roughness was determined by Visioscan. Each data point is the average of 20 or 21 test subjects.

Figure 2:
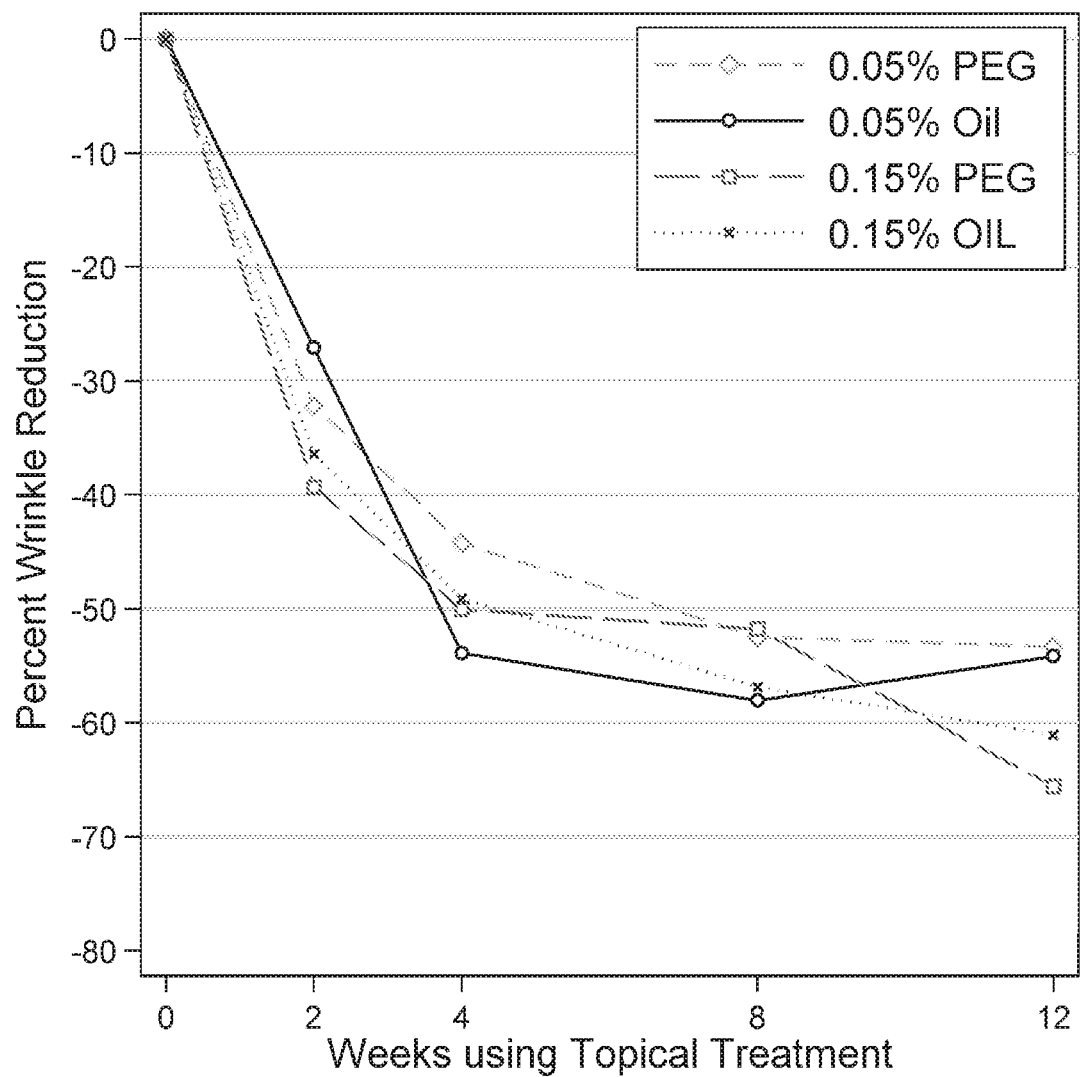

FIG. 2 is a line graph showing the average percent wrinkle reduction from baseline of test subjects skin after topical treatment of the periorbital areas by compound #222 (0.05% in oil, 0.05% in PEG, 0.15% in oil, and 0.15% in PEG). Wrinkle reduction was determined by Visioscan. Each data point is the average of 20 or 21 test subjects.

DETAILED DESCRIPTION

Provided herein are γ-diketones useful for treating, protecting, and improving the condition and/or aesthetic appearance of skin, for example, treating, preventing, ameliorating, reducing and/or eliminating, and/or improving the appearance of fine lines and/or wrinkles of skin. The inventors have discovered that in some embodiments, application of the γ-diketones provided herein can increase collagen replacement and retention, and can also, in some embodiments, increase cellular proliferation of the epidermis and dermis.

Cosmetic or dermopharmaceutical compositions comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a dermatologically acceptable salt thereof, and a dermatologically acceptable carrier are also provided herein.

Compounds

Some embodiments of the present disclosure include compounds of Formula (I):

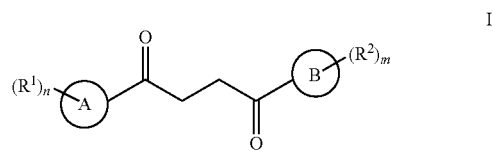

or salts, dermatologically acceptable salts, or prodrugs thereof.

In some embodiments of Formula I, Ring A is a 7-12 membered heteroaryl, wherein a carbon atom on the ring is attached to the carbonyl carbon.

In some embodiments of Formula I, Ring A is a 7-12 membered heteroaryl, wherein a carbon atom on the benzene ring is attached to the carbonyl carbon.

In some embodiments of Formula I, Ring A is a 7-12 membered heteroaryl, wherein a carbon atom on the heteroaromatic ring is attached to the carbonyl carbon.

In some embodiments of Formula I, Ring A is a 7-12 membered heteroaryl, wherein a carbon atom on the heterocyclic aliphatic ring is attached to the carbonyl carbon.

In some embodiments of Formula I, Ring B is selected from the group consisting of phenyl and a 5-6 membered heteroaryl, with the proviso that a carbon atom on the ring is attached to the carbonyl carbon.

In some embodiments of Formula I, $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula I, $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula I, $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula I, $R^2$ is a substituent attached to Ring B and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula I, each $R^3$ is independently selected from the group consisting of H, unsubstituted —$C_{1-6}$ alkyl and —$C_{1-3}$ haloalkyl.

In some embodiments of Formula I, each $R^{3b}$ is independently selected from the group consisting of H and unsubstituted —$C_{1-3}$ alkyl.

In some embodiments of Formula I, n is 0 to 10. In some embodiments of Formula I, n is 1 to 10.

In some embodiments of Formula I, m is 0 to 5.

In some embodiments of Formula I, m is 1 to 5.

In some embodiments of Formula I, Ring A is a 9-membered bicyclic heteroaryl ring containing 1-3 heteroatoms selected from the group consisting of N, O, and S.

In some embodiments of Formula I, Ring A is a 10-membered bicyclic heteroaryl ring containing 1-3 heteroatoms selected from the group consisting of N, O, and S.

In some embodiments of Formula I, Ring A is selected from the group consisting of:

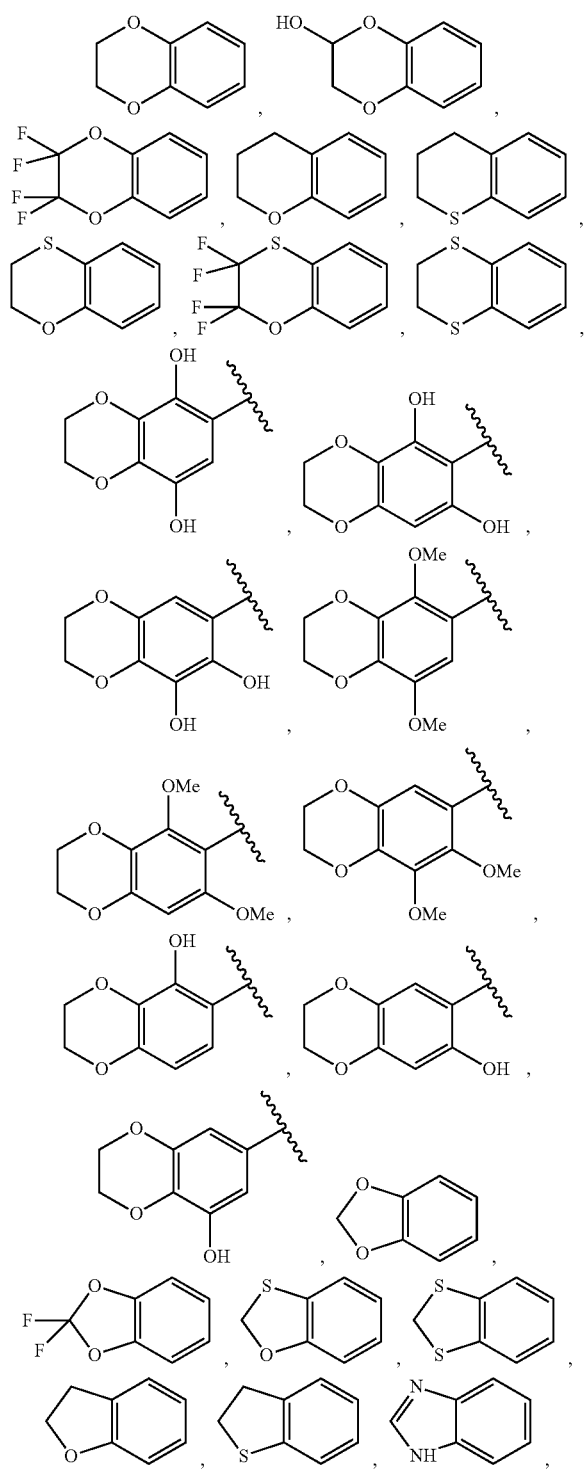

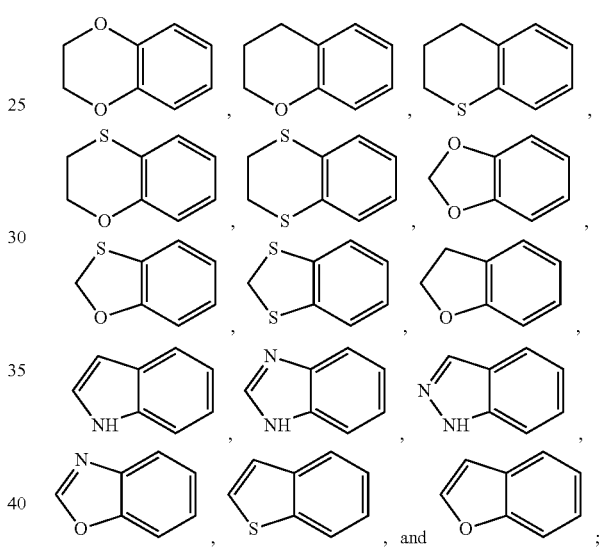

wherein, unless otherwise designated, the carbonyl carbon of Formula I can form a bond with any unsubstituted carbon on Ring A.

In some embodiments of Formula I, Ring A is selected from the group consisting of:

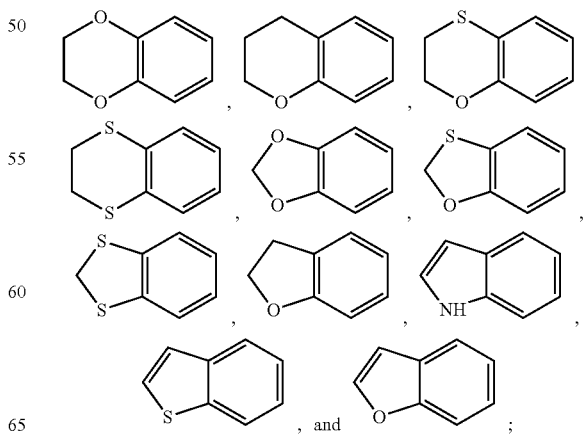

wherein the carbonyl carbon of Formula I can form a bond with any unsubstituted carbon on Ring A.

In some embodiments of Formula I, Ring A is selected from the group consisting of:

wherein the carbonyl carbon of Formula I can form a bond with any unsubstituted carbon on the Ring A.

In some embodiments of Formula I, Ring A is selected from the group consisting of:

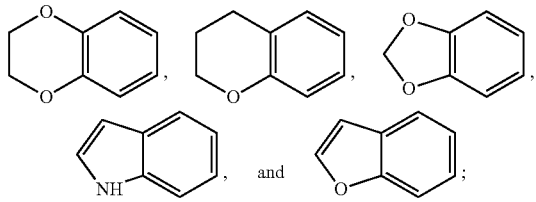

wherein the carbonyl carbon of Formula I can form a bond with any unsubstituted carbon on the Ring A.

In some embodiments of Formula I, Ring A is selected from the group consisting of

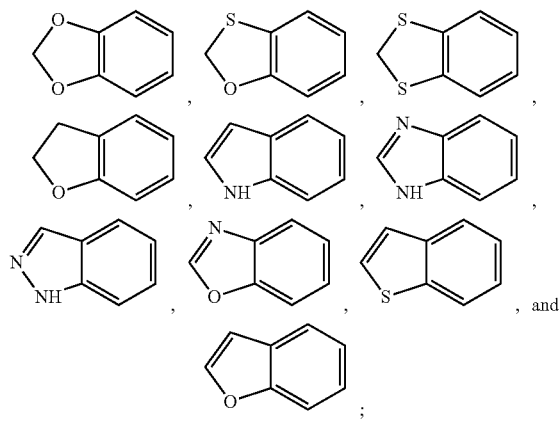

wherein the carbonyl carbon of Formula I can form a bond with any unsubstituted carbon on the Ring A.

In some embodiments of Formula I, Ring A is selected from the group consisting of

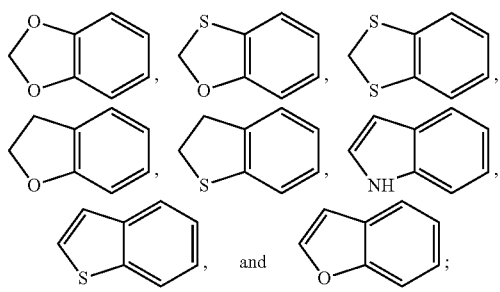

wherein the carbonyl carbon of Formula I can form a bond with any unsubstituted carbon on the Ring A.

In some embodiments of Formula I, Ring A is selected from the group consisting of

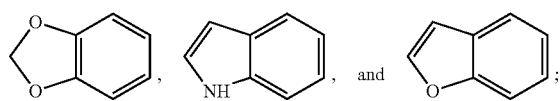

wherein the carbonyl carbon of Formula I can form a bond with any unsubstituted carbon on the Ring A.

In some embodiments of Formula I, Ring A is selected from the group consisting of

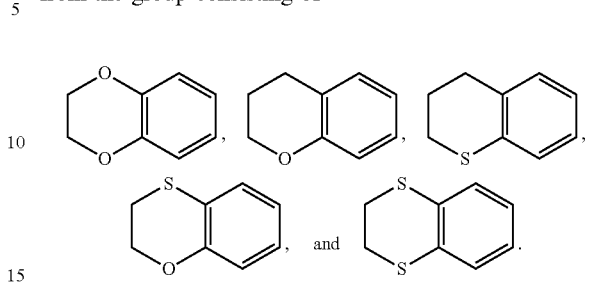

In some embodiments, Ring A is selected from the group consisting of

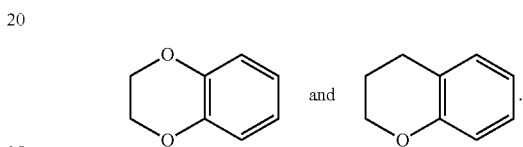

Some embodiments of Formula I include compounds of Formula (Ia):

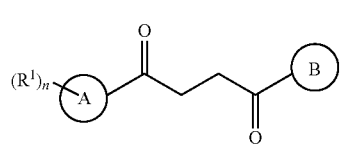

or salts, dermatologically acceptable salts, or prodrugs thereof.

In some embodiments of Formula Ia, Ring A is

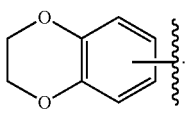

In some embodiments of Formula Ia, Ring B is selected from the group consisting of

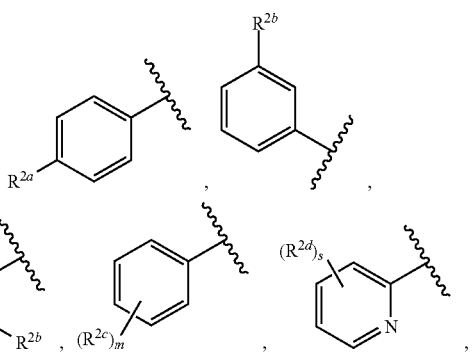

-continued

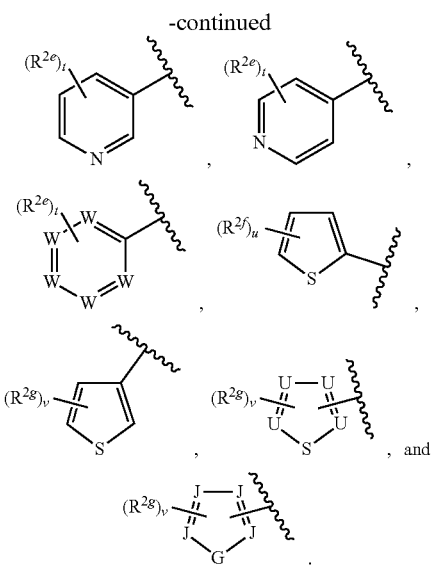

In some embodiments of Formula Ia, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula Ia, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula Ia, $R^{2a}$ is a substituent attached to the para position of phenyl and selected from the group consisting of unsubstituted —$C_{1-6}$ alkyl, —$CH_2OH$, —$CH_2N(R^{3b})_2$, —$C_{1-3}$ haloalkyl, Cl, Br, I, —$OR^{3a}$, and CN.

In some embodiments of Formula Ia, $R^{2b}$ is one substituent attached to the meta or ortho position of phenyl and selected from the group consisting of unsubstituted —$C_{1-6}$ alkyl, —$CH_2OH$, —$CH_2N(R^{3b})_2$, —$C_{1-3}$ haloalkyl, halide, —$OR^{3a}$, and CN.

In some embodiments of Formula Ia, $R^{2c}$ is a substituent attached to the phenyl and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; m is 2 to 5.

In some embodiments of Formula Ia, $R^{2d}$ is a substituent attached to the heteroaryl ring and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; s is 1 to 4.

In some embodiments of Formula Ia, $R^{2e}$ is a substituent attached to the heteroaryl ring and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; t is 1 to 4.

In some embodiments of Formula Ia, $R^{2e}$ is a substituent attached to the heteroaryl ring and are independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN; t is 0 to 4.

In some embodiments of Formula Ia, $R^{2f}$ is a substituent attached to the heteroaryl ring and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; u is 1 to 3.

In some embodiments of Formula Ia, $R^{2g}$ is a substituent attached to the heteroaryl ring and are independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN; v is 1 to 3.

In some embodiments of Formula Ia, $R^{2g}$ is a substituent attached to the heteroaryl ring and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; v is 0 to 3.

In some embodiments of Formula Ia, each $R^3$ is independently selected from the group consisting of H, unsubstituted —$C_{1-6}$ alkyl and —$C_{1-3}$ haloalkyl.

In some embodiments of Formula Ia, each $R^{3a}$ is independently selected from the group consisting of unsubstituted —$C_{2-6}$ alkyl and —$C_{1-3}$ haloalkyl.

In some embodiments of Formula Ia, each $R^{3b}$ is independently selected from the group consisting of H and unsubstituted —$C_{1-3}$ alkyl.

In some embodiments of Formula Ia, each W is independently N or C.

In some embodiments of Formula Ia, at least two W must be N.

In some embodiments of Formula Ia, each U is independently N or C.

In some embodiments of Formula Ia, at least one U must be N and at least one U must be C.

In some embodiments of Formula Ia, G is NH or O.

In some embodiments of Formula Ia, each J is independently N or C.

In some embodiments of Formula Ia, at least one J must be C.

In some embodiments of Formula Ia, n is 0 to 7.

In some embodiments of Formula Ia, n is 1 to 7.

In some embodiments of Formula Ia, Ring A is selected from the group consisting of

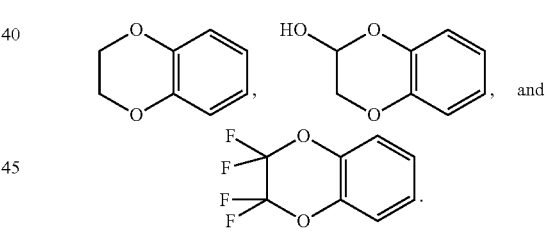

In some embodiments of Formula Ia, Ring B is selected from the group consisting of

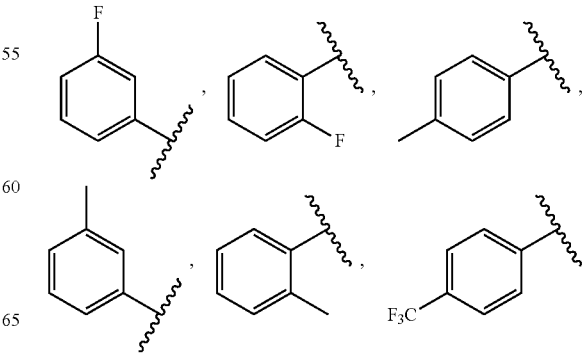

-continued
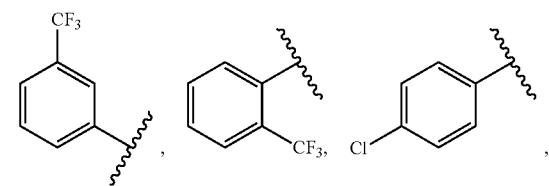
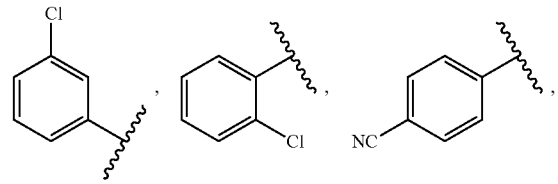
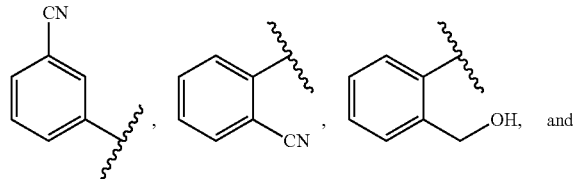
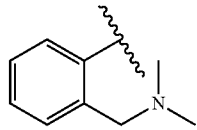
In some embodiments of Formula Ia, Ring B is selected from the group consisting of
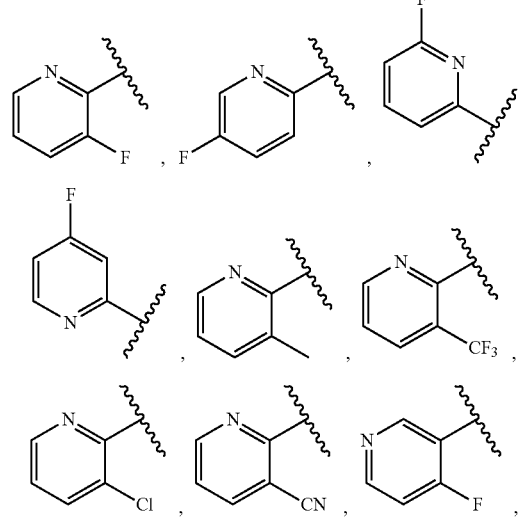
-continued
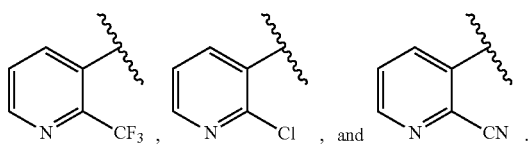
In some embodiments of Formula Ia, Ring B is selected from the group consisting of
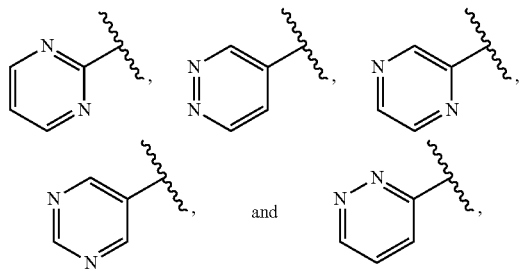
In some embodiments of Formula Ia, Ring B is selected from the group consisting of
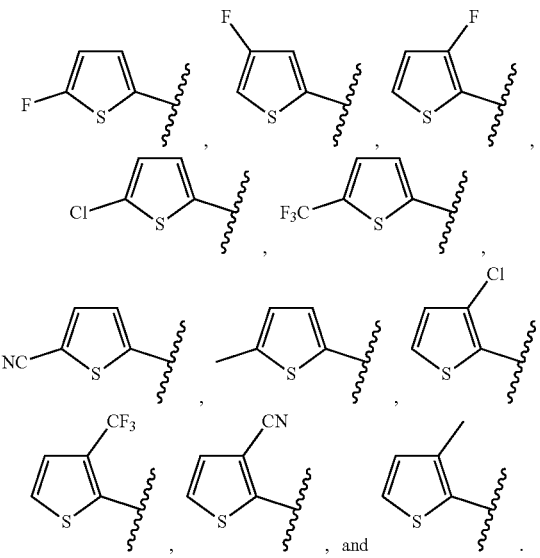
In some embodiments of Formula Ia, Ring B is selected from the group consisting of
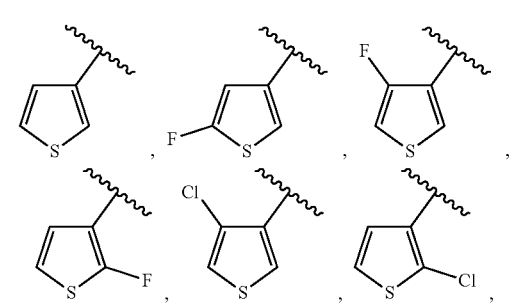

-continued

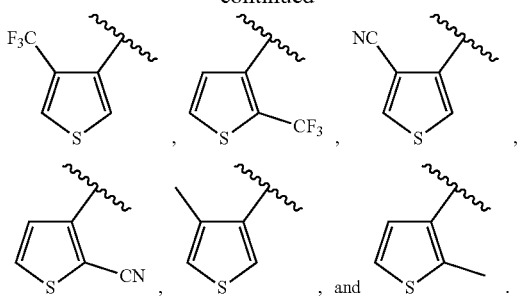

, and

In some embodiments of Formula Ia, Ring B is selected from the group consisting of

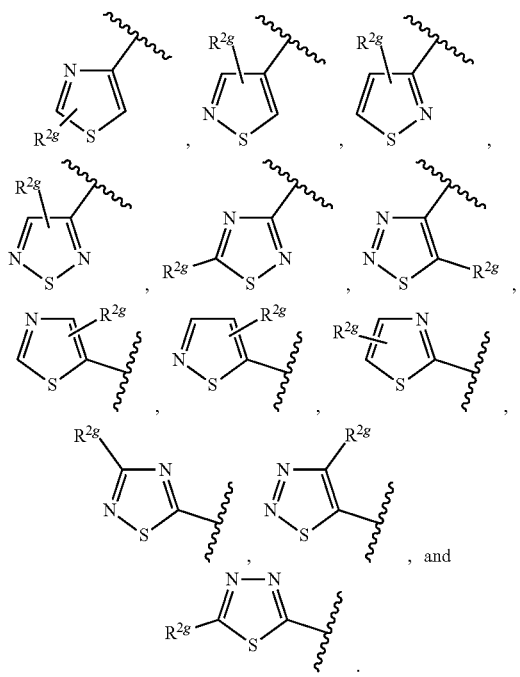

In some embodiments of Formula Ia, Ring B is selected from the group consisting of

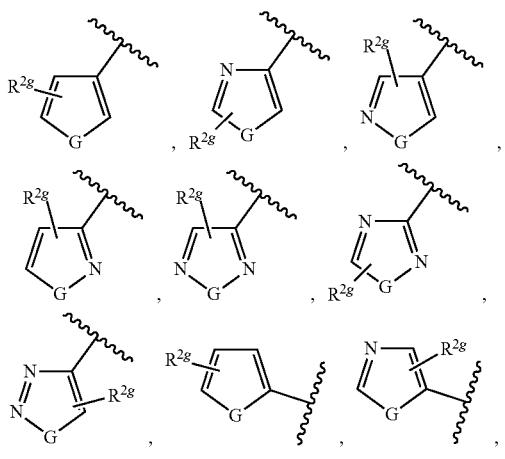

-continued

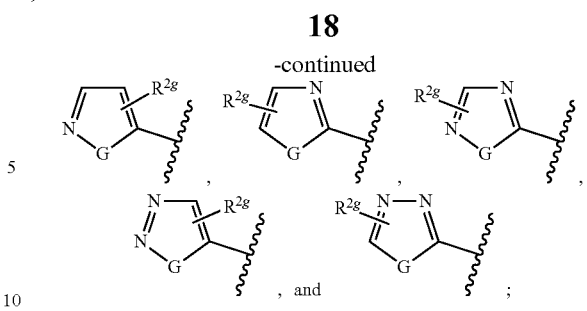

, and

In some embodiments of Formula Ia, t is 0.
In some embodiments of Formula Ia, at least one $R^{2e}$ is a halide.
In some embodiments of Formula Ia, at least one $R^{2e}$ is F.
In some embodiments of Formula Ia, at least one $R^{2e}$ is Cl.
In some embodiments of Formula Ia, at least one $R^{2e}$ is Me.
In some embodiments of Formula Ia, at least one $R^{2e}$ is OH.
In some embodiments of Formula Ia, at least one $R^{2e}$ is OMe.
In some embodiments of Formula Ia, at least one $R^{2e}$ is $CF_3$.
In some embodiments of Formula Ia, at least one $R^{2e}$ is CN.
In some embodiments of Formula Ia, t is 1 and $R^{2e}$ is F.
In some embodiments of Formula Ia, t is 2 and both $R^{2e}$ are F.
In some embodiments of Formula Ia, t is 1 and $R^{2e}$ is Me.
In some embodiments of Formula Ia, t is 2 and both $R^{2e}$ are Me.
In some embodiments of Formula Ia, t is 1 and $R^{2e}$ is $CF_3$.
In some embodiments of Formula Ia, t is 2 and both $R^{2e}$ are $CF_3$.
In some embodiments of Formula Ia, t is 1 and $R^{2e}$ is OMe.
In some embodiments of Formula Ia, t is 2 and both $R^{2e}$ are OMe.
In some embodiments of Formula Ia, t is 2 and one $R^{2e}$ is F and the other $R^{2e}$ is Me.
In some embodiments of Formula Ia, t is 2 and one $R^{2e}$ is F and the other $R^{2e}$ is $CF_3$.
In some embodiments of Formula Ia, t is 2 and one $R^{2e}$ is F and the other $R^{2e}$ is OMe.
In some embodiments of Formula Ia, t is 1 and $R^{2e}$ is CN.
In some embodiments of Formula Ia, t is 2 and both $R^{2e}$ are CN.
In some embodiments of Formula Ia, t is 2 and one $R^{2e}$ is F and the other $R^{2e}$ is CN.
In some embodiments of Formula Ia, at least one $R^{2e}$ is —$C_{1-2}$ alkyl.
In some embodiments of Formula Ia, at least one $R^{2e}$ is —$C_{1-3}$ alkyl.
In some embodiments of Formula Ia, at least one $R^{2e}$ is —$C_{1-4}$ alkyl.
In some embodiments of Formula Ia, at least one $R^{2e}$ is —$C_{1-5}$ alkyl.
In some embodiments of Formula Ia, at least one $R^{2e}$ is —$C_{1-6}$ alkyl.
In some embodiments of Formula Ia, at least one $R^{2e}$ is —$C_{2-6}$ alkyl.
In some embodiments of Formula Ia, at least one $R^{2e}$ is —$C_{3-6}$ alkyl.
In some embodiments of Formula Ia, at least one $R^{2e}$ is —$C_{4-6}$ alkyl.

In some embodiments of Formula Ia, at least one $R^{2e}$ is —$C_{2-5}$ alkyl.

In some embodiments of Formula Ia, at least one $R^{2e}$ is —$C_{3-4}$ alkyl.

In some embodiments of Formula Ia, at least one $R^{2f}$ is halide.

In some embodiments of Formula Ia, at least one $R^{2f}$ is F.

In some embodiments of Formula Ia, at least one $R^{2f}$ is Cl.

In some embodiments of Formula Ia, at least one $R^{2f}$ is Me.

In some embodiments of Formula Ia, at least one $R^{2f}$ is OH.

In some embodiments of Formula Ia, at least one $R^{2f}$ is OMe.

In some embodiments of Formula Ia, at least one $R^{2f}$ is $CF_3$.

In some embodiments of Formula Ia, at least one $R^{2f}$ is CN.

In some embodiments of Formula Ia, u is 1 and $R^{2f}$ is F.

In some embodiments of Formula Ia, u is 2 and both $R^{2f}$ are F.

In some embodiments of Formula Ia, u is 1 and $R^{2f}$ is Me.

In some embodiments of Formula Ia, u is 2 and both $R^{2f}$ are Me.

In some embodiments of Formula Ia, u is 1 and $R^{2f}$ is $CF_3$.

In some embodiments of Formula Ia, u is 2 and both $R^{2f}$ are $CF_3$.

In some embodiments of Formula Ia, u is 1 and $R^{2f}$ is OMe.

In some embodiments of Formula Ia, u is 2 and both $R^{2f}$ are OMe.

In some embodiments of Formula Ia, u is 2 and one $R^{2f}$ is F and the other $R^{2f}$ is Me.

In some embodiments of Formula Ia, u is 2 and one $R^{2f}$ is F and the other $R^{2f}$ is $CF_3$.

In some embodiments of Formula Ia, u is 2 and one $R^{2f}$ is F and the other $R^{2f}$ is OMe.

In some embodiments of Formula Ia, u is 1 and $R^{2f}$ is CN.

In some embodiments of Formula Ia, u is 2 and both $R^{2f}$ are CN.

In some embodiments of Formula Ia, u is 2 and one $R^{2f}$ is F and the other $R^{2f}$ is CN.

In some embodiments of Formula Ia, at least one $R^{2f}$ is —$C_{1-2}$ alkyl.

In some embodiments of Formula Ia, at least one $R^{2f}$ is —$C_{1-3}$ alkyl.

In some embodiments of Formula Ia, at least one $R^{2f}$ is —$C_{1-4}$ alkyl.

In some embodiments of Formula Ia, at least one $R^{2f}$ is —$C_{1-5}$ alkyl.

In some embodiments of Formula Ia, at least one $R^{2f}$ is —$C_{1-6}$ alkyl.

In some embodiments of Formula Ia, at least one $R^{2f}$ is —$C_{2-6}$ alkyl.

In some embodiments of Formula Ia, at least one $R^{2f}$ is —$C_{3-6}$ alkyl.

In some embodiments of Formula Ia, at least one $R^{2f}$ is —$C_{4-6}$ alkyl.

In some embodiments of Formula Ia, at least one $R^{2f}$ is —$C_{2-5}$ alkyl.

In some embodiments of Formula Ia, at least one $R^{2f}$ is —$C_{3-4}$ alkyl.

In some embodiments of Formula Ia, v is 0.

In some embodiments of Formula Ia, v is 1.

In some embodiments of Formula Ia, v is 2.

In some embodiments of Formula Ia, at least one $R^{2g}$ is halide.

In some embodiments of Formula Ia, at least one $R^{2g}$ is F.

In some embodiments of Formula Ia, at least one $R^{2g}$ is Cl.

In some embodiments of Formula Ia, at least one $R^{2g}$ is Me.

In some embodiments of Formula Ia, at least one $R^{2g}$ is OH.

In some embodiments of Formula Ia, at least one $R^{2g}$ is OMe.

In some embodiments of Formula Ia, at least one $R^{2g}$ is $CF_3$.

In some embodiments of Formula Ia, at least one $R^{2g}$ is CN.

In some embodiments of Formula Ia, v is 1 and $R^{2g}$ is F.

In some embodiments of Formula Ia, v is 2 and both $R^{2g}$ are F.

In some embodiments of Formula Ia, v is 1 and $R^{2g}$ is Me.

In some embodiments of Formula Ia, v is 2 and both $R^{2g}$ are Me.

In some embodiments of Formula Ia, v is 1 and $R^{2g}$ is $CF_3$.

In some embodiments of Formula Ia, v is 2 and both $R^{2g}$ are $CF_3$.

In some embodiments of Formula Ia, v is 1 and $R^{2g}$ is OMe.

In some embodiments of Formula Ia, v is 2 and both $R^{2g}$ are OMe.

In some embodiments of Formula Ia, v is 2 and one $R^{2g}$ is F and the other $R^{2g}$ is Me.

In some embodiments of Formula Ia, v is 2 and one $R^{2g}$ is F and the other $R^{2g}$ is $CF_3$.

In some embodiments of Formula Ia, v is 2 and one $R^{2g}$ is F and the other $R^{2g}$ is OMe.

In some embodiments of Formula Ia, v is 1 and $R^{2g}$ is CN.

In some embodiments of Formula Ia, v is 2 and both $R^{2g}$ are CN.

In some embodiments of Formula Ia, v is 2 and one $R^{2g}$ is F and the other $R^{2g}$ is CN.

In some embodiments of Formula Ia, at least one $R^{2g}$ is —$C_{1-2}$ alkyl.

In some embodiments of Formula Ia, at least one $R^{2g}$ is —$C_{1-3}$ alkyl.

In some embodiments of Formula Ia, at least one $R^{2g}$ is —$C_{1-4}$ alkyl.

In some embodiments of Formula Ia, at least one $R^{2g}$ is —$C_{1-5}$ alkyl.

In some embodiments of Formula Ia, at least one $R^{2g}$ is —$C_{1-6}$ alkyl.

In some embodiments of Formula Ia, at least one $R^{2g}$ is —$C_{2-6}$ alkyl.

In some embodiments of Formula Ia, at least one $R^{2g}$ is —$C_{3-6}$ alkyl.

In some embodiments of Formula Ia, at least one $R^{2g}$ is —$C_{4-6}$ alkyl.

In some embodiments of Formula Ia, at least one $R^{2g}$ is —$C_{2-5}$ alkyl.

In some embodiments of Formula Ia, at least one $R^{2g}$ is —$C_{3-4}$ alkyl.

Some embodiments of Formula I include compounds of Formula (Ib):

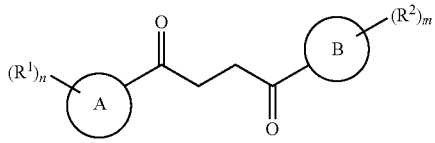

or salts, dermatologically acceptable salts, or prodrugs thereof.

In some embodiments of Formula Ib, Ring A is

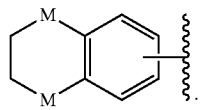

In some embodiments of Formula Ib, Ring B is selected from the group consisting of phenyl and a 5-6 membered heteroaryl, wherein a carbon atom on the ring is attached to the carbonyl carbon.

In some embodiments of Formula Ib, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula Ib, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula Ib, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ib, each $R^2$ is a substituent attached to Ring B and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ib, each $R^3$ is independently selected from the group consisting of H, unsubstituted —$C_{1-6}$ alkyl and —$C_{1-3}$ haloalkyl.

In some embodiments of Formula Ib, each $R^{3b}$ is independently selected from the group consisting of H and unsubstituted —$C_{1-3}$ alkyl.

In some embodiments of Formula Ib, each M is independently selected from the group consisting of N, C, S and O.

In some embodiments of Formula Ib, both M are not O.
In some embodiments of Formula Ib, both M are not C.
In some embodiments of Formula Ib, m is 0 to 5.
In some embodiments of Formula Ib, m is 1 to 5.
In some embodiments of Formula Ib, n is 0 to 10.
In some embodiments of Formula Ib, n is 1 to 10.
In some embodiments of Formula Ib, Ring A is selected from the group consisting of

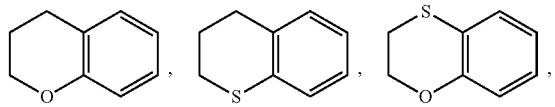

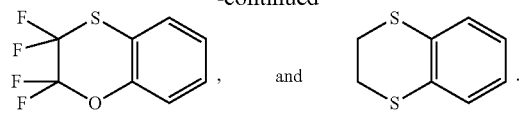 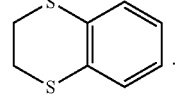

Some embodiments of Formula I include compounds of Formula (Ic):

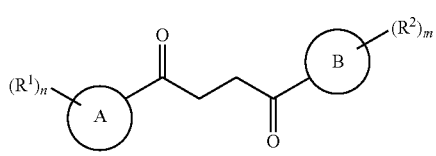

or salts, dermatologically acceptable salts, or prodrugs thereof.

In some embodiments of Formula Ic, Ring A is

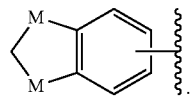

In some embodiments of Formula Ic, Ring B is selected from the group consisting of phenyl and a 5-6 membered heteroaryl, wherein a carbon atom on the ring is attached to the carbonyl carbon.

In some embodiments of Formula Ic, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula Ic, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula Ic, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ic, each $R^2$ is a substituent attached to Ring B and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ic, each $R^3$ is independently selected from the group consisting of H, unsubstituted —$C_{1-6}$ alkyl and —$C_{1-3}$ haloalkyl.

In some embodiments of Formula Ic, each $R^{3b}$ is independently selected from the group consisting of H and unsubstituted —$C_{1-3}$ alkyl.

In some embodiments of Formula Ic, each M is independently selected from the group consisting of N, C, S and O.

In some embodiments of Formula Ic, if one M is C, the other M is selected from the group consisting of N, S, and O.

In some embodiments of Formula Ic, m is 0 to 5.
In some embodiments of Formula Ic, m is 1 to 5.
In some embodiments of Formula Ic, n is 0 to 10.
In some embodiments of Formula Ic, n is 1 to 10.

In some embodiments of Formula Ic, Ring A is selected from the group consisting of

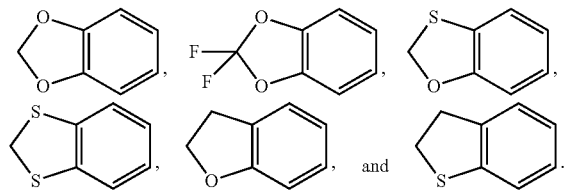

and

Some embodiments of Formula I include compounds of Formula (Id):

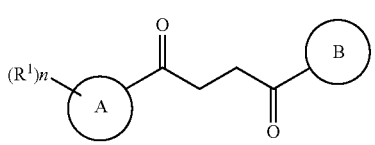

or salts, dermatologically acceptable salts, or prodrugs thereof.

In some embodiments of Formula Id, Ring A is

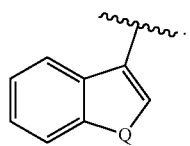

In some embodiments of Formula Id, Ring B is selected from the group consisting of

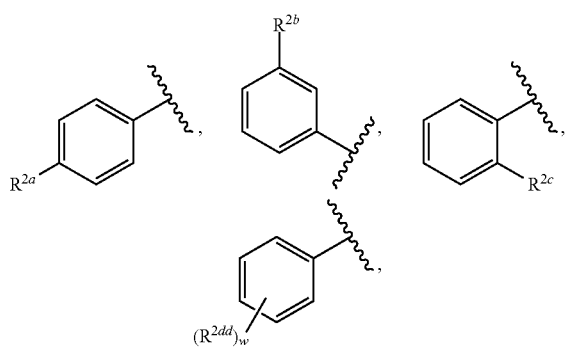

and a 5-6 membered heteroaryl($R^{2ee}$)$_y$, wherein a carbon atom on the ring is attached to the carbonyl carbon.

In some embodiments of Formula Id, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula Id, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula Id, $R^{2a}$ is one substituent attached to the para position of phenyl and is selected from the group consisting of H, unsubstituted —$C_{1-6}$ alkyl, —$CH_2OH$, —$CH_2N(R^{3b})_2$, —$C_{1-3}$ haloalkyl, Cl, Br, I, —$OR^3$a, and CN.

In some embodiments of Formula Id, $R^{2b}$ is one substituent attached to the meta position of phenyl and is selected from the group consisting of H, unsubstituted —$C_{2-6}$ alkyl, —$CH_2OH$, —$CH_2N(R^{3b})_2$, —$C_{1-3}$ haloalkyl, F, I, —$OR^3$, and CN.

In some embodiments of Formula Id, $R^{2c}$ is one substituent attached to the ortho position of phenyl and is selected from the group consisting of unsubstituted —$C_{1-6}$ alkyl, —$CH_2OH$, —$CH_2N(R^{3b})_2$, —$C_{1-3}$ haloalkyl, F, Br, I, —$OR^3$, and CN.

In some embodiments of Formula Id, $R^{2dd}$ is a substituent attached to the phenyl and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; w is 1 to 5.

In some embodiments of Formula Id, $R^{2ee}$ is a substituent attached to the heteroaryl ring and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; y is 0 to 3.

In some embodiments of Formula Id, $R^{2c}$ is a F.
In some embodiments of Formula Id, $R^{2c}$ is a Me.
In some embodiments of Formula Id, $R^{2c}$ is a OH.
In some embodiments of Formula Id, $R^{2c}$ is a OMe.
In some embodiments of Formula Id, $R^{2c}$ is a $CF_3$.
In some embodiments of Formula Id, $R^{2c}$ is a CN.
In some embodiments of Formula Id, $R^{2c}$ is a —$C_{1-2}$ alkyl.
In some embodiments of Formula Id, $R^{2c}$ is a —$C_{1-3}$ alkyl.
In some embodiments of Formula Id, $R^{2c}$ is a —$C_{1-4}$ alkyl.
In some embodiments of Formula Id, $R^{2c}$ is a —$C_{1-5}$ alkyl.
In some embodiments of Formula Id, $R^{2c}$ is a —$C_{1-6}$ alkyl.
In some embodiments of Formula Id, $R^{2c}$ is a —$C_{2-6}$ alkyl.
In some embodiments of Formula Id, $R^{2c}$ is a —$C_{3-6}$ alkyl.
In some embodiments of Formula Id, $R^{2c}$ is a —$C_{4-6}$ alkyl.
In some embodiments of Formula Id, $R^{2c}$ is a —$C_{2-5}$ alkyl.
In some embodiments of Formula Id, $R^{2c}$ is a —$C_{3-4}$ alkyl.
In some embodiments of Formula Id, at least one $R^{2dd}$ is F.
In some embodiments of Formula Id, at least one $R^{2dd}$ is Cl.
In some embodiments of Formula Id, at least one $R^{2dd}$ is Me.
In some embodiments of Formula Id, at least one $R^{2dd}$ is OH.
In some embodiments of Formula Id, at least one $R^{2dd}$ is OMe.
In some embodiments of Formula Id, at least one $R^{2dd}$ is $CF_3$.
In some embodiments of Formula Id, at least one $R^{2dd}$ is CN.
In some embodiments, of Formula Id, w is 2 to 5.
In some embodiments, of Formula Id, w is 1.
In some embodiments, of Formula Id, w is 2.

In some embodiments of Formula Id, w is 1 and $R^{2dd}$ is F.

In some embodiments of Formula Id, w is 2 and both $R^{2dd}$ are F.

In some embodiments of Formula Id, w is 1 and $R^{2dd}$ is Me.

In some embodiments of Formula Id, w is 2 and both $R^{2dd}$ are Me.

In some embodiments of Formula Id, w is 1 and $R^{2dd}$ is $CF_3$.

In some embodiments of Formula Id, w is 2 and both $R^{2dd}$ are $CF_3$.

In some embodiments of Formula Id, w is 1 and $R^{2dd}$ is OMe.

In some embodiments of Formula Id, w is 2 and both $R^{2dd}$ are OMe.

In some embodiments of Formula Id, w is 2 and one $R^{2dd}$ is F and the other $R^{2dd}$ is Me.

In some embodiments of Formula Id, w is 2 and one $R^{2dd}$ is F and the other $R^{2dd}$ is $CF_3$.

In some embodiments of Formula Id, w is 2 and one $R^{2dd}$ is F and the other $R^{2dd}$ is OMe.

In some embodiments of Formula Id, w is 1 and $R^{2dd}$ is CN.

In some embodiments of Formula Id, w is 2 and both $R^{2dd}$ are CN.

In some embodiments of Formula Id, w is 2 and one $R^{2dd}$ is F and the other $R^{2dd}$ is CN.

In some embodiments of Formula Id, at least one $R^{2dd}$ is $—C_{1-2}$ alkyl.

In some embodiments of Formula Id, at least one $R^{2dd}$ is $—C_{1-3}$ alkyl.

In some embodiments of Formula Id, at least one $R^{2dd}$ is $—C_{1-4}$ alkyl.

In some embodiments of Formula Id, at least one $R^{2dd}$ is $—C_{1-5}$ alkyl.

In some embodiments of Formula Id, at least one $R^{2dd}$ is $—C_{1-6}$ alkyl.

In some embodiments of Formula Id, at least one $R^{2dd}$ is $—C_{2-6}$ alkyl.

In some embodiments of Formula Id, at least one $R^{2dd}$ is $—C_{3-6}$ alkyl.

In some embodiments of Formula Id, at least one $R^{2dd}$ is $—C_{4-6}$ alkyl.

In some embodiments of Formula Id, at least one $R^{2dd}$ is $—C_{2-5}$ alkyl.

In some embodiments of Formula Id, at least one $R^{2dd}$ is $—C_{3-4}$ alkyl.

In some embodiments of Formula Id, y is 0.
In some embodiments of Formula Id, y is 1.
In some embodiments of Formula Id, y is 2.
In some embodiments of Formula Id, at least one $R^{2ee}$ is halide.

In some embodiments of Formula Id, at least one $R^{2ee}$ is F.

In some embodiments of Formula Id, at least one $R^{2ee}$ is Cl.

In some embodiments of Formula Id, at least one $R^{2ee}$ is Me.

In some embodiments of Formula Id, at least one $R^{2ee}$ is OH.

In some embodiments of Formula Id, at least one $R^{2ee}$ is OMe.

In some embodiments of Formula Id, at least one $R^{2ee}$ is $CF_3$.

In some embodiments of Formula Id, at least one $R^{2ee}$ is CN.

In some embodiments of Formula Id, y is 1 and $R^{2ee}$ is F.
In some embodiments of Formula Id, y is 2 and both $R^{2ee}$ are F.

In some embodiments of Formula Id, y is 1 and $R^{2ee}$ is Me.

In some embodiments of Formula Id, y is 2 and both $R^{2ee}$ are Me.

In some embodiments of Formula Id, y is 1 and $R^{2ee}$ is $CF_3$.

In some embodiments of Formula Id, y is 2 and both $R^{2ee}$ are $CF_3$.

In some embodiments of Formula Id, y is 1 and $R^{2ee}$ is OMe.

In some embodiments of Formula Id, y is 2 and both $R^{2ee}$ are OMe.

In some embodiments of Formula Id, y is 2 and one $R^{2ee}$ is F and the other $R^{2ee}$ is Me.

In some embodiments of Formula Id, y is 2 and one $R^{2ee}$ is F and the other $R^{2ee}$ is $CF_3$.

In some embodiments of Formula Id, y is 2 and one $R^{2ee}$ is F and the other $R^{2ee}$ is OMe.

In some embodiments of Formula Id, y is 1 and $R^{2ee}$ is CN.

In some embodiments of Formula Id, y is 2 and both $R^{2ee}$ are CN.

In some embodiments of Formula Id, y is 2 and one $R^{2ee}$ is F and the other $R^{2ee}$ is CN.

In some embodiments of Formula Id, at least one $R^{2ee}$ is $—C_{1-2}$ alkyl.

In some embodiments of Formula Id, at least one $R^{2ee}$ is $—C_{1-3}$ alkyl.

In some embodiments of Formula Id, at least one $R^{2ee}$ is $—C_{1-4}$ alkyl.

In some embodiments of Formula Id, at least one $R^{2ee}$ is $—C_{1-5}$ alkyl.

In some embodiments of Formula Id, at least one $R^{2ee}$ is $—C_{1-6}$ alkyl.

In some embodiments of Formula Id, at least one $R^{2ee}$ is $—C_{2-6}$ alkyl.

In some embodiments of Formula Id, at least one $R^{2ee}$ is $—C_{3-6}$ alkyl.

In some embodiments of Formula Id, at least one $R^{2ee}$ is $—C_{4-6}$ alkyl.

In some embodiments of Formula Id, at least one $R^{2ee}$ is $—C_{2-5}$ alkyl.

In some embodiments of Formula Id, at least one $R^{2ee}$ is $—C_{3-4}$ alkyl.

In some embodiments of Formula Id, each $R^3$ is independently selected from the group consisting of H, unsubstituted $—C_{1-6}$ alkyl and $—C_{1-3}$ haloalkyl.

In some embodiments of Formula Id, each $R^{3a}$ is independently selected from the group consisting of H, unsubstituted $—C_{2-6}$ alkyl and $—C_{1-3}$ haloalkyl.

In some embodiments of Formula Id, each $R^{3b}$ is independently selected from the group consisting of H and unsubstituted $—C_{1-3}$ alkyl.

In some embodiments of Formula Id, Q is S or NH.
In some embodiments of Formula Id, n is 0 to 5.
In some embodiments of Formula Id, n is 1 to 5.
In some embodiments of Formula Id, Ring A is selected from the group consisting of

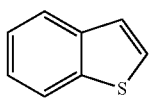 and 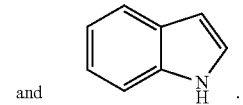

In some embodiments of Formula Id, $R^{2a}$ is H.
In some embodiments of Formula Id, $R^{2b}$ is H.
In some embodiments of Formula Id, w is 0.

Some embodiments of Formula I include compounds of Formula (Ie):

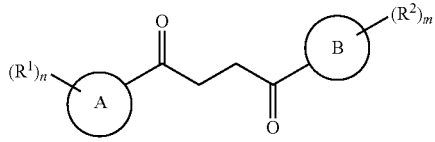

Ie or salts, dermatologically acceptable salts, or prodrugs thereof.

In some embodiments of Formula Ie, Ring A is

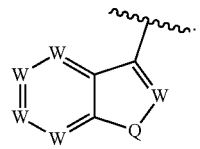

In some embodiments of Formula Ie, Ring B is selected from the group consisting of phenyl and a 5-6 membered heteroaryl, wherein a carbon atom on the ring is attached to the carbonyl carbon.

In some embodiments of Formula Ie, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula Ie, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula Ie, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ie, each $R^2$ is a substituent attached to Ring B and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ie, each $R^3$ is independently selected from the group consisting of H, unsubstituted —$C_{1-6}$ alkyl and —$C_{1-3}$ haloalkyl.

In some embodiments of Formula Ie, each $R^{3b}$ is independently selected from the group consisting of H and unsubstituted —$C_{1-3}$ alkyl.

In some embodiments of Formula Ie, each W is independently N or C.

In some embodiments of Formula Ie, at least one W must be N.

In some embodiments of Formula Ie, Q is S or NH.
In some embodiments of Formula Ie, m is 0 to 5.
In some embodiments of Formula Ie, m is 1 to 5.
In some embodiments of Formula Ie, n is 0 to 4.
In some embodiments of Formula Ie, n is 1 to 4.

In some embodiments of Formula Ie, Ring A is selected from the group consisting of

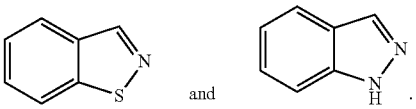 [SMILES: c1ccc2sncc2c1 ; c1ccc2[nH]ncc2c1]

Some embodiments of Formula I include compounds of Formula (If):

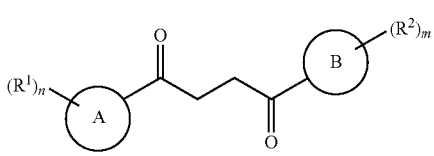

If or salts, dermatologically acceptable salts, or prodrugs thereof.

In some embodiments of Formula If, Ring A is

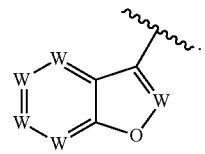

In some embodiments of Formula If, Ring B is selected from the group consisting of phenyl and a 5-6 membered heteroaryl, wherein a carbon atom on the ring is attached to the carbonyl carbon.

In some embodiments of Formula If, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula If, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula If, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula If, each $R^2$ is a substituent attached to Ring B and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula If, each $R^3$ is independently selected from the group consisting of H, unsubstituted —$C_{1-6}$ alkyl and —$C_{1-3}$ haloalkyl.

In some embodiments of Formula If, each $R^{3b}$ is independently selected from the group consisting of H and unsubstituted —$C_{1-3}$ alkyl.

In some embodiments of Formula If, each W is independently N or C.

In some embodiments of Formula If, m is 0 to 5.
In some embodiments of Formula If, m is 1 to 5.
In some embodiments of Formula If, n is 0 to 5.
In some embodiments of Formula If, n is 1 to 5.

In some embodiments of Formula If, Ring A is selected from the group consisting of

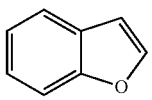 and 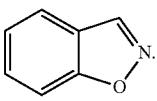

Some embodiments of Formula I include compounds of Formula (Ig):

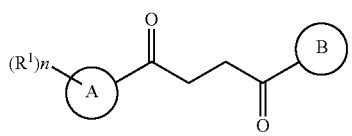

Ig or salts, dermatologically acceptable salts, or prodrugs thereof.

In some embodiments of Formula Ig, Ring A is

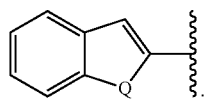

In some embodiments of Formula Ig, Ring B is selected from the group consisting of

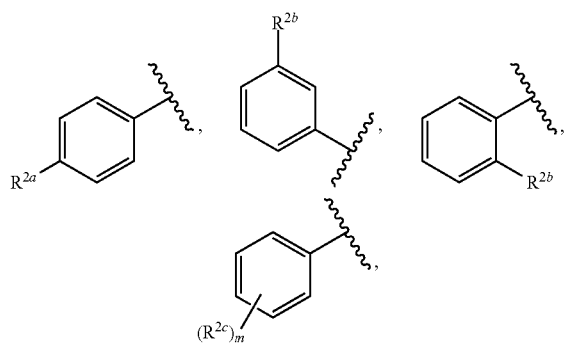

and a 5-6 membered heteroaryl$(R^{2d})_s$, wherein a carbon atom on the ring is attached to the carbonyl carbon.

In some embodiments of Formula Ig, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula Ig, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula Ig, $R^{2a}$ is one substituent attached to the para position of phenyl and is selected from the group consisting of unsubstituted —$C_{1-6}$ alkyl, —$CH_2OH$, —$CH_2N(R^{3b})_2$, —$C_{1-3}$ haloalkyl, F, I, —$OR^3$, and CN.

In some embodiments of Formula Ig, $R^{2b}$ is one substituent attached to the meta or ortho position of phenyl and is selected from the group consisting of unsubstituted —$C_{2-6}$ alkyl, —$CH_2OH$, —$CH_2N(R^{3b})_2$, —$C_{1-3}$ haloalkyl, halide, —$OR^3$, and CN.

In some embodiments of Formula Ig, $R^{2c}$ is a substituent attached to the phenyl and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; m is 2-5.

In some embodiments of Formula Ig, $R^{2d}$ is a substituent attached to the heteroaryl ring and are independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN; s is 1-3.

In some embodiments of Formula Ig, $R^{2d}$ is a substituent attached to the heteroaryl ring and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN; s is 0-4.

In some embodiments of Formula Ig, each $R^3$ is independently selected from the group consisting of H, unsubstituted —$C_{1-6}$ alkyl and —$C_{1-3}$ haloalkyl.

In some embodiments of Formula Ig, each $R^{3b}$ is independently selected from the group consisting of H and unsubstituted —$C_{1-3}$ alkyl.

In some embodiments of Formula Ig, Q is selected from the group consisting of O, S, and NH.

In some embodiments of Formula Ig, n is 0 to 5.
In some embodiments of Formula Ig, n is 1 to 5.
In some embodiments of Formula Ig, Ring A is selected from the group consisting of

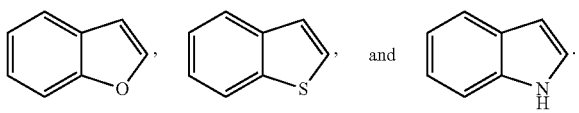

In some embodiments of Formula Ig, $R^{2a}$ is a F.
In some embodiments of Formula Ig, $R^{2a}$ is a OH.
In some embodiments of Formula Ig, $R^{2a}$ is a OMe.
In some embodiments of Formula Ig, at least one $R^{2d}$ is —$CH_2OH$.
In some embodiments of Formula Ig, at least one $R^{2d}$ is —$CH_2N(R^{3b})_2$.
In some embodiments of Formula Ig, at least one $R^{2d}$ is —$CH_2NH_2$.
In some embodiments of Formula Ig, at least one $R^{2d}$ is —$CH_2NHMe$.
In some embodiments of Formula Ig, at least one $R^{2d}$ is —$CH_2NMe_2$.
In some embodiments of Formula Ig, at least one $R^{2d}$ is —$CH_2NHEt$.
In some embodiments of Formula Ig, at least one $R^{2d}$ is —$CH_2N(Me)(Et)$.
In some embodiments of Formula Ig, at least one $R^{2d}$ is —$CH_2NEt_2$.

Some embodiments of Formula I include compounds of Formula (Ih):

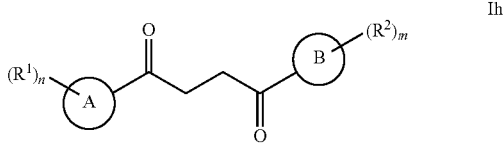

Ih or salts, dermatologically acceptable salts, or prodrugs thereof.

In some embodiments of Formula Ih, Ring A is

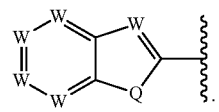

In some embodiments of Formula Ih, Ring B is selected from the group consisting of phenyl and a 5-6 membered heteroaryl, wherein a carbon atom on the ring is attached to the carbonyl carbon.

In some embodiments of Formula Ih, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula Ih, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula Ih, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ih, each $R^2$ is a substituent attached to Ring B and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ih, each $R^3$ is independently selected from the group consisting of H, unsubstituted —$C_{1-6}$ alkyl and —$C_{1-3}$ haloalkyl.

In some embodiments of Formula Ih, each $R^{3b}$ is independently selected from the group consisting of H and unsubstituted —$C_{1-3}$ alkyl.

In some embodiments of Formula Ih, each W is independently N or C.

In some embodiments of Formula Ih, at least one W must be N.

In some embodiments of Formula Ih, Q is selected from the group consisting of O, S, and NH.

In some embodiments of Formula Ih, m is 0 to 5.
In some embodiments of Formula Ih, m is 1 to 5.
In some embodiments of Formula Ih, n is 0 to 4.
In some embodiments of Formula Ih, n is 1 to 4.
In some embodiments of Formula Ih, Ring A is selected from the group consisting of

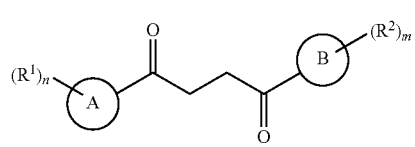

Some embodiments of Formula I include compounds of Formula (Ii):

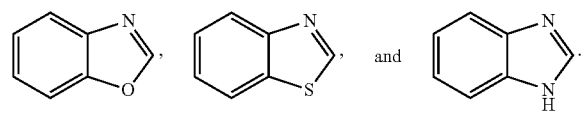

Ii or salts, dermatologically acceptable salts, or prodrugs thereof.

In some embodiments of Formula Ii, Ring A is

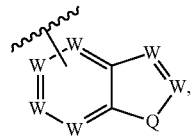

wherein a carbon atom on the ring is attached to the carbonyl carbon.

In some embodiments of Formula Ii, Ring B is selected from the group consisting of phenyl and a 5-6 membered heteroaryl, wherein a carbon atom on the ring is attached to the carbonyl carbon.

In some embodiments of Formula Ii, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, and CN.

In some embodiments of Formula Ii, each $R^1$ is a substituent attached to Ring A and is independently selected at each occurrence from the group consisting of unsubstituted —$C_{1-6}$ alkyl, —$C_{1-3}$ haloalkyl, halide, —$OR^3$, and CN.

In some embodiments of Formula Ii, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ii, each $R^2$ is a substituent attached to Ring B and is independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, and CN.

In some embodiments of Formula Ii, each $R^3$ is independently selected from the group consisting of H, unsubstituted —$C_{1-6}$ alkyl and —$C_{1-3}$ haloalkyl.

In some embodiments of Formula Ii, each $R^{3b}$ is independently selected from the group consisting of H and unsubstituted —$C_{1-3}$ alkyl.

In some embodiments of Formula Ii, each W is independently N or C.

In some embodiments of Formula Ii, at least one W is C

In some embodiments of Formula Ii, Q is selected from the group consisting of O, S, and N.

In some embodiments of Formula Ii, m is 0 to 5.
In some embodiments of Formula Ii, m is 1 to 5.
In some embodiments of Formula Ii, n is 0 to 7.
In some embodiments of Formula Ii, n is 1 to 7.
In some embodiments of Formula Ii, Ring A is selected from the group consisting of

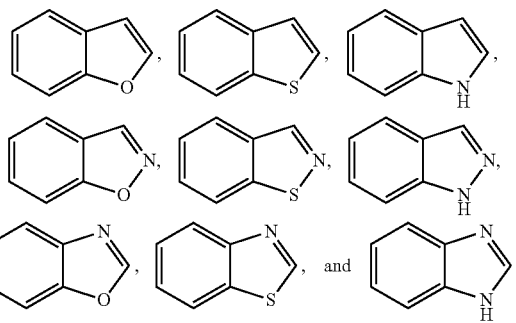

In some embodiments of Formula I, Ia, Ib, Ic, Id, Ie, If, Ig, Ih, and Ii, —$C_{1-3}$ haloalkyl is $CF_3$.

In some embodiments of Formula I, Ia, Ib, Ic, Id, Ie, If, Ig, Ih, and Ii, $R^1$ is selected from the group consisting of F, Cl, Me, OMe, OH, $CF_3$, and CN.

In some embodiments of Formula I, Ia, Ib, Ic, Id, Ie, If, Ig, Ih, and Ii, n is 0.

In some embodiments of Formula I, Ia, Ib, Ic, Id, Ie, If, Ig, Ih, and Ii, at least one $R^1$ is a halide.

In some embodiments of Formula I, Ia, Ib, Ic, Id, Ie, If, Ig, Ih, and Ii, at least one $R^1$ is F.

In some embodiments of Formula I, Ia, Ib, Ic, Id, Ie, If, Ig, Ih, and Ii, at least one $R^1$ is Cl.

In some embodiments of Formula I, Ia, Ib, Ic, Id, Ie, If, Ig, Ih, and Ii, at least one $R^1$ is Me.

In some embodiments of Formula I, Ia, Ib, Ic, Id, Ie, If, Ig, Ih, and Ii, at least one $R^1$ is OH.

In some embodiments of Formula I, Ia, Ib, Ic, Id, Ie, If, Ig, Ih, and Ii, at least one $R^1$ is OMe.

In some embodiments of Formula I, Ia, Ib, Ic, Id, Ie, If, Ig, Ih, and Ii, at least one $R^1$ is $CF_3$.

In some embodiments of Formula I, Ia, Ib, Ic, Id, Ie, If, Ig, Ih, and Ii, at least one $R^1$ is CN.

In some embodiments of Formula I, Ia, Ib, Ic, Id, Ie, If, Ig, Ih, and Ii, n is 0 to 8.

In some embodiments of Formula I, Ia, Ib, Ic, Id, Ie, If, Ig, Ih, and Ii, n is 0 to 6.

In some embodiments of Formula I, Ia, Ib, Ic, Id, Ie, If, Ig, Ih, and Ii, n is 0 to 4.

In some embodiments of Formula I, Ia, Ib, Ic, Id, Ie, If, Ig, Ih, and Ii, n is 0 to 2.

In some embodiments of Formula I, Ia, Ib, Ic, Id, Ie, If, Ig, Ih, and Ii, $R^1$ is F; and n is 1.

In some embodiments of Formula I, Ia, Ib, Ic, Id, Ie, If, Ig, Ih, and Ii, $R^1$ is F; and n is 1 or 2.

In some embodiments of Formula I, Ia, Ib, Ic, Id, Ie, If, Ig, Ih, and Ii, $R^1$ is F; and n is 3 or 4.

In some embodiments of Formula I, Ia, Ib, Ic, Id, Ie, If, Ig, Ih, and Ii, $R^1$ is OH; and n is 1 or 2.

In some embodiments of Formula I, Ia, Ib, Ic, Id, Ie, If, Ig, Ih, and Ii, $R^1$ is OMe; and n is 1 or 2.

In some embodiments of Formula I, Ia, Ib, Ic, Id, Ie, If, Ig, Ih, and Ii, at least one $R^1$ is —$C_{1-2}$ alkyl.

In some embodiments of Formula I, Ia, Ib, Ic, Id, Ie, If, Ig, Ih, and Ii, at least one $R^1$ is —$C_{1-3}$ alkyl.

In some embodiments of Formula I, Ia, Ib, Ic, Id, Ie, If, Ig, Ih, and Ii, at least one $R^1$ is —$C_{1-4}$ alkyl.

In some embodiments of Formula I, Ia, Ib, Ic, Id, Ie, If, Ig, Ih, and Ii, at least one $R^1$ is —$C_{1-5}$ alkyl.

In some embodiments of Formula I, Ia, Ib, Ic, Id, Ie, If, Ig, Ih, and Ii, at least one $R^1$ is —$C_{1-6}$ alkyl.

In some embodiments of Formula I, Ia, Ib, Ic, Id, Ie, If, Ig, Ih, and Ii, at least one $R^1$ is —$C_{2-6}$ alkyl.

In some embodiments of Formula I, Ia, Ib, Ic, Id, Ie, If, Ig, Ih, and Ii, at least one $R^1$ is —$C_{3-6}$ alkyl.

In some embodiments of Formula I, Ia, Ib, Ic, Id, Ie, If, Ig, Ih, and Ii, at least one $R^1$ is —$C_{4-6}$ alkyl.

In some embodiments, each $R^1$ is the same.

In some embodiments of Formula I, Ia, Ib, Ic, Id, Ie, If, Ig, Ih, and Ii, $R^1$ is independently selected at each occurrence from the group consisting of F, Cl, Me, OMe, OH, $CF_3$, and CN; and n is 1 or 2.

In some embodiments of Formula I, Ib, Ic, Ie, If, Ih, and Ii, Ring B is phenyl.

In some embodiments of Formula I, Ib, Ic, Ie, If, Ih, and Ii, Ring B is a 5-membered heteroaryl containing 1-3 heteroatoms selected from the group consisting of N, O, and S.

In some embodiments of Formula I, Ib, Ic, Ie, If, Ih, and Ii, Ring B is a 6-membered heteroaryl containing 1-2 nitrogen atoms.

In some embodiments of Formula Ia, at least one $R^{2d}$, $R^{2e}$, $R^{2f}$, or $R^{2g}$ is —$CH_2OH$.

In some embodiments of Formula Ia, Id, and Ig, at least one $R^{2a}$, $R^{2b}$, or $R^{2c}$ is —$CH_2OH$.

In some embodiments of Formula Id, at least one $R^{2dd}$ or $R^{2ee}$ is —$CH_2OH$.

In some embodiments of Formula I, Ib, Ic, Ie, If, Ig, Ih, and Ii, at least one $R^2$ is —$CH_2OH$.

In some embodiments of Formula Ia, at least one $R^{2d}$, $R^{2e}$, $R^{2f}$, or $R^{2g}$ is —$CH_2N(R^{3b})_2$.

In some embodiments of Formula Ia, Id, and Ig, at least one $R^{2a}$, $R^{2b}$, or $R^{2c}$ is —$CH_2N(R^{3b})_2$.

In some embodiments of Formula Id, at least one $R^{2dd}$ or $R^{2ee}$ is —$CH_2N(R^{3b})_2$.

In some embodiments of Formula I, Ib, Ic, Ie, If, Ig, Ih, and Ii, at least one $R^2$ is —$CH_2N(R^{3b})_2$.

In some embodiments of Formula Ia, at least one $R^{2d}$, $R^{2e}$, $R^{2f}$, or $R^{2g}$ is —$CH_2NH_2$.

In some embodiments of Formula Ia, Id, and Ig, at least one $R^{2a}$, $R^{2b}$, or $R^{2c}$ is —$CH_2NH_2$.

In some embodiments of Formula Id, at least one $R^{2dd}$ or $R^{2ee}$ is —$CH_2NH_2$.

In some embodiments of Formula I, Ib, Ic, Ie, If, Ig, Ih, and Ii, at least one $R^2$ is —$CH_2NH_2$.

In some embodiments of Formula Ia, at least one $R^{2d}$, $R^{2e}$, $R^{2f}$, or $R^{2g}$ is —$CH_2NHMe$.

In some embodiments of Formula Ia, Id, and Ig, at least one $R^{2a}$, $R^{2b}$, or $R^{2c}$ is —$CH_2NHMe$.

In some embodiments of Formula Id, at least one $R^{2dd}$ or $R^{2ee}$ is —$CH_2NHMe$.

In some embodiments of Formula I, Ib, Ic, Ie, If, Ig, Ih, and Ii, at least one $R^2$ is —$CH_2NHMe$.

In some embodiments of Formula Ia, at least one $R^{2d}$, $R^{2e}$, $R^{2f}$, or $R^{2g}$ is —$CH_2NMe_2$.

In some embodiments of Formula Ia, Id, and Ig, at least one $R^{2a}$, $R^{2b}$, or $R^{2c}$ is —$CH_2NMe_2$.

In some embodiments of Formula Id, at least one $R^{2dd}$ or $R^{2ee}$ is —$CH_2NMe_2$.

In some embodiments of Formula I, Ib, Ic, Ie, If, Ig, Ih, and Ii, at least one $R^2$ is —$CH_2NMe_2$.

In some embodiments of Formula Ia, at least one $R^{2d}$, $R^{2e}$, $R^{2f}$, or $R^{2g}$ is —$CH_2NHEt$.

In some embodiments of Formula Ia, Id, and Ig, at least one $R^{2a}$, $R^{2b}$, or $R^{2c}$ is —$CH_2NHEt$.

In some embodiments of Formula Id, at least one $R^{2dd}$ or $R^{2ee}$ is —$CH_2NHEt$.

In some embodiments of Formula I, Ib, Ic, Ie, If, Ig, Ih, and Ii, at least one $R^2$ is —$CH_2NHEt$.

In some embodiments of Formula Ia, at least one $R^{2d}$, $R^{2e}$, $R^{2f}$, or $R^{2g}$ is —$CH_2N(Me)(Et)$.

In some embodiments of Formula Ia, Id, and Ig, at least one $R^{2a}$, $R^{2b}$, or $R^{2c}$ is —$CH_2N(Me)(Et)$.

In some embodiments of Formula Id, at least one $R^{2dd}$ or $R^{2ee}$ is —$CH_2N(Me)(Et)$.

In some embodiments of Formula I, Ib, Ic, Ie, If, Ig, Ih, and Ii, at least one $R^2$ is —$CH_2N(Me)(Et)$.

In some embodiments of Formula Ia, at least one $R^{2d}$, $R^{2e}$, $R^{2f}$, or $R^{2g}$ is —$CH_2NEt_2$.

In some embodiments of Formula Ia, Id, and Ig, at least one $R^{2a}$, $R^{2b}$, or $R^{2c}$ is —$CH_2NEt_2$.

In some embodiments of Formula Id, at least one $R^{2dd}$ or $R^{2ee}$ is —CH$_2$NEt$_2$.

In some embodiments of Formula I, Ib, Ic, Ie, If, Ig, Ih, and Ii, at least one $R^2$ is —CH$_2$NEt$_2$.

In some embodiments of Formula I, Ib, Ic, Ie, If, Ih, and Ii, at least one $R^2$ is independently selected at each occurrence from the group consisting of F, Cl, Me, OMe, OH, CF$_3$, and CN.

In some embodiments of Formula I, Ib, Ic, Ie, If, Ih, and Ii, m is 0.

In some embodiments of Formula I, Ib, Ic, Ie, If, Ih, and Ii, at least one $R^2$ is halide.

In some embodiments of Formula I, Ib, Ic, Ie, If, Ih, and Ii, at least one $R^2$ is F.

In some embodiments of Formula I, Ib, Ic, Ie, If, Ih, and Ii, at least one $R^2$ is Cl.

In some embodiments of Formula I, Ib, Ic, Ie, If, Ih, and Ii, at least one $R^2$ is Me.

In some embodiments of Formula I, Ib, Ic, Ie, If, Ih, and Ii, at least one $R^2$ is OH.

In some embodiments of Formula I, Ib, Ic, Ie, If, Ih, and Ii, at least one $R^2$ is OMe.

In some embodiments of Formula I, Ib, Ic, Ie, If, Ih, and Ii, at least one $R^2$ is CF$_3$.

In some embodiments of Formula I, Ib, Ic, Ie, If, Ih, and Ii, at least one $R^2$ is CN.

In some embodiments of Formula I, Ib, Ic, Ie, If, Ih, and Ii, m is 0 to 4.

In some embodiments of Formula I, Ib, Ic, Ie, If, Ih, and Ii, m is 0 to 2.

In some embodiments of Formula I, Ib, Ic, Ie, If, Ih, and Ii, m is 1.

In some embodiments of Formula I, Ib, Ic, Ie, If, Ih, and Ii, m is 2.

In some embodiments of Formula I, Ib, Ic, Ie, If, Ih, and Ii, $R^2$ is F; and m is 1.

In some embodiments of Formula I, Ib, Ic, Ie, If, Ih, and Ii, $R^2$ is F; and m is 2.

In some embodiments of Formula I, Ib, Ic, Ie, If, Ih, and Ii, $R^2$ is Me; and m is 1.

In some embodiments of Formula I, Ib, Ic, Ie, If, Ih, and Ii, $R^2$ is Me; and m is 2.

In some embodiments of Formula I, Ib, Ic, Ie, If, Ih, and Ii, $R^2$ is CF$_3$; and m is 1.

In some embodiments of Formula I, Ib, Ic, Ie, If, Ih, and Ii, $R^2$ is CF$_3$; and m is 2.

In some embodiments of Formula I, Ib, Ic, Ie, If, Ih, and Ii, $R^2$ is OMe; and m is 1.

In some embodiments of Formula I, Ib, Ic, Ie, If, Ih, and Ii, $R^2$ is OMe; and m is 2.

In some embodiments of Formula I, Ib, Ic, Ie, If, Ih, and Ii, $R^2$ is F and Me; and m is 2.

In some embodiments of Formula I, Ib, Ic, Ie, If, Ih, and Ii, $R^2$ is F and CF$_3$; and m is 2.

In some embodiments of Formula I, Ib, Ic, Ie, If, Ih, and Ii, $R^2$ is F and OMe; and m is 2.

In some embodiments of Formula I, Ib, Ic, Ie, If, Ih, and Ii, $R^2$ is CN; and m is 1.

In some embodiments of Formula I, Ib, Ic, Ie, If, Ih, and Ii, $R^2$ is CN; and m is 2.

In some embodiments of Formula I, Ib, Ic, Ie, If, Ih, and Ii, $R^2$ is F and CN; and m is 2.

In some embodiments of Formula I, Ib, Ic, Ie, If, Ih, and Ii, at least one $R^2$ is —C$_{1-2}$ alkyl.

In some embodiments of Formula I, Ib, Ic, Ie, If, Ih, and Ii, at least one $R^2$ is —C$_{1-3}$ alkyl.

In some embodiments of Formula I, Ib, Ic, Ie, If, Ih, and Ii, at least one $R^2$ is —C$_{1-4}$ alkyl.

In some embodiments of Formula I, Ib, Ic, Ie, If, Ih, and Ii, at least one $R^2$ is —C$_{1-5}$ alkyl.

In some embodiments of Formula I, Ib, Ic, Ie, If, Ih, and Ii, at least one $R^2$ is —C$_{1-6}$ alkyl.

In some embodiments of Formula I, Ib, Ic, Ie, If, Ih, and Ii, at least one $R^2$ is —C$_{2-6}$ alkyl.

In some embodiments of Formula I, Ib, Ic, Ie, If, Ih, and Ii, at least one $R^2$ is —C$_{3-6}$ alkyl.

In some embodiments of Formula I, Ib, Ic, Ie, If, Ih, and Ii, at least one $R^2$ is —C$_{4-6}$ alkyl.

In some embodiments of Formula I, Ia, Ib, Ic, Id, Ie, If, Ig, Ih, and Ii, $R^3$ is —C$_{1-2}$ alkyl.

In some embodiments of Formula I, Ia, Ib, Ic, Id, Ie, If, Ig, Ih, and Ii, $R^3$ is —C$_{1-3}$ alkyl.

In some embodiments of Formula I, Ia, Ib, Ic, Id, Ie, If, Ig, Ih, and Ii, $R^3$ is —C$_{1-4}$ alkyl.

In some embodiments of Formula I, Ia, Ib, Ic, Id, Ie, If, Ig, Ih, and Ii, $R^3$ is —C$_{1-5}$ alkyl.

In some embodiments of Formula I, Ia, Ib, Ic, Id, Ie, If, Ig, Ih, and Ii, $R^3$ is —C$_{1-6}$ alkyl.

In some embodiments of Formula I, Ia, Ib, Ic, Id, Ie, If, Ig, Ih, and Ii, $R^3$ and/or $R^{3a}$ is —C$_{2-6}$ alkyl.

In some embodiments of Formula I, Ia, Ib, Ic, Id, Ie, If, Ig, Ih, and Ii, $R^3$ and/or $R^{3a}$ is —C$_{3-6}$ alkyl.

In some embodiments of Formula I, Ia, Ib, Ic, Id, Ie, If, Ig, Ih, and Ii, $R^3$ and/or $R^{3a}$ is —C$_{4-6}$ alkyl.

In some embodiments of Formula I, Ia, Ib, Ic, Id, Ie, If, Ig, Ih, and Ii, $R^3$ and/or $R^{3a}$ is —C$_{2-5}$ alkyl.

In some embodiments of Formula I, Ia, Ib, Ic, Id, Ie, If, Ig, Ih, and Ii, $R^3$ and/or $R^{3a}$ is —C$_{3-4}$ alkyl.

In some embodiments of Formula I, Ib, Ic, Ie, If, Ih, and Ii, Ring B is a phenyl or 6-membered heteroaryl; $R^2$ is selected from the group consisting of F, Cl, Me, OMe, OH, CF$_3$, and CN; m is 1; and $R^2$ is attached to an ortho carbon of the 6-membered ring.

In some embodiments of Formula I, Ib, Ic, Ie, If, Ih, and Ii, Ring B is a phenyl; $R^2$ is selected from the group consisting of F, Cl, Me, OMe, OH, CF$_3$; and CN; m is 1; and $R^2$ is attached to an ortho position of the phenyl ring.

In some embodiments of Formula I, Ib, Ic, Ie, If, Ih, and Ii, Ring B is a pyridine; $R^2$ is selected from the group consisting of F, Cl, Me, OMe, OH, CF$_3$, and CN; m is 1; and $R^2$ is attached to an ortho carbon of the pyridine ring.

In some embodiments of Formula I, Ib, Ic, Ie, If, Ih, and Ii,

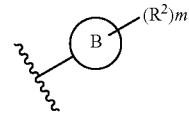

is selected from the group consisting of:

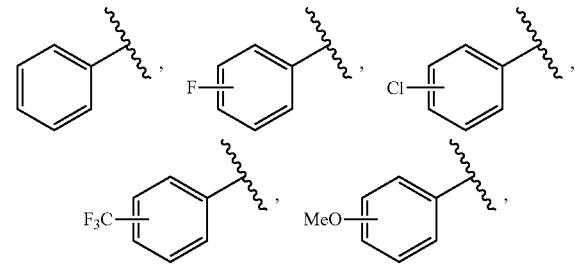

-continued

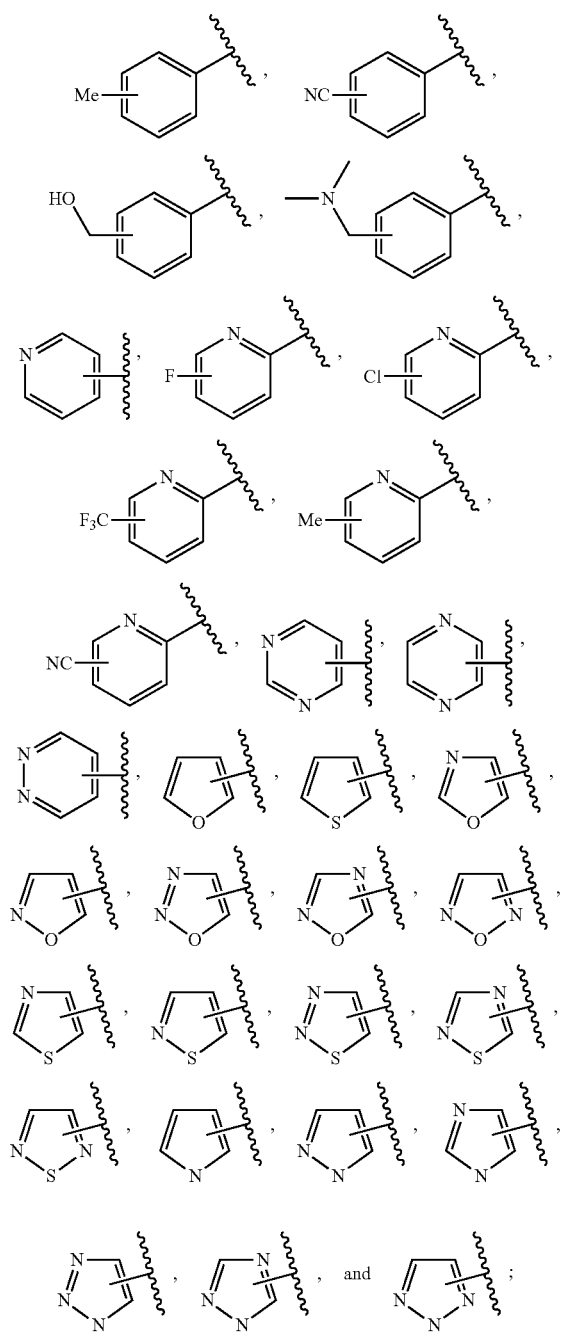

wherein the carbonyl carbon of Formula I, Ib, Ic, 1e, If, Ih, and Ii, can form a bond with any unsubstituted carbon on the Ring B.

In some embodiments of Formula I, Ib, Ic, Ie, If, Ih, and Ii,

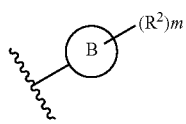

is selected from the group consisting of:

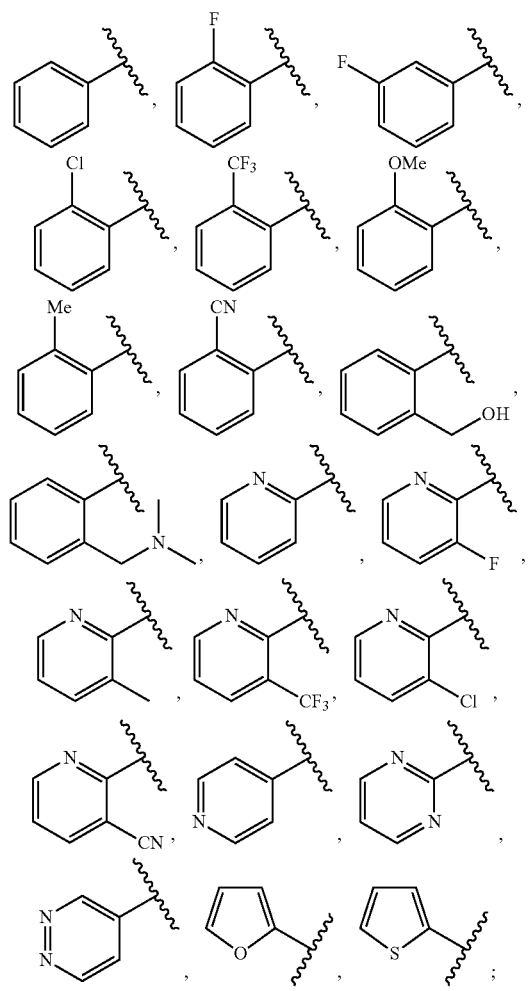

wherein the carbonyl carbon of Formula I, Ib, Ic, Ie, If, Ih, and Ii, can form a bond with any unsubstituted carbon on the Ring B.

In some embodiments of Formula I, Ib, Ic, Ie, If, Ih, and Ii,

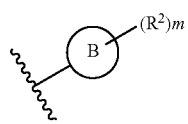

is selected from the group consisting of:

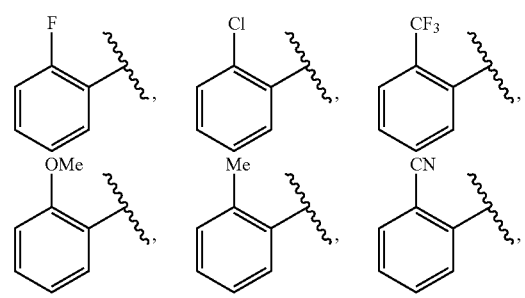

-continued

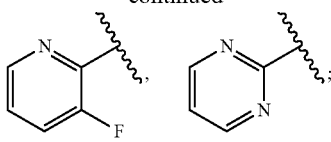

wherein the carbonyl carbon of Formula I, Ib, Ic, Ie, If, Ih, and Ii, can form a bond with any unsubstituted carbon on the Ring B.

In some embodiments of Formula I, Ib, Ic, Ie, If, Ih, and Ii,

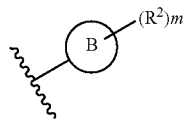

is selected from the group consisting of

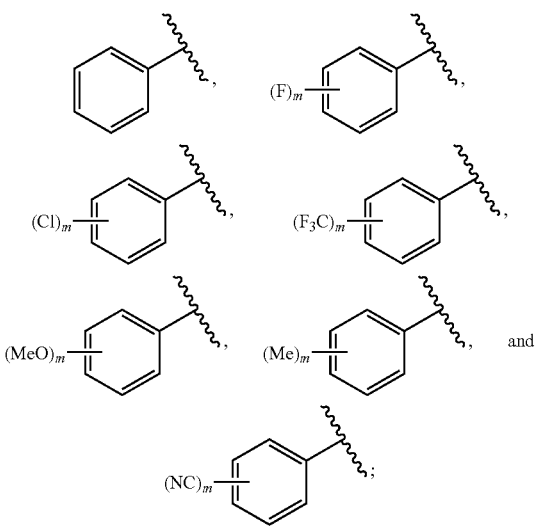

m is 1 or 2.

In some embodiments of Formula I, Ib, Ic, Ie, If, Ih, and Ii,

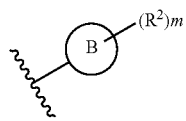

is selected from the group consisting of

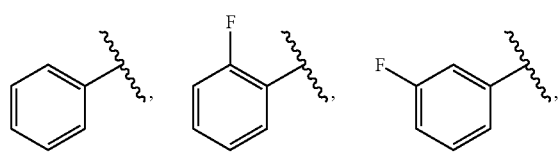

-continued

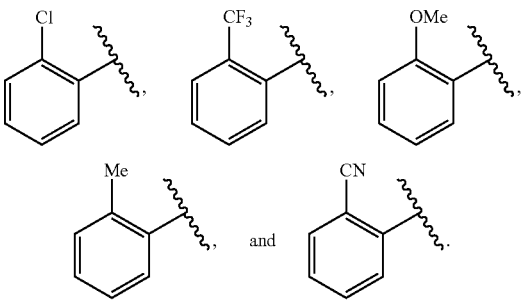

In some embodiments of Formula I, Ib, Ic, Ie, If, Ih, and Ii,

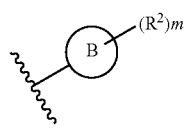

is selected from the group consisting of

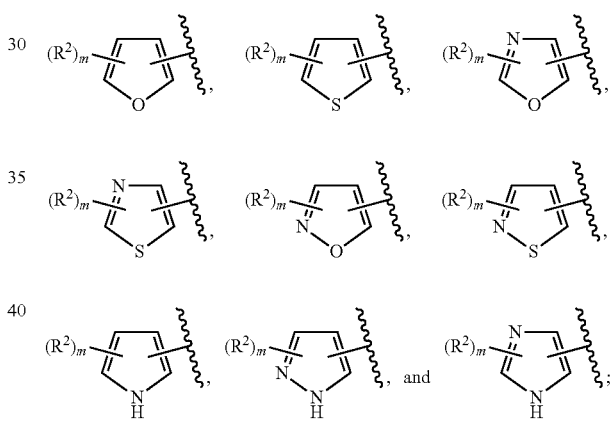

and m is 0 to 2.

In some embodiments of Formula I, Ib, Ic, Ie, If, Ih, and Ii,

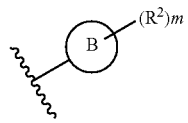

is selected from the group consisting of

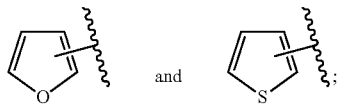

and m is 0.

In some embodiments of Formula I, Ib, Ic, Ie, If, Ih, and Ii,

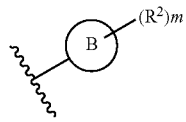

is selected from the group consisting of

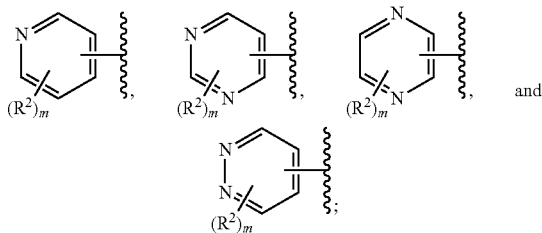

and m is 0 to 2.

In some embodiments of Formula I, Ib, Ic, Ie, If, Ih, and Ii,

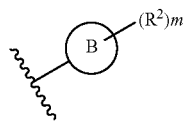

is selected from the group consisting of

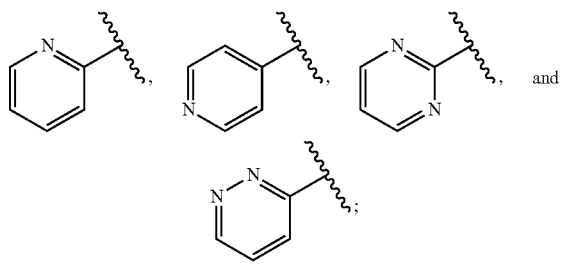

and m is 0.

In some embodiments of Formula Ia and Id, $R^{2a}$ is a Cl.
In some embodiments of Formula Ia, Id, and Ig, $R^{2a}$ is a Me.
In some embodiments of Formula Ia, Id, and Ig, $R^{2a}$ is a $CF_3$.
In some embodiments of Formula Ia, Id, and Ig, $R^{2a}$ is a CN.
In some embodiments of Formula Ia, Id, and Ig, $R^{2a}$ is a Me.
In some embodiments of Formula Ia, Id, and Ig, $R^{2a}$ is a $CF_3$.
In some embodiments of Formula Ia, Id, and Ig, $R^{2a}$ is a CN.
In some embodiments of Formula Ia, Id, and Ig, $R^{2a}$ is a —$C_{1-2}$ alkyl.
In some embodiments of Formula Ia, Id, and Ig, $R^{2a}$ is a —$C_{1-3}$ alkyl.
In some embodiments of Formula Ia, Id, and Ig, $R^{2a}$ is a —$C_{1-4}$ alkyl.
In some embodiments of Formula Ia, Id, and Ig, $R^{2a}$ is a —$C_{1-5}$ alkyl.
In some embodiments of Formula Ia, Id, and Ig, $R^{2a}$ is a —$C_{1-6}$ alkyl.
In some embodiments of Formula Ia, Id, and Ig, $R^{2a}$ is a —$C_{2-6}$ alkyl.
In some embodiments of Formula Ia, Id, and Ig, $R^{2a}$ is a —$C_{3-6}$ alkyl.
In some embodiments of Formula Ia, Id, and Ig, $R^{2a}$ is a —$C_{4-6}$ alkyl.
In some embodiments of Formula Ia, Id, and Ig, $R^{2a}$ is a —$C_{2-5}$ alkyl.
In some embodiments of Formula Ia, Id, and Ig, $R^{2a}$ is a —$C_{3-4}$ alkyl.
In some embodiments of Formula Ia and Ig, $R^{2b}$ is a halide.
In some embodiments of Formula Ia, Id, and Ig, $R^{2b}$ is a F.
In some embodiments of Formula Ia and Ig, $R^{2b}$ is a Cl.
In some embodiments of Formula Ia, $R^{2b}$ is a Me.
In some embodiments of Formula Id and Ig, $R^{2b}$ is a OH.
In some embodiments of Formula Id and Ig, $R^{2b}$ is a OMe.
In some embodiments of Formula Ia, Id, and Ig, $R^{2b}$ is a $CF_3$.
In some embodiments of Formula Ia, Id, and Ig, $R^{2b}$ is a CN.
In some embodiments of Formula Ia, $R^{2b}$ is a —$C_{1-2}$ alkyl.
In some embodiments of Formula Ia, $R^{2b}$ is a —$C_{1-3}$ alkyl.
In some embodiments of Formula Ia, $R^{2b}$ is a —$C_{1-4}$ alkyl.
In some embodiments of Formula Ia, $R^{2b}$ is a —$C_{1-5}$ alkyl.
In some embodiments of Formula Ia, $R^{2b}$ is a —$C_{1-6}$ alkyl.
In some embodiments of Formula Ia, Id, and Ig, $R^{2b}$ is a —$C_{2-6}$ alkyl.
In some embodiments of Formula Ia, Id, and Ig, $R^{2b}$ is a —$C_{3-6}$ alkyl.
In some embodiments of Formula Ia, Id, and Ig, $R^{2b}$ is a —$C_{4-6}$ alkyl.
In some embodiments of Formula Ia, Id, and Ig, $R^{2b}$ is a —$C_{2-5}$ alkyl.
In some embodiments of Formula Ia, Id, and Ig, $R^{2b}$ is a —$C_{3-4}$ alkyl.
In some embodiments of Formula Ia and Ig, at least one $R^{2c}$ is halide.
In some embodiments of Formula Ia and Ig, at least one $R^{2c}$ is F.
In some embodiments of Formula Ia and Ig, at least one $R^{2C}$ is Cl.
In some embodiments of Formula Ia and Ig, at least one $R^{2C}$ is Me.
In some embodiments of Formula Ia and Ig, at least one $R^{2C}$ is OH.
In some embodiments of Formula Ia and Ig, at least one $R^{2C}$ is OMe.
In some embodiments of Formula Ia and Ig, at least one $R^{2c}$ is $CF_3$.
In some embodiments of Formula Ia and Ig, at least one $R^{2C}$ is CN.
In some embodiments of Formula Ia and Ig, $R^{2C}$ is a F.
In some embodiments of Formula Ia and Ig, $R^{2C}$ is F and m is 1.
In some embodiments of Formula Ia and Ig, $R^{2C}$ is Me and m is 1.
In some embodiments of Formula Ia and Ig, $R^{2c}$ is Me and m is 2.

In some embodiments of Formula Ia and Ig, $R^{2c}$ is $CF_3$ and m is 1.

In some embodiments of Formula Ia and Ig, $R^{2c}$ is $CF_3$ and m is 2.

In some embodiments of Formula Ia and Ig, $R^{2c}$ is OMe and m is 1.

In some embodiments of Formula Ia and Ig, $R^{2c}$ is OMe and m is 2.

In some embodiments of Formula Ia and Ig, m is 2 and one $R^{2c}$ is F and the other $R^{2c}$ is Me.

In some embodiments of Formula Ia and Ig, m is 2 and one $R^{2c}$ is F and the other $R^{2c}$ is $CF_3$.

In some embodiments of Formula Ia and Ig, m is 2 and one $R^{2c}$ is F and the other $R^{2c}$ is OMe.

In some embodiments of Formula Ia and Ig, $R^{2c}$ is CN and m is 1.

In some embodiments of Formula Ia and Ig, $R^{2c}$ is CN and m is 2.

In some embodiments of Formula Ia and Ig, m is 2 and one $R^{2c}$ is F and the other $R^{2c}$ is CN.

In some embodiments of Formula Ia and Ig, at least one $R^{2c}$ is —$C_{1-2}$ alkyl.

In some embodiments of Formula Ia and Ig, at least one $R^{2c}$ is —$C_{1-3}$ alkyl.

In some embodiments of Formula Ia and Ig, at least one $R^{2c}$ is —$C_{1-4}$ alkyl.

In some embodiments of Formula Ia and Ig, at least one $R^{2c}$ is —$C_{1-5}$ alkyl.

In some embodiments of Formula Ia and Ig, at least one $R^{2c}$ is —$C_{1-6}$ alkyl.

In some embodiments of Formula Ia and Ig, at least one $R^{2c}$ is —$C_{2-6}$ alkyl.

In some embodiments of Formula Ia and Ig, at least one $R^{2c}$ is —$C_{3-6}$ alkyl.

In some embodiments of Formula Ia and Ig, at least one $R^{2c}$ is —$C_{4-6}$ alkyl.

In some embodiments of Formula Ia and Ig, at least one $R^{2c}$ is —$C_{2-5}$ alkyl.

In some embodiments of Formula Ia and Ig, at least one $R^{2c}$ is —$C_{3-4}$ alkyl.

In some embodiments of Formula Ia and Ig, at least one $R^{2d}$ is halide.

In some embodiments of Formula Ia and Ig, at least one $R^{2d}$ is F.

In some embodiments of Formula Ia and Ig, at least one $R^{2d}$ is Cl.

In some embodiments of Formula Ia and Ig, at least one $R^{2d}$ is Me.

In some embodiments of Formula Ia and Ig, at least one $R^{2d}$ is OH.

In some embodiments of Formula Ia and Ig, at least one $R^{2d}$ is OMe.

In some embodiments of Formula Ia and Ig, at least one $R^{2d}$ is $CF_3$.

In some embodiments of Formula Ia and Ig, at least one $R^{2d}$ is CN.

In some embodiments of Formula Ia and Ig, s is 1 and $R^{2d}$ is F.

In some embodiments of Formula Ia and Ig, s is 2 and both $R^{2d}$ are F.

In some embodiments of Formula Ia and Ig, s is 1 and $R^{2d}$ is Me.

In some embodiments of Formula Ia and Ig, s is 2 and both $R^{2d}$ are Me.

In some embodiments of Formula Ia and Ig, s is 1 and $R^{2d}$ is $CF_3$.

In some embodiments of Formula Ia and Ig, s is 2 and both $R^{2d}$ are $CF_3$.

In some embodiments of Formula Ia and Ig, s is 1 and $R^{2d}$ is OMe.

In some embodiments of Formula Ia and Ig, s is 2 and both $R^{2d}$ are OMe.

In some embodiments of Formula Ia and Ig, s is 2 and one $R^{2d}$ is F and the other $R^{2d}$ is Me.

In some embodiments of Formula Ia and Ig, s is 2 and one $R^{2d}$ is F and the other $R^{2d}$ is $CF_3$.

In some embodiments of Formula Ia and Ig, s is 2 and one $R^{2d}$ is F and the other $R^{2d}$ is OMe.

In some embodiments of Formula Ia and Ig, s is 1 and $R^{2d}$ is CN.

In some embodiments of Formula Ia and Ig, s is 2 and both $R^{2d}$ are CN.

In some embodiments of Formula Ia and Ig, s is 2 and one $R^{2d}$ is F and the other $R^{2d}$ is CN.

In some embodiments of Formula Ia and Ig, at least one $R^{2d}$ is —$C_{1-2}$ alkyl.

In some embodiments of Formula Ia and Ig, at least one $R^{2d}$ is —$C_{1-3}$ alkyl.

In some embodiments of Formula Ia and Ig, at least one $R^{2d}$ is —$C_{1-4}$ alkyl.

In some embodiments of Formula Ia and Ig, at least one $R^{2d}$ is —$C_{1-5}$ alkyl.

In some embodiments of Formula Ia and Ig, at least one $R^{2d}$ is —$C_{1-6}$ alkyl.

In some embodiments of Formula Ia and Ig, at least one $R^{2d}$ is —$C_{2-6}$ alkyl.

In some embodiments of Formula Ia and Ig, at least one $R^{2d}$ is —$C_{3-6}$ alkyl.

In some embodiments of Formula Ia and Ig, at least one $R^{2d}$ is —$C_{4-6}$ alkyl.

In some embodiments of Formula Ia and Ig, at least one $R^{2d}$ is —$C_{2-5}$ alkyl.

In some embodiments of Formula Ia and Ig, at least one $R^{2d}$ is —$C_{3-4}$ alkyl.

Some embodiments of the present disclosure include compounds of Formula (II):

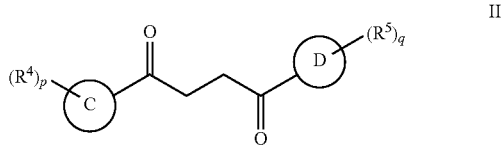

or salts, dermatologically acceptable salts, or prodrugs thereof.

In some embodiments of Formula II, Ring C is a 5-6 membered heteroaryl, wherein a carbon atom on the ring is attached to the carbonyl carbon.

In some embodiments of Formula II, Ring D is selected from the group consisting of phenyl and a 5-6 membered heteroaryl, wherein a carbon atom on the ring is attached to the carbonyl carbon.

In some embodiments of Formula II, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, and CN.

In some embodiments of Formula II, each $R^4$ is a substituent attached to Ring C and is independently selected at each occurrence from the group consisting of unsubstituted —$C_{1-6}$ alkyl, —$C_{1-3}$ haloalkyl, halide, —$OR^6$, and CN.

In some embodiments of Formula II, each $R^5$ is a substituent attached to Ring D and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN.

In some embodiments of Formula II, each $R^5$ is a substituent attached to Ring D and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN.

In some embodiments of Formula II, each $R^6$ is independently selected from the group consisting of H, unsubstituted —$C_{1-6}$ alkyl and —$C_{1-3}$ haloalkyl.

In some embodiments of Formula II, each $R^{6b}$ is independently selected from the group consisting of H and unsubstituted —$C_{1-3}$ alkyl.

In some embodiments of Formula II, each q is 0 to 4.
In some embodiments of Formula II, each q is 1 to 4.
In some embodiments of Formula II, each p is 0 to 5.
In some embodiments of Formula II, each p is 1 to 5.

In some embodiments of Formula II, Ring C is a 5-membered heteroaryl ring containing 1-3 heteroatoms selected from the group consisting of N, O, and S.

In some embodiments of Formula II,

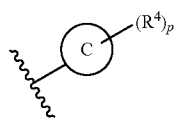

is selected from the group consisting of

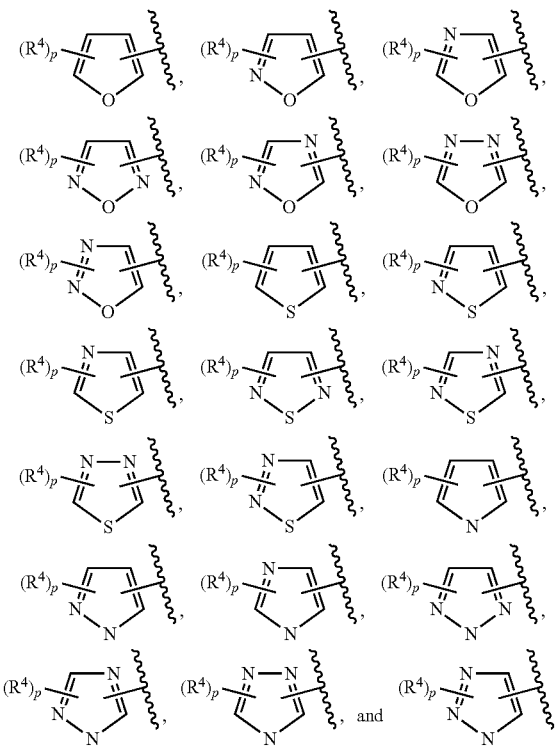

and p is 0 to 2.

In some embodiments of Formula II, p is 0.

In some embodiments of Formula II,

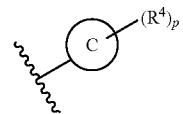

is

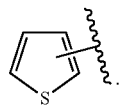

In some embodiments of Formula II, Ring C is a 6-membered heteroaryl ring containing 1-2 nitrogens.

In some embodiments of Formula II,

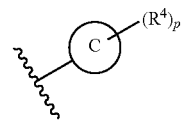

is selected from the group consisting of

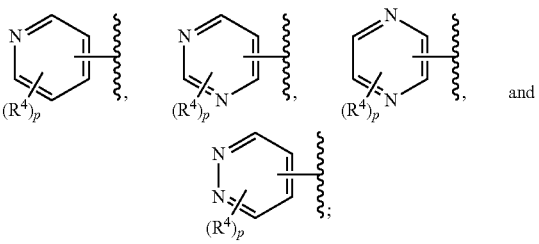

and p is 0 to 2.

In some embodiments of Formula II,

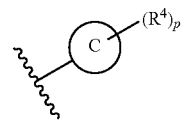

is

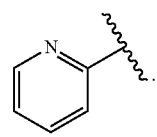

In some embodiments of Formula II, each $R^4$ is independently selected from the group consisting of F, Cl, Me, OMe, OH, $CF_3$, and CN.

In some embodiments of Formula II, Ring C is selected from the group consisting of:

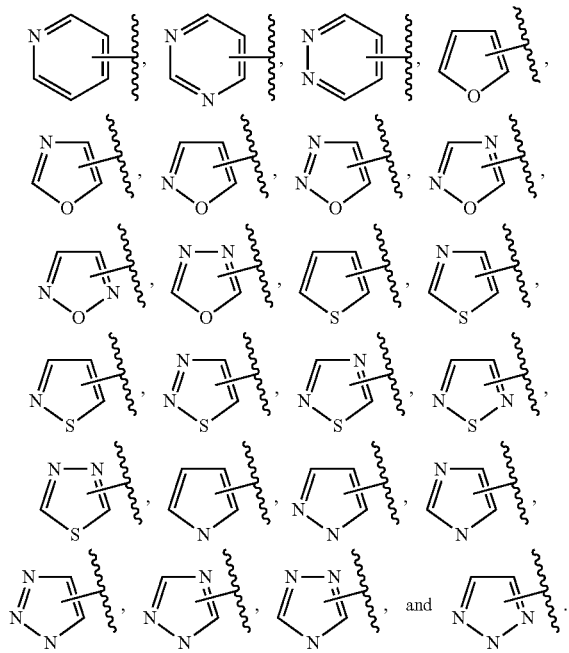

In some embodiments of Formula II, Ring D is a phenyl or 6-membered heteroaryl; $R^5$ is selected from the group consisting of F, Cl, Me, OMe, OH, $CF_3$ and CN; q is 1; and $R^5$ is attached to an ortho carbon of the 6-membered ring.

In some embodiments of Formula II, Ring D is a phenyl, $R^5$ is selected from the group consisting of F, Cl, Me, OMe, OH, $CF_3$ and CN; q is 1; and $R^5$ is attached to an ortho position of the phenyl ring.

In some embodiments of Formula II, Ring D is a pyridine, $R^5$ is selected from the group consisting of F, Cl, Me, OMe, OH, $CF_3$ and CN; q is 1; and $R^5$ is attached to an ortho carbon of the pyridine ring.

In some embodiments of Formula II,

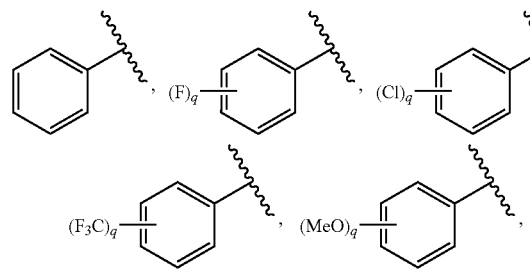

is selected from the group consisting of:

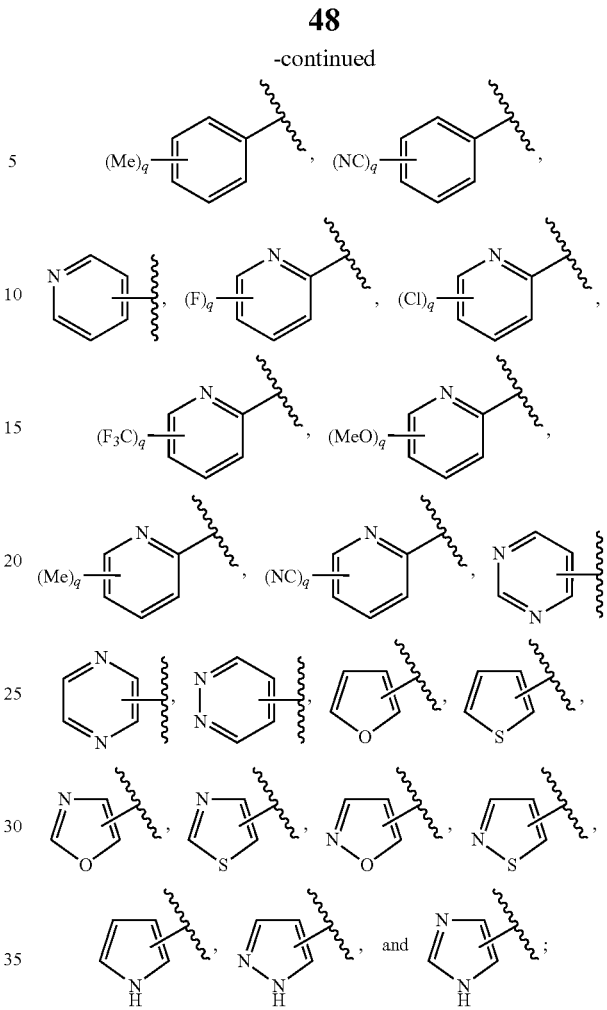

wherein the carbonyl carbon of Formula II can form a bond with any unsubstituted carbon on the Ring D; and q is 1 or 2.

In some embodiments of Formula II, q is 0.

In some embodiments of Formula II,

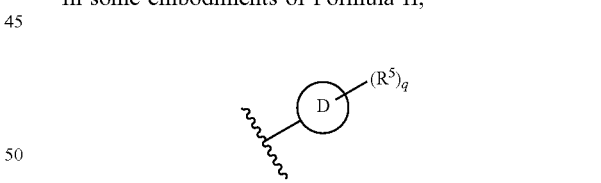

is selected from the group consisting of:

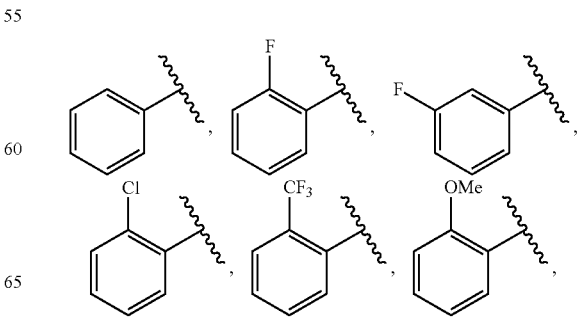

-continued

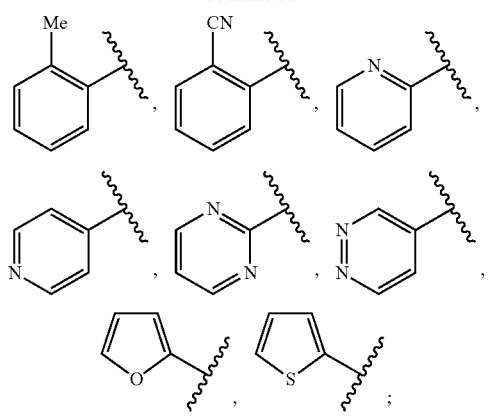

wherein the carbonyl carbon of Formula II can form a bond with any unsubstituted carbon on the Ring D.

In some embodiments of Formula II,

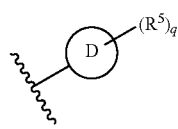

is selected from the group consisting of:

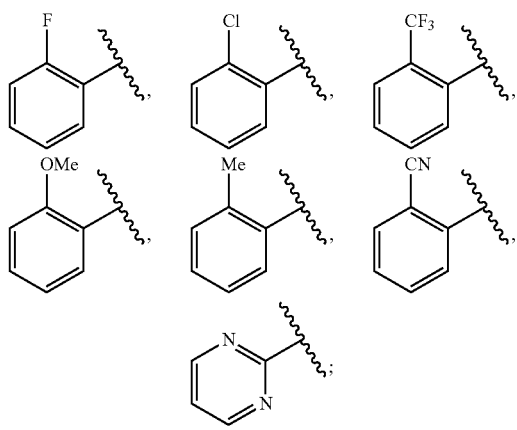

wherein the carbonyl carbon of Formula II can form a bond with any unsubstituted carbon on the Ring D.

Some embodiments of Formula II include compounds of Formula (IIa):

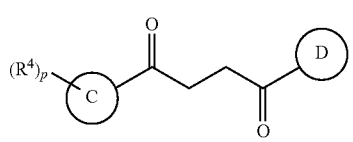

IIa or salts, dermatologically acceptable salts, or prodrugs thereof.

In some embodiments of Formula IIa, Ring C is

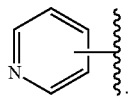

In some embodiments of Formula IIa, Ring D is selected from the group consisting of

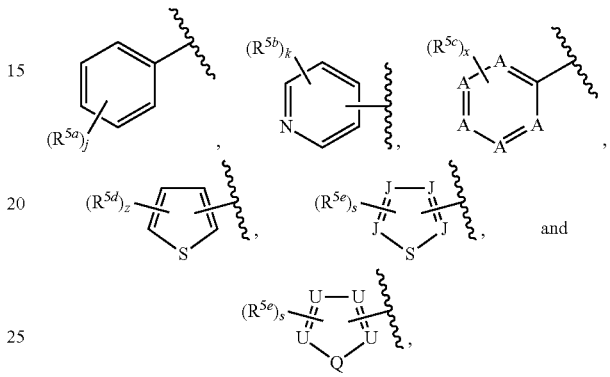

and wherein a carbon atom on the ring is attached to the carbonyl carbon.

In some embodiments of Formula IIa, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, and CN.

In some embodiments of Formula IIa, each $R^4$ is a substituent attached to Ring C and is independently selected at each occurrence from the group consisting of unsubstituted —$C_{1-6}$ alkyl, —$C_{1-3}$ haloalkyl, halide, —$OR^6$, and CN.

In some embodiments of Formula IIa, $R^{5a}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6a$, and CN; j is 1 to 5.

In some embodiments of Formula IIa, $R^{5b}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, F, I, —$OR^{6a}$, and CN; k is 1 to 4.

In some embodiments of Formula IIa, $R^{5c}$ is a substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN; x is 1 to 3.

In some embodiments of Formula IIa, $R^{5c}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN; x is 0 to 3.

In some embodiments of Formula IIa, x is 0.

In some embodiments of Formula IIa, $R^{5d}$ is a substituent attached to the ring and are independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN; z is 1 or 2.

In some embodiments of Formula IIa, $R^{5e}$ is a substituent attached to the ring and are independently selected at each occurrence from the group consisting of H, unsubstituted —C$_{1-6}$ alkyl, —CH$_2$OH, —CH$_2$N(R$^{6b}$)$_2$, —C$_{1-3}$ haloalkyl, halide, —OR$^6$, and CN; s is 1 to 3.

In some embodiments of Formula IIa, R$^{5e}$ is a substituent attached to the ring and are independently selected at each occurrence from the group consisting of unsubstituted —C$_{1-6}$ alkyl, —CH$_2$OH, —CH$_2$N(R$^{6b}$)$_2$, —C$_{1-3}$ haloalkyl, halide, —OR$^6$, and CN; s is 0 to 3.

In some embodiments of Formula IIa, each R$^6$ is independently selected from the group consisting of H, unsubstituted —C$_{1-6}$ alkyl and —C$_{1-3}$ haloalkyl.

In some embodiments of Formula IIa, each R$^{6a}$ is independently selected from the group consisting of H, unsubstituted —C$_{2-6}$ alkyl and —C$_{1-3}$ haloalkyl.

In some embodiments of Formula IIa, each R$^{6b}$ is independently selected from the group consisting of H and unsubstituted —C$_{1-3}$ alkyl.

In some embodiments of Formula IIa, each A is independently N or C.

In some embodiments of Formula IIa, at least two A must be N.

In some embodiments of Formula IIa, each J is independently N or C.

In some embodiments of Formula IIa, at least one J must be N and at least one J must be C.

In some embodiments of Formula IIa, each U is independently N or C.

In some embodiments of Formula IIa, at least one U must be C.

In some embodiments of Formula IIa, Q is O or N.
In some embodiments of Formula IIa, p is 0 to 4.
In some embodiments of Formula IIa, p is 1 to 4.
In some embodiments of Formula IIa, Ring D is selected from the group consisting of

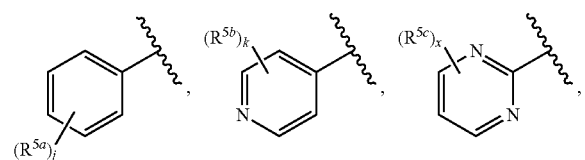
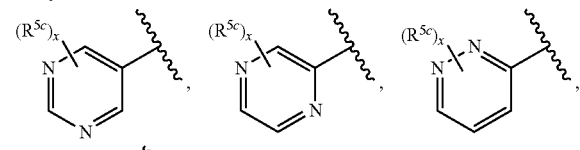
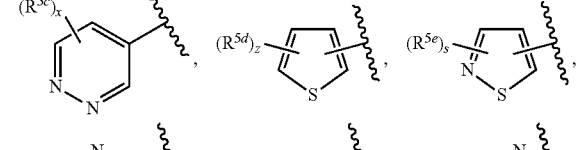
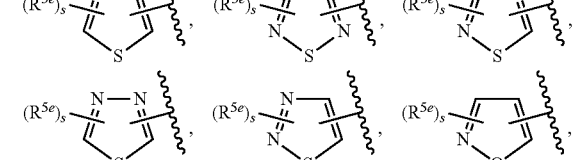
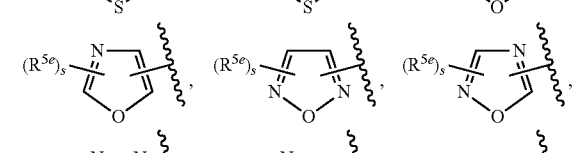
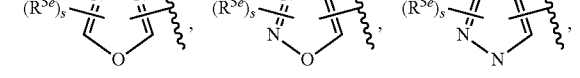

-continued

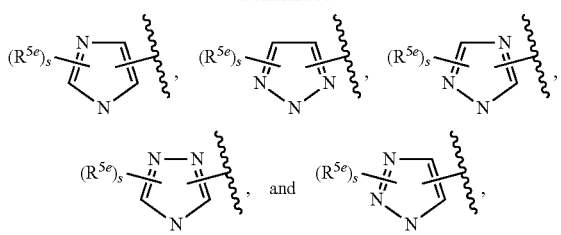

wherein a carbon atom on the ring is attached to the carbonyl carbon.

In some embodiments of Formula IIa, Ring D is selected from the group consisting of:

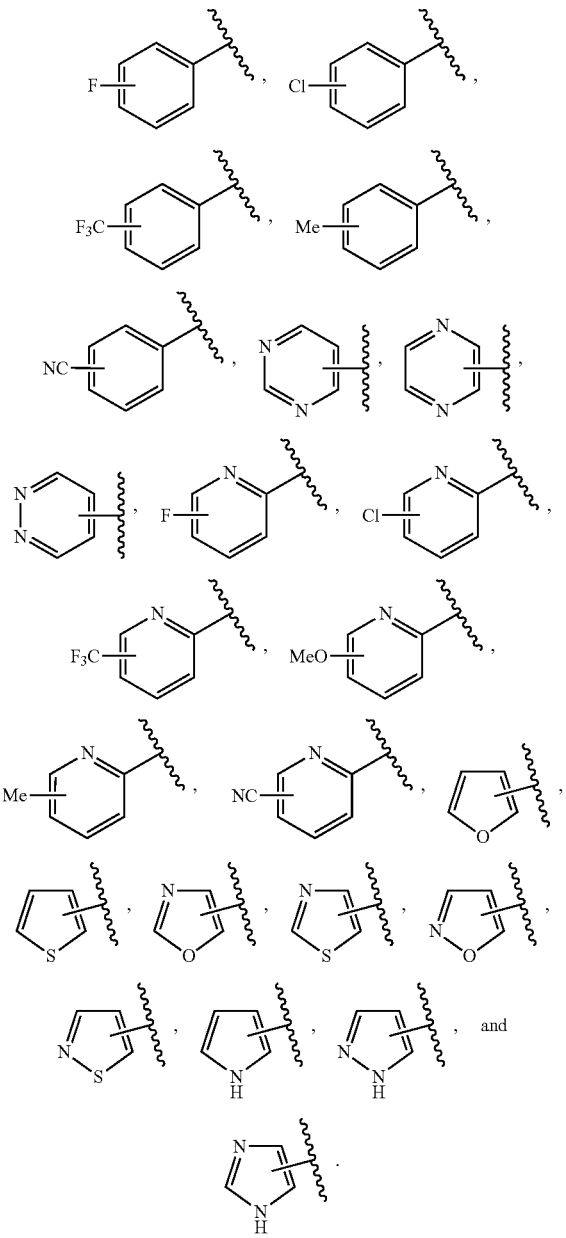

Some embodiments of Formula II include compounds of Formula (IIb):

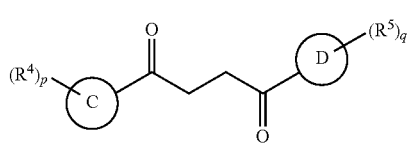

or salts, dermatologically acceptable salts, or prodrugs thereof.

In some embodiments of Formula IIb, Ring C is

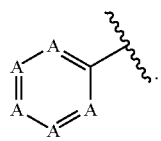

In some embodiments of Formula IIb, Ring D is selected from the group consisting of phenyl and a 5-6 membered heteroaryl, wherein a carbon atom on the ring is attached to the carbonyl carbon.

In some embodiments of Formula IIb, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6a$, and CN.

In some embodiments of Formula IIb, each $R^4$ is a substituent attached to Ring C and is independently selected at each occurrence from the group consisting of unsubstituted —$C_{1-6}$ alkyl, —$C_{1-3}$ haloalkyl, halide, —$OR^6a$, and CN.

In some embodiments of Formula IIb, each $R^5$ is a substituent attached to Ring D and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN.

In some embodiments of Formula IIb, each $R^5$ is a substituent attached to Ring D and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN.

In some embodiments of Formula IIb, each $R^6$ is independently selected from the group consisting of H, unsubstituted —$C_{1-6}$ alkyl, and —$C_{1-3}$ haloalkyl.

In some embodiments of Formula IIb, each $R^{6a}$ is independently selected from the group consisting of unsubstituted —$C_{1-6}$ alkyl and —$C_{1-3}$ haloalkyl.

In some embodiments of Formula IIb, each $R^{6b}$ is independently selected from the group consisting of H and unsubstituted —$C_{1-3}$ alkyl.

In some embodiments of Formula IIb, each A is independently N or C.

In some embodiments of Formula IIb, at least two A must be N.

In some embodiments of Formula IIb, p is 0 to 3.
In some embodiments of Formula IIb, p is 1 to 3.
In some embodiments of Formula IIb, q is 1 to 5.
In some embodiments of Formula IIb, q is 0 to 5.

In some embodiments of Formula IIb, Ring C is selected from the group consisting of

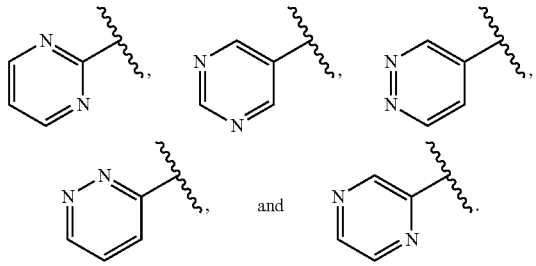

In some embodiments of Formula II and IIb, Ring D is phenyl.

In some embodiments of Formula II and IIb,

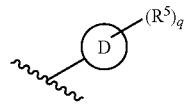

is selected from the group consisting of

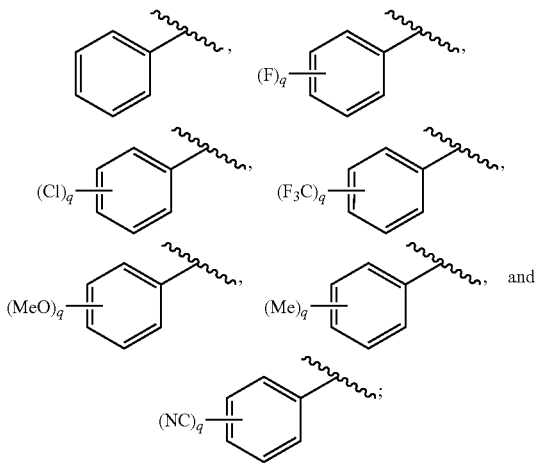

and q is 1 or 2.

In some embodiments of Formula II and IIb,

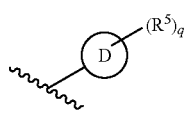

is selected from the group consisting of

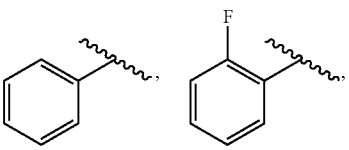

-continued

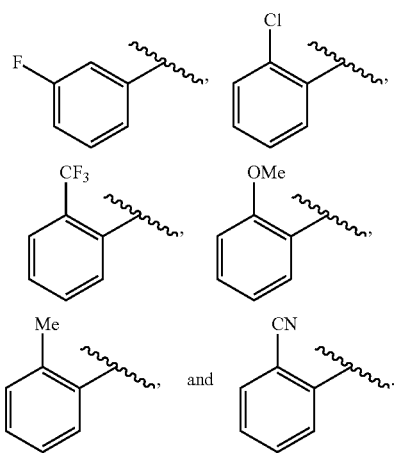

In some embodiments of Formula II and IIb, Ring D is a 5-membered heteroaryl containing 1-3 heteroatoms selected from the group consisting of N, O, and S.

In some embodiments of Formula II and IIb,

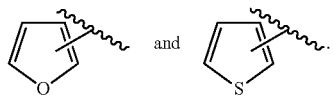

is selected from the group consisting of

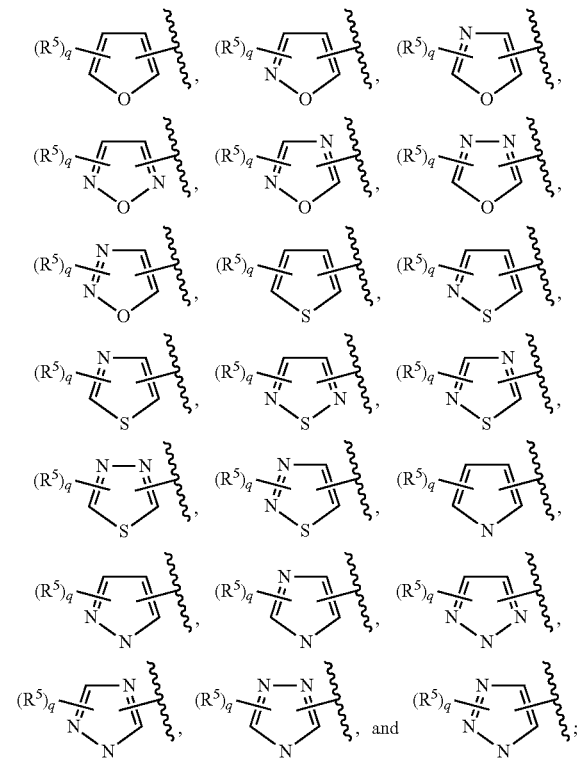

and q is 0 to 2.

In some embodiments of Formula II and IIb,

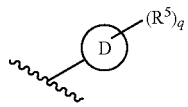

is selected from the group consisting of

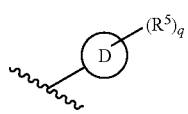

In some embodiments of Formula II and IIb, Ring D is a 6-membered heteroaryl containing 1-2 nitrogen atoms.

In some embodiments of Formula II and IIb,

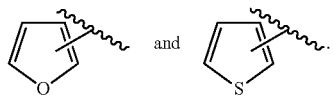

is selected from the group consisting of

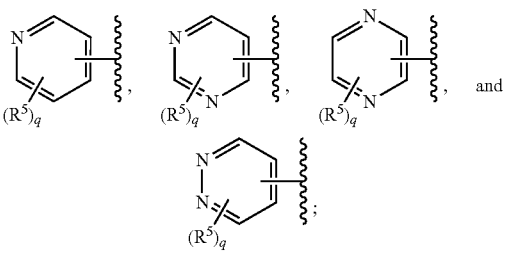

and q is 0 to 2.

In some embodiments of Formula II and IIb,

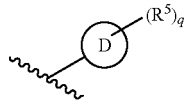

is selected from the group consisting of

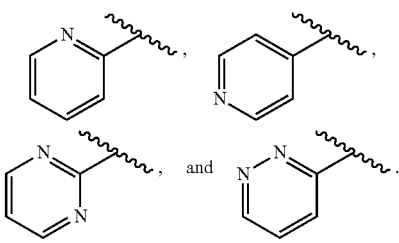

In some embodiments of Formula II and IIb, at least one $R^5$ is —$CH_2OH$.

In some embodiments of Formula II and IIb, at least one $R^5$ is —$CH_2N(R^{3b})_2$.

In some embodiments of Formula II and IIb, at least one $R^5$ is —CH$_2$NH$_2$.
In some embodiments of Formula II and IIb, at least one $R^5$ is —CH$_2$NHMe.
In some embodiments of Formula II and IIb, at least one $R^5$ is —CH$_2$NMe$_2$.
In some embodiments of Formula II and IIb, at least one $R^5$ is —CH$_2$NHEt.
In some embodiments of Formula II and IIb, at least one $R^5$ is —CH$_2$N(Me)(Et).
In some embodiments of Formula II and IIb, at least one $R^5$ is —CH$_2$NEt$_2$.
In some embodiments of Formula II and IIb, each $R^5$ is independently selected from the group consisting of F, Cl, Me, OMe, OH, CF$_3$, and CN.
In some embodiments of Formula II and IIb, $R^5$ is a halide.
In some embodiments of Formula II and IIb, $R^5$ is F.
In some embodiments of Formula II and IIb, $R^5$ is Cl.
In some embodiments of Formula II and IIb, $R^5$ is Me.
In some embodiments of Formula II and IIb, $R^5$ is OH.
In some embodiments of Formula II and IIb, $R^5$ is OMe.
In some embodiments of Formula II and IIb, $R^5$ is CF$_3$.
In some embodiments of Formula II and IIb, $R^5$ is CN.
In some embodiments of Formula II and IIb, q is 1-4.
In some embodiments of Formula II and IIb, q is 1-2.
In some embodiments of Formula II and IIb, q is 0.
In some embodiments of Formula II and IIb, q is 1.
In some embodiments of Formula II and IIb, q is 2.
In some embodiments of Formula II and IIb, $R^5$ is F; and q is 1.
In some embodiments of Formula II and IIb, $R^5$ is F; and q is 2.
In some embodiments of Formula II and IIb, $R^5$ is Me; and q is 1.
In some embodiments of Formula II and IIb, $R^5$ is Me; and q is 2.
In some embodiments of Formula II and IIb, $R^5$ is CF$_3$; and q is 1.
In some embodiments of Formula II and IIb, $R^5$ is CF$_3$; and q is 2.
In some embodiments of Formula II and IIb, $R^5$ is OMe; and q is 1.
In some embodiments of Formula II and IIb, $R^5$ is OMe; and q is 2.
In some embodiments of Formula II and IIb, $R^5$ is F and Me; and q is 2.
In some embodiments of Formula II and IIb, $R^5$ is F and CF$_3$; and q is 2.
In some embodiments of Formula II and IIb, $R^5$ is F and OMe; and q is 2.
In some embodiments of Formula II and IIb, $R^5$ is CN; and q is 1.
In some embodiments of Formula II and IIb, $R^5$ is CN; and q is 2.
In some embodiments of Formula II and IIb, $R^5$ is F and CN; and q is 2.
In some embodiments of Formula II and IIb, at least one $R^5$ is —C$_{1-2}$ alkyl.
In some embodiments of Formula II and IIb, at least one $R^5$ is —C$_{1-3}$ alkyl.
In some embodiments of Formula II and IIb, at least one $R^5$ is —C$_{1-4}$ alkyl.
In some embodiments of Formula II and IIb, at least one $R^5$ is —C$_{1-5}$ alkyl.
In some embodiments of Formula II and IIb, at least one $R^5$ is —C$_{1-6}$ alkyl.
In some embodiments of Formula II and IIb, at least one $R^5$ is —C$_{2-6}$ alkyl.
In some embodiments of Formula II and IIb, at least one $R^5$ is —C$_{3-6}$ alkyl.
In some embodiments of Formula II and IIb, at least one $R^5$ is —C$_{4-6}$ alkyl.
In some embodiments of Formula II and IIb, at least one $R^5$ is —C$_{2-5}$ alkyl.
In some embodiments of Formula II and IIb, at least one $R^5$ is —C$_{3-5}$ alkyl.

Some embodiments of Formula II include compounds of Formula (IIc):

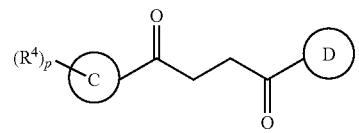

or salts, dermatologically acceptable salts, or prodrugs thereof.

In some embodiments of Formula IIc, Ring C is

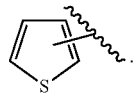

In some embodiments of Formula IIc, Ring D is selected from the group consisting of

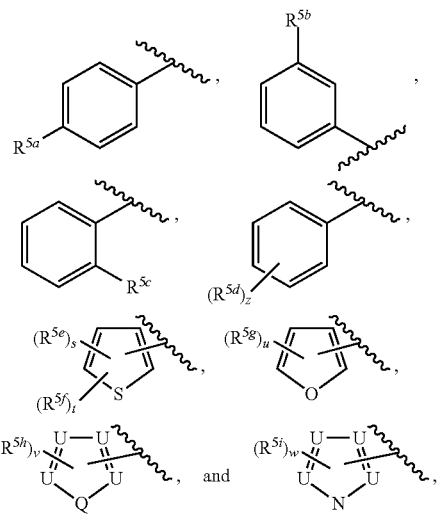

wherein a carbon atom on the ring is attached to the carbonyl carbon.

In some embodiments of Formula IIc, each $R^4$ is a substituent attached to Ring C and is independently selected at each occurrence from the group consisting of H, unsubstituted —C$_{1-6}$ alkyl, —C$_{1-3}$ haloalkyl, halide, —OR$^6$, and CN.

In some embodiments of Formula IIc, each $R^4$ is a substituent attached to Ring C and is independently selected at each occurrence from the group consisting of unsubstituted —C$_{1-6}$ alkyl, —C$_{1-3}$ haloalkyl, halide, —OR$^6$, and CN.

In some embodiments of Formula IIc, $R^{5a}$ is one substituent attached to the para position of phenyl and is selected from the group consisting of unsubstituted —$C_2$-6 alkyl, —$CH_2OH$, —$CH_2N(R^{6b})_2$, —$C_{2-3}$ haloalkyl, iodide, —$OR^6a$, and CN.

In some embodiments of Formula IIc, $R^{5b}$ is one substituent attached to the meta position of phenyl and is selected from the group consisting of unsubstituted —$C_{1-6}$ alkyl, —$CH_2OH$, —$CH_2N(R^{6b})_2$, —$C_{2-3}$ haloalkyl, halide, —$OR^{6a}$, and CN.

In some embodiments of Formula IIc, $R^{5c}$ is one substituent attached to the ortho position of phenyl and is selected from the group consisting of unsubstituted —$C_{1-6}$ alkyl, —$CH_2OH$, —$CH_2N(R^{6b})_2$, —$C_{1-3}$ haloalkyl, F, Br, I, —$OR^6a$, and CN.

In some embodiments of Formula IIc, $R^{5d}$ is a substituent attached to the phenyl and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6a$, and CN; z is 2 to 5.

In some embodiments of Formula IIc, $R^{5e}$ is a substituent attached to the ring and is selected from the group consisting of unsubstituted —$C_{2-5}$ alkyl, —$CH_2OH$, —$CH_2N(R^{6b})_2$, —$C_{1-3}$ haloalkyl, F, I, —$OR^6$, and CN; s is 1.

In some embodiments of Formula IIc, $R^{5f}$ is a substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, F, Br, I, —$OR^6$, and CN; t is 1 or 2.

In some embodiments of Formula IIc, $R^{5f}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, F, Br, I, —$OR^6$, and CN; t is 0 to 2.

In some embodiments of Formula IIc, $R^{5g}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN; u is 1 to 3.

In some embodiments of Formula IIc, $R^{5h}$ is a substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN; v is 1 or 2.

In some embodiments of Formula IIc, $R^{5h}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN; v is 0 to 2.

In some embodiments of Formula IIc, $R^{5i}$ is substituent attached to the ring and is independently selected at each occurrence from the group consisting of H, H, unsubstituted —$C_{1-6}$ alkyl, —$CH_2OH$, —$CH_2N(R^{6b})_2$, —$C_{1-3}$ haloalkyl, halide, —$OR^6$, and CN; w is 1 to 4.

In some embodiments of Formula IIc, $R^{5i}$ is substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN; w is 0 to 4.

In some embodiments of Formula IIc, each $R^6$ is independently selected from the group consisting of H, unsubstituted —$C_{1-6}$ alkyl, and —$C_{1-3}$ haloalkyl.

In some embodiments of Formula IIc, each $R^{6a}$ is independently selected from the group consisting of unsubstituted —$C_{2-6}$ alkyl and —$C_{1-3}$ haloalkyl.

In some embodiments of Formula IIc, each $R^{6b}$ is independently selected from the group consisting of H and unsubstituted —$C_{1-3}$ alkyl.

In some embodiments of Formula IIc, each U is independently N or C.

In some embodiments of Formula IIc, at least one U must be C.

In some embodiments of Formula IIc, Q is S or O.

In some embodiments of Formula IIc, at least one U must be N and at least one U must be C.

In some embodiments of Formula IIc, p is 0 to 3.

In some embodiments of Formula IIc, p is 1 to 3.

In some embodiments of Formula IIc, Ring D is selected from the group consisting of

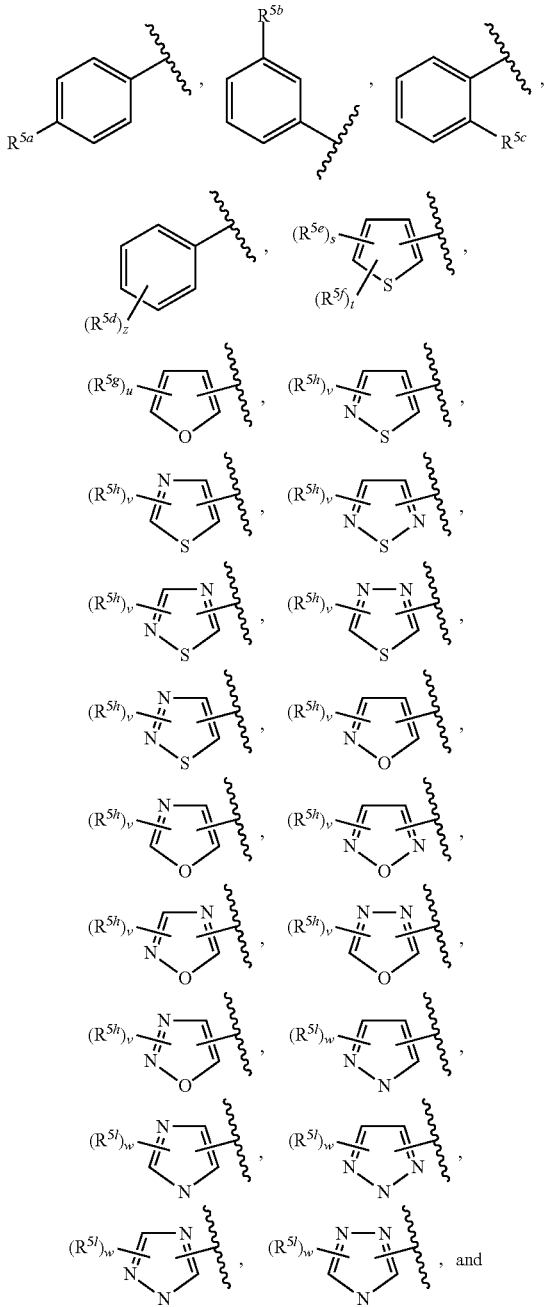

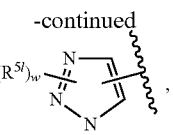

wherein a carbon atom on the ring is attached to the carbonyl carbon.

In some embodiments of Formula IIc, t is 0.
In some embodiments of Formula IIc, v is 0.
In some embodiments of Formula IIc, w is 0.
In some embodiments of Formula IIc, $R^{5a}$, $R^{5b}$, or $R^{5c}$ is a CN.
In some embodiments of Formula IIc, $R^{5b}$ or $R^{5c}$ is a halide.
In some embodiments of Formula IIc, $R^{5b}$ or $R^{5c}$ is a F.
In some embodiments of Formula IIc, $R^{5b}$ is a Cl.
In some embodiments of Formula IIc, $R^{5b}$ or $R^{5c}$ is a Me.
In some embodiments of Formula IIc, $R^{5c}$ is a $CF_3$.
In some embodiments of Formula IIc, $R^{5b}$ or $R^{5c}$ is a $—C_{1-2}$ alkyl.
In some embodiments of Formula IIc, $R^{5b}$ or $R^{5c}$ is a $—C_{1-3}$ alkyl.
In some embodiments of Formula IIc, $R^{5b}$ or $R^{5c}$ is a $—C_{1-4}$ alkyl.
In some embodiments of Formula IIc, $R^{5b}$ or $R^{5c}$ is a $—C_{1-5}$ alkyl.
In some embodiments of Formula IIc, $R^{5b}$ or $R^{5c}$ is a $—C_{1-6}$ alkyl.
In some embodiments of Formula IIc, $R^{5a}$, $R^{5b}$, or $R^{5c}$ is a $—C_{2-6}$ alkyl.
In some embodiments of Formula IIc, $R^{5a}$, $R^{5b}$, or $R^{5c}$ is a $—C_{3-6}$ alkyl.
In some embodiments of Formula IIc, $R^{5a}$, $R^{5b}$, or $R^{5c}$ is a $—C_{4-6}$ alkyl.
In some embodiments of Formula IIc, $R^{5a}$, $R^{5b}$, or $R^{5c}$ is a $—C_{2-5}$ alkyl.
In some embodiments of Formula IIc, $R^{5a}$, $R^{5b}$, or $R^{5c}$ is a $—C_{3-5}$ alkyl.
In some embodiments of Formula IIc, at least one $R^{5f}$, $R^{5g}$, $R^{5h}$, or $R^{5i}$ is halide.
In some embodiments of Formula IIc, at least one $R^{5f}$, $R^{5g}$, $R^{5h}$, or $R^{5i}$ is F.
In some embodiments of Formula IIc, at least one $R^{5f}$, $R^{5g}$, $R^{5h}$, or $R^{5i}$ is Cl.
In some embodiments of Formula IIc, at least one $R^{5f}$, $R^{5g}$, $R^{5h}$, or $R^{5i}$ is Me.
In some embodiments of Formula IIc, at least one $R^{5f}$, $R^{5g}$, $R^{5h}$, or $R^{5i}$ is OH.
In some embodiments of Formula IIc, at least one $R^{5f}$, $R^{5g}$, $R^{5h}$, or $R^{5i}$ is OMe.
In some embodiments of Formula IIc, at least one $R^{5f}$, $R^{5g}$, $R^{5h}$, or $R^{5i}$ is $CF_3$.
In some embodiments of Formula IIc, at least one $R^{5f}$, $R^{5g}$, $R^{5h}$, or $R^{5i}$ is CN.
In some embodiments of Formula IIc, t is 1.
In some embodiments of Formula IIc, t is 2.
In some embodiments of Formula IIc, t is 1 and $R^{5f}$ is F.
In some embodiments of Formula IIc, t is 2 and both $R^{5f}$ are F.
In some embodiments of Formula IIc, t is 1 and $R^{5f}$ is Me.
In some embodiments of Formula IIc, t is 2 and both $R^{5f}$ are Me.
In some embodiments of Formula IIc, t is 1 and $R^{5f}$ is $CF_3$.
In some embodiments of Formula IIc, t is 2 and both $R^{5f}$ are $CF_3$.
In some embodiments of Formula IIc, t is 1 and $R^{5f}$ is OMe.
In some embodiments of Formula IIc, t is 2 and both $R^{5f}$ are OMe.
In some embodiments of Formula IIc, t is 2 and one $R^{5f}$ is F and the other $R^{5f}$ is OMe.
In some embodiments of Formula IIc, t is 2 and one $R^{5f}$ is F and the other $R^{5f}$ is $CF_3$.
In some embodiments of Formula IIc, t is 2 and one $R^{5f}$ is F and the other $R^{5f}$ is OMe.
In some embodiments of Formula IIc, t is 1 and $R^{5f}$ is CN.
In some embodiments of Formula IIc, t is 2 and both $R^{5f}$ are CN.
In some embodiments of Formula IIc, t is 2 and one $R^{5f}$ is F and the other $R^{5f}$ is CN.
In some embodiments of Formula IIc, at least one $R^{5f}$, $R^{5g}$, $R^{5h}$, or $R^{5i}$ is $—C_{1-2}$ alkyl.
In some embodiments of Formula IIc, at least one $R^{5f}$, $R^{5g}$, $R^{5h}$, or $R^{5i}$ is $—C_{1-3}$ alkyl.
In some embodiments of Formula IIc, at least one $R^{5f}$, $R^{5g}$, $R^{5h}$, or $R^{5i}$ is $—C_{1-4}$ alkyl.
In some embodiments of Formula IIc, at least one $R^{5f}$, $R^{5g}$, $R^{5h}$, or $R^{5i}$ is $—C_{1-5}$ alkyl.
In some embodiments of Formula IIc, at least one $R^{5f}$, $R^{5g}$, $R^{5h}$, or $R^{5i}$ is $—C_{1-6}$ alkyl.
In some embodiments of Formula IIc, at least one $R^{5f}$, $R^{5g}$, $R^{5h}$, or $R^{5i}$ is $—C_{2-6}$ alkyl.
In some embodiments of Formula IIc, at least one $R^{5f}$, $R^{5g}$, $R^{5h}$, or $R^{5i}$ is $—C_{3-6}$ alkyl.
In some embodiments of Formula IIc, at least one $R^{5f}$, $R^{5g}$, $R^{5h}$, or $R^{5i}$ is $—C_{4-6}$ alkyl.
In some embodiments of Formula IIc, at least one $R^{5f}$, $R^{5g}$, $R^{5h}$, or $R^{5i}$ is $—C_{2-5}$ alkyl.
In some embodiments of Formula IIc, at least one $R^{5f}$, $R^{5g}$, $R^{5h}$, or $R^{5i}$ is $—C_{3-5}$ alkyl.
In some embodiments of Formula IIc, u is 1.
In some embodiments of Formula IIc, u is 2.
In some embodiments of Formula IIc, u is 1 and $R^{5g}$ is F.
In some embodiments of Formula IIc, u is 2 and both $R^{5g}$ are F.
In some embodiments of Formula IIc, u is 1 and $R^{5g}$ is Me.
In some embodiments of Formula IIc, u is 2 and both $R^{5g}$ are Me.
In some embodiments of Formula IIc, u is 1 and $R^{5g}$ is $CF_3$.
In some embodiments of Formula IIc, u is 2 and both $R^{5g}$ are $CF_3$.
In some embodiments of Formula IIc, u is 1 and $R^{5g}$ is OMe.
In some embodiments of Formula IIc, u is 2 and both $R^{5g}$ are OMe.
In some embodiments of Formula IIc, u is 2 and one $R^{5g}$ is F and the other $R^{5g}$ is OMe.
In some embodiments of Formula IIc, u is 2 and one $R^{5g}$ is F and the other $R^{5g}$ is $CF_3$.
In some embodiments of Formula IIc, u is 2 and one $R^{5g}$ is F and the other $R^{5g}$ is OMe.
In some embodiments of Formula IIc, u is 1 and $R^{5g}$ is CN.
In some embodiments of Formula IIc, u is 2 and both $R^{5g}$ are CN.
In some embodiments of Formula IIc, u is 2 and one $R^{5g}$ is F and the other $R^{5g}$ is CN.
In some embodiments of Formula IIc, v is 1.
In some embodiments of Formula IIc, v is 2.
In some embodiments of Formula IIc, v is 1 and $R^{5h}$ is F.

In some embodiments of Formula IIc, v is 2 and both $R^{5h}$ are F.
In some embodiments of Formula IIc, v is 1 and $R^{5h}$ is Me.
In some embodiments of Formula IIc, v is 2 and both $R^{5h}$ are Me.
In some embodiments of Formula IIc, v is 1 and $R^{5h}$ is $CF_3$.
In some embodiments of Formula IIc, v is 2 and both $R^{5h}$ are $CF_3$.
In some embodiments of Formula IIc, v is 1 and $R^{5h}$ is OMe.
In some embodiments of Formula IIc, v is 2 and both $R^{5h}$ are OMe.
In some embodiments of Formula IIc, v is 2 and one $R^{5h}$ is F and the other $R^{5h}$ is OMe.
In some embodiments of Formula IIc, v is 2 and one $R^{5h}$ is F and the other $R^{5h}$ is $CF_3$.
In some embodiments of Formula IIc, v is 2 and one $R^{5h}$ is F and the other $R^{5h}$ is OMe.
In some embodiments of Formula IIc, v is 1 and $R^{5h}$ is CN.
In some embodiments of Formula IIc, v is 2 and both $R^{5h}$ are CN.
In some embodiments of Formula IIc, v is 2 and one $R^{5h}$ is F and the other $R^{5h}$ is CN.
In some embodiments of Formula IIc, w is 1.
In some embodiments of Formula IIc, w is 2.
In some embodiments of Formula IIc, w is 1 and $R^{5i}$ is F.
In some embodiments of Formula IIc, w is 2 and both $R^{5i}$ are F.
In some embodiments of Formula IIc, w is 1 and $R^{5i}$ is Me.
In some embodiments of Formula IIc, w is 2 and both $R^{5i}$ are Me.
In some embodiments of Formula IIc, w is 1 and $R^{5i}$ is $CF_3$.
In some embodiments of Formula IIc, w is 2 and both $R^{5i}$ are $CF_3$.
In some embodiments of Formula IIc, w is 1 and $R^{5i}$ is OMe.
In some embodiments of Formula IIc, w is 2 and both $R^{5i}$ are OMe.
In some embodiments of Formula IIc, w is 2 and one $R^{5i}$ is F and the other $R^{5i}$ is OMe.
In some embodiments of Formula IIc, w is 2 and one $R^{5i}$ is F and the other $R^{5i}$ is $CF_3$.
In some embodiments of Formula IIc, w is 2 and one $R^{5i}$ is F and the other $R^{5i}$ is OMe.
In some embodiments of Formula IIc, w is 1 and $R^{5i}$ is CN.
In some embodiments of Formula IIc, w is 2 and both $R^{5i}$ are CN.
In some embodiments of Formula IIc, w is 2 and one $R^{5i}$ is F and the other $R^{5i}$ is CN.
In some embodiments of Formula IIc, at least one $R^{5f}$, $R^{5g}$, $R^{5h}$, or $R^{5i}$ is —$CH_2OH$.
In some embodiments of Formula IIc, at least one $R^{5f}$, $R^{5g}$, $R^{5h}$, or $R^{5i}$ is —$CH_2N(R^{3b})_2$.
In some embodiments of Formula IIc, at least one $R^{5f}$, $R^{5g}$, $R^{5h}$, or $R^{5i}$ is —$CH_2NH_2$.
In some embodiments of Formula IIc, at least one $R^{5f}$, $R^{5g}$, $R^{5h}$, or $R^{5i}$ is —$CH_2NHMe$.
In some embodiments of Formula IIc, at least one $R^{5f}$, $R^{5g}$, $R^{5h}$, or $R^{5i}$ is —$CH_2NMe_2$.
In some embodiments of Formula IIc, at least one $R^{5f}$, $R^{5g}$, $R^{5h}$, or $R^{5i}$ is —$CH_2NHEt$.
In some embodiments of Formula IIc, at least one $R^{5f}$, $R^{5g}$, $R^{5h}$, or $R^{5i}$ is —$CH_2N(Me)(Et)$.
In some embodiments of Formula IIc, at least one $R^{5f}$, $R^{5g}$, $R^{5h}$, or $R^{5i}$ is —$CH_2NEt_2$.

Some embodiments of Formula II include compounds of Formula (IId):

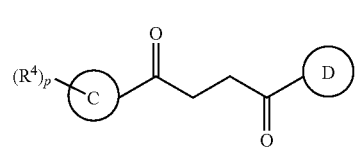

or salts, dermatologically acceptable salts, or prodrugs thereof.

In some embodiments of Formula IId, Ring C is

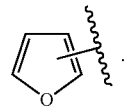

In some embodiments of Formula IId, Ring D is selected from the group consisting of

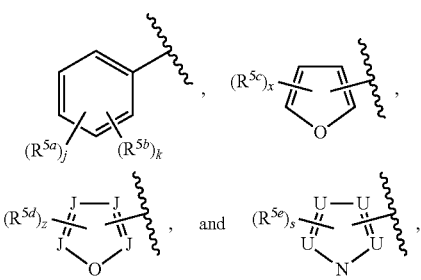

wherein a carbon atom on the ring is attached to the carbonyl carbon.

In some embodiments of Formula IId, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, and CN.

In some embodiments of Formula IId, each $R^4$ is a substituent attached to Ring C and is independently selected at each occurrence from the group consisting of unsubstituted —$C_{1-6}$ alkyl, —$C_{1-3}$ haloalkyl, halide, —$OR^6$, and CN.

In some embodiments of Formula IId, $R^{5a}$ is a substituent attached to the ring and is selected from the group consisting of unsubstituted —$C_{2-6}$ alkyl, —$CH_2OH$, —$CH_2N(R^{6b})_2$, —$C_{1-3}$ haloalkyl, halide, —$OR^{6a}$, and CN; j is 1

In some embodiments of Formula IId, $R^{5b}$ is a substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^{6a}$, and CN; k is 1 to 4.

In some embodiments of Formula IId, $R^{5b}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^{6a}$, and CN; k is 0 to 4.

In some embodiments of Formula IId, $R^{5c}$ is a substituent attached to the ring and is independently selected at each occurrence from the group consisting of unsubstituted —$C_{2-5}$ alkyl, —$CH_2OH$, —$CH_2N(R^{6b})_2$, —$C_{1-3}$ haloalkyl, halide, —$OR^6$, and CN; x is 1 to 3.

In some embodiments of Formula IId, $R^{5d}$ is a substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN; z is 1 or 2.

In some embodiments of Formula IId, $R^{5d}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN; z is 0 to 2.

In some embodiments of Formula IId, $R^{5e}$ is a substituent attached to the ring and is independently selected at each occurrence from the group consisting of H, H, unsubstituted —$C_{1-6}$ alkyl, —$CH_2OH$, —$CH_2N(R^{6b})_2$, —$C_{1-3}$ haloalkyl, halide, —$OR^6$, and CN; s is 1 to 4.

In some embodiments of Formula IId, $R^{5e}$ is a substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN; s is 0 to 4.

In some embodiments of Formula IId, each $R^6$ is independently selected from the group consisting of H, unsubstituted —$C_{1-6}$ alkyl, and —$C_{1-3}$ haloalkyl.

In some embodiments of Formula IId, each $R^{6a}$ is independently selected from the group consisting of unsubstituted —$C_{2-6}$ alkyl and —$C_{1-3}$ haloalkyl.

In some embodiments of Formula IId, each $R^{6b}$ is independently selected from the group consisting of H and unsubstituted —$C_{1-3}$ alkyl.

In some embodiments of Formula IId, each J is independently N or C.

In some embodiments of Formula IId, at least one J must be N and at least one J must be C.

In some embodiments of Formula IId, each U is independently N or C.

In some embodiments of Formula IId, at least one U must be C.

In some embodiments of Formula IId, p is 1 to 3.
In some embodiments of Formula IId, p is 0 to 3.
In some embodiments of Formula IId, Ring D is selected from the group consisting of

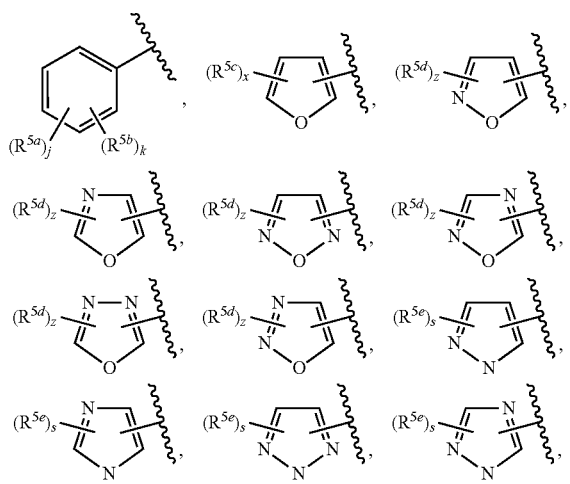

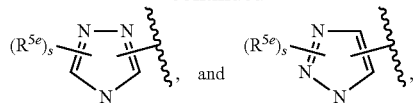

wherein a carbon atom on the ring is attached to the carbonyl carbon.

In some embodiments of Formula IId, k is 0.

Some embodiments of Formula II include compounds of Formula (IIe):

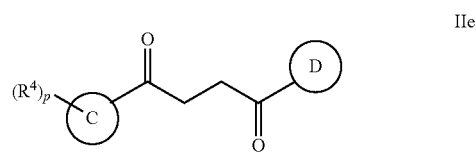

or salts, dermatologically acceptable salts, or prodrugs thereof.

In some embodiments of Formula IIe, Ring C is

wherein a carbon atom on the ring is attached to the carbonyl carbon.

In some embodiments of Formula IIe, Ring D is selected from the group consisting of

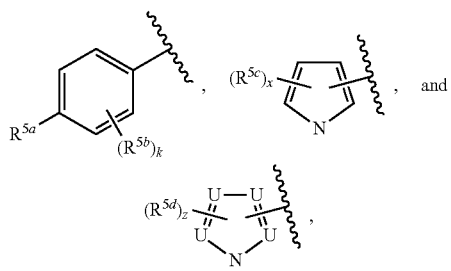

wherein a carbon atom on the ring is attached to the carbonyl carbon.

In some embodiments of Formula IIe, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, and CN.

In some embodiments of Formula IIe, each $R^4$ is a substituent attached to Ring C and is independently selected at each occurrence from the group consisting of unsubstituted —$C_{1-6}$ alkyl, —$C_{1-3}$ haloalkyl, halide, —$OR^6$, and CN.

In some embodiments of Formula IIe, $R^{5a}$ is one substituent attached to the para position of phenyl and is selected from the group consisting of H, unsubstituted —$C_{1-6}$ alkyl, —$CH_2OH$, —$CH_2N(R^{6b})_2$, —$C_{1-3}$ haloalkyl, F, Br, I, —$OR^6$, and CN.

In some embodiments of Formula IIe, $R^{5b}$ is a substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN; k is 1 to 4.

In some embodiments of Formula IIe, $R^{5b}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN; k is 0 to 4.

In some embodiments of Formula IIe, $R^{5c}$ is a substituent attached to the ring and is independently selected at each occurrence from the group consisting of unsubstituted —$C_{2-5}$ alkyl, —$CH_2OH$, —$CH_2N(R^{6b})_2$, —$C_{1-3}$ haloalkyl, halide, —$OR^6$, and CN; x is 1 to 4.

In some embodiments of Formula IIe, $R^{5d}$ is a substituent attached to the ring and is independently selected at each occurrence from the group consisting of H, unsubstituted —$C_{2-6}$ alkyl, —$CH_2OH$, —$CH_2N(R^{6b})_2$, —$C_{1-3}$ haloalkyl, halide, —$OR^{6a}$, and CN; z is 1 or 2.

In some embodiments of Formula Ie, $R^{5d}$ is a substituent attached to the ring and is independently selected at each occurrence from the group consisting of unsubstituted —$C_{2-6}$ alkyl, —$CH_2OH$, —$CH_2N(R^{6b})_2$, —$C_{1-3}$ haloalkyl, halide, —$OR^{6a}$, and CN; z is 0 to 2.

In some embodiments of Formula IIe, each $R^6$ is independently selected from the group consisting of H, unsubstituted —$C_{1-6}$ alkyl, and —$C_{1-3}$ haloalkyl.

In some embodiments of Formula IIe, each $R^{6a}$ is independently selected from the group consisting of unsubstituted —$C_{1-6}$ alkyl and —$C_{1-3}$ haloalkyl.

In some embodiments of Formula IIe, each $R^{6b}$ is independently selected from the group consisting of H and unsubstituted —$C_{1-3}$ alkyl.

In some embodiments of Formula IIe, each A is independently N or C.

In some embodiments of Formula IIe, at least one A must be C.

In some embodiments of Formula IIe, each U is independently N or C.

In some embodiments of Formula IIe, at least one U must be N and at least one U must be C.

In some embodiments of Formula IIe, p is 0 to 4.

In some embodiments of Formula IIe, p is 1 to 4.

In some embodiments of Formula IIe, Ring C is selected from the group consisting of

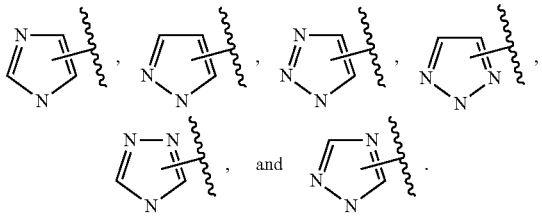

In some embodiments of Formula Ie, Ring D is selected from the group consisting of

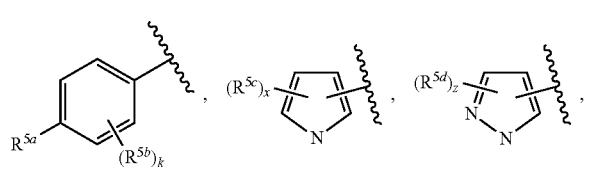

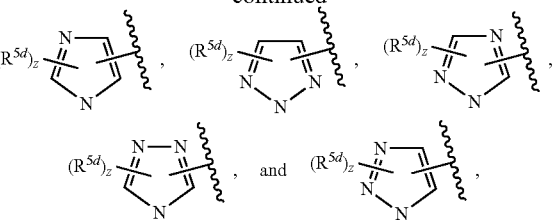

wherein a carbon atom on the ring is attached to the carbonyl carbon.

In some embodiments of Formula Ie, $R^{5a}$ is a OMe.
In some embodiments of Formula IIe, $R^{5a}$ is a halide.
In some embodiments of Formula IIe, $R^{5a}$ is a F.
In some embodiments of Formula IIe, $R^{5a}$ is a Me.
In some embodiments of Formula IIe, $R^{5a}$ is a OH.
In some embodiments of Formula IIe, $R^{5a}$ is a $CF_3$.
In some embodiments of Formula IIe, $R^{5a}$ is a CN.
In some embodiments of Formula IIe, $R^{5a}$ is a —$C_{1-2}$ alkyl.
In some embodiments of Formula Ie, $R^{5a}$ is a —$C_{1-3}$ alkyl.
In some embodiments of Formula IIe, $R^{5a}$ is a —$C_{1-4}$ alkyl.
In some embodiments of Formula IIe, $R^{5a}$ is a —$C_{1-5}$ alkyl.
In some embodiments of Formula IIe, $R^{5a}$ is a —$C_{1-6}$ alkyl.
In some embodiments of Formula IIe, $R^{5a}$ is a —$C_{2-6}$ alkyl.
In some embodiments of Formula IIe, $R^{5a}$ is a —$C_{3-6}$ alkyl.
In some embodiments of Formula IIe, $R^{5a}$ is a —$C_{4-6}$ alkyl.
In some embodiments of Formula IIe, $R^{5a}$ is a —$C_{2-5}$ alkyl.
In some embodiments of Formula IIe, $R^{5a}$ is a —$C_{3-5}$ alkyl.

In some embodiments of Formula IId and IIe, z is 0.

Some embodiments of Formula II include compounds of Formula (IIf):

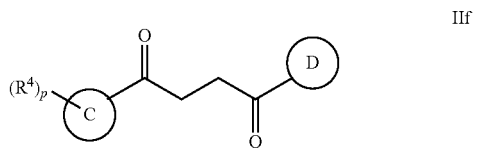

or salts, dermatologically acceptable salts, or prodrugs thereof.

In some embodiments of Formula IIf, Ring C is

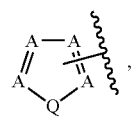

wherein a carbon atom on the ring is attached to the carbonyl carbon.

In some embodiments of Formula IIf, Ring D is selected from the group consisting of

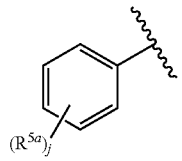

and a 5-membered heteroaryl($R^{5b}$)$_k$, wherein a carbon atom on the ring is attached to the carbonyl carbon.

In some embodiments of Formula IIf, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, and CN.

In some embodiments of Formula IIf, each $R^4$ is a substituent attached to Ring C and is independently selected at each occurrence from the group consisting of unsubstituted —$C_{1-6}$ alkyl, —$C_{1-3}$ haloalkyl, halide, —$OR^6$, and CN.

In some embodiments of Formula IIf, $R^{5a}$ is a substituent attached to phenyl and is selected from the group consisting of H, unsubstituted —$C_{1-6}$ alkyl, —$CH_2OH$, —$CH_2N(R^{6b})_2$, —$C_{1-3}$ haloalkyl, halide, —$OR^6a$, and CN; j is 1 to 5

In some embodiments of Formula IIf, $R^{5a}$ is a substituent attached to phenyl and is selected from the group consisting of unsubstituted —$C_{1-6}$ alkyl, —$CH_2OH$, —$CH_2N(R^{6b})_2$, —$C_{1-3}$ haloalkyl, halide, —$OR^{6a}$, and CN; j is 0 to 5

In some embodiments of Formula IIf, $R^{5b}$ is a substituent attached to the ring and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, and CN; k is 1 to 4.

In some embodiments of Formula IIf, $R^{5b}$ is a substituent attached to the ring and is independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, and CN; k is 0 to 4.

In some embodiments of Formula IIf, each $R^6$ is independently selected from the group consisting of H, unsubstituted —$C_{1-6}$ alkyl, and —$C_{1-3}$ haloalkyl.

In some embodiments of Formula IIf, each $R^{6a}$ is independently selected from the group consisting of unsubstituted —$C_{2-6}$ alkyl and —$C_{1-3}$ haloalkyl.

In some embodiments of Formula IIf, each $R^{6b}$ is independently selected from the group consisting of H and unsubstituted —$C_{1-3}$ alkyl.

In some embodiments of Formula IIf, each A is independently N or C.

In some embodiments of Formula IIf, at least one A must be N and at least one A must be C.

In some embodiments of Formula IIf, Q is S or O.

In some embodiments of Formula IIf, p is 0 to 4.

In some embodiments of Formula IIf, p is 1 to 4.

In some embodiments of Formula IIf, Ring C is selected from the group consisting of

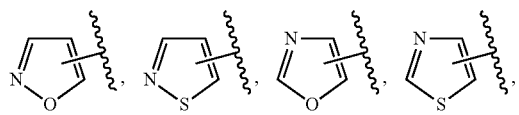

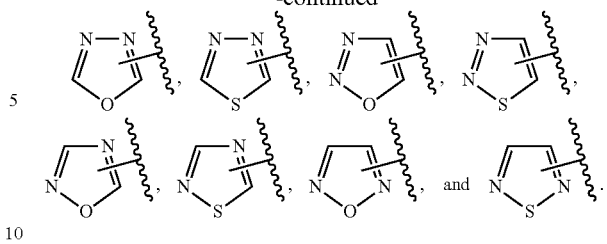

In some embodiments of Formula IIf, Ring D is selected from the group consisting of

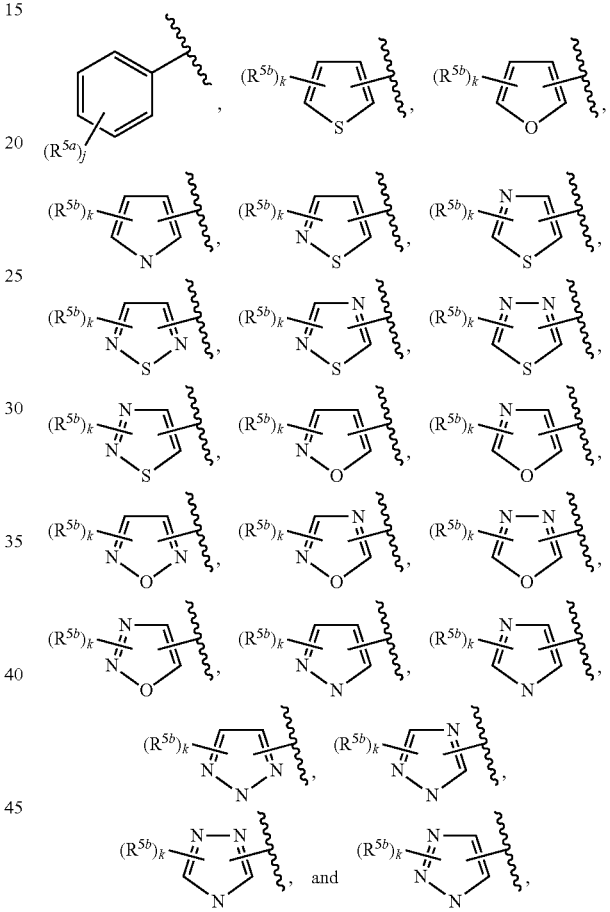

wherein a carbon atom on the ring is attached to the carbonyl carbon.

In some embodiments of Formula IIe and IIf, k is 0.

In some embodiments of Formula II, IIa, IIc, IId, IIe, and IIf, each $R^4$ is independently selected from the group consisting of F, Cl, Me, OMe, OH, $CF_3$ and CN; and p is 0 to 2.

In some embodiments of Formula II, IIa, IIb, IIc, IId, IIe, and IIf, —$C_{1-3}$ haloalkyl is —$CF_3$.

In some embodiments of Formula II, IIa, IIb, IIc, IId, IIe, and IIf, p is 0.

In some embodiments of Formula II, IIa, IIb, IIc, IId, IIe, and IIf, at least one $R^4$ is a halide.

In some embodiments of Formula II, IIa, IIb, IIc, IId, IIe, and IIf, at least one $R^4$ is F.

In some embodiments of Formula II, IIa, IIb, IIc, IId, IIe, and IIf, at least one $R^4$ is Cl.

In some embodiments of Formula II, IIa, IIb, IIc, IId, IIe, and IIf, at least one $R^4$ is Me.

In some embodiments of Formula II, IIa, IIc, IId, IIe, and IIf, at least one $R^4$ is OH.

In some embodiments of Formula II, IIa, IIb, IIc, IId, IIe, and IIf, at least one $R^4$ is OMe.

In some embodiments of Formula II, IIa, IIb, IIc, IId, IIe, and IIf, at least one $R^4$ is $CF_3$.

In some embodiments of Formula II, IIa, IIb, IIc, IId, IIe, and IIf, at least one $R^4$ is CN.

In some embodiments of Formula II, IIa, IIb, IIc, IId, IIe, and IIf, p is 0-3.

In some embodiments of Formula II, IIa, IIb, IIc, IId, IIe, and IIf, p is 0-2.

In some embodiments of Formula II, IIa, IIb, IIc, IId, IIe, and IIf, p is 2.

In some embodiments of Formula II, IIa, IIb, IIc, IId, IIe, and IIf, p is 1.

In some embodiments of Formula II, IIa, IIb, IIc, IId, IIe, and IIf, $R^4$ is F; and p is 1.

In some embodiments of Formula II, IIa, IIb, IIc, IId, IIe, and IIf, $R^4$ is F; and p is 2.

In some embodiments of Formula II, IIa, IIc, IId, IIe, and IIf, $R^4$ is OH; and p is 1.

In some embodiments of Formula II, IIa, IIb, IIc, IId, IIe, and IIf, $R^4$ is OMe; and p is 1-2.

In some embodiments of Formula II, IIa, IIb, IIc, IId, IIe, and IIf, at least one $R^4$ is —$C_{1-2}$ alkyl.

In some embodiments of Formula II, IIa, IIb, IIc, IId, IIe, and IIf, at least one $R^4$ is —$C_{1-3}$ alkyl.

In some embodiments of Formula II, IIa, IIb, IIc, IId, IIe, and IIf, at least one $R^4$ is —$C_{1-4}$ alkyl.

In some embodiments of Formula II, IIa, IIb, IIc, IId, IIe, and IIf, at least one $R^4$ is —$C_{1-5}$ alkyl.

In some embodiments of Formula II, IIa, IIb, IIc, IId, IIe, and IIf, at least one $R^4$ is —$C_{1-6}$ alkyl.

In some embodiments of Formula II, IIa, IIb, IIc, IId, IIe, and IIf, at least one $R^4$ is —$C_{2-6}$ alkyl.

In some embodiments of Formula II, IIa, IIb, IIc, IId, IIe, and IIf, at least one $R^4$ is —$C_{3-6}$ alkyl.

In some embodiments of Formula II, IIa, IIb, IIc, IId, IIe, and IIf, at least one $R^4$ is —$C_{4-6}$ alkyl.

In some embodiments of Formula II, IIa, IIb, IIc, IId, IIe, and IIf, at least one $R^4$ is —$C_{2-5}$ alkyl.

In some embodiments of Formula II, IIa, IIb, IIc, IId, IIe, and IIf, at least one $R^4$ is —$C_{3-5}$ alkyl.

In some embodiments of Formula IIa, IIc, IId, IIe, and IIf, at least one $R^{5a}$ or $R^{5b}$ is —$CH_2OH$.

In some embodiments of Formula IIa, IIc, IId, IIe, and IIf, at least one $R^{5a}$ or $R^{5b}$ is —$CH_2N(R^{3b})_2$.

In some embodiments of Formula IIa, IIc, IId, IIe, and IIf, at least one $R^{5a}$ or $R^{5b}$ is —$CH_2NH_2$.

In some embodiments of Formula IIa, IIc, IId, IIe, and IIf, at least one $R^{5a}$ or $R^{5b}$ is —$CH_2NHMe$.

In some embodiments of Formula IIa, IIc, IId, IIe, and IIf, at least one $R^{5a}$ or $R^{5b}$ is —$CH_2NMe_2$.

In some embodiments of Formula IIa, IIc, IId, IIe, and IIf, at least one $R^{5a}$ or $R^{5b}$ is —$CH_2NHEt$.

In some embodiments of Formula IIa, IIc, IId, IIe, and IIf, at least one $R^{5a}$ or $R^{5b}$ is —$CH_2N(Me)(Et)$.

In some embodiments of Formula IIa, IIc, IId, IIe, and IIf, at least one $R^{5a}$ or $R^{5b}$ is —$CH_2NEt_2$.

In some embodiments of Formula IIa, IIc, IId, and IIe, at least one $R^{5c}$ or $R^{5d}$ is —$CH_2OH$.

In some embodiments of Formula IIa, IIc, IId, and IIe, at least one $R^{5c}$ or $R^{5d}$ is —$CH_2N(R^{3b})_2$.

In some embodiments of Formula IIa, IIc, IId, and IIe, at least one $R^{5c}$ or $R^{5d}$ is —$CH_2NH_2$.

In some embodiments of Formula IIa, IIc, IId, and IIe, at least one $R^{5c}$ or $R^{5d}$ is —$CH_2NHMe$.

In some embodiments of Formula IIa, IIc, IId, and IIe, at least one $R^{5c}$ or $R^{5d}$ is —$CH_2NMe_2$.

In some embodiments of Formula IIa, IIc, IId, and IIe, at least one $R^{5c}$ or $R^{5d}$ is —$CH_2NHEt$.

In some embodiments of Formula IIa, IIc, IId, and IIe, at least one $R^{5c}$ or $R^{5d}$ is —$CH_2N(Me)(Et)$.

In some embodiments of Formula IIa, IIc, IId, and IIe, at least one $R^{5c}$ or $R^{5d}$ is —$CH_2NEt_2$.

In some embodiments of Formula IIa, IIc, and IId, at least one $R^{5e}$ is —$CH_2OH$.

In some embodiments of Formula IIa, IIc, and IId, at least one $R^{5e}$ is —$CH_2N(R^{3b})_2$.

In some embodiments of Formula IIa, IIc, and IId, at least one $R^{5e}$ is —$CH_2NH_2$.

In some embodiments of Formula IIa, IIc, and IId, at least one $R^{5e}$ is —$CH_2NHMe$.

In some embodiments of Formula IIa, IIc, and IId, at least one $R^{5e}$ is —$CH_2NMe_2$.

In some embodiments of Formula IIa, IIc, and IId, at least one $R^{5e}$ is —$CH_2NHEt$.

In some embodiments of Formula IIa, IIc, and IId, at least one $R^e$ is —$CH_2N(Me)(Et)$.

In some embodiments of Formula IIa, IIc, and IId, at least one $R^{5e}$ is —$CH_2NEt_2$.

In some embodiments of Formula II, IIa, IIb, IIc, IId, IIe, and IIf, $R^6$ is —$C_{1-2}$ alkyl.

In some embodiments of Formula II, IIa, IIb, IIc, IId, IIe, and IIf, $R^6$ is —$C_{1-3}$ alkyl.

In some embodiments of Formula II, IIa, IIb, IIc, IId, IIe, and IIf, $R^6$ is —$C_{1-4}$ alkyl.

In some embodiments of Formula II, IIa, IIb, IIc, IId, IIe, and IIf, $R^6$ is —$C_{1-5}$ alkyl.

In some embodiments of Formula II, IIa, IIb, IIc, IId, IIe, and IIf, $R^6$ is —$C_{1-6}$ alkyl.

In some embodiments of Formula II, IIa, IIb, IIc, IId, IIe, and IIf, $R^6$ is —$C_{2-6}$ alkyl.

In some embodiments of Formula II, IIa, IIb, IIc, IId, IIe, and IIf, $R^6$ is —$C_{3-6}$ alkyl.

In some embodiments of Formula II, IIa, IIb, IIc, IId, IIe, and IIf, $R^6$ is —$C_{4-6}$ alkyl.

In some embodiments of Formula II, IIa, IIb, IIc, IId, IIe, and IIf, $R^6$ is —$C_{2-5}$ alkyl.

In some embodiments of Formula II, IIa, IIb, IIc, IId, IIe, and IIf, $R^6$ is —$C_{3-5}$ alkyl.

In some embodiments of Formula IIa, IId, and IIf, at least one $R^{5a}$ is halide.

In some embodiments of Formula IId, IIe, and IIf, at least one $R^{5b}$ is halide.

In some embodiments of Formula IIa, IId, and IIe, at least one $R^{5c}$ is halide.

In some embodiments of Formula IIa, IIc, IId, and IIe, at least one $R^{5d}$ is halide.

In some embodiments of Formula IIa and IId, at least one $R^{5e}$ is halide.

In some embodiments of Formula IIa, IId, and IIf, at least one $R^{5a}$ is F.

In some embodiments of Formula IIa, IId, IIe, and IIf, at least one $R^{5b}$ is F.

In some embodiments of Formula IIa, IId, and IIe, at least one $R^{5c}$ is F.

In some embodiments of Formula IIa, IIc, IId, and IIe, at least one $R^{5d}$ is F.

In some embodiments of Formula IIa, IIc, and IId, at least one $R^{5e}$ is F.

In some embodiments of Formula IIa and IId, at least one $R^{5a}$ or $R^{5e}$ is Cl.

In some embodiments of Formula IId, IIe, and IIf, at least one $R^{5b}$ is Cl.

In some embodiments of Formula IIa, IId, and IIe, at least one $R^{5c}$ is Cl.

In some embodiments of Formula IIa, IIc, IId, IIe, and IIf, at least one $R^{5d}$ is Cl.

In some embodiments of Formula IIa and IIf, at least one $R^{5a}$ is Me.

In some embodiments of Formula IIa, IId, IIe, and IIf, at least one $R^{5b}$ is Me.

In some embodiments of Formula IIa, at least one $R^{5c}$ is Me.

In some embodiments of Formula IIa, IIc, and IIf, at least one $R^{5d}$ is Me.

In some embodiments of Formula IIa and IId, at least one $R^{5e}$ is Me.

In some embodiments of Formula IIa, at least one $R^{5a}$ is OH.

In some embodiments of Formula IIa, IIe, and IIf, at least one $R^{5b}$ is OH.

In some embodiments of Formula IIa, IId, and IIe, at least one $R^{5c}$ is OH.

In some embodiments of Formula IIa and IId, at least one $R^{5d}$ is OH.

In some embodiments of Formula IIa, IIc, and IId, at least one $R^{5e}$ is OH.

In some embodiments of Formula IIe and IIf, at least one $R^{5b}$ is OMe.

In some embodiments of Formula IIa, IId, and IIe, at least one $R^{5c}$ or $R^{5d}$ is OMe.

In some embodiments of Formula IIa, IIc, and IId, at least one $R^{5e}$ is OMe.

In some embodiments of Formula IIa, IId, and IIf, at least one $R^{5a}$ is $CF_3$.

In some embodiments of Formula IIa, IId, IIe, and IIf, at least one $R^{5b}$ is $CF_3$.

In some embodiments of Formula IIa, IId, and IIe, at least one $R^{5c}$ is $CF_3$.

In some embodiments of Formula IIa, IIc, IId, and IIe, at least one $R^{5d}$ is $CF_3$.

In some embodiments of Formula IIa, IIc, and IId, at least one $R^{5e}$ is $CF_3$.

In some embodiments of Formula IIa, IId, and IIf, at least one $R^{5a}$ is CN.

In some embodiments of Formula IIa, IId, IIe, and IIf, at least one $R^{5b}$ is CN.

In some embodiments of Formula IIa, IId, and IIe, at least one $R^{5c}$ is CN.

In some embodiments of Formula IIa, IIc, IId, and IIe, at least one $R^{5d}$ is CN.

In some embodiments of Formula IIa, IIc, and IId, at least one $R^{5e}$ is CN.

In some embodiments of Formula IIa and IIf, at least one $R^{5a}$ is $—C_{1-2}$ alkyl.

In some embodiments of Formula IIa and IIf, at least one $R^{5a}$ is $—C_{1-3}$ alkyl.

In some embodiments of Formula IIa and IIf, at least one $R^{5a}$ is $—C_{1-4}$ alkyl.

In some embodiments of Formula IIa and IIf, at least one $R^{5a}$ is $—C_{1-5}$ alkyl.

In some embodiments of Formula IIa and IIf, at least one $R^{5a}$ is $—C_{1-6}$ alkyl.

In some embodiments of Formula IIa, IId, IIe, and IIf, at least one $R^{5a}$, $R^{5b}$, $R^{5c}$, $R^{5d}$, or $R^{5e}$ is $—C_{2-6}$ alkyl.

In some embodiments of Formula IIa, IId, IIe, and IIf, at least one $R^{5a}$, $R^{5b}$, $R^{5c}$, $R^{5d}$, or $R^{5e}$ is $—C_{3-6}$ alkyl.

In some embodiments of Formula IIa, IId, IIe, and IIf, at least one $R^{5a}R^{5b}$, $R^{5c}$, $R^{5d}$, or $R^{5e}$ is $—C_{4-6}$ alkyl.

In some embodiments of Formula IIa, IId, IIe, and IIf, at least one $R^{5a}$, $R^{5b}$, $R^{5c}$, $R^{5d}$, or $R^{5e}$ is $—C_{2-5}$ alkyl.

In some embodiments of Formula IIa, IId, IIe, and IIf, at least one $R^{5a}$, $R^{5b}$, $R^{5c}$, $R^{5d}$, or $R^{5e}$ is $—C_{3-5}$ alkyl.

In some embodiments of Formula IIa, IId, IIe, and IIf, at least one $R^{5b}$ is $—C_{1-3}$ alkyl.

In some embodiments of Formula IIa, IId, IIe, and IIf, at least one $R^{5b}$ is $—C_{1-4}$ alkyl.

In some embodiments of Formula IIa, IId, IIe, and IIf, at least one $R^{5b}$ is $—C_{1-5}$ alkyl.

In some embodiments of Formula IIa, IId, IIe, and IIf, at least one $R^{5b}$ is $—C_{1-6}$ alkyl.

In some embodiments of Formula IIa, at least one $R^{5c}$ is $—C_{1-3}$ alkyl.

In some embodiments of Formula IIa, at least one $R^{5c}$ is $—C_{1-4}$ alkyl.

In some embodiments of Formula IIa, at least one $R^{5c}$ is $—C_{1-5}$ alkyl.

In some embodiments of Formula IIa, at least one $R^{5c}$ is $—C_{1-6}$ alkyl.

In some embodiments of Formula IIa, IIc, and IId, at least one $R^{5d}$ is $—C_{1-3}$ alkyl.

In some embodiments of Formula IIa, IIc, and IId, at least one $R^{5d}$ is $—C_{1-4}$ alkyl.

In some embodiments of Formula IIa, IIc, and IId, at least one $R^{5d}$ is $—C_{1-5}$ alkyl.

In some embodiments of Formula IIa, IIc, and IId, at least one $R^{5d}$ is $—C_{1-6}$ alkyl.

In some embodiments of Formula IIa and IId, at least one $R^{5e}$ is $—C_{1-3}$ alkyl.

In some embodiments of Formula IIa and IId, at least one $R^{5e}$ is $—C_{1-4}$ alkyl.

In some embodiments of Formula IIa and IId, at least one $R^{5e}$ is $—C_{1-5}$ alkyl.

In some embodiments of Formula IIa and IId, at least one $R^{5e}$ is $—C_{1-6}$ alkyl.

In some embodiments of Formula IIa, IId, and IIf, j is 1 and $R^{5a}$ is F.

In some embodiments of Formula IIa, IId, and IIf, j is 2 and both $R^{5a}$ are F.

In some embodiments of Formula IIa and IIf, j is 1 and $R^{5a}$ is Me.

In some embodiments of Formula IIa and IIf, j is 2 and both $R^{5a}$ are Me.

In some embodiments of Formula IIa, IId, and IIf, j is 1 and $R^{5a}$ is $CF_3$.

In some embodiments of Formula IIa, IId, and IIf, j is 2 and both $R^{5a}$ are $CF_3$.

In some embodiments of Formula IIa and IIf, j is 2 and one $R^{5a}$ is F and the other $R^{5a}$ is Me.

In some embodiments of Formula IIa, IId, and IIf, j is 2 and one $R^{5a}$ is F and the other $R^{5a}$ is $CF_3$.

In some embodiments of Formula IIa, IId, and IIf, j is 1 and $R^{5a}$ is CN.

In some embodiments of Formula IIa, IId, and IIf, j is 2 and both $R^{5a}$ are CN.

In some embodiments of Formula IIa, IId, and IIf, j is 2 and one $R^{5a}$ is F and the other $R^{5a}$ is CN.

In some embodiments of Formula IIa, IId, IIe, and IIf, k is 1 and $R^{5b}$ is F.

In some embodiments of Formula IIa, IId, IIe, and IIf, k is 2 and both $R^{5b}$ are F.
In some embodiments of Formula IIa, IId, IIe, and IIf, k is 1 and $R^{5b}$ is Me.
In some embodiments of Formula IIa, IId, IIe, and IIf, k is 2 and both $R^{5b}$ are Me.
In some embodiments of Formula IIa, IId, IIe, and IIf, k is 1 and $R^{5b}$ is $CF_3$.
In some embodiments of Formula IIa, IId, IIe, and IIf, k is 2 and both $R^{5b}$ are $CF_3$.
In some embodiments of Formula IIa, IId, IIe, and IIf, k is 2 and one $R^{5b}$ is F and the other $R^{5b}$ is Me.
In some embodiments of Formula IIa, IId, IIe, and IIf, k is 2 and one $R^{5b}$ is F and the other $R^{5b}$ is $CF_3$.
In some embodiments of Formula IIa, IId, IIe, and IIf, k is 1 and $R^{5b}$ is CN.
In some embodiments of Formula IIa, IId, IIe, and IIf, k is 2 and both $R^{5b}$ are CN.
In some embodiments of Formula IIa, IId, IIe, and IIf, k is 2 and one $R^{5b}$ is F and the other $R^{5b}$ is CN.
In some embodiments of Formula IIa, IId, and IIe, x is 1 and $R^{5c}$ is F.
In some embodiments of Formula IIa, IId, and IIe, x is 2 and both $R^{5c}$ are F.
In some embodiments of Formula IIa, x is 1 and $R^{5c}$ is Me.
In some embodiments of Formula IIa, x is 2 and both $R^{5c}$ are Me.
In some embodiments of Formula IIa, IId, and IIe, x is 1 and $R^{5c}$ is $CF_3$.
In some embodiments of Formula IIa, IId, and IIe, x is 2 and both $R^{5c}$ are $CF_3$.
In some embodiments of Formula IIa, IId, and IIe, x is 1 and $R^{5c}$ is OMe.
In some embodiments of Formula IIa, IId, and IIe, x is 2 and both $R^{5c}$ are OMe.
In some embodiments of Formula IIa, x is 2 and one $R^{5c}$ is F and the other $R^{5c}$ is Me.
In some embodiments of Formula IIa, IId, and IIe, x is 2 and one $R^{5c}$ is F and the other $R^{5c}$ is $CF_3$.
In some embodiments of Formula IIa, IId, and IIe, x is 2 and one $R^{5c}$ is F and the other $R^{5c}$ is OMe.
In some embodiments of Formula IIa, IId, and IIe, x is 1 and $R^{5c}$ is CN.
In some embodiments of Formula IIa, IId, and IIe, x is 2 and both $R^{5c}$ are CN.
In some embodiments of Formula IIa, IId, and IIe, x is 2 and one $R^{5c}$ is F and the other $R^{5c}$ is CN.
In some embodiments of Formula IIa, IIc, IId, and IIe, z is 1 and $R^{5d}$ is F.
In some embodiments of Formula IIa, IIc, IId, and IIe, z is 2 and both $R^{5d}$ are F.
In some embodiments of Formula IIa, IIc, and IIf, z is 1 and $R^{5d}$ is Me.
In some embodiments of Formula IIa, IIc, and IIf, z is 2 and both $R^{5d}$ are Me.
In some embodiments of Formula IIa, IIc, IId, and IIe, z is 1 and $R^{5d}$ is $CF_3$.
In some embodiments of Formula IIa, IIc, IId, and IIe, z is 2 and both $R^{5d}$ are $CF_3$.
In some embodiments of Formula IIa, IId, and IIe, z is 1 and $R^{5d}$ is OMe.
In some embodiments of Formula IIa, IId, and IIe, z is 2 and both $R^{5d}$ are OMe.
In some embodiments of Formula IIa and IIc, z is 2 and one $R^{5d}$ is F and the other $R^{5d}$ is Me.
In some embodiments of Formula IIa, IIc, IId, and IIe, z is 2 and one $R^{5d}$ is F and the other $R^{5d}$ is $CF_3$.
In some embodiments of Formula IIa, IId, and IIe, z is 2 and one $R^{5d}$ is F and the other $R^{5d}$ is OMe.
In some embodiments of Formula IIa, IIc, IId, and IIe, z is 1 and $R^{5d}$ is CN.
In some embodiments of Formula IIa, IIc, IId, and IIe, z is 2 and both $R^{5d}$ are CN.
In some embodiments of Formula IIa, IIc, IId, and IIe, z is 2 and one $R^{5d}$ is F and the other $R^{5d}$ is CN.
In some embodiments of Formula IIa and IId, s is 0.
In some embodiments of Formula IIa and IId, s is 1.
In some embodiments of Formula IIa and IId, s is 2.
In some embodiments of Formula IIa, IIc, and IId, s is 1 and $R^{5e}$ is F.
In some embodiments of Formula IIa, IIc, and IId, s is 2 and both $R^{5e}$ are F.
In some embodiments of Formula IIa and IId, s is 1 and $R^{5e}$ is Me.
In some embodiments of Formula IIa and IId, s is 2 and both $R^{5e}$ are Me.
In some embodiments of Formula IIa, IIc, and IId, s is 1 and $R^{5e}$ is $CF_3$.
In some embodiments of Formula IIa, IIc, and IId, s is 2 and both $R^{5e}$ are $CF_3$.
In some embodiments of Formula IIa, IIc, and IId, s is 1 and $R^{5e}$ is OMe.
In some embodiments of Formula IIa, IIc, and IId, s is 2 and both $R^{5e}$ are OMe.
In some embodiments of Formula IIa and IId, s is 2 and one $R^{5e}$ is F and the other $R^{5e}$ is Me.
In some embodiments of Formula IIa, IIc, and IId, s is 2 and one $R^{5e}$ is F and the other $R^{5e}$ is $CF_3$.
In some embodiments of Formula IIa, IIc, and IId, s is 2 and one $R^{5e}$ is F and the other $R^{5e}$ is OMe.
In some embodiments of Formula IIa, IIc, and IId, s is 1 and $R^{5e}$ is CN.
In some embodiments of Formula IIa, IIc, and IId, s is 2 and both $R^{5e}$ are CN.
In some embodiments of Formula IIa, IIc, and IId, s is 2 and one $R^{5e}$ is F and the other $R^{5e}$ is CN.

Some embodiments of the present disclosure include compounds of Formula (III):

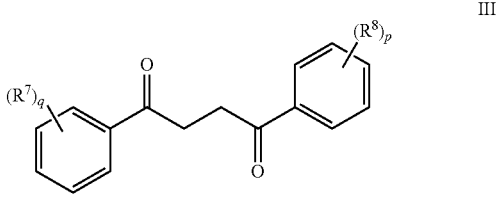

or salts, dermatologically acceptable salts or prodrugs thereof.

In some embodiments of Formula III, each $R^7$ is a substituent attached to the phenyl ring and is independently selected at each occurrence from the group consisting of unsubstituted —$C_{1-6}$ alkyl, —$CH_2OH$, —$CH_2N(R^{9a})_2$, —$C_{1-3}$ haloalkyl, halide, —$OR^9$, and CN.

In some embodiments of Formula III, each $R^8$ is a substituent attached to the phenyl ring and is independently selected at each occurrence from the group consisting of H, unsubstituted —$C_{1-6}$ alkyl, —$CH_2OH$, —$CH_2N(R^{9a})_2$, —$C_{1-3}$ haloalkyl, halide, —$OR^9$, and CN.

In some embodiments of Formula III, each $R^8$ is a substituent attached to the phenyl ring and is independently selected at each occurrence from the group consisting of unsubstituted —$C_{1-6}$ alkyl, —$CH_2OH$, —$CH_2N(R^{9a})_2$, —$C_{1-3}$ haloalkyl, halide, —$OR^9$, and CN.

In some embodiments of Formula III, each $R^9$ is independently selected from the group consisting of H, unsubstituted —$C_{1-6}$ alkyl, and —$C_{1-3}$ haloalkyl.

In some embodiments of Formula III, each $R^{9a}$ is independently selected from the group consisting of H and unsubstituted —$C_{1-3}$ alkyl.

In some embodiments of Formula III, each q is 1 to 5.

In some embodiments of Formula III, each $R^7$ is independently selected from the group consisting of F, Cl, Me, OMe, OH, $CF_3$ and CN.

In some embodiments of Formula III, at least one $R^7$ is halide.

In some embodiments of Formula III, at least one $R^7$ is F.
In some embodiments of Formula III, at least one $R^7$ is Cl.
In some embodiments of Formula III, at least one $R^7$ is Me.
In some embodiments of Formula III, at least one $R^7$ is OH.
In some embodiments of Formula III, at least one $R^7$ is OMe.
In some embodiments of Formula III, at least one $R^7$ is $CF_3$.
In some embodiments of Formula III, at least one $R^7$ is CN.
In some embodiments of Formula III, q is 1 to 4.
In some embodiments of Formula III, q is 1 to 3.
In some embodiments of Formula III, q is 1 or 2.
In some embodiments of Formula III, q is 2.
In some embodiments of Formula III, q is 1.
In some embodiments of Formula III, q is 1 and $R^7$ is F.
In some embodiments of Formula III, q is 2 and both $R^7$ are F.
In some embodiments of Formula III, q is 1 and $R^7$ is Me.
In some embodiments of Formula III, q is 2 and both $R^7$ are Me.
In some embodiments of Formula III, q is 1 and $R^7$ is $CF_3$.
In some embodiments of Formula III, q is 2 and both $R^7$ are $CF_3$.
In some embodiments of Formula III, q is 1 and $R^7$ is OMe.
In some embodiments of Formula III, q is 2 and both $R^7$ are OMe.
In some embodiments of Formula III, q is 2 and one $R^7$ is F and the other $R^7$ is Me.
In some embodiments of Formula III, q is 2 and one $R^7$ is F and the other $R^7$ is $CF_3$.
In some embodiments of Formula III, q is 2 and one $R^7$ is F and the other $R^7$ is OMe.
In some embodiments of Formula III, q is 1 and $R^7$ is CN.
In some embodiments of Formula III, q is 2 and both $R^7$ are CN.
In some embodiments of Formula III, q is 2 and one $R^7$ is F and the other $R^7$ is CN.
In some embodiments of Formula III, at least one $R^7$ is —$C_{1-2}$ alkyl.
In some embodiments of Formula III, at least one $R^7$ is —$C_{1-3}$ alkyl.
In some embodiments of Formula III, at least one $R^7$ is —$C_{1-4}$ alkyl.
In some embodiments of Formula III, at least one $R^7$ is —$C_{1-5}$ alkyl.

In some embodiments of Formula III, at least one $R^7$ is —$C_{1-6}$ alkyl.
In some embodiments of Formula III, at least one $R^7$ is —$C_{2-6}$ alkyl.
In some embodiments of Formula III, at least one $R^7$ is —$C_{3-6}$ alkyl.
In some embodiments of Formula III, at least one $R^7$ is —$C_{4-6}$ alkyl.
In some embodiments of Formula III, at least one $R^7$ is —$C_{2-5}$ alkyl.
In some embodiments of Formula III, at least one $R^7$ is —$C_{3-5}$ alkyl.

In some embodiments of Formula III, at least one $R^8$ is independently selected from the group consisting of H, F, Cl, Me, OMe, OH, $CF_3$ and CN.

In some embodiments of Formula III, at least one $R^8$ is halide.

In some embodiments of Formula III, at least one $R^8$ is F.
In some embodiments of Formula III, at least one $R^8$ is Cl.
In some embodiments of Formula III, at least one $R^8$ is Me.
In some embodiments of Formula III, at least one $R^8$ is OH.
In some embodiments of Formula III, at least one $R^8$ is OMe.
In some embodiments of Formula III, at least one $R^8$ is $CF_3$.
In some embodiments of Formula III, at least one $R^8$ is CN.
In some embodiments of Formula III, p is 0 to 4.
In some embodiments of Formula III, p is 0 to 3.
In some embodiments of Formula III, p is 0 to 2.
In some embodiments of Formula III, p is 1 to 4.
In some embodiments of Formula III, p is 1 to 3.
In some embodiments of Formula III, p is 1 or 2.
In some embodiments of Formula III, p is 2.
In some embodiments of Formula III, p is 1.
In some embodiments of Formula III, p is 0.
In some embodiments of Formula III, p is 1 and $R^8$ is F.
In some embodiments of Formula III, p is 2 and both $R^8$ are F.
In some embodiments of Formula III, p is 1 and $R^8$ is Me.
In some embodiments of Formula III, p is 2 and both $R^8$ are Me.
In some embodiments of Formula III, p is 1 and $R^8$ is $CF_3$.
In some embodiments of Formula III, p is 2 and both $R^8$ are $CF_3$.
In some embodiments of Formula III, p is 1 and $R^8$ is OMe.
In some embodiments of Formula III, p is 2 and both $R^8$ are OMe.
In some embodiments of Formula III, p is 2 and one $R^8$ is F and the other $R^8$ is Me.
In some embodiments of Formula III, p is 2 and one $R^8$ is F and the other $R^8$ is $CF_3$.
In some embodiments of Formula III, p is 2 and one $R^8$ is F and the other $R^8$ is OMe.
In some embodiments of Formula III, p is 1 and $R^8$ is CN.
In some embodiments of Formula III, p is 2 and both $R^8$ are CN.
In some embodiments of Formula III, p is 2 and one $R^8$ is F and the other $R^8$ is CN.
In some embodiments of Formula III, at least one $R^8$ is —$C_{1-2}$ alkyl.
In some embodiments of Formula III, at least one $R^8$ is —$C_{1-3}$ alkyl.

In some embodiments of Formula III, at least one $R^8$ is —$C_{1-4}$ alkyl.
In some embodiments of Formula III, at least one $R^8$ is —$C_{1-5}$ alkyl.
In some embodiments of Formula III, at least one $R^8$ is —$C_{1-6}$ alkyl.
In some embodiments of Formula III, at least one $R^8$ is —$C_{2-6}$ alkyl.
In some embodiments of Formula III, at least one $R^8$ is —$C_{3-6}$ alkyl.
In some embodiments of Formula III, at least one $R^8$ is —$C_{4-6}$ alkyl.
In some embodiments of Formula III, at least one $R^8$ is —$C_{2-5}$ alkyl.
In some embodiments of Formula III, at least one $R^8$ is —$C_{3-5}$ alkyl.
In some embodiments of Formula III, $R^9$ is —$C_{1-2}$ alkyl.
In some embodiments of Formula III, $R^9$ is —$C_{1-3}$ alkyl.
In some embodiments of Formula III, $R^9$ is —$C_{1-4}$ alkyl.
In some embodiments of Formula III, $R^9$ is —$C_{1-5}$ alkyl.
In some embodiments of Formula III, $R^9$ is —$C_{1-6}$ alkyl.
In some embodiments of Formula III, $R^9$ is —$C_{2-6}$ alkyl.
In some embodiments of Formula III, $R^9$ is —$C_{3-6}$ alkyl.
In some embodiments of Formula III, $R^9$ is —$C_{4-6}$ alkyl.
In some embodiments of Formula III, $R^9$ is —$C_{2-5}$ alkyl.
In some embodiments of Formula III, $R^9$ is —$C_{3-5}$ alkyl.
In some embodiments of Formula III, at least one $R^7$ and/or $R^8$ is —$CH_2OH$.
In some embodiments of Formula III, at least one $R^7$ and/or $R^8$ is —$CH_2N(R^{9a})_2$.
In some embodiments of Formula III, at least one $R^7$ and/or $R^8$ is —$CH_2NH_2$.
In some embodiments of Formula III, at least one $R^7$ and/or $R^8$ is —$CH_2NHMe$.
In some embodiments of Formula III, at least one $R^7$ and/or $R^8$ is —$CH_2NMe_2$.
In some embodiments of Formula III, at least one $R^7$ and/or $R^8$ is —$CH_2NHEt$.
In some embodiments of Formula III, at least one $R^7$ and/or $R^8$ is —$CH_2N(Me)(Et)$.
In some embodiments of Formula III, at least one $R^7$ and/or $R^8$ is —$CH_2NEt_2$.
Some embodiments of Formula III include compounds of Formula (IIIa):

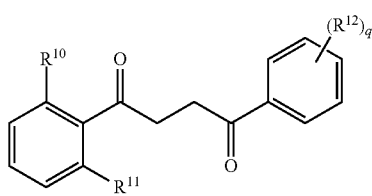

or salts, dermatologically acceptable salts, or prodrugs thereof.

In some embodiments of Formula IIIa, $R^{10}$ is one substituent attached to the ortho position of phenyl and is selected from the group consisting of H, unsubstituted —$C_{1-6}$ alkyl, —$C_{1-3}$ haloalkyl, halide, —$OR^{13}$, and CN.

In some embodiments of Formula IIIa, $R^{11}$ is one substituent attached to the ortho position of phenyl and is selected from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN.

In some embodiments of Formula IIIa, each $R^{12}$ is a substituent attached to the phenyl ring and is independently selected at each occurrence from the group consisting of H, unsubstituted —$C_{1-6}$ alkyl, —$CH_2OH$, —$CH_2N(R^{13b})_2$, —$C_{1-3}$ haloalkyl, halide, —$OR^{13}$, and CN.

In some embodiments of Formula IIIa, each $R^{12}$ is a substituent attached to the phenyl ring and is independently selected at each occurrence from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN.

In some embodiments of Formula IIIa, each $R^{13}$ is independently selected from the group consisting of unsubstituted —$C_{1-6}$ alkyl and —$C_{1-3}$ haloalkyl.

In some embodiments of Formula IIIa, each $R^{13b}$ is independently selected from the group consisting of H and unsubstituted —$C_{1-3}$ alkyl.

In some embodiments of Formula IIIa, q is 0 to 5.
In some embodiments of Formula IIIa, q is 1 to 5.
In some embodiments of Formula IIIa, at least one $R^{12}$ is selected from the group consisting of H, F, Cl, Me, OMe, $CF_3$, and CN.
In some embodiments of Formula IIIa, q is 0.
In some embodiments of Formula IIIa, at least one $R^{12}$ is a halide.
In some embodiments of Formula IIIa, at least one $R^{12}$ is F.
In some embodiments of Formula IIIa, at least one $R^{12}$ is Cl.
In some embodiments of Formula IIIa, at least one $R^{12}$ is Me.
In some embodiments of Formula IIIa, at least one $R^{12}$ is OH.
In some embodiments of Formula IIIa, at least one $R^{12}$ is OMe.
In some embodiments of Formula IIIa, at least one $R^{12}$ is $CF_3$.
In some embodiments of Formula IIIa, at least one $R^{12}$ is CN.
In some embodiments of Formula IIIa, q is 1 and $R^{12}$ is F.
In some embodiments of Formula IIIa, q is 2 and both $R^{12}$ are F.
In some embodiments of Formula IIIa, q is 1 and $R^{12}$ is Me.
In some embodiments of Formula IIIa, q is 2 and both $R^{12}$ are Me.
In some embodiments of Formula IIIa, q is 1 and $R^{12}$ is $CF_3$.
In some embodiments of Formula IIIa, q is 2 and both $R^{12}$ are $CF_3$.
In some embodiments of Formula IIIa, q is 1 and $R^{12}$ is OMe.
In some embodiments of Formula IIIa, q is 2 and both $R^{12}$ are OMe.
In some embodiments of Formula IIIa, q is 2 and one $R^{12}$ is F and the other $R^{12}$ is Me.
In some embodiments of Formula IIIa, q is 2 and one $R^{12}$ is F and the other $R^{12}$ is $CF_3$.
In some embodiments of Formula IIIa, q is 2 and one $R^{12}$ is F and the other $R^{12}$ is OMe.
In some embodiments of Formula IIIa, q is 1 and $R^{12}$ is CN.
In some embodiments of Formula IIIa, q is 2 and both $R^{12}$ are CN.
In some embodiments of Formula IIIa, q is 2 and one $R^{12}$ is F and the other $R^{12}$ is CN.

In some embodiments of Formula IIIa, q is 1 and $R^{12}$ is F or Cl.

In some embodiments of Formula IIIa, at least one $R^{12}$ is —$C_{1-2}$ alkyl.

In some embodiments of Formula IIIa, at least one $R^{12}$ is —$C_{1-3}$ alkyl.

In some embodiments of Formula IIIa, at least one $R^{12}$ is —$C_{1-4}$ alkyl.

In some embodiments of Formula IIIa, at least one $R^{12}$ is —$C_{1-5}$ alkyl.

In some embodiments of Formula IIIa, at least one $R^{12}$ is —$C_{1-6}$ alkyl.

In some embodiments of Formula IIIa, at least one $R^{12}$ is —$C_{2-6}$ alkyl.

In some embodiments of Formula IIIa, at least one $R^{12}$ is —$C_{3-6}$ alkyl.

In some embodiments of Formula IIIa, at least one $R^{12}$ is —$C_{4-6}$ alkyl.

In some embodiments of Formula IIIa, at least one $R^{12}$ is —$C_{2-5}$ alkyl.

In some embodiments of Formula IIIa, at least one $R^{12}$ is —$C_{3-5}$ alkyl.

Some embodiments of Formula III include compounds of Formula (IIIb):

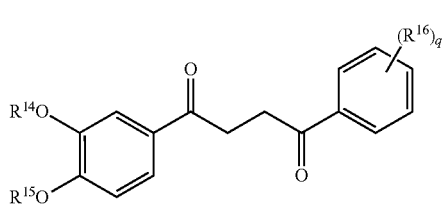

IIIb or salts, dermatologically acceptable salts, or prodrugs thereof.

In some embodiments of Formula IIIb, $R^{14}$ is selected from the group consisting of unsubstituted —$C_{1-6}$ alkyl and —$C_{1-3}$ haloalkyl.

In some embodiments of Formula IIIb, $R^{15}$ is selected from the group consisting of unsubstituted —$C_{1-6}$ alkyl and —$C_{1-3}$ haloalkyl.

In some embodiments of Formula IIIb, each $R^{16}$ is a substituent attached to the phenyl ring and is independently selected at each occurrence from the group consisting of unsubstituted —$C_{1-6}$ alkyl, —$CH_2OH$, —$CH_2N(R^{17b})_2$, —$C_{1-3}$ haloalkyl, halide, —$OR^{17}$, and CN.

In some embodiments of Formula IIIb, each $R^{17}$ is independently selected from the group consisting of unsubstituted —$C_{1-6}$ alkyl and —$C_{1-3}$ haloalkyl.

In some embodiments of Formula IIIb, each $R^{17b}$ is independently selected from the group consisting of H and unsubstituted —$C_{1-3}$ alkyl.

In some embodiments of Formula IIIb, each q is 0 to 5.

In some embodiments of Formula IIIb, at least one $R^{16}$ is selected from the group consisting of H, F, Cl, Me, OMe, $CF_3$, and CN.

In some embodiments of Formula IIIb, q is 0.

In some embodiments of Formula IIIb, at least one $R^{16}$ is OH.

In some embodiments of Formula IIIb, at least one $R^{16}$ is OMe.

In some embodiments of Formula IIIb, q is 1 and $R^{16}$ is F.

In some embodiments of Formula IIIb, q is 2 and both $R^{16}$ are F.

In some embodiments of Formula IIIb, q is 1 and $R^{16}$ is Me.

In some embodiments of Formula IIIb, q is 2 and both $R^{16}$ are Me.

In some embodiments of Formula IIIb, q is 1 and $R^{16}$ is $CF_3$.

In some embodiments of Formula IIIb, q is 2 and both $R^{16}$ are $CF_3$.

In some embodiments of Formula IIIb, q is 1 and $R^{16}$ is OMe.

In some embodiments of Formula IIIb, q is 2 and both $R^{16}$ are OMe.

In some embodiments of Formula IIIb, q is 2 and one $R^{16}$ is F and the other $R^{16}$ is Me.

In some embodiments of Formula IIIb, q is 2 and one $R^{16}$ is F and the other $R^{16}$ is $CF_3$.

In some embodiments of Formula IIIb, q is 2 and one $R^{16}$ is F and the other $R^{16}$ is OMe.

In some embodiments of Formula IIIb, q is 1 and $R^{16}$ is CN.

In some embodiments of Formula IIIb, q is 2 and both $R^{16}$ are CN.

In some embodiments of Formula IIIb, q is 2 and one $R^{16}$ is F and the other $R^{16}$ is CN.

In some embodiments of Formula IIIb, at least one $R^{16}$ is —$CH_2OH$.

In some embodiments of Formula IIIb, at least one $R^{16}$ is —$CH_2N(R^{17b})_2$.

In some embodiments of Formula IIIb, at least one $R^{16}$ is —$CH_2NH_2$.

In some embodiments of Formula IIIb, at least one $R^{16}$ is —$CH_2NHMe$.

In some embodiments of Formula IIIb, at least one $R^{16}$ is —$CH_2NMe_2$.

In some embodiments of Formula IIIb, at least one $R^{16}$ is —$CH_2NHEt$.

In some embodiments of Formula IIIb, at least one $R^{16}$ is —$CH_2N(Me)(Et)$.

In some embodiments of Formula IIIb, at least one $R^{16}$ is —$CH_2NEt_2$.

In some embodiments of Formula IIIb, $R^{17}$ is —$C_{1-2}$ alkyl.

In some embodiments of Formula IIIb, $R^{17}$ is —$C_{1-3}$ alkyl.

In some embodiments of Formula IIIb, $R^{17}$ is —$C_{1-4}$ alkyl.

In some embodiments of Formula IIIb, $R^{17}$ is —$C_{1-5}$ alkyl.

In some embodiments of Formula IIIb, $R^{17}$ is —$C_{1-6}$ alkyl.

In some embodiments of Formula IIIb, $R^{17}$ is —$C_{2-6}$ alkyl.

In some embodiments of Formula IIIb, $R^{17}$ is —$C_{3-6}$ alkyl.

In some embodiments of Formula IIIb, $R^{17}$ is —$C_{4-6}$ alkyl.

In some embodiments of Formula IIIb, $R^{17}$ is —$C_{2-5}$ alkyl.

In some embodiments of Formula IIIb, $R^{17}$ is —$C_{3-5}$ alkyl.

Some embodiments of Formula III include compounds of Formula

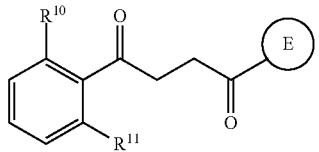

or salts, dermatologically acceptable salts, or prodrugs thereof.

In some embodiments of Formula IIIc, Ring E is selected from the group consisting of

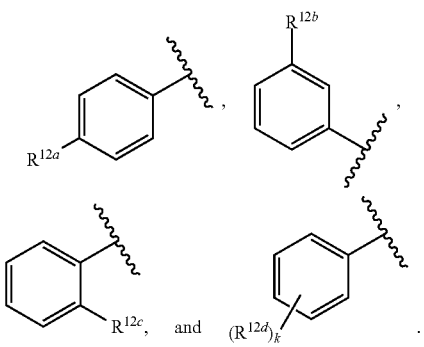

In some embodiments of Formula IIIc, $R^{10}$ is one substituent attached to the ortho position of the phenyl ring and is selected from the group consisting of H, unsubstituted —$C_{1-6}$ alkyl, —$C_{1-3}$ haloalkyl, halide, —$OR^{13}$, and CN.

In some embodiments of Formula IIIc, $R^{11}$ is one substituent attached to the ortho position of the phenyl ring and is selected from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN.

In some embodiments of Formula IIIc, $R^{12a}$ is one substituent attached to the para position of the phenyl ring and is selected at each occurrence from the group consisting of unsubstituted —$C_{2-6}$ alkyl, —$CH_2OH$, —$CH_2N(R^{13b})_2$, —$C_{2-3}$ haloalkyl, Cl, I, —OEt, and CN.

In some embodiments of Formula IIIc, $R^{12b}$ is one substituent attached to the meta position of the phenyl ring and is selected at each occurrence from the group consisting of unsubstituted —$C_{2-6}$ alkyl, —$CH_2OH$, —$CH_2N(R^{13b})_2$, —$C_{1-3}$ haloalkyl, iodide, and —$OR^{13a}$.

In some embodiments of Formula IIIc, $R^{12c}$ is one substituent attached to the ortho position of the phenyl ring and is selected at each occurrence from the group consisting of unsubstituted —$C_{2-6}$ alkyl, —$CH_2OH$, —$CH_2N(R^{13b})_2$, —$C_{1-3}$ haloalkyl, F, I, —$OR^{13a}$, and CN.

In some embodiments of Formula IIIc, $R^{12d}$ is a substituents attached to the ring and are independently selected at each occurrence from the group consisting of unsubstituted —$C_{1-6}$ alkyl, —$CH_2OH$, —$CH_2N(R^{13b})_2$, —$C_{1-3}$ haloalkyl, F, Br, I, —$OR^{13}$, and CN; k is 2 to 5.

In some embodiments of Formula IIIc, each $R^{13}$ is independently selected from the group consisting of unsubstituted —$C_{1-6}$ alkyl and —$C_{1-3}$ haloalkyl.

In some embodiments of Formula IIIc, each $R^{13a}$ is independently selected from the group consisting of unsubstituted —$C_{2-6}$ alkyl and —$C_{1-3}$ haloalkyl.

In some embodiments of Formula IIIc, each $R^{13b}$ is independently selected from the group consisting of H and unsubstituted —$C_{1-3}$ alkyl.

In some embodiments of Formula IIIc, at least one $R^{12d}$ is —$C_{2-6}$ alkyl.
In some embodiments of Formula IIIc, at least one $R^{12d}$ is —$C_{2-5}$ alkyl.
In some embodiments of Formula IIIc, at least one $R^{12d}$ is —$C_{2-4}$ alkyl.
In some embodiments of Formula IIIc, at least one $R^{12d}$ is —$C_{3-6}$ alkyl.
In some embodiments of Formula IIIc, at least one $R^{12d}$ is —$C_{4-6}$ alkyl.
In some embodiments of Formula IIIc, $R^{12a}$, $R^{12b}$, $R^{12c}$, and/or $R^{13a}$ is —$C_{2-6}$ alkyl.
In some embodiments of Formula IIIc, $R^{12a}$, $R^{12b}$, $R^{12c}$, and/or $R^{13a}$ is —$C_{2-5}$ alkyl.
In some embodiments of Formula IIIc, $R^{12a}$, $R^{12b}$, $R^{12c}$, and/or $R^{13a}$ is —$C_{2-4}$ alkyl.
In some embodiments of Formula IIIc, $R^{12a}$, $R^{12b}$, $R^{12c}$, and/or $R^{13a}$ is —$C_{3-6}$ alkyl.
In some embodiments of Formula IIIc, $R^{12a}$, $R^{12b}$, $R^{12c}$, and/or $R^{13a}$ is —$C_{4-6}$ alkyl.
In some embodiments of Formula IIIc, at least one $R^{12d}$ is Me.
In some embodiments of Formula IIIc, at least one $R^{12d}$ is $CF_3$.
In some embodiments of Formula IIIc, $R^{13a}$ is Me.
In some embodiments of Formula IIIc, $R^{12b}$, $R^{12c}$, and/or $R^{13a}$ is $CF_3$.
In some embodiments of Formula IIIc, at least one $R^{12d}$ is F.
In some embodiments of Formula IIIc, $R^{12c}$ is F.
In some embodiments of Formula IIIc, $R^{12a}$ is Cl.
In some embodiments of Formula IIIc, at least one $R^{12d}$ is CN.
In some embodiments of Formula IIIc, at least one $R^{12d}$ is —$CH_2OH$.
In some embodiments of Formula IIIc, at least one $R^{12d}$ is —$CH_2N(R^{13b})_2$.
In some embodiments of Formula IIIc, at least one $R^{12d}$ is —$CH_2NH_2$.
In some embodiments of Formula IIIc, at least one $R^{12d}$ is —$CH_2NHMe$.
In some embodiments of Formula IIIc, at least one $R^{12d}$ is —$CH_2NMe_2$.
In some embodiments of Formula IIIc, at least one $R^{12d}$ is —$CH_2NHEt$.
In some embodiments of Formula IIIc, at least one $R^{12d}$ is —$CH_2N(Me)(Et)$.
In some embodiments of Formula IIIc, $R^{12a}$, $R^{12c}$, or $R^{12c}$ is CN.
In some embodiments of Formula IIIc, $R^{12a}$, $R^{12b}$, or $R^{12c}$ is —$CH_2OH$.
In some embodiments of Formula IIIc, $R^{12a}$, $R^{12b}$, or $R^{12c}$ is —$CH_2N(R^{13b})_2$.
In some embodiments of Formula IIIc, $R^{12a}$, $R^{12b}$, or $R^{12c}$ is —$CH_2NH_2$.
In some embodiments of Formula IIIc, $R^{12a}$, $R^{12b}$, or $R^{12c}$ is —$CH_2NHMe$.
In some embodiments of Formula IIIc, $R^{12a}$, $R^{12b}$, or $R^{12c}$ is —$CH_2NMe_2$.
In some embodiments of Formula IIIc, $R^{12a}$, $R^{12b}$, or $R^{12c}$ is —$CH_2NHEt$.
In some embodiments of Formula IIIc, $R^{12a}$, $R^{12b}$, or $R^{12c}$ is —$CH_2N(Me)(Et)$.

In some embodiments of Formula IIIa and IIIc, $R^{11}$ is —$CH_2NEt_2$.

In some embodiments of Formula IIIa and IIIc, $R^{10}$ is selected from the group consisting of H, F, Cl, Me, OMe, $CF_3$, and CN.

In some embodiments of Formula IIIa and IIIc, $R^{11}$ is selected from the group consisting of F, Cl, Me, OMe, $CF_3$, and CN.

In some embodiments of Formula IIIa and IIIc, $R^{10}$ is H; and $R^{11}$ is F.

In some embodiments of Formula IIIa and IIIc, $R^{10}$ is H; and $R^{11}$ is Cl.

In some embodiments of Formula IIIa and IIIc, $R^{10}$ is H; and $R^{11}$ is Me.

In some embodiments of Formula IIIa and IIIc, $R^{10}$ is H; and $R^{11}$ is OMe.

In some embodiments of Formula IIIa and IIIc, $R^{10}$ is H; and $R^{11}$ is $CF_3$.

In some embodiments of Formula IIIa and IIIc, $R^{10}$ is H; and $R^{11}$ is CN.

In some embodiments of Formula IIIa and IIIc, $R^{10}$ is F; and $R^{11}$ is F.

In some embodiments of Formula IIIa and IIIc, $R^{10}$ is F; and $R^{11}$ is Cl.

In some embodiments of Formula IIIa and IIIc, $R^{10}$ is F; and $R^{11}$ is Me.

In some embodiments of Formula IIIa and IIIc, $R^{10}$ is F; and $R^{11}$ is OMe.

In some embodiments of Formula IIIa and IIIc, $R^{10}$ is F; and $R^{11}$ is $CF_3$.

In some embodiments of Formula IIIa and IIIc, $R^{10}$ is F; and $R^{11}$ is CN.

In some embodiments of Formula IIIa and IIIc, $R^{10}$ is —$C_{1-2}$ alkyl.

In some embodiments of Formula IIIa and IIIc, $R^{10}$ is —$C_{1-3}$ alkyl.

In some embodiments of Formula IIIa and IIIc, $R^{10}$ is —$C_{1-4}$ alkyl.

In some embodiments of Formula IIIa and IIIc, $R^{10}$ is —$C_{1-5}$ alkyl.

In some embodiments of Formula IIIa and IIIc, $R^{10}$ is —$C_{1-6}$ alkyl.

In some embodiments of Formula IIIa and IIIc, $R^{10}$ is —$C_{2-6}$ alkyl.

In some embodiments of Formula IIIa and IIIc, $R^{10}$ is —$C_{3-6}$ alkyl.

In some embodiments of Formula IIIa and IIIc, $R^{10}$ is —$C_{4-6}$ alkyl.

In some embodiments of Formula IIIa and IIIc, $R^{10}$ is —$C_{2-5}$ alkyl.

In some embodiments of Formula IIIa and IIIc, $R^{10}$ is —$C_{3-5}$ alkyl.

In some embodiments of Formula IIIa and IIIc, $R^{11}$ is —$C_{1-2}$ alkyl.

In some embodiments of Formula IIIa and IIIc, $R^{11}$ is —$C_{1-3}$ alkyl.

In some embodiments of Formula IIIa and IIIc, $R^{11}$ is —$C_{1-4}$ alkyl.

In some embodiments of Formula IIIa and IIIc, $R^{11}$ is —$C_{1-5}$ alkyl.

In some embodiments of Formula IIIa and IIIc, $R^{11}$ is —$C_{1-6}$ alkyl.

In some embodiments of Formula IIIa and IIIc, $R^{11}$ is —$C_{2-6}$ alkyl.

In some embodiments of Formula IIIa and IIIc, $R^{11}$ is —$C_{3-6}$ alkyl.

In some embodiments of Formula IIIa and IIIc, $R^{11}$ is —$C_{4-6}$ alkyl.

In some embodiments of Formula IIIa and IIIc, $R^{11}$ is —$C_{2-5}$ alkyl.

In some embodiments of Formula IIIa and IIIc, $R^{11}$ is —$C_{3-5}$ alkyl.

In some embodiments of Formula IIIa and IIIc, q is 1 to 4.

In some embodiments of Formula IIIa and IIIc, q is 1 to 3.

In some embodiments of Formula IIIa, q is 1 or 2.

In some embodiments of Formula IIIa and IIIc, q is 2.

In some embodiments of Formula IIIa and IIIc, q is 1.

In some embodiments of Formula IIIa and IIIc, $R^{11}$ is —$CH_2OH$.

In some embodiments of Formula IIIa and IIIc, $R^{11}$ is a —$CH_2N(R^{13b})_2$.

In some embodiments of Formula IIIa and IIIc, $R^{11}$ is a —$CH_2NH_2$.

In some embodiments of Formula IIIa and IIIc, $R^{11}$ is a —$CH_2NHMe$.

In some embodiments of Formula IIIa and IIIc, $R^{11}$ is a —$CH_2NMe_2$.

In some embodiments of Formula IIIa and IIIc, $R^{11}$ is a —$CH_2NHEt$.

In some embodiments of Formula IIIa and IIIc, $R^{11}$ is a —$CH_2N(Me)(Et)$.

In some embodiments of Formula IIIa and IIIc, $R^{11}$ is a —$CH_2NEt_2$.

In some embodiments of Formula IIIa and IIIc, $R^{13}$ is a —$C_{1-2}$ alkyl.

In some embodiments of Formula IIIa and IIIc, $R^{13}$ is —$C_{1-3}$ alkyl.

In some embodiments of Formula IIIa and IIIc, $R^{13}$ is —$C_{1-4}$ alkyl.

In some embodiments of Formula IIIa and IIIc, $R^{13}$ is —$C_{1-5}$ alkyl.

In some embodiments of Formula IIIa and IIIc, $R^{13}$ is a —$C_{1-6}$ alkyl.

In some embodiments of Formula IIIa and IIIc, $R^{13}$ is a —$C_{2-6}$ alkyl.

In some embodiments of Formula IIIa and IIIc, $R^{13}$ is a —$C_{3-6}$ alkyl.

In some embodiments of Formula IIIa and IIIc, $R^{13}$ is a —$C_{4-6}$ alkyl.

In some embodiments of Formula IIIa and IIIc, $R^{13}$ is a —$C_{2-5}$ alkyl.

In some embodiments of Formula IIIa and IIIc, $R^{13}$ is a —$C_{3-5}$ alkyl.

Some embodiments of Formula III include compounds of Formula (IIId):

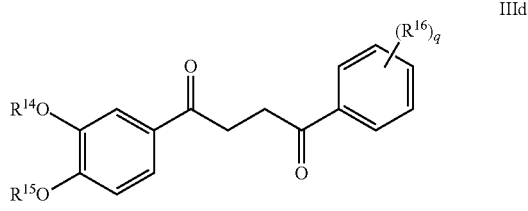

or salts, dermatologically acceptable salts, or prodrugs thereof.

In some embodiments of Formula IIId, $R^{14}$ is selected from the group consisting of unsubstituted —$C_{1-6}$ alkyl and —$C_{1-3}$ haloalkyl.

In some embodiments of Formula IIId, $R^{15}$ is selected from the group consisting of unsubstituted —$C_{1-6}$ alkyl and —$C_{1-3}$ haloalkyl.

In some embodiments of Formula IIId, each $R^{16}$ is a substituent attached to the phenyl ring and is independently selected at each occurrence from the group consisting of unsubstituted —$C_{1-6}$ alkyl, —$CH_2OH$, —$CH_2N(R^{17b})_2$, —$C_{1-3}$ haloalkyl, halide, —$OR^{17}a$, and CN.

In some embodiments of Formula IIId, each $R^{17a}$ is independently selected from the group consisting of unsubstituted —$C_{3-6}$ alkyl and —$C_{1-3}$ haloalkyl.

In some embodiments of Formula IIId, each $R^{17b}$ is independently selected from the group consisting of H and unsubstituted —$C_{1-3}$ alkyl.

In some embodiments of Formula IIId, q is 1 to 5.

In some embodiments of Formula IIId, $R^{17a}$ is —$C_{3-6}$ alkyl.

In some embodiments of Formula IIId, $R^{17a}$ is —$C_{4-6}$ alkyl.

In some embodiments of Formula IIId, $R^{17a}$ is —$C_{3-5}$ alkyl.

In some embodiments of Formula IIId, at least one $R^{16}$ is —$CH_2OH$.

In some embodiments of Formula IIId, at least one $R^{16}$ is —$CH_2N(R^{17b})_2$.

In some embodiments of Formula IIId, at least one $R^{16}$ is —$CH_2NH_2$.

In some embodiments of Formula IIId, at least one $R^{16}$ is —$CH_2NHMe$.

In some embodiments of Formula IIId, at least one $R^{16}$ is —$CH_2NMe_2$.

In some embodiments of Formula IIId, at least one $R^{16}$ is —$CH_2NHEt$.

In some embodiments of Formula IIId, at least one $R^{16}$ is —$CH_2N(Me)(Et)$.

In some embodiments of Formula IIId, at least one $R^{16}$ is —$CH_2NEt_2$.

In some embodiments of Formula IIIa, IIIb, IIIc, and IIId, —$C_{1-3}$ haloalkyl is —$CF_3$.

In some embodiments of Formula IIIb and IIId, $R^{14}$ is Me

In some embodiments of Formula IIIb and IIId, $R^{14}$ is Et.

In some embodiments of Formula IIIb and IIId, $R^{14}$ is —$C_{1-2}$ alkyl.

In some embodiments of Formula IIIb and IIId, $R^{14}$ is —$C_{1-3}$ alkyl.

In some embodiments of Formula IIIb and IIId, $R^{14}$ is —$C_{1-4}$ alkyl.

In some embodiments of Formula IIIb and IIId, $R^{14}$ is —$C_{1-5}$ alkyl.

In some embodiments of Formula IIIb and IIId, $R^{14}$ is —$C_{1-6}$ alkyl.

In some embodiments of Formula IIIb and IIId, $R^{14}$ is —$C_{2-6}$ alkyl.

In some embodiments of Formula IIIb and IIId, $R^{14}$ is —$C_{3-6}$ alkyl.

In some embodiments of Formula IIIb and IIId, $R^{14}$ is —$C_{4-6}$ alkyl.

In some embodiments of Formula IIIb and IIId, $R^{14}$ is —$C_{2-5}$ alkyl.

In some embodiments of Formula IIIb and IIId, $R^{14}$ is —$C_{3-5}$ alkyl.

In some embodiments of Formula IIIb and IIId, $R^{14}$ is —$C_{1-2}$ haloalkyl.

In some embodiments of Formula IIIb and IIId, $R^{14}$ is —$C_{1-3}$ haloalkyl.

In some embodiments of Formula IIIb and IIId, $R^{14}$ is —$C_{2-3}$ haloalkyl.

In some embodiments of Formula IIIb and IIId, $R^{14}$ is $CF_3$.

In some embodiments of Formula IIIb and IIId, $R^{15}$ is Me

In some embodiments of Formula IIIb and IIId, $R^{15}$ is Et.

In some embodiments of Formula IIIb and IIId, $R^{15}$ is —$C_{1-2}$ alkyl.

In some embodiments of Formula IIIb and IIId, $R^{15}$ is —$C_{1-3}$ alkyl.

In some embodiments of Formula IIIb and IIId, $R^{15}$ is —$C_{1-4}$ alkyl.

In some embodiments of Formula IIIb and IIId, $R^{15}$ is —$C_{1-5}$ alkyl.

In some embodiments of Formula IIIb and IIId, $R^{15}$ is —$C_{1-6}$ alkyl.

In some embodiments of Formula IIIb and IIId, $R^{15}$ is —$C_{2-6}$ alkyl.

In some embodiments of Formula IIIb and IIId, $R^{15}$ is —$C_{3-6}$ alkyl.

In some embodiments of Formula IIIb and IIId, $R^{15}$ is —$C_{4-6}$ alkyl.

In some embodiments of Formula IIIb and IIId, $R^{15}$ is —$C_{2-5}$ alkyl.

In some embodiments of Formula IIIb and IIId, $R^{15}$ is —$C_{3-5}$ alkyl.

In some embodiments of Formula IIIb and IIId, $R^{15}$ is —$C_{1-2}$ haloalkyl.

In some embodiments of Formula IIIb and IIId, $R^{15}$ is —$C_{1-3}$ haloalkyl.

In some embodiments of Formula IIIb and IIId, $R^{15}$ is —$C_{2-3}$ haloalkyl.

In some embodiments of Formula IIIb and IIId, $R^{15}$ is $CF_3$.

In some embodiments of Formula IIIb and IIId, at least one $R^{16}$ is a halide.

In some embodiments of Formula IIIb and IIId, at least one $R^{16}$ is F.

In some embodiments of Formula IIIb and IIId, at least one $R^{16}$ is Cl.

In some embodiments of Formula IIIb and IIId, at least one $R^{16}$ is Me.

In some embodiments of Formula IIIb and IIId, at least one $R^{16}$ is $CF_3$.

In some embodiments of Formula IIIb and IIId, at least one $R^{16}$ is CN.

In some embodiments of Formula IIIb and IIId, q is 1 to 4.

In some embodiments of Formula IIIb and IIId, q is 1 to 3.

In some embodiments of Formula IIIb and IIId, q is 1 or 2.

In some embodiments of Formula IIIb and IIId, q is 2.

In some embodiments of Formula IIIb and IIId, q is 1.

In some embodiments of Formula IIIb and IIId, q is 1 and $R^{16}$ is F or Cl.

In some embodiments of Formula IIIb and IIId, at least one $R^{16}$ is —$C_{1-2}$ alkyl.

In some embodiments of Formula IIIb and IIId, at least one $R^{16}$ is —$C_{1-3}$ alkyl.

In some embodiments of Formula IIIb and IIId, at least one $R^{16}$ is —$C_{1-4}$ alkyl.

In some embodiments of Formula IIIb and IIId, at least one $R^{16}$ is —$C_{1-5}$ alkyl.

In some embodiments of Formula IIIb and IIId, at least one $R^{16}$ is —$C_{1-6}$ alkyl.

In some embodiments of Formula IIIb and IIId, at least one $R^{16}$ is —$C_{2-6}$ alkyl.

n some embodiments of Formula IIIb and IIId, at least one $R^{16}$ is —$C_{3-6}$ alkyl.

In some embodiments of Formula IIIb and IIId, at least one $R^{16}$ is —$C_{4-6}$ alkyl.

In some embodiments of Formula IIIb and IIId, at least one $R^{16}$ is —$C_{2-5}$ alkyl.

In some embodiments of Formula IIIb and IIId, at least one $R^{16}$ is —$C_{3-5}$ alkyl.

Some embodiments of the present disclosure include compounds of Formula (IV):

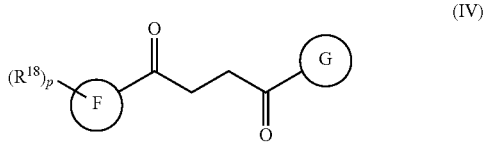

(IV)

or salts, dermatologically acceptable salts, or prodrugs thereof.

In some embodiments of Formula IV, Ring Ring F is

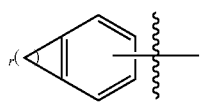

In some embodiments of Formula IV, Ring G is selected from the group consisting of

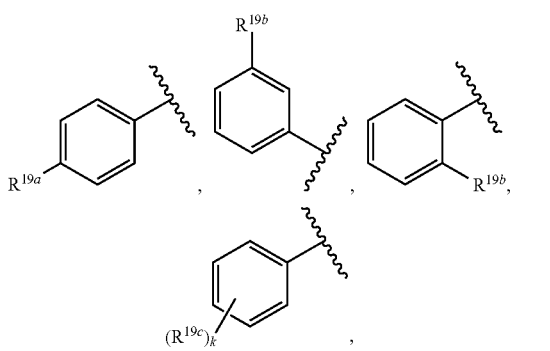

and a 5-6 membered heteroaryl$(R^{19d})_z$, wherein a carbon atom on the ring is attached to the carbonyl carbon.

In some embodiments of Formula IV, each $R^{18}$ is a substituent attached to Ring F and is independently selected at each occurrence from the group consisting of H, —$C_{1-3}$ haloalkyl, halide, —$OR^{20}$, and CN.

In some embodiments of Formula IV, each $R^{18}$ is a substituent attached to Ring F and is independently selected at each occurrence from the group consisting of —$C_{1-3}$ haloalkyl, halide, —$OR^{20}$, and CN.

In some embodiments of Formula IV, $R^{19a}$ is a substituent attached to the para position of phenyl and is selected from the group consisting of H, unsubstituted —$C_{2-6}$ alkyl, —$CH_2OH$, —$CH_2N(R^{21})_2$, —$C_{1-3}$ haloalkyl, F, Br, I, —$OR^{20}$, and CN.

In some embodiments of Formula IV, $R^{19b}$ is a substituent attached to the meta or ortho position of phenyl and is selected from the group consisting of H, unsubstituted —$C_{2-6}$ alkyl, —$CH_2OH$, —$CH_2N(R^{21})_2$, —$C_{1-3}$ haloalkyl, halide, —$OR^{20}$, and CN.

In some embodiments of Formula IV, $R^{19c}$ is a substituent attached to the phenyl and is independently selected at each occurrence from the group consisting of H, —$CH_2OH$, —$CH_2N(R^{21})_2$, —$C_{1-3}$ haloalkyl, halide, —$OR^{20}$, and CN; k is 2 to 5.

In some embodiments of Formula IV, $R^{19c}$ is a substituent attached to the phenyl and is independently selected at each occurrence from the group consisting of —$CH_2OH$, —$CH_2N(R^{21})_2$, —$C_{1-3}$ haloalkyl, halide, —$OR^{20}$, and CN; k is 0 to 5.

In some embodiments of Formula IV, $R^{19d}$ is a substituent attached to the heteroaryl ring and is independently selected at each occurrence from the group consisting of H, —$CH_2OH$, —$CH_2N(R^{21})_2$, —$C_{1-3}$ haloalkyl, halide, —$OR^{20}$, and CN; z is 0 to 4.

In some embodiments of Formula IV, $R^{19d}$ is a substituent attached to the heteroaryl ring and is independently selected at each occurrence from the group consisting of —$CH_2OH$, —$CH_2N(R^{21})_2$, —$C_{1-3}$ haloalkyl, halide, —$OR^{20}$, and CN; z is 1 to 4.

In some embodiments of Formula IV, each $R^{20}$ is independently selected from the group consisting of H, unsubstituted —$C_{3-6}$ alkyl, and —$C_{1-3}$ haloalkyl.

In some embodiments of Formula IV, each $R^{21}$ is independently selected from the group consisting of H and unsubstituted —$C_{1-3}$ alkyl.

In some embodiments of Formula IV, p is 0 to 13.

In some embodiments of Formula IV, p is 1 to 13.

In some embodiments of Formula IV, p is 0.

In some embodiments of Formula IV, r is 1 to 5.

In some embodiments of Formula IV,

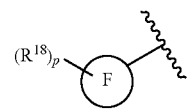

is selected from the group consisting of:

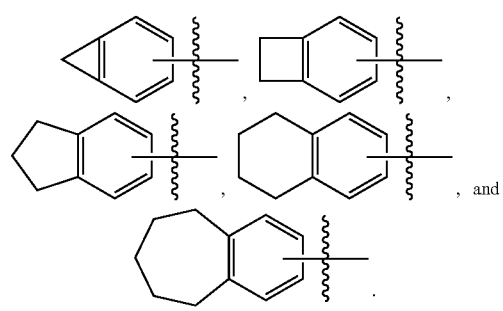

, and

In some embodiments of Formula IV,

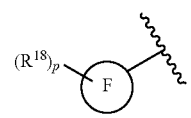

is selected from the group consisting of:

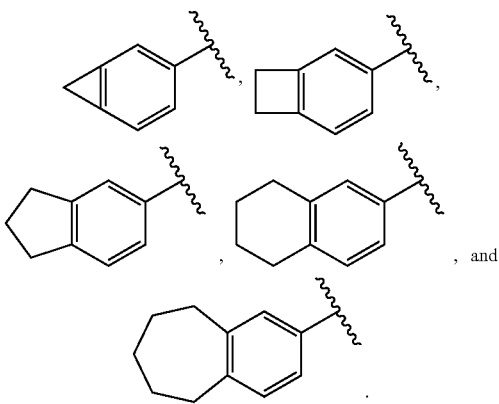

In some embodiments of Formula IV, at least one $R^{19c}$ or $R^{19d}$ is selected from the group consisting of H, F, Cl, Me, OMe, $CF_3$, and CN.

In some embodiments of Formula IV, at least one $R^{19c}$ or $R^{19d}$ is halide.

In some embodiments of Formula IV, at least one $R^{19c}$ or $R^{19d}$ is F.

In some embodiments of Formula IV, at least one $R^{19c}$ or $R^{19d}$ is Cl.

In some embodiments of Formula IV, at least one $R^{19c}$ or $R^{19d}$ is Me.

In some embodiments of Formula IV, at least one $R^{19c}$ or $R^{19d}$ is OH.

In some embodiments of Formula IV, at least one $R^{19c}$ or $R^{19d}$ is OMe.

In some embodiments of Formula IV, at least one $R^{19c}$ or $R^{19d}$ is $CF_3$.

In some embodiments of Formula IV, at least one $R^{19c}$ or $R^{19d}$ is CN.

In some embodiments of Formula IV, $R^{19b}$ is selected from the group consisting of H, F, Cl, Me, OMe, $CF_3$, and CN.

In some embodiments of Formula IV, $R^{19a}$ or $R^{19b}$ is H.

In some embodiments of Formula IV, $R^{19a}$ or $R^{19b}$ is halide.

In some embodiments of Formula IV, $R^{19a}$ or $R^{19b}$ is F.

In some embodiments of Formula IV, $R^{19a}$ or $R^{19b}$ is Cl.

In some embodiments of Formula IV, $R^{19a}$ or $R^{19b}$ is Me.

In some embodiments of Formula IV, $R^{19a}$ or $R^{19b}$ is OH.

In some embodiments of Formula IV, $R^{19a}$ or $R^{19b}$ is OMe.

In some embodiments of Formula IV, $R^{19a}$ or $R^{19b}$ is $CF_3$.

In some embodiments of Formula IV, $R^{19a}$ or $R^{19b}$ is CN.

In some embodiments of Formula IV, z is 1.

In some embodiments of Formula IV, z is 2.

In some embodiments of Formula IV, z is 2 and both $R^{19d}$ are F.

In some embodiments of Formula IV, z is 2 and both $R^{19d}$ are Me.

In some embodiments of Formula IV, z is 2 and both $R^{19d}$ are $CF_3$.

In some embodiments of Formula IV, z is 2 and both $R^{19d}$ are OMe.

In some embodiments of Formula IV, z is 2 and one $R^{19d}$ is F and the other $R^{19d}$ is Me.

In some embodiments of Formula IV, z is 2 and one $R^{19d}$ is F and the other $R^{19d}$ is $CF_3$.

In some embodiments of Formula IV, z is 2 and one $R^{19d}$ is F and the other $R^{19d}$ is OMe.

In some embodiments of Formula IV, z is 2 and both $R^{19d}$ are CN.

In some embodiments of Formula IV, z is 2 and one $R^{19d}$ is F and the other $R^{19d}$ is CN.

In some embodiments of Formula IV, z is 2 and one $R^{19d}$ is F and the other $R^{19d}$ is Cl.

In some embodiments of Formula IV, at least one $R^{19c}$ or $R^{19d}$ is —$C_{1-2}$ alkyl.

In some embodiments of Formula IV, at least one $R^{19c}$ or $R^{19d}$ is —$C_{1-3}$ alkyl.

In some embodiments of Formula IV, at least one $R^{19c}$ or $R^{19d}$ is —$C_{1-4}$ alkyl.

In some embodiments of Formula IV, at least one $R^{19c}$ or $R^{19d}$ is —$C_{1-5}$ alkyl.

In some embodiments of Formula IV, at least one $R^{19c}$ or $R^{19d}$ is —$C_{1-6}$ alkyl.

In some embodiments of Formula IV, at least one $R^{19c}$ or $R^{19d}$ is —$C_{2-6}$ alkyl.

In some embodiments of Formula IV, at least one $R^{19c}$ or $R^{19d}$ is —$C_{3-6}$ alkyl.

In some embodiments of Formula IV, at least one $R^{19c}$ or $R^{19d}$ is —$C_{4-6}$ alkyl.

In some embodiments of Formula IV, at least one $R^{19c}$ or $R^{19d}$ is —$C_{2-5}$ alkyl.

In some embodiments of Formula IV, at least one $R^{19c}$ or $R^{19d}$ is —$C_{3-5}$ alkyl.

In some embodiments of Formula IV, at least one $R^{19c}$ or $R^{19d}$ is —$CH_2OH$.

In some embodiments of Formula IV, at least one $R^{19c}$ or $R^{19d}$ is —$CH_2N(R^{13b})_2$.

In some embodiments of Formula IV, at least one $R^{19c}$ or $R^{19d}$ is —$CH_2NH_2$.

In some embodiments of Formula IV, at least one $R^{19c}$ or $R^{19d}$ is —$CH_2NHMe$.

In some embodiments of Formula IV, at least one $R^{19c}$ or $R^{19d}$ is —$CH_2NMe_2$.

In some embodiments of Formula IV, at least one $R^{19c}$ or $R^{19d}$ is —$CH_2NHEt$.

In some embodiments of Formula IV, at least one $R^{19c}$ or $R^{19d}$ is —$CH_2N(Me)(Et)$.

In some embodiments of Formula IV, at least one $R^{19c}$ or $R^{19d}$ is —$CH_2NEt_2$.

In some embodiments of Formula IV, $R^{19a}$ or $R^{19b}$ is —$C_{1-2}$ alkyl.

In some embodiments of Formula IV, $R^{19a}$ or $R^{19b}$ is —$C_{1-3}$ alkyl.

In some embodiments of Formula IV, $R^{19a}$ or $R^{19b}$ is —$C_{1-4}$ alkyl.

In some embodiments of Formula IV, $R^{19a}$ or $R^{19b}$ is —$C_{1-5}$ alkyl.

In some embodiments of Formula IV, $R^{19a}$ or $R^{19b}$ is —$C_{1-6}$ alkyl.

In some embodiments of Formula IV, $R^{19a}$ or $R^{19b}$ is —$C_{2-6}$ alkyl.

In some embodiments of Formula IV, $R^{19a}$ or $R^{19b}$ is —$C_{3-6}$ alkyl.

In some embodiments of Formula IV, $R^{19a}$ or $R^{19b}$ is —$C_{4-6}$ alkyl.

In some embodiments of Formula IV, $R^{19a}$ or $R^{19b}$ is —$C_{2-5}$ alkyl.

In some embodiments of Formula IV, $R^{19a}$ or $R^{19b}$ is —$C_{3-5}$ alkyl.

In some embodiments of Formula IV, $R^{19a}$ or $R^{19b}$ is —$CH_2OH$.

In some embodiments of Formula IV, $R^{19a}$ or $R^{19b}$ is —CH$_2$N(R$^{13b}$)$_2$.

In some embodiments of Formula IV, $R^{19a}$ or $R^{19b}$ is —CH$_2$NH$_2$.

In some embodiments of Formula IV, $R^{19a}$ or $R^{19b}$ is —CH$_2$NHMe.

In some embodiments of Formula IV, $R^{19a}$ or $R^{19b}$ is —CH$_2$NMe$_2$.

In some embodiments of Formula IV, $R^{19a}$ or $R^{19b}$ is —CH$_2$NHEt.

In some embodiments of Formula IV, $R^{19a}$ or $R^{19b}$ is —CH$_2$N(Me)(Et).

In some embodiments of Formula IV, $R^{19a}$ or $R^{19b}$ is —CH$_2$NEt$_2$.

In some embodiments of Formula IV,

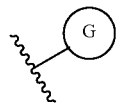

is selected from the group consisting of:

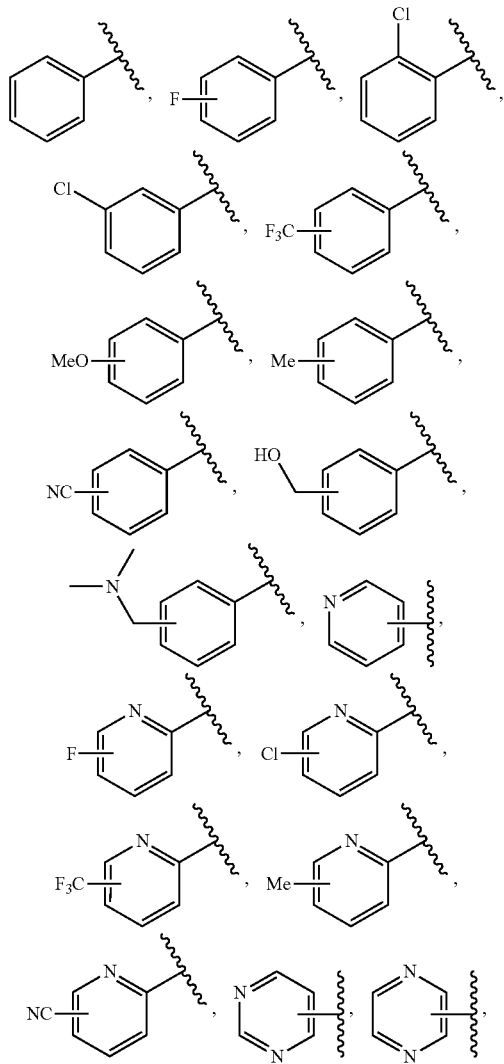

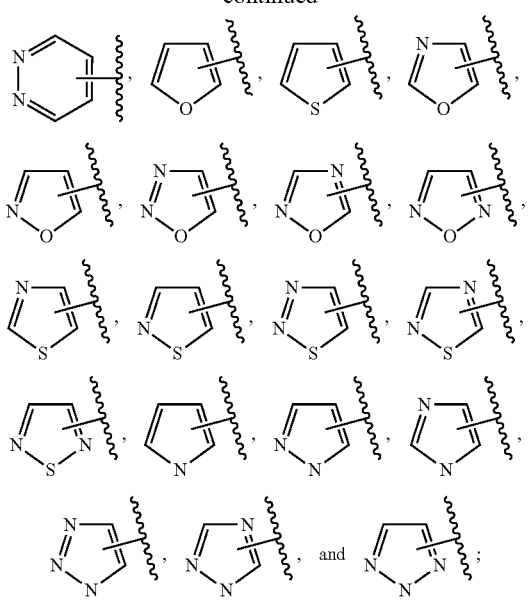

wherein the carbonyl carbon of Formula IV can form a bond with any unsubstituted carbon on the Ring G.

In some embodiments of Formula IV,

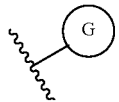

is selected from the group consisting of:

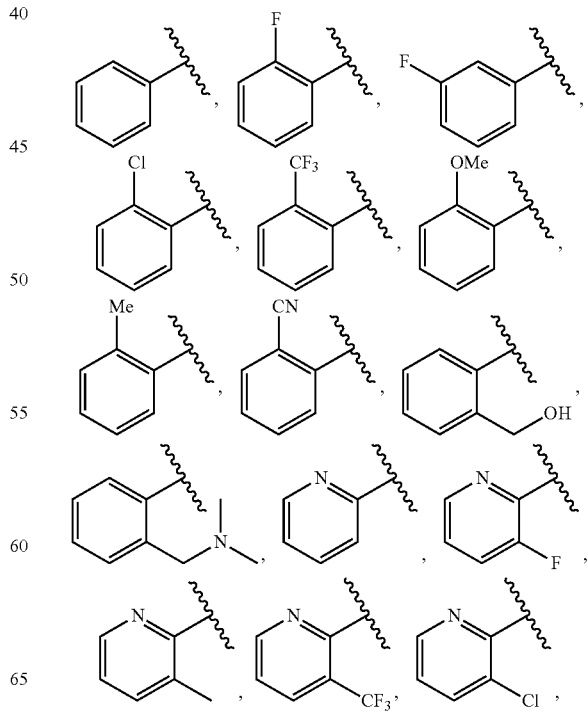

-continued
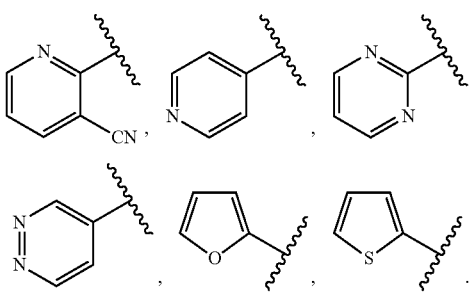
In some embodiments of Formula IV,
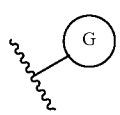
is selected from the group consisting of:
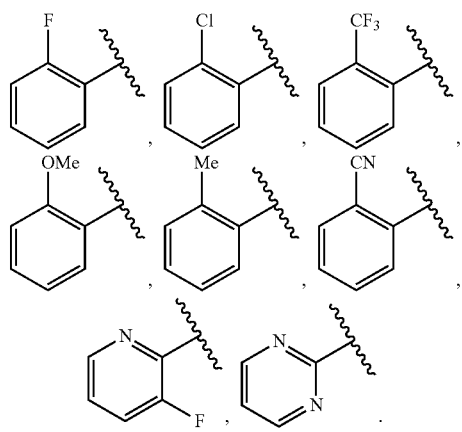
In some embodiments of Formula IV, —C$_{1-3}$ haloalkyl is —CF$_3$.
Illustrative compounds of Formulas I, Ia, Ib, Ic, Id, Ie, If, Ig, Ih, Ii, II, IIa, IIb, IIc, IId, IIe, IIf, III, IIIa, IIIb, IIIc, IIId, and IV are shown in Table 1.
TABLE 1
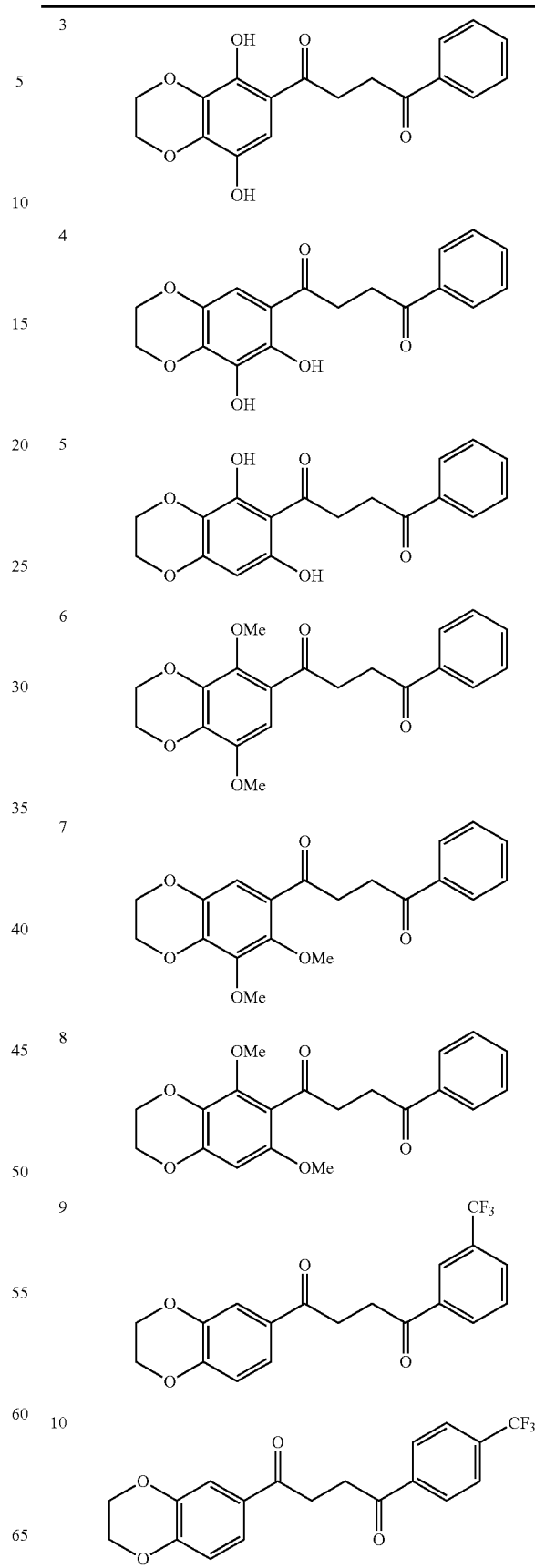

TABLE 1-continued
| 11 | 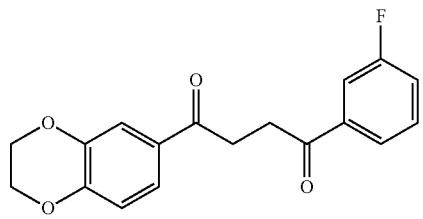 |
| --- | --- |
| 12 | 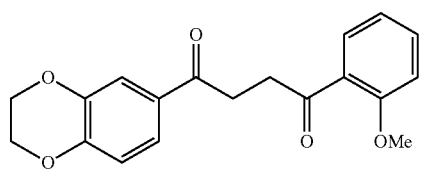 |
| 13 | 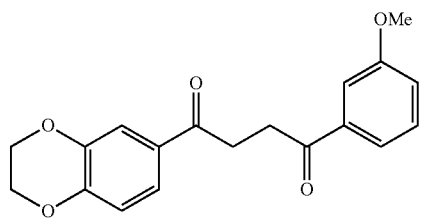 [SMILES: COc1cccc(C(=O)CCC(=O)c2ccc3c(c2)OCCO3)c1] |
| 14 | 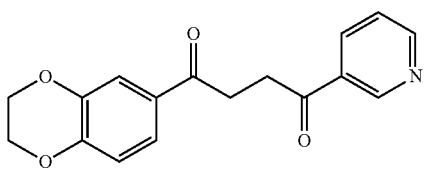 [SMILES: O=C(CCC(=O)c1ccc2c(c1)OCCO2)c1cccnc1] |
| 15 | 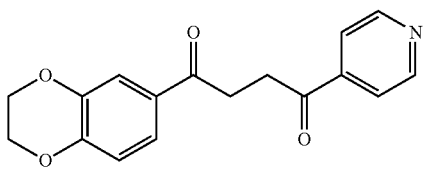 [SMILES: O=C(CCC(=O)c1ccc2c(c1)OCCO2)c1ccncc1] |
| 16 | 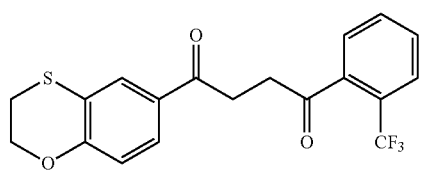 |
| 17 | 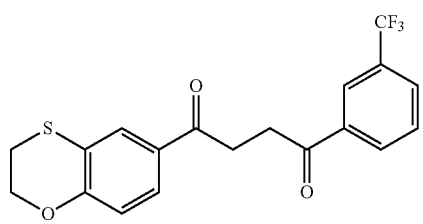 [SMILES: O=C(CCC(=O)c1ccc2c(c1)SCCO2)c1cccc(C(F)(F)F)c1] |
TABLE 1-continued
| 18 | 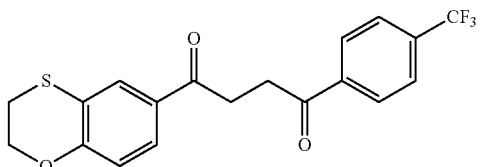 |
| --- | --- |
| 19 | 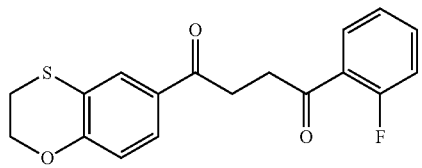 [SMILES: O=C(CCC(=O)c1ccccc1F)c1ccc2c(c1)SCCO2] |
| 20 | 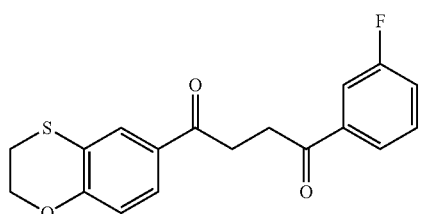 [SMILES: O=C(CCC(=O)c1ccc2c(c1)OCCC2)c1cccc(F)c1] |
| 21 | 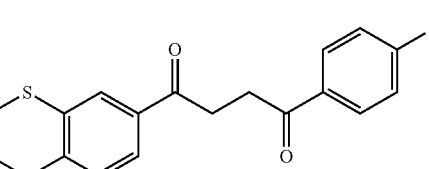 |
| 22 | 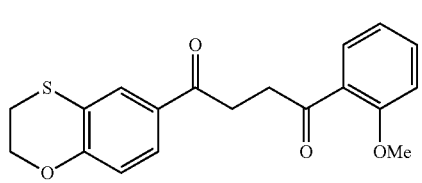 |
| 23 | 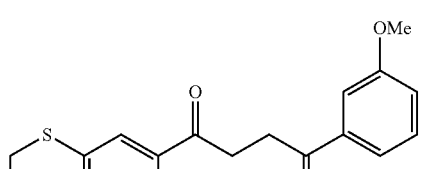 |
| 24 | 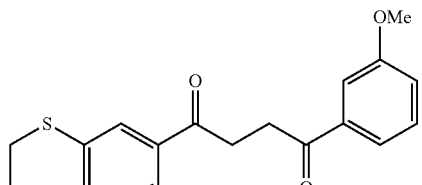 |
| 25 | 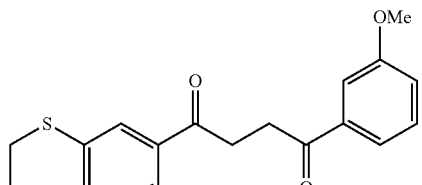 |

TABLE 1-continued
| | | | | |
|---|---|---|---|---|
| 26 | 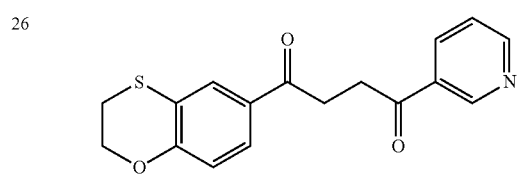 | | 34 | 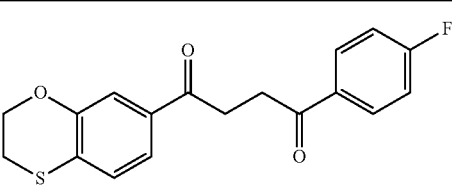 |
| 27 | | | 35 | |
| 28 | 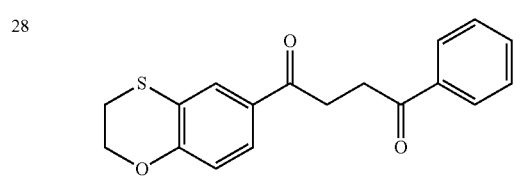 | | 36 | |
| 29 | | | 37 | 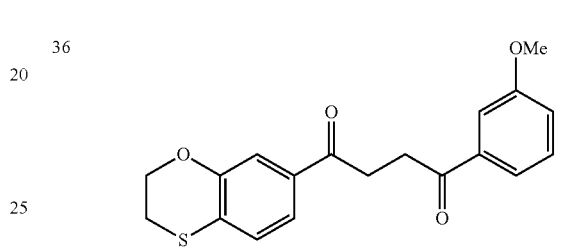 |
| 30 | 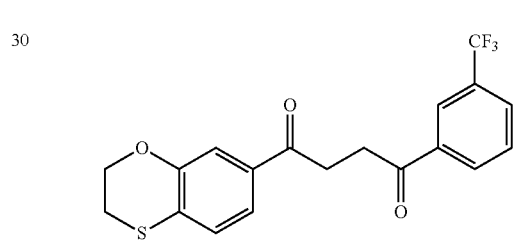 | | 38 | |
| 31 | | | 39 | 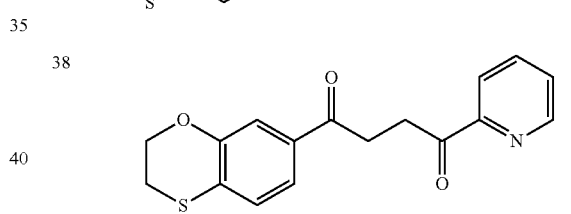 |
| 32 |  | | 40 | |
| 33 | 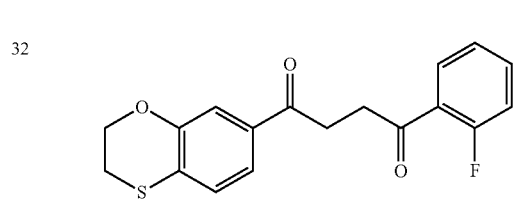 | | 41 | 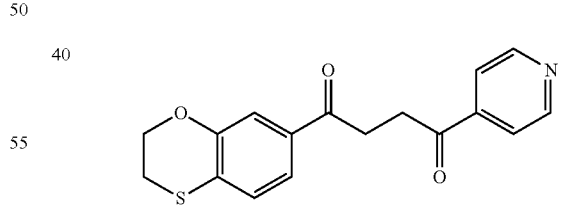 |

TABLE 1-continued
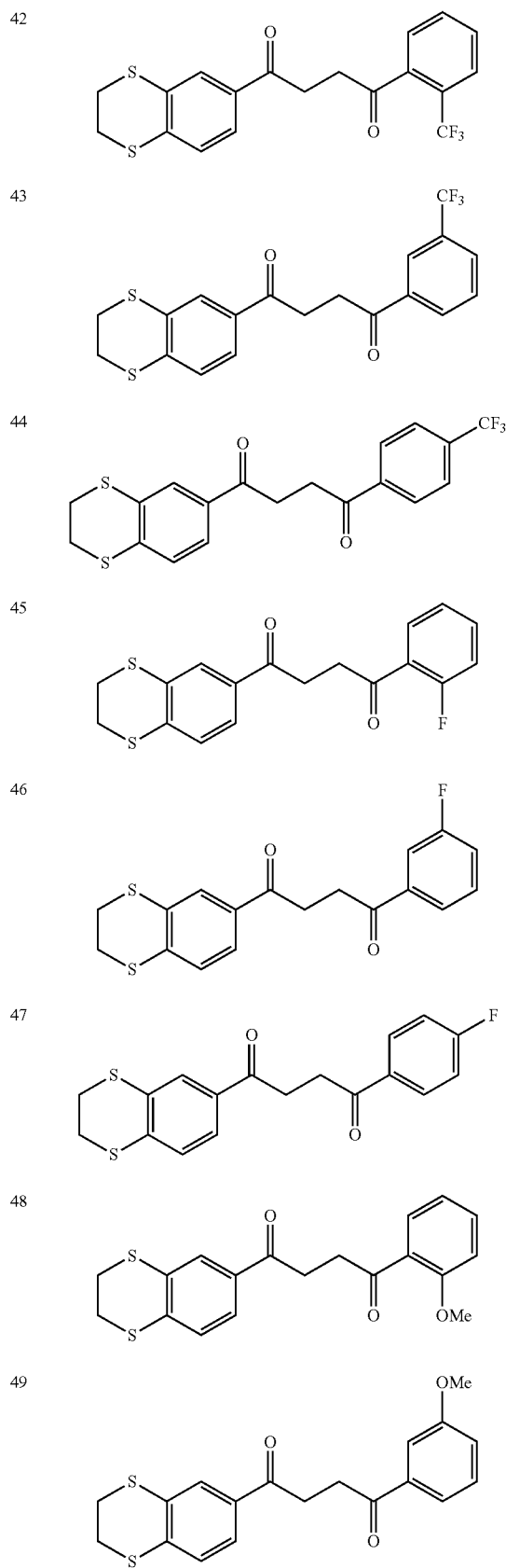
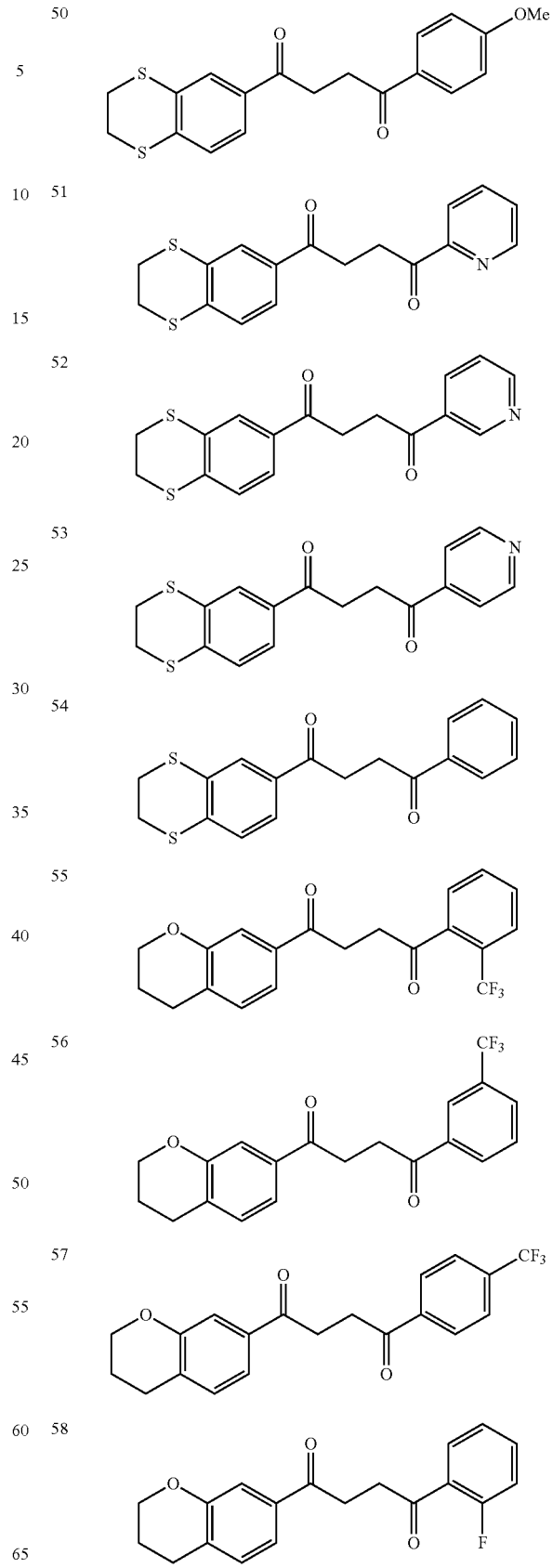

TABLE 1-continued
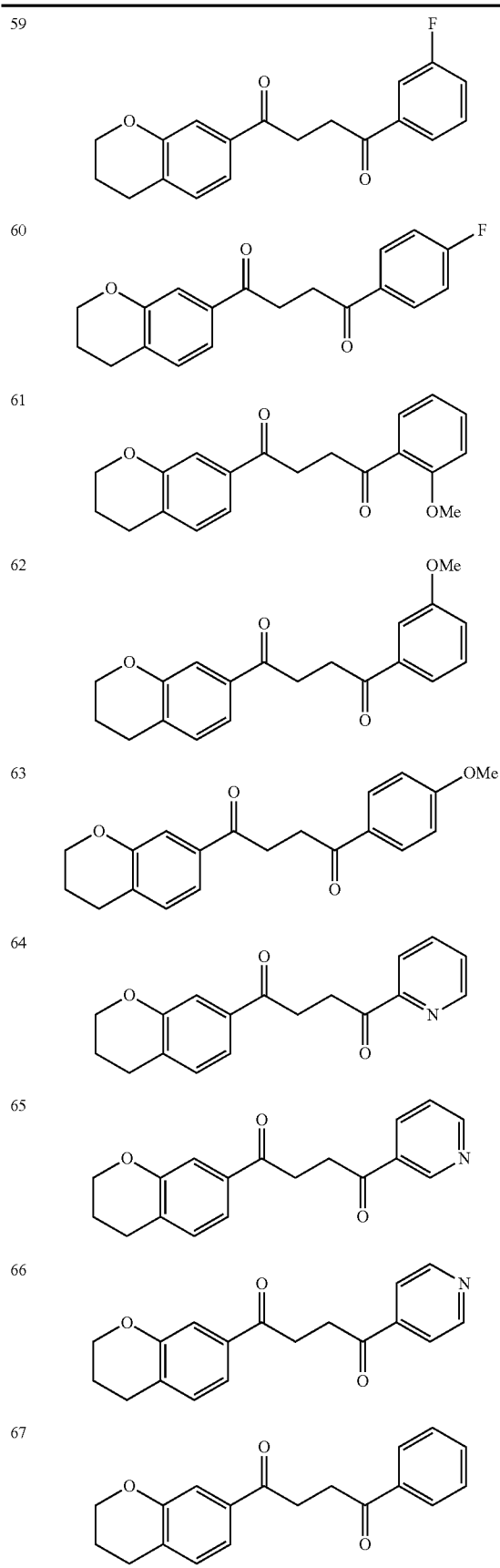
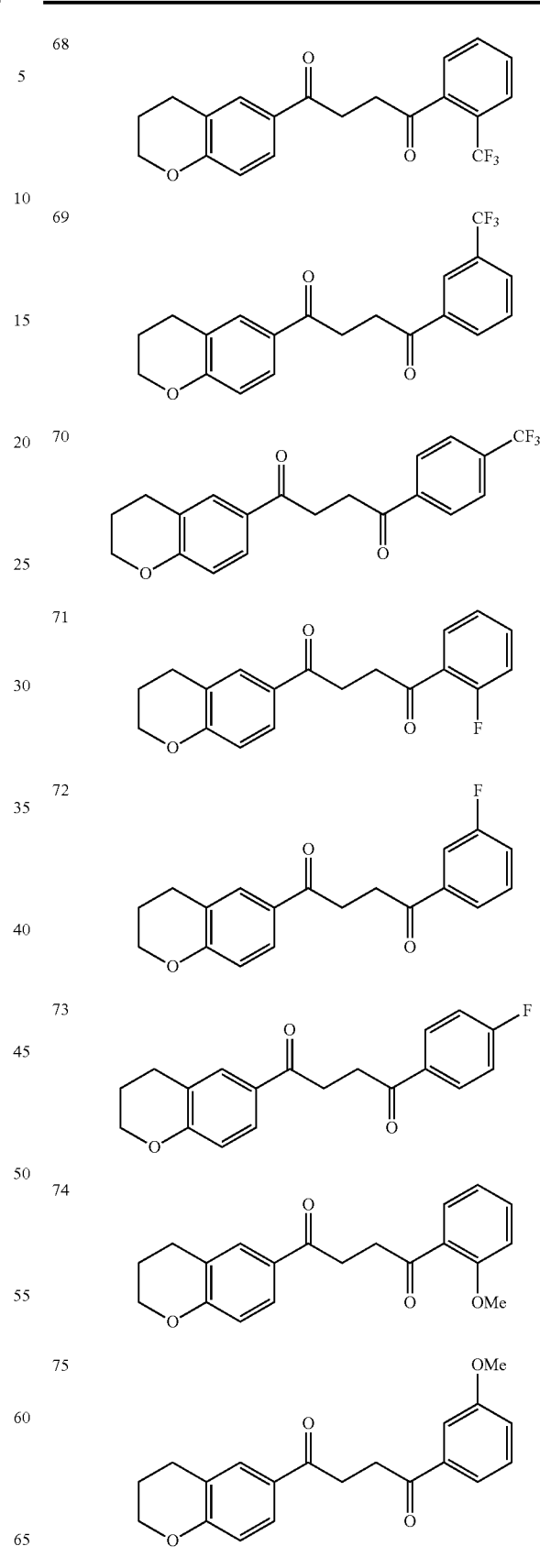

TABLE 1-continued
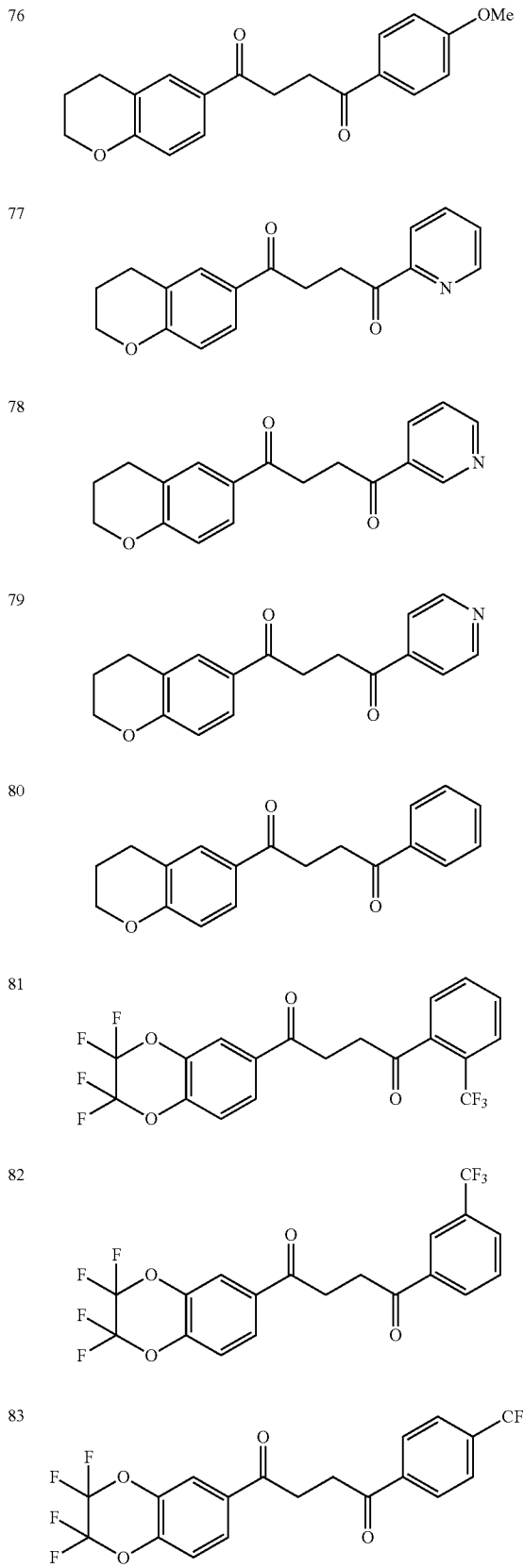
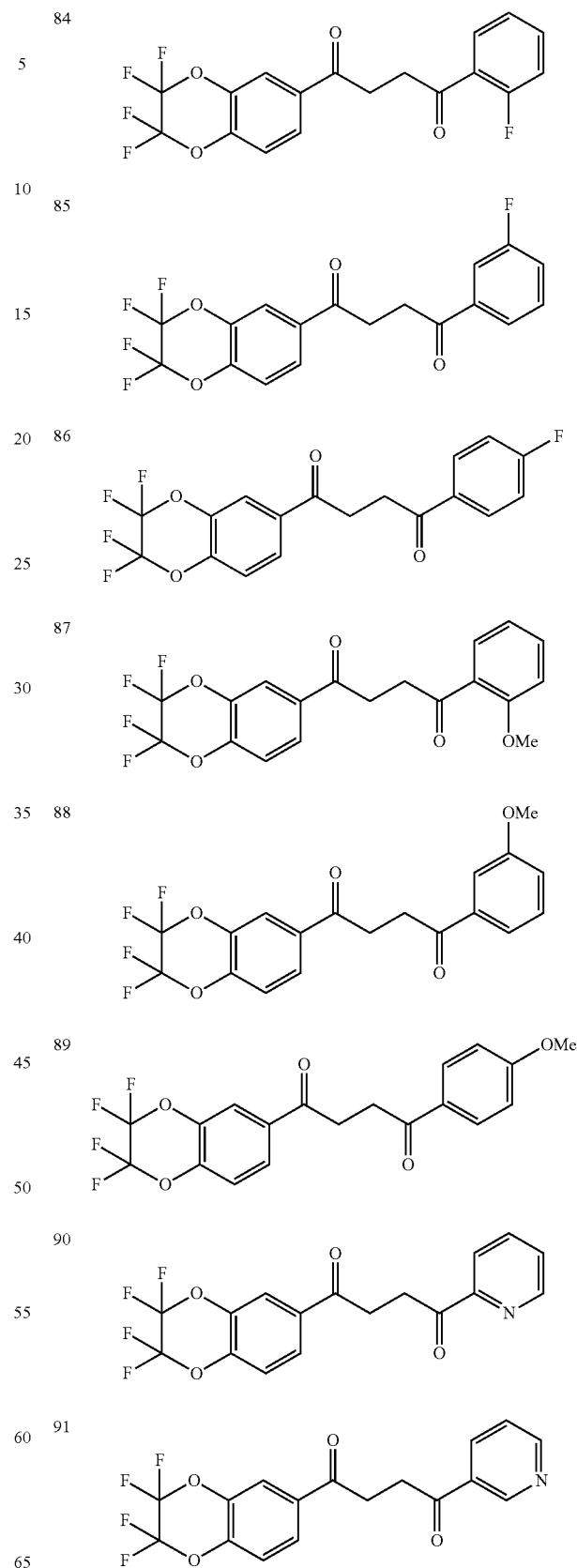

TABLE 1-continued
| | |
|---|---|
| 92 | 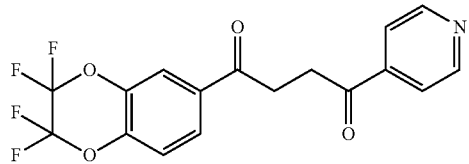 [SMILES: O=C(CCC(=O)c1ccc2c(c1)OC(F)(F)C(F)(F)O2)c1ccncc1] |
| 93 | 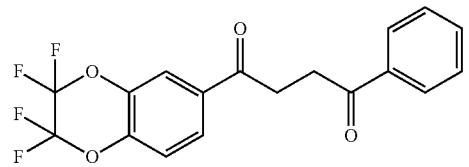 |
| 94 | 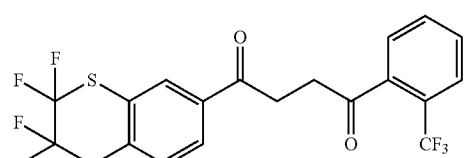 |
| 95 | 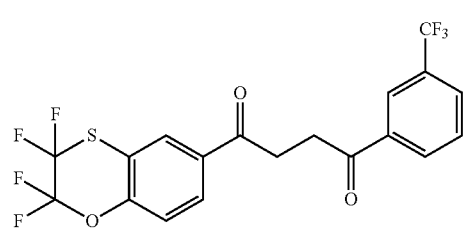 [SMILES: O=C(CCC(=O)c1ccc2c(c1)SC(F)(F)C(F)(F)O2)c1cccc(C(F)(F)F)c1] |
| 96 | 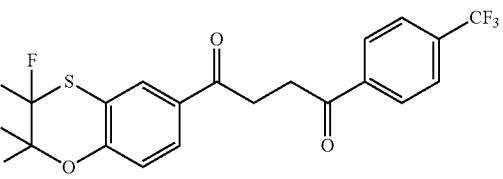 |
| 97 | 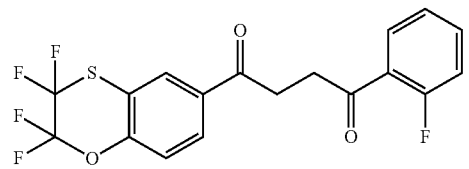 [SMILES: O=C(CCC(=O)c1ccccc1F)c1ccc2c(c1)SC(F)(F)C(F)(F)O2] |
| 98 | 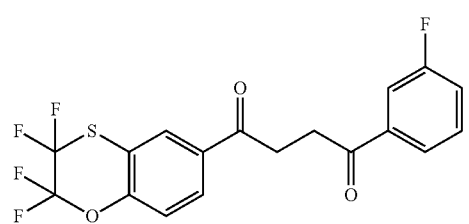 [SMILES: O=C(CCC(=O)c1ccc2c(c1)SC(F)(F)C(F)(F)O2)c1cccc(F)c1] |
| 99 | 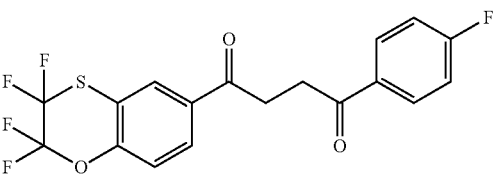 |
TABLE 1-continued
| | |
|---|---|
| 100 | 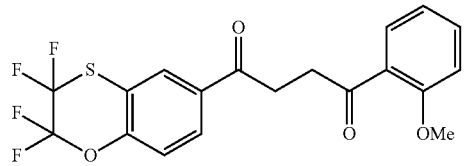 |
| 101 | 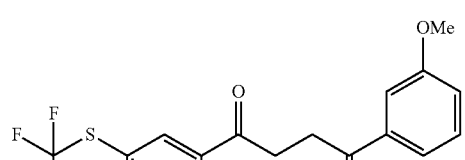 |
| 102 | 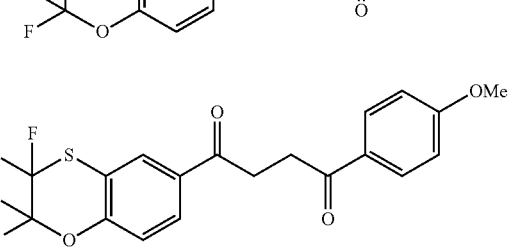 |
| 103 | 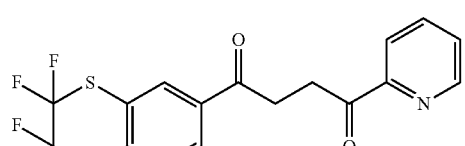 |
| 104 | 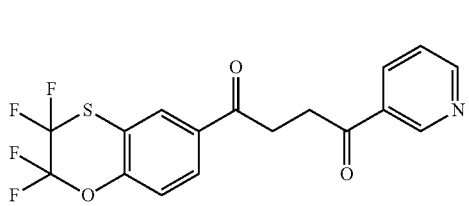 |
| 105 | 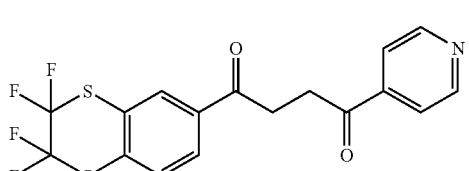 |
| 106 | 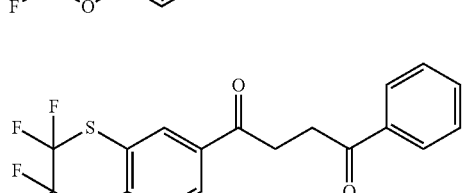 |
| 107 | 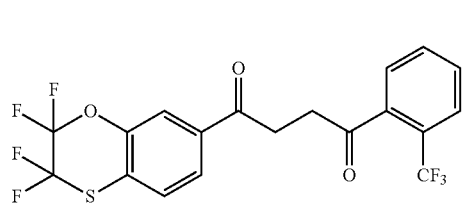 |

TABLE 1-continued
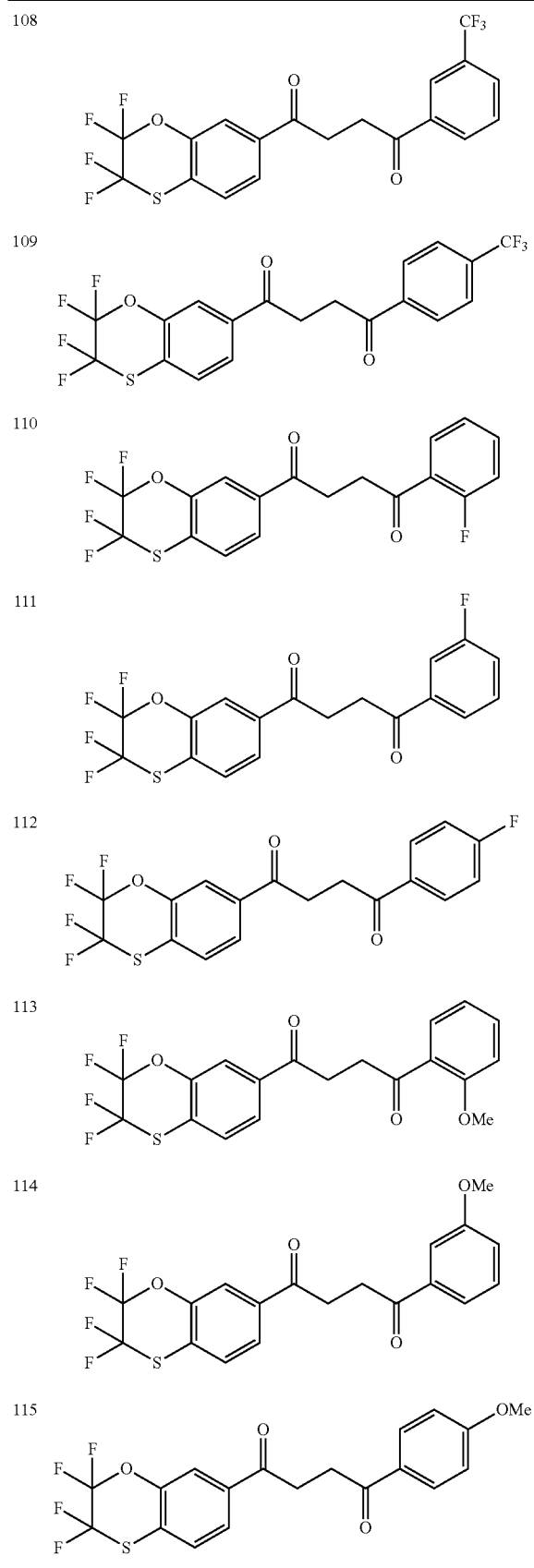
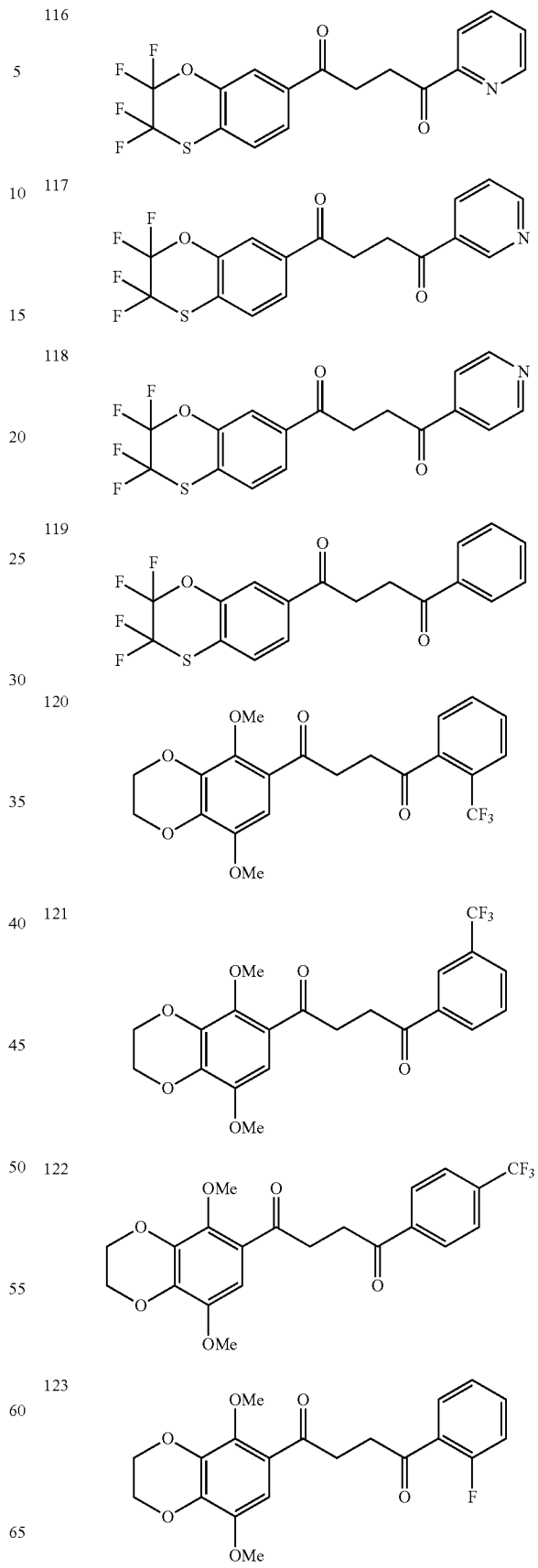

TABLE 1-continued
| | |
|---|---|
| 124 | 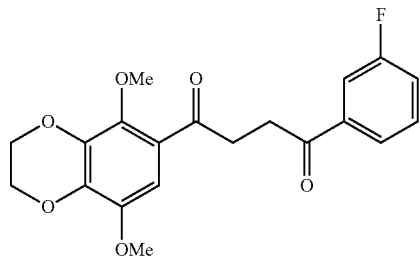 [SMILES: COc1cc(C(=O)CCC(=O)c2cccc(F)c2)c(OC)c2c1OCCO2] |
| 125 | 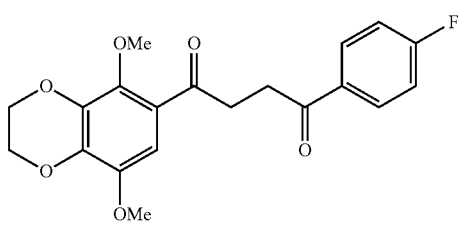 [SMILES: COc1cc(C(=O)CCC(=O)c2ccc(F)cc2)c(OC)c2c1OCCO2] |
| 126 | 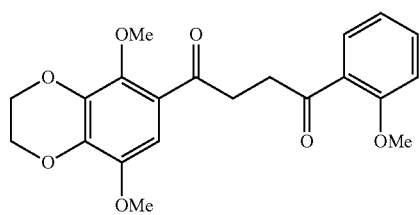 [SMILES: COc1ccccc1C(=O)CCC(=O)c1cc(OC)c2c(c1OC)OCCO2] |
| 127 | 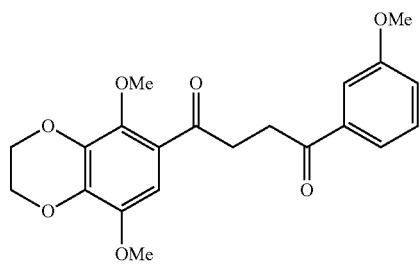 [SMILES: COc1cccc(C(=O)CCC(=O)c2cc(OC)c3c(c2OC)OCCO3)c1] |
| 128 | 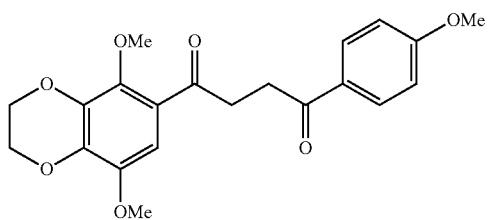 [SMILES: COc1ccc(C(=O)CCC(=O)c2cc(OC)c3c(c2OC)OCCO3)cc1] |
| 129 | 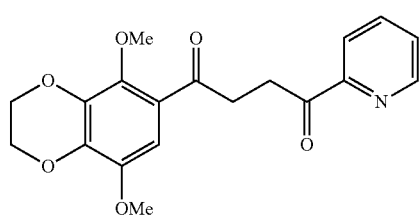 [SMILES: COc1cc(C(=O)CCC(=O)c2ccccn2)c(OC)c2c1OCCO2] |
| 130 | 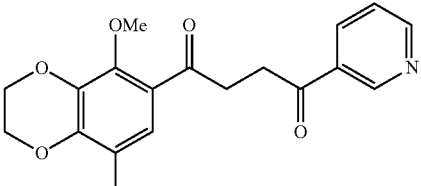 |
| 131 | 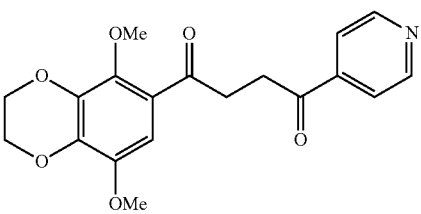 [SMILES: COc1cc(C(=O)CCC(=O)c2ccncc2)c(OC)c2c1OCCO2] |
| 132 | 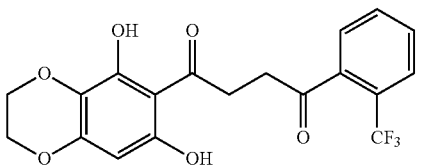 [SMILES: O=C(CCC(=O)c1c(O)cc2c(c1O)OCCO2)c1ccccc1C(F)(F)F] |
| 133 | 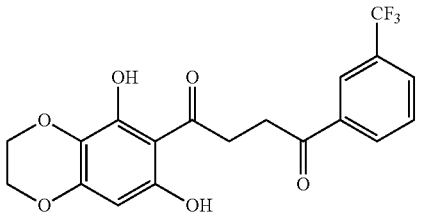 [SMILES: O=C(CCC(=O)c1c(O)cc2c(c1O)OCCO2)c1cccc(C(F)(F)F)c1] |
| 134 | 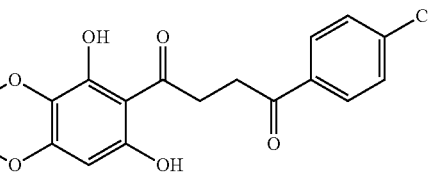 |
| 135 | 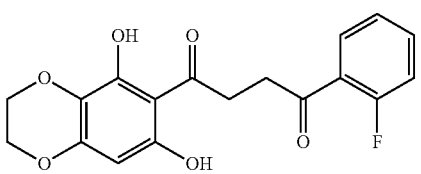 |
| 136 | 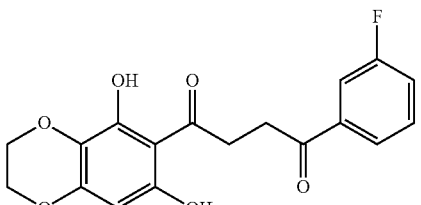 |
| 137 | 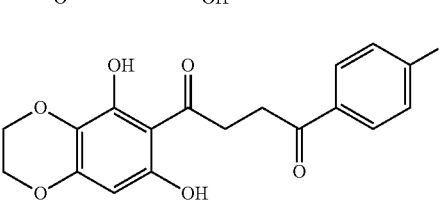 |

TABLE 1-continued
| | | | |
|---|---|---|---|
| 138 | 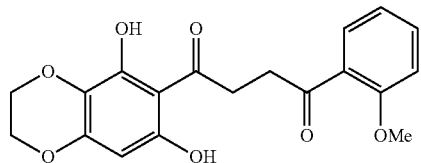 [SMILES: COc1ccccc1C(=O)CCC(=O)c1c(O)cc2c(c1O)OCCO2] | 146 | 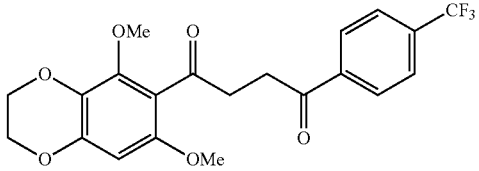 |
| 139 | 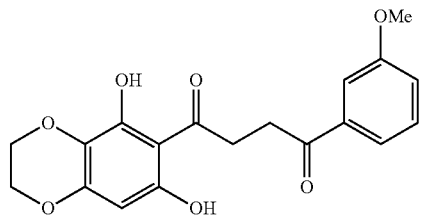 [SMILES: COc1cccc(C(=O)CCC(=O)c2c(O)cc3c(c2O)OCCO3)c1] | 147 | 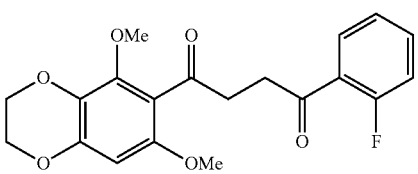 |
| 140 | 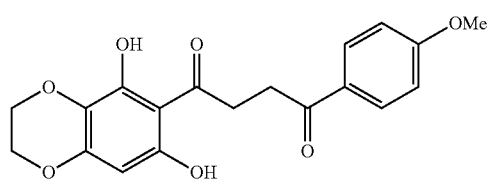 [SMILES: COc1ccc(C(=O)CCC(=O)c2c(O)cc3c(c2O)OCCO3)cc1] | 148 | 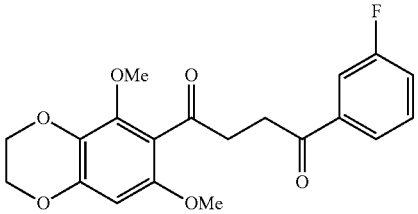 |
| 141 | 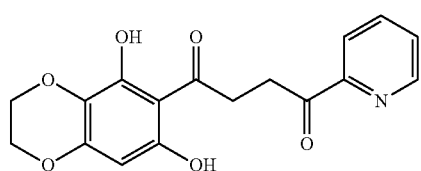 [SMILES: O=C(CCC(=O)c1c(O)cc2c(c1O)OCCO2)c1ccccn1] | 149 | 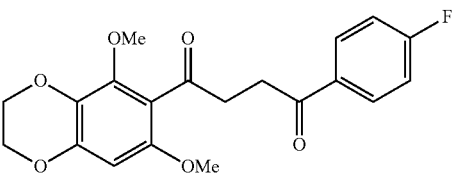 |
| 142 | 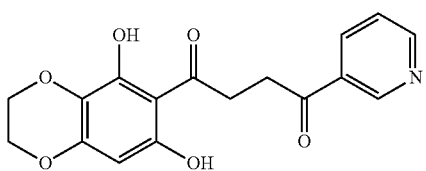 [SMILES: O=C(CCC(=O)c1c(O)cc2c(c1O)OCCO2)c1cccnc1] | 150 | 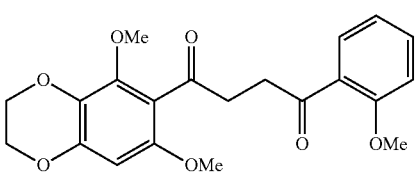 |
| 143 | 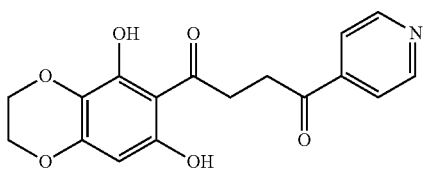 [SMILES: O=C(CCC(=O)c1c(O)cc2c(c1O)OCCO2)c1ccncc1] | 151 | 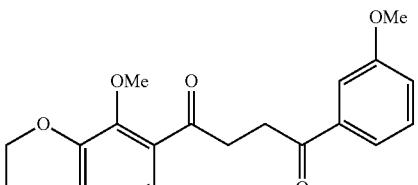 |
| 144 | 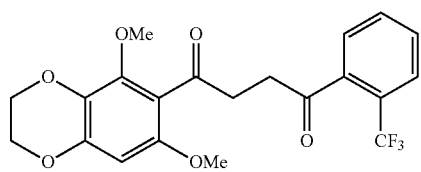 [SMILES: COc1cc2c(c(OC)c1C(=O)CCC(=O)c1ccccc1C(F)(F)F)OCCO2] | 152 | 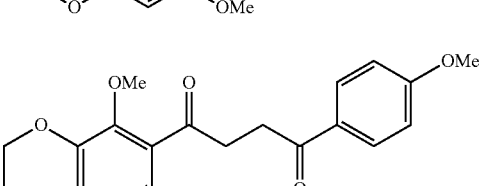 |
| 145 | 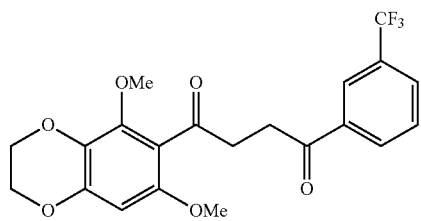 [SMILES: COc1cc2c(c(OC)c1C(=O)CCC(=O)c1cccc(C(F)(F)F)c1)OCCO2] | 153 | 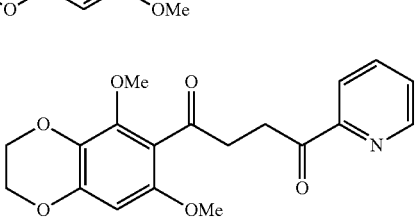 |

TABLE 1-continued
| 154 | 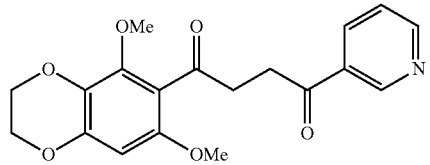 [SMILES: COc1cc2c(c(OC)c1C(=O)CCC(=O)c1cccnc1)OCCO2] |
| 155 | 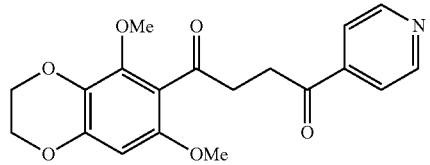 |
| 156 | 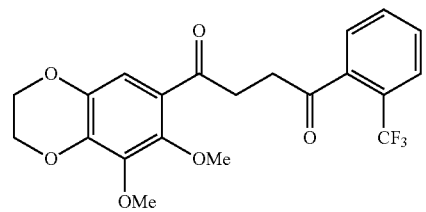 [SMILES: COc1c(C(=O)CCC(=O)c2ccccc2C(F)(F)F)cc2c(c1OC)OCCO2] |
| 157 | 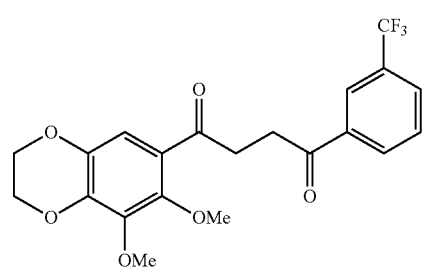 |
| 158 | 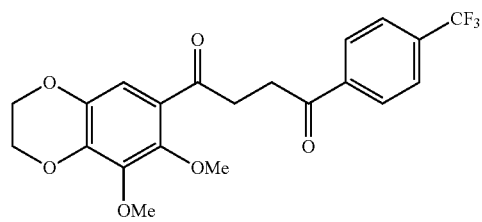 [SMILES: COc1c(C(=O)CCC(=O)c2ccc(C(F)(F)F)cc2)cc2c(c1OC)OCCO2] |
| 159 | 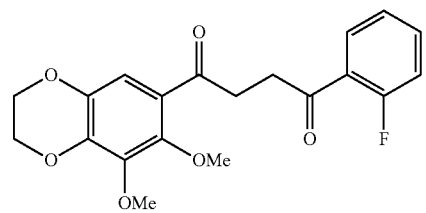 [SMILES: COc1c(C(=O)CCC(=O)c2ccccc2F)cc2c(c1OC)OCCO2] |
| 160 | 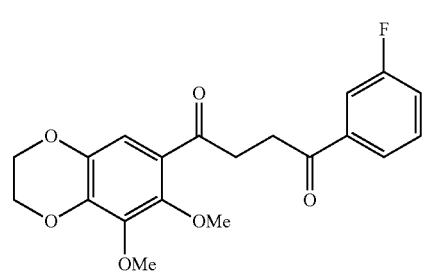 [SMILES: COc1c(C(=O)CCC(=O)c2cccc(F)c2)cc2c(c1OC)OCCO2] |
TABLE 1-continued
| 161 | 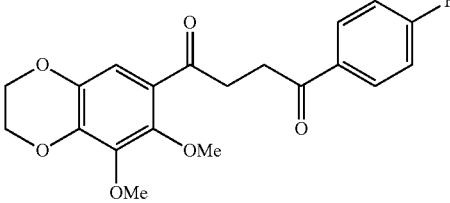 |
| 162 | 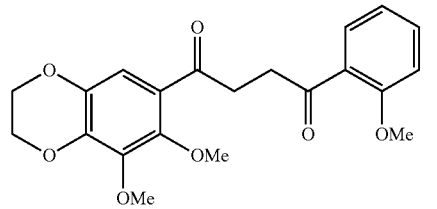 [SMILES: COc1ccccc1C(=O)CCC(=O)c1cc2c(c(OC)c1OC)OCCO2] |
| 163 | 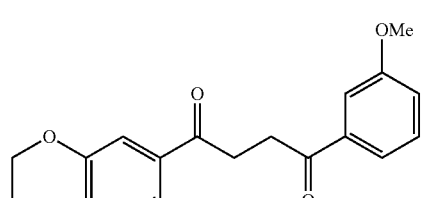 |
| 164 | 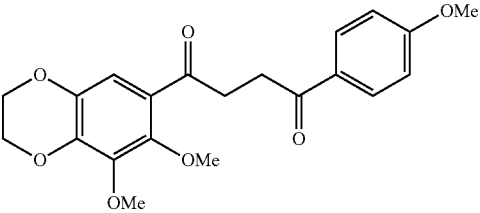 [SMILES: COc1ccc(C(=O)CCC(=O)c2cc3c(c(OC)c2OC)OCCO3)cc1] |
| 165 | 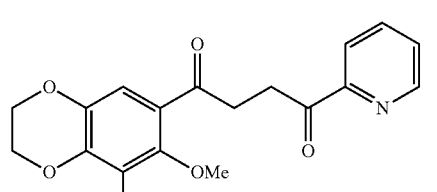 |
| 166 | 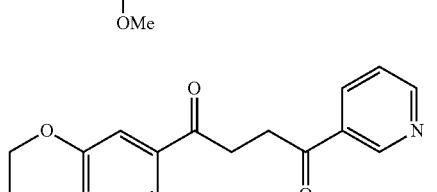 |
| 167 | 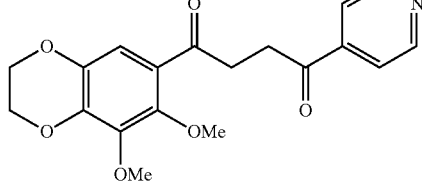 |

TABLE 1-continued
168 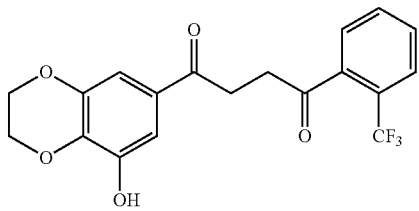 [SMILES: O=C(CCC(=O)c1ccccc1C(F)(F)F)c1cc(O)c2c(c1)OCCO2]
169 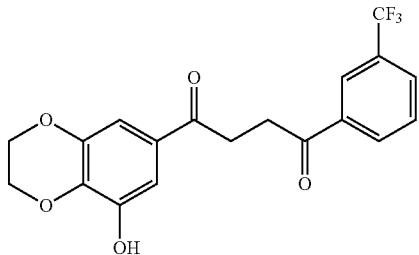 [SMILES: O=C(CCC(=O)c1cc(O)c2c(c1)OCCO2)c1cccc(C(F)(F)F)c1]
170 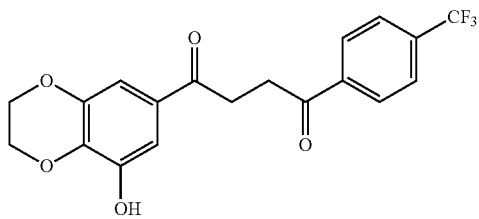 [SMILES: O=C(CCC(=O)c1cc(O)c2c(c1)OCCO2)c1ccc(C(F)(F)F)cc1]
171 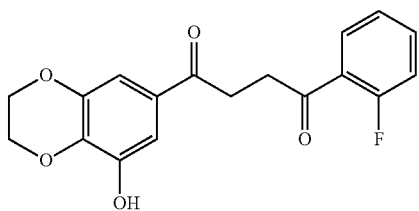 [SMILES: O=C(CCC(=O)c1ccccc1F)c1cc(O)c2c(c1)OCCO2]
172 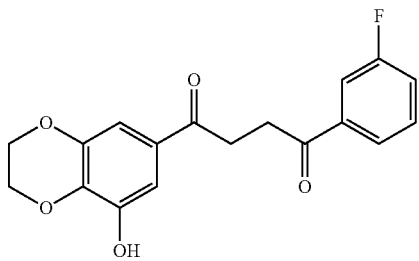 [SMILES: O=C(CCC(=O)c1cc(O)c2c(c1)OCCO2)c1cccc(F)c1]
173 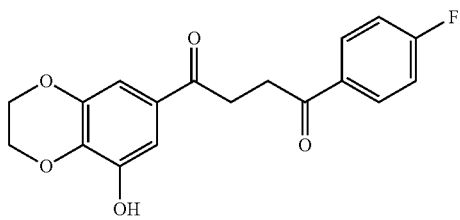 [SMILES: O=C(CCC(=O)c1cc(O)c2c(c1)OCCO2)c1ccc(F)cc1]
174 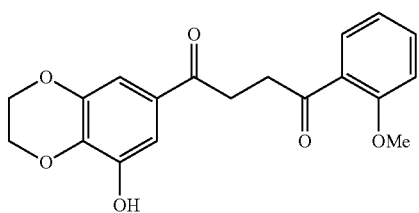 [SMILES: COc1ccccc1C(=O)CCC(=O)c1cc(O)c2c(c1)OCCO2]
TABLE 1-continued
175 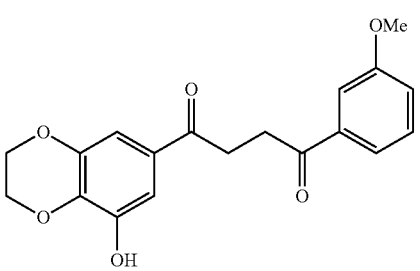 [SMILES: COc1cccc(C(=O)CCC(=O)c2cc(O)c3c(c2)OCCO3)c1]
176 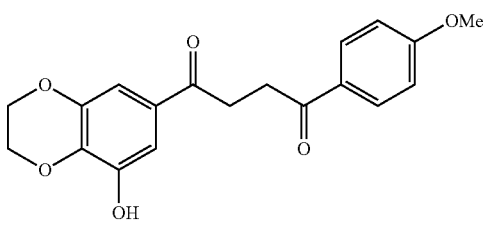 [SMILES: COc1ccc(C(=O)CCC(=O)c2cc(O)c3c(c2)OCCO3)cc1]
177 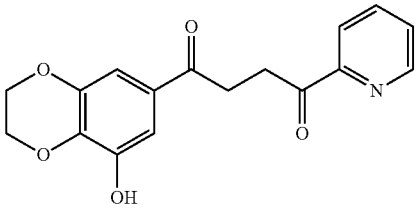 [SMILES: O=C(CCC(=O)c1ccccn1)c1cc(O)c2c(c1)OCCO2]
178 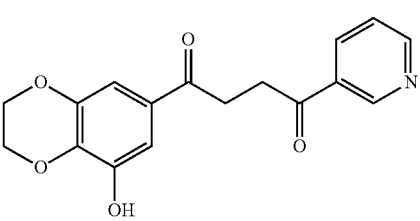 [SMILES: O=C(CCC(=O)c1cc(O)c2c(c1)OCCO2)c1cccnc1]
179 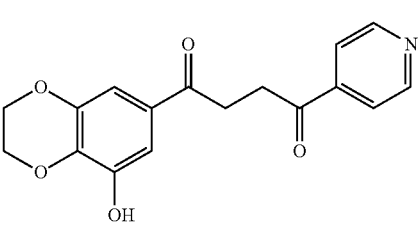 [SMILES: O=C(CCC(=O)c1cc(O)c2c(c1)OCCO2)c1ccncc1]
180 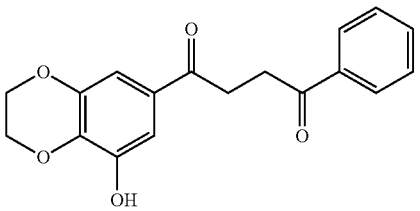 [SMILES: O=C(CCC(=O)c1cc(O)c2c(c1)OCCO2)c1ccccc1]
181 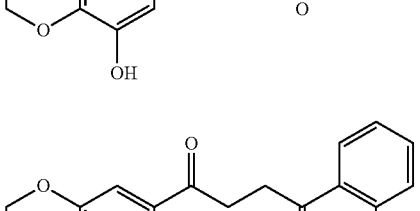

TABLE 1-continued
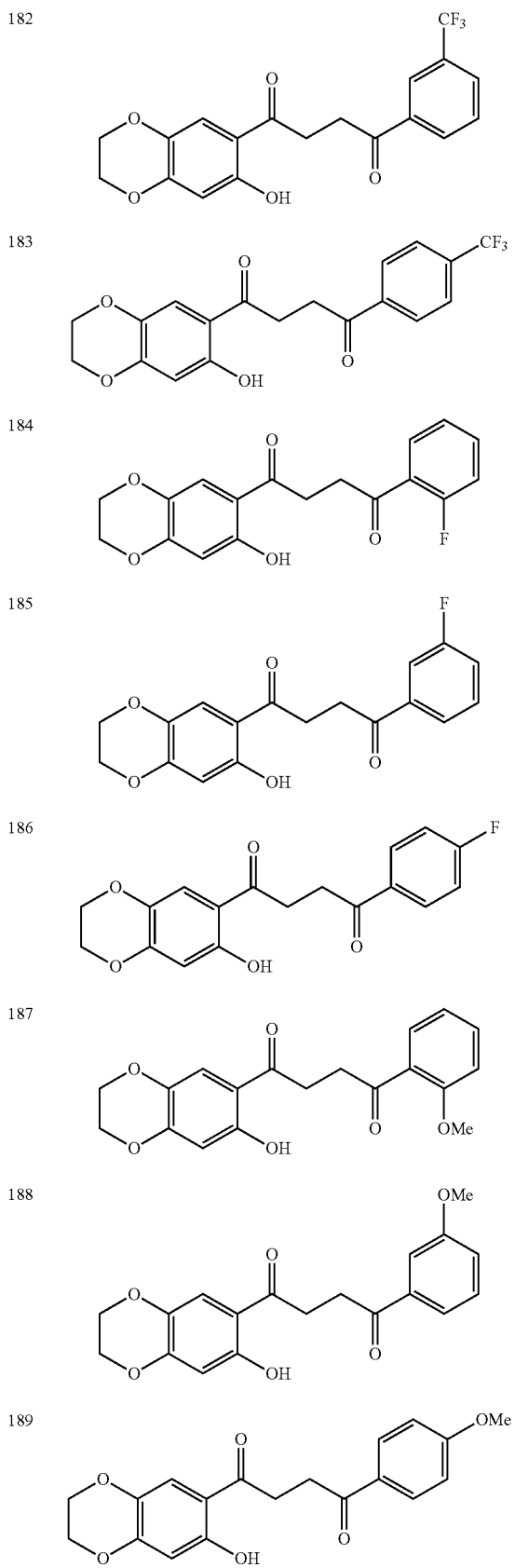
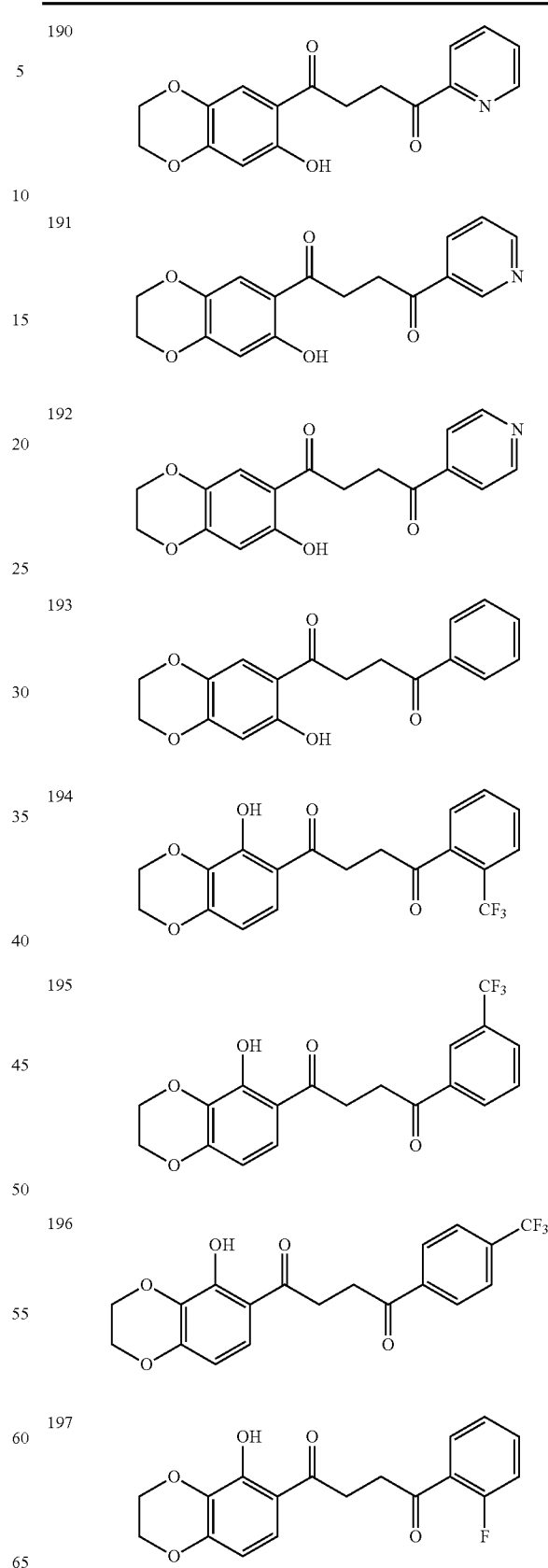

TABLE 1-continued
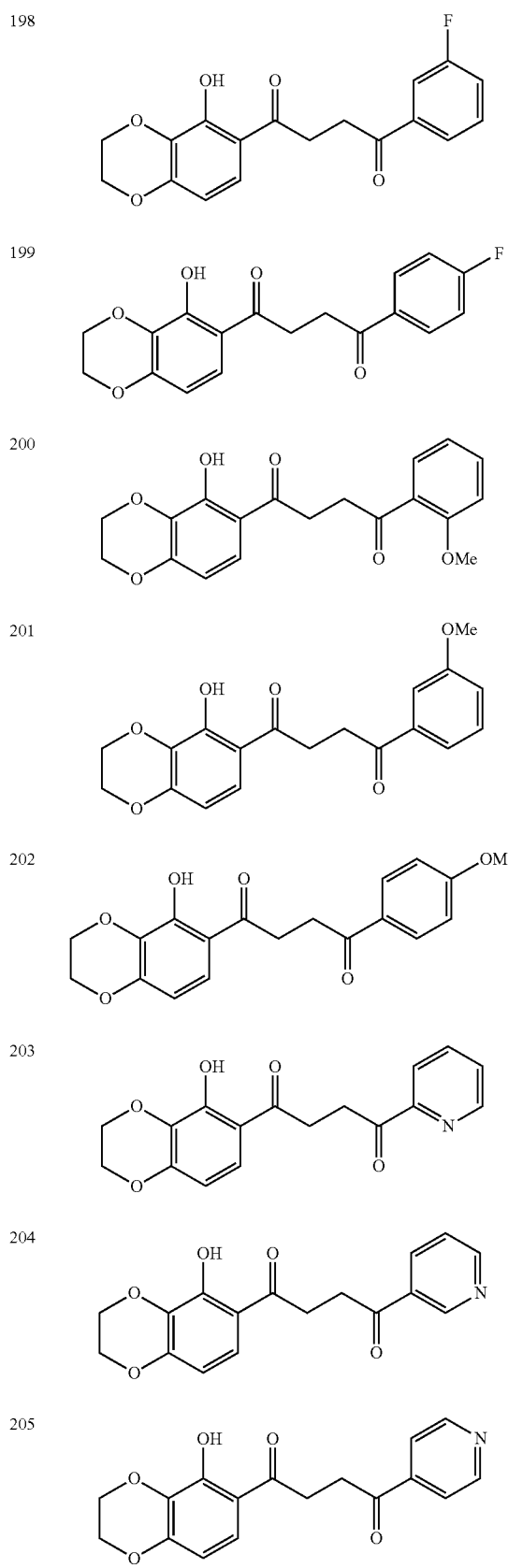
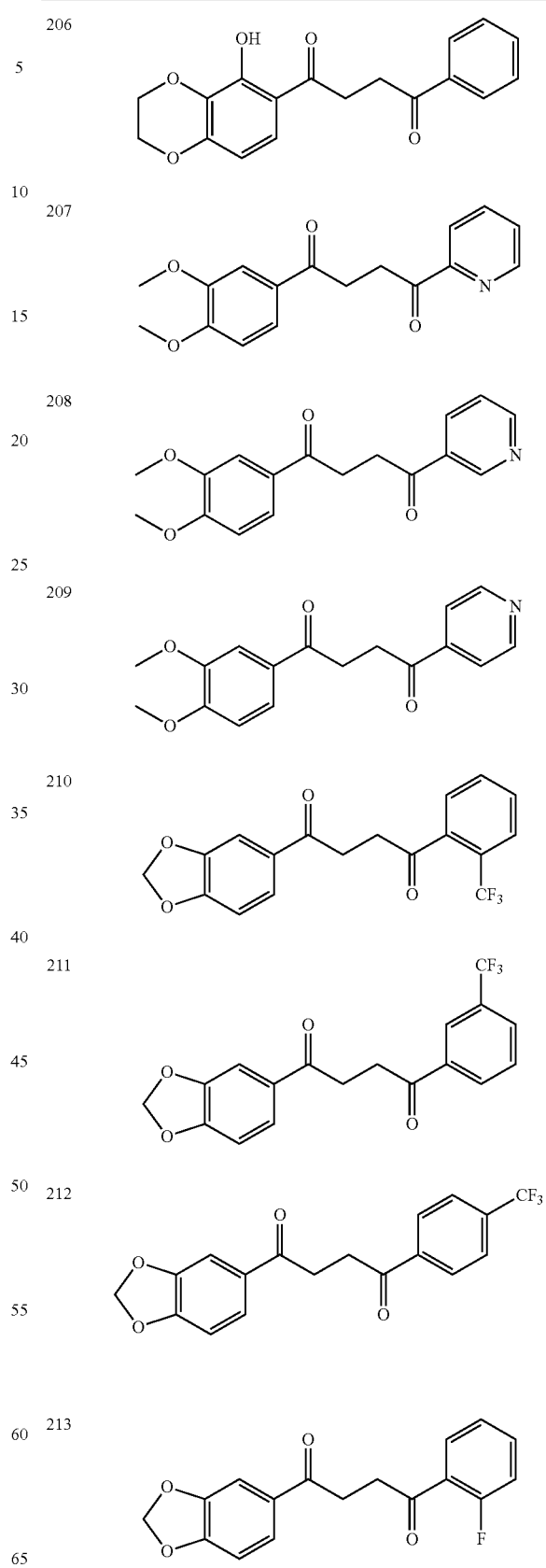

TABLE 1-continued
| 214 | 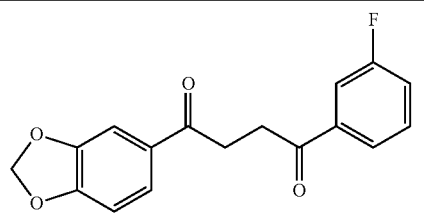 |
| --- | --- |
| 215 | 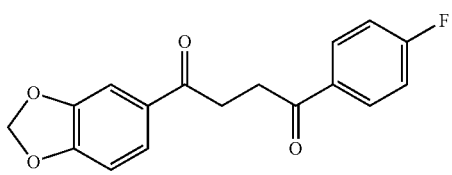 [SMILES: O=C(CCC(=O)c1ccc2c(c1)OCO2)c1ccc(F)cc1] |
| 216 | 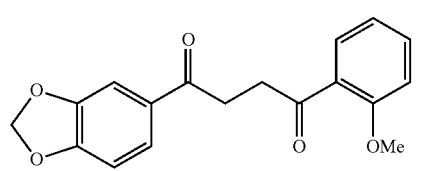 |
| 217 | 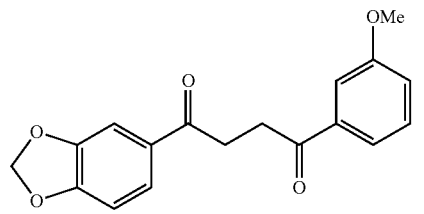 [SMILES: COc1cccc(C(=O)CCC(=O)c2ccc3c(c2)OCO3)c1] |
| 218 | 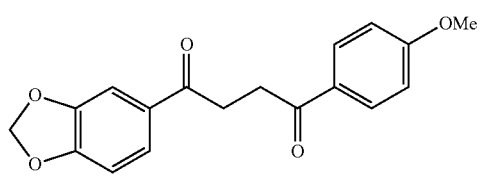 [SMILES: COc1ccc(C(=O)CCC(=O)c2ccc3c(c2)OCO3)cc1] |
| 219 | 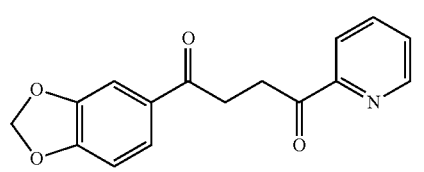 |
| 220 | 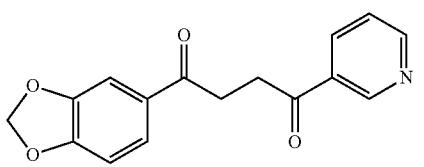 [SMILES: O=C(CCC(=O)c1ccc2c(c1)OCO2)c1cccnc1] |
| 221 | 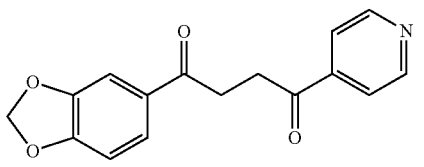 [SMILES: O=C(CCC(=O)c1ccc2c(c1)OCO2)c1ccncc1] |
| 222 | 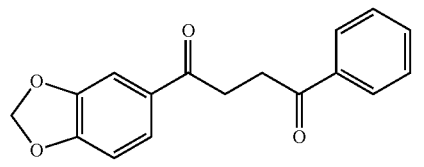 [SMILES: O=C(CCC(=O)c1ccc2c(c1)OCO2)c1ccccc1] |
| 223 | 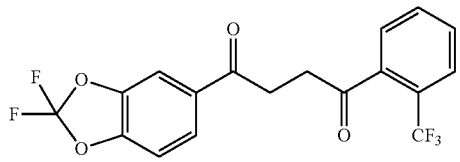 [SMILES: O=C(CCC(=O)c1ccccc1C(F)(F)F)c1ccc2c(c1)OC(F)(F)O2] |
| 224 | 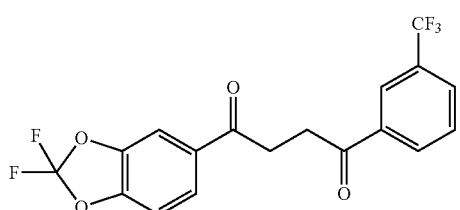 |
| 225 | 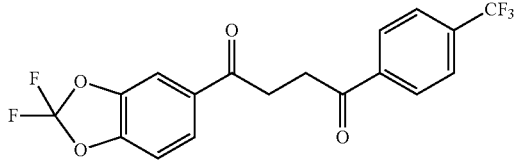 [SMILES: O=C(CCC(=O)c1ccc2c(c1)OC(F)(F)O2)c1ccc(C(F)(F)F)cc1] |
| 226 | 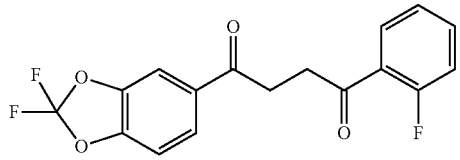 [SMILES: O=C(CCC(=O)c1ccccc1F)c1ccc2c(c1)OC(F)(F)O2] |
| 227 | 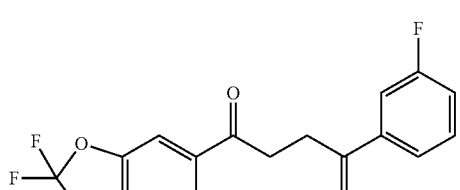 |
| 228 | 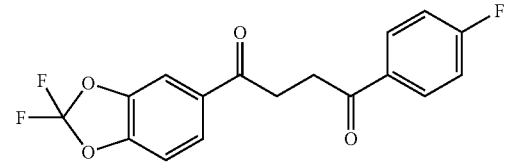 [SMILES: O=C(CCC(=O)c1ccc2c(c1)OC(F)(F)O2)c1ccc(F)cc1] |
| 229 | 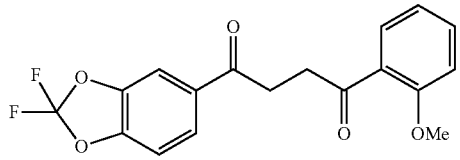 [SMILES: COc1ccccc1C(=O)CCC(=O)c1ccc2c(c1)OC(F)(F)O2] |
| 230 | 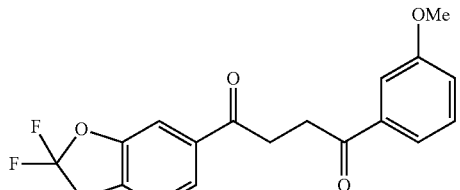 |

TABLE 1-continued
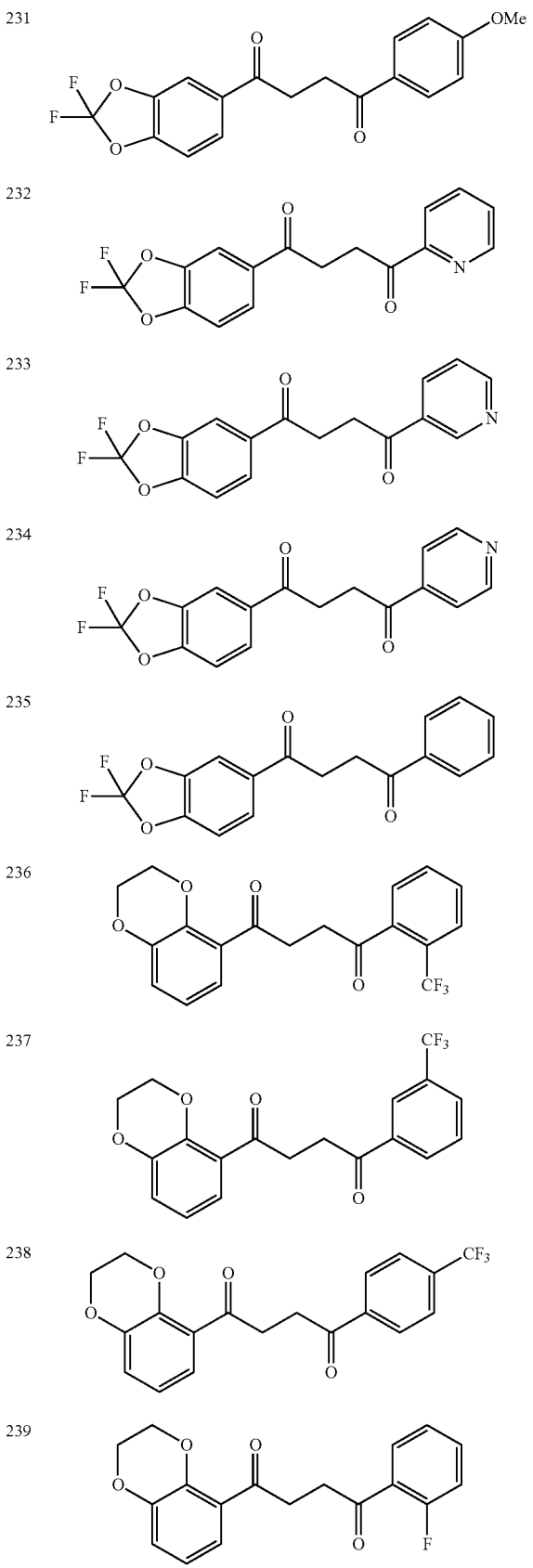
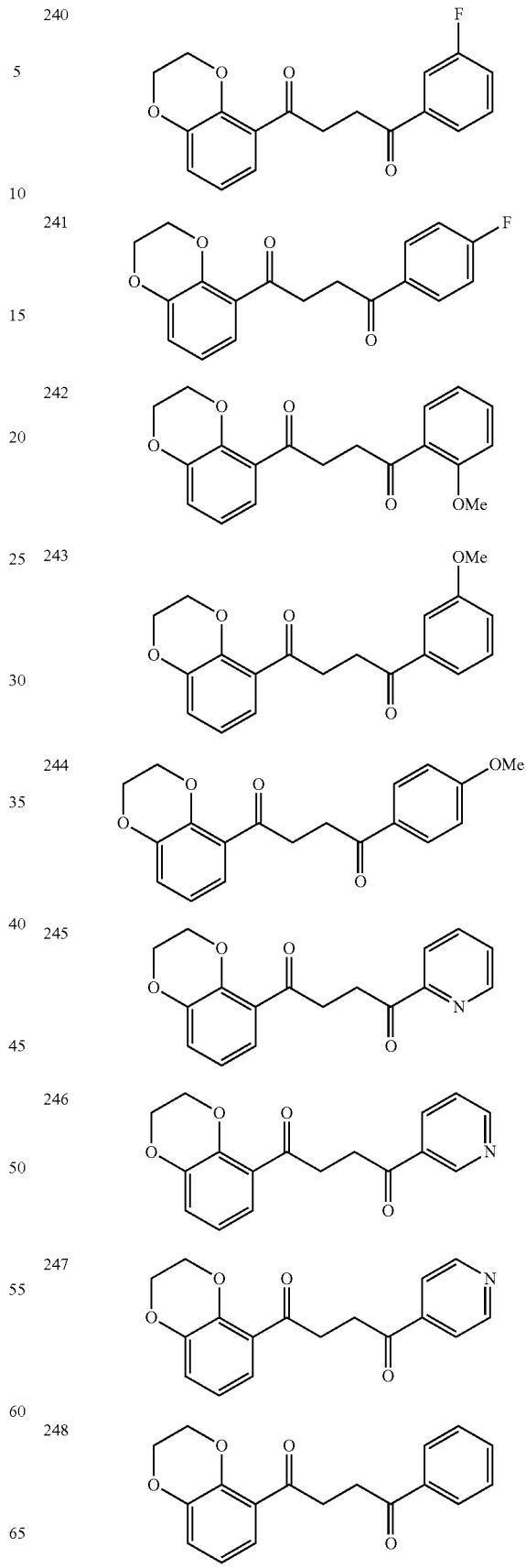

TABLE 1-continued
249 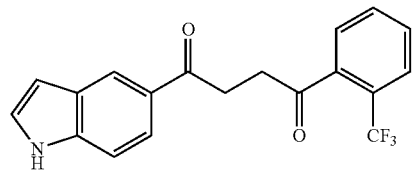
250 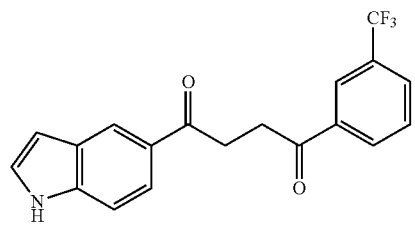
251 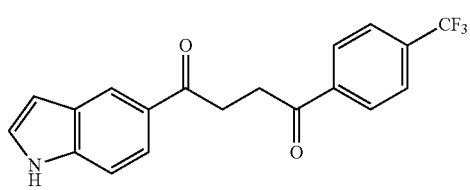 [SMILES: O=C(CCC(=O)c1ccc2[nH]ccc2c1)c1ccc(C(F)(F)F)cc1]
252 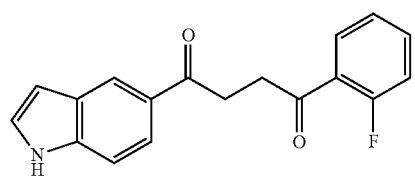
253 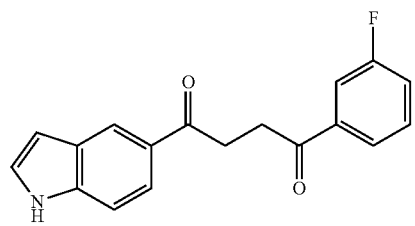
254 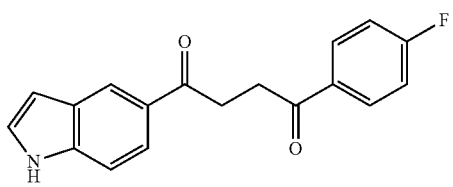 [SMILES: O=C(CCC(=O)c1ccc2[nH]ccc2c1)c1ccc(F)cc1]
255 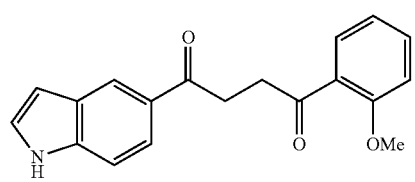 [SMILES: COc1ccccc1C(=O)CCC(=O)c1ccc2[nH]ccc2c1]
256 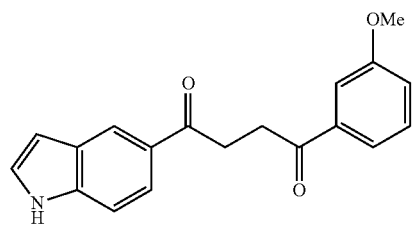 [SMILES: COc1cccc(C(=O)CCC(=O)c2ccc3[nH]ccc3c2)c1]
TABLE 1-continued
257 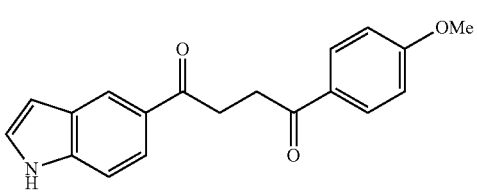 [SMILES: COc1ccc(C(=O)CCC(=O)c2ccc3[nH]ccc3c2)cc1]
258 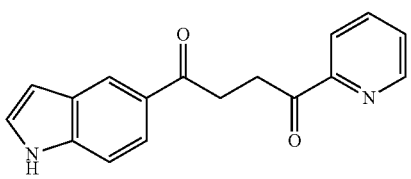
259 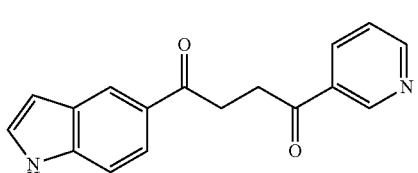
260 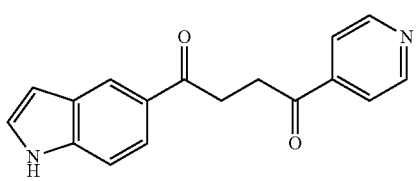 [SMILES: O=C(CCC(=O)c1ccc2[nH]ccc2c1)c1ccncc1]
261 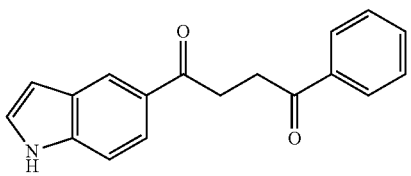 [SMILES: O=C(CCC(=O)c1ccc2[nH]ccc2c1)c1ccccc1]
262 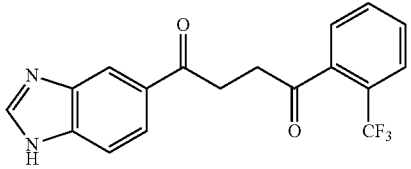
263 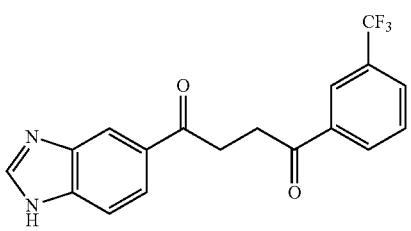 [SMILES: O=C(CCC(=O)c1ccc2[nH]cnc2c1)c1cccc(C(F)(F)F)c1]
264 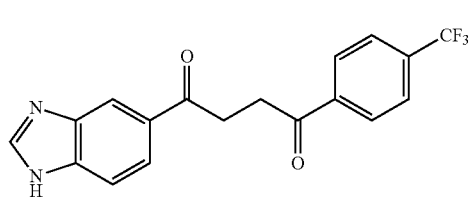

TABLE 1-continued
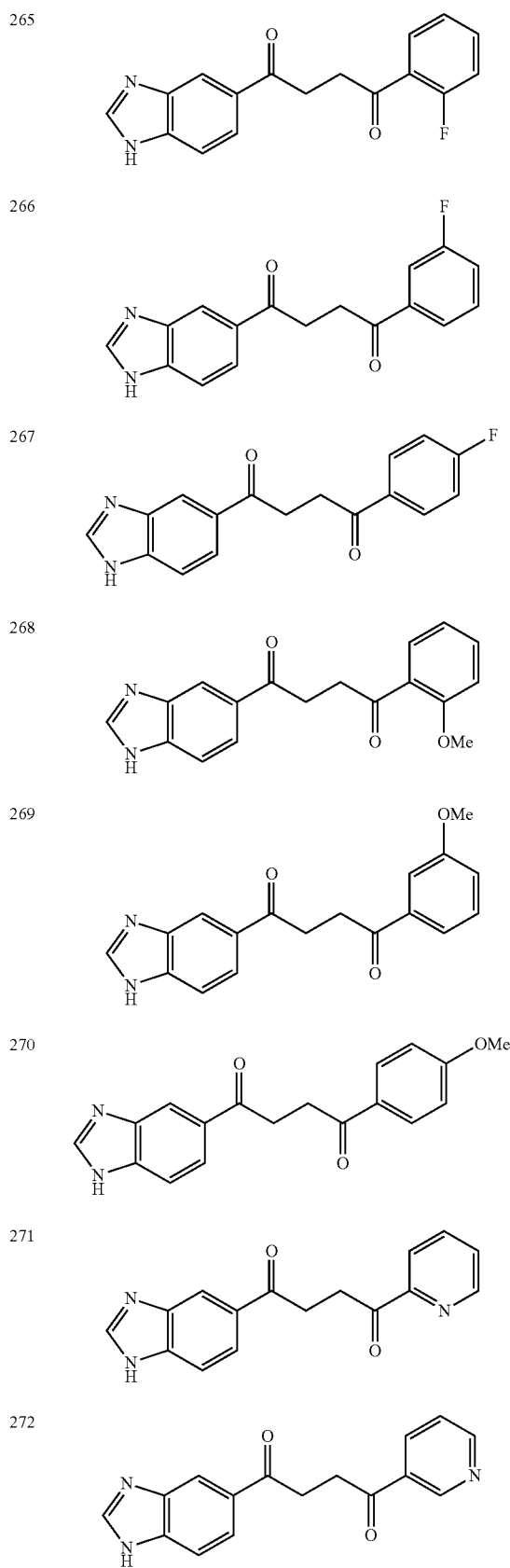
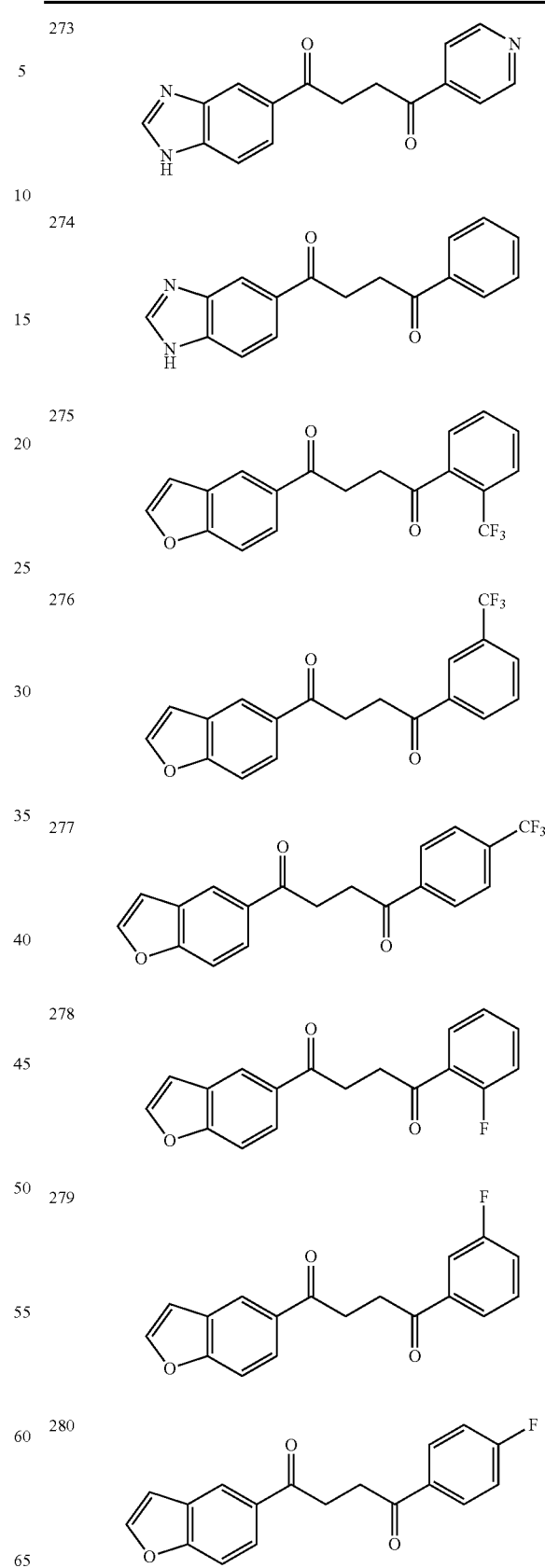

TABLE 1-continued
| | |
|---|---|
| 281 | 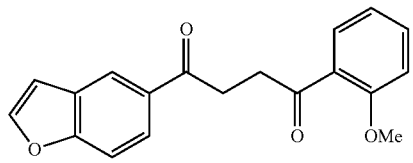 [SMILES: COc1ccccc1C(=O)CCC(=O)c1ccc2occc2c1] |
| 282 | 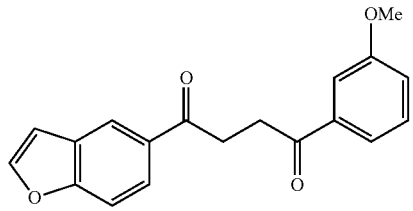 |
| 283 | 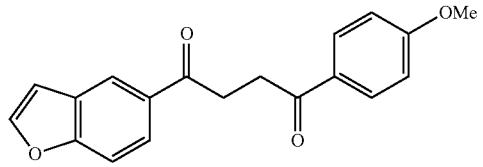 [SMILES: COc1ccc(C(=O)CCC(=O)c2ccc3occc3c2)cc1] |
| 284 | 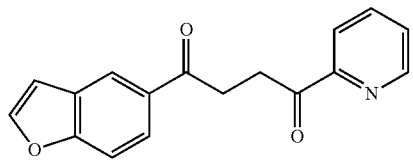 |
| 285 | 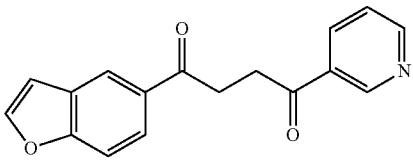 [SMILES: O=C(CCC(=O)c1ccc2occc2c1)c1cccnc1] |
| 286 | 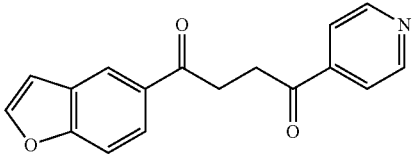 |
| 287 | 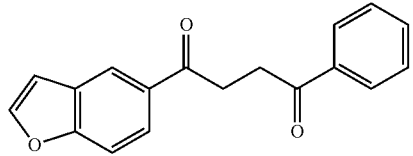 |
| 288 | 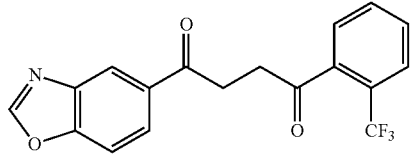 |
| 289 | 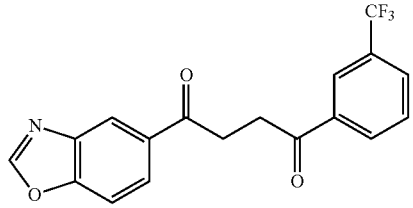 |
| 290 | 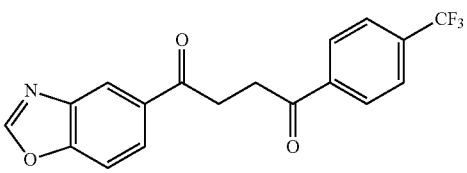 [SMILES: O=C(CCC(=O)c1ccc2ocnc2c1)c1ccc(C(F)(F)F)cc1] |
| 291 | 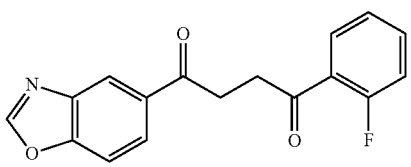 |
| 292 | 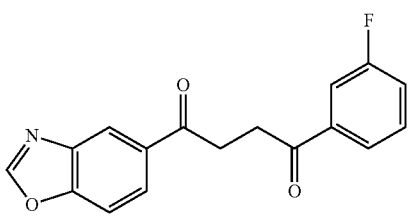 [SMILES: O=C(CCC(=O)c1ccc2ocnc2c1)c1cccc(F)c1] |
| 293 | 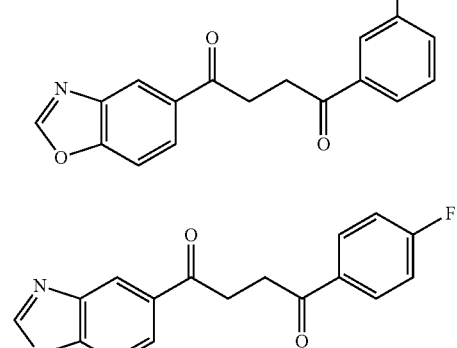 |
| 294 | 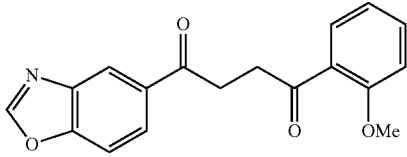 |
| 295 | 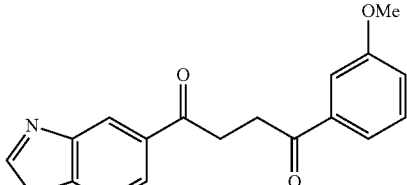 |
| 296 | 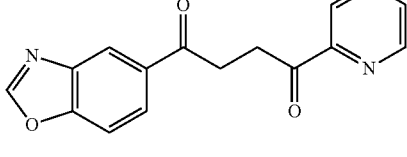 |
| 297 | 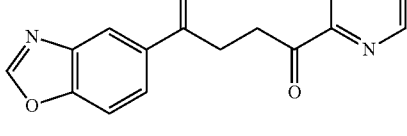 |

TABLE 1-continued
| | |
|---|---|
| 298 | 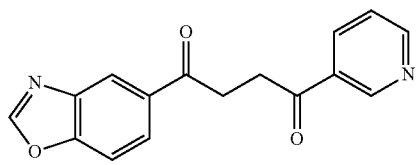 [SMILES: O=C(CCC(=O)c1ccc2ocnc2c1)c1cccnc1] |
| 299 | 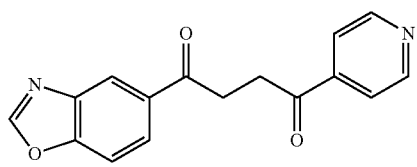 [SMILES: O=C(CCC(=O)c1ccc2ocnc2c1)c1ccncc1] |
| 300 | 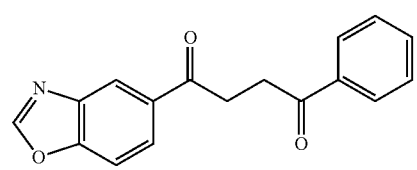 [SMILES: O=C(CCC(=O)c1ccc2ocnc2c1)c1ccccc1] |
| 301 | 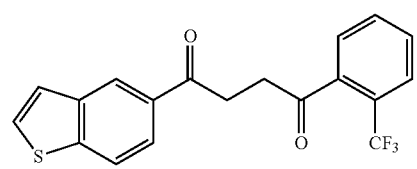 |
| 302 | 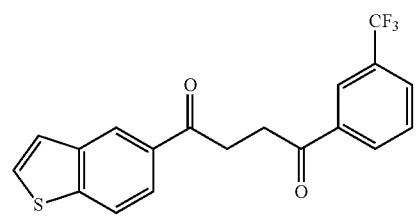 [SMILES: O=C(CCC(=O)c1ccc2sccc2c1)c1cccc(C(F)(F)F)c1] |
| 303 | 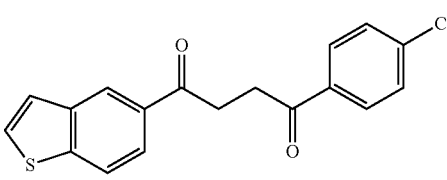 |
| 304 | 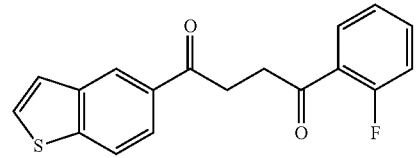 [SMILES: O=C(CCC(=O)c1ccccc1F)c1ccc2sccc2c1] |
| 305 | 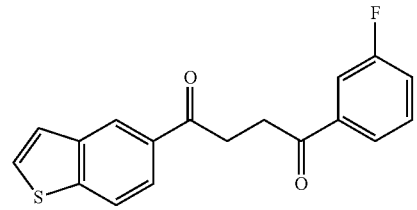 [SMILES: O=C(CCC(=O)c1ccc2sccc2c1)c1cccc(F)c1] |
| 306 | 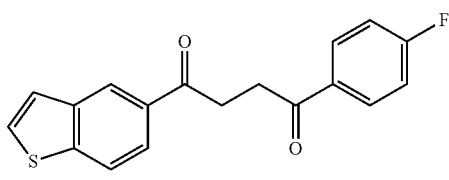 |
TABLE 1-continued
| | |
|---|---|
| 307 | 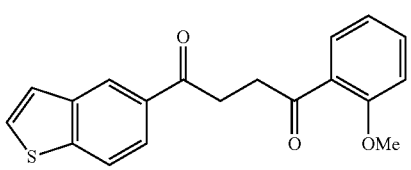 [SMILES: COc1ccccc1C(=O)CCC(=O)c1ccc2sccc2c1] |
| 308 | 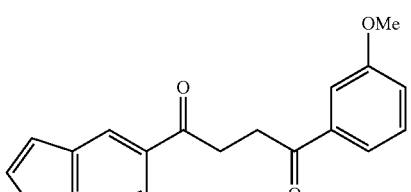 |
| 309 | 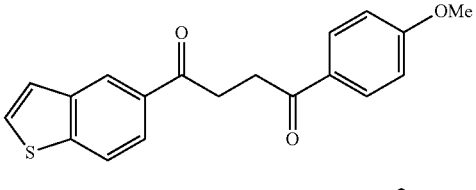 |
| 310 | 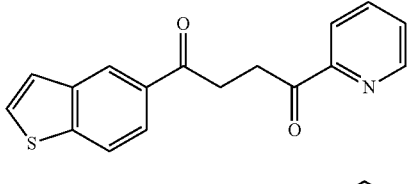 |
| 311 | 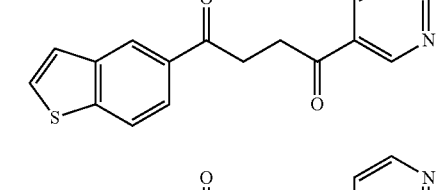 |
| 312 | 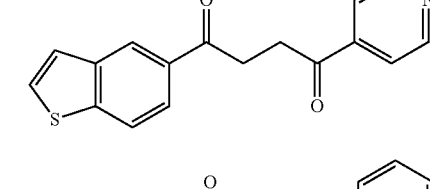 |
| 313 | 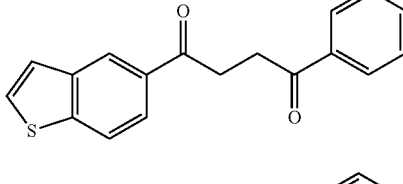 |
| 314 | 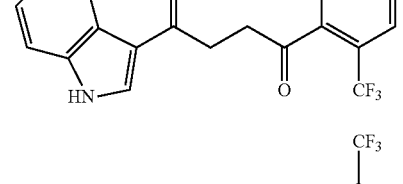 |
| 315 | 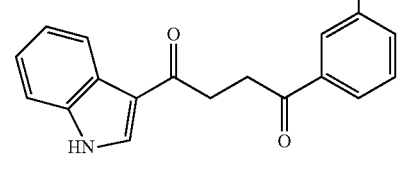 |

TABLE 1-continued
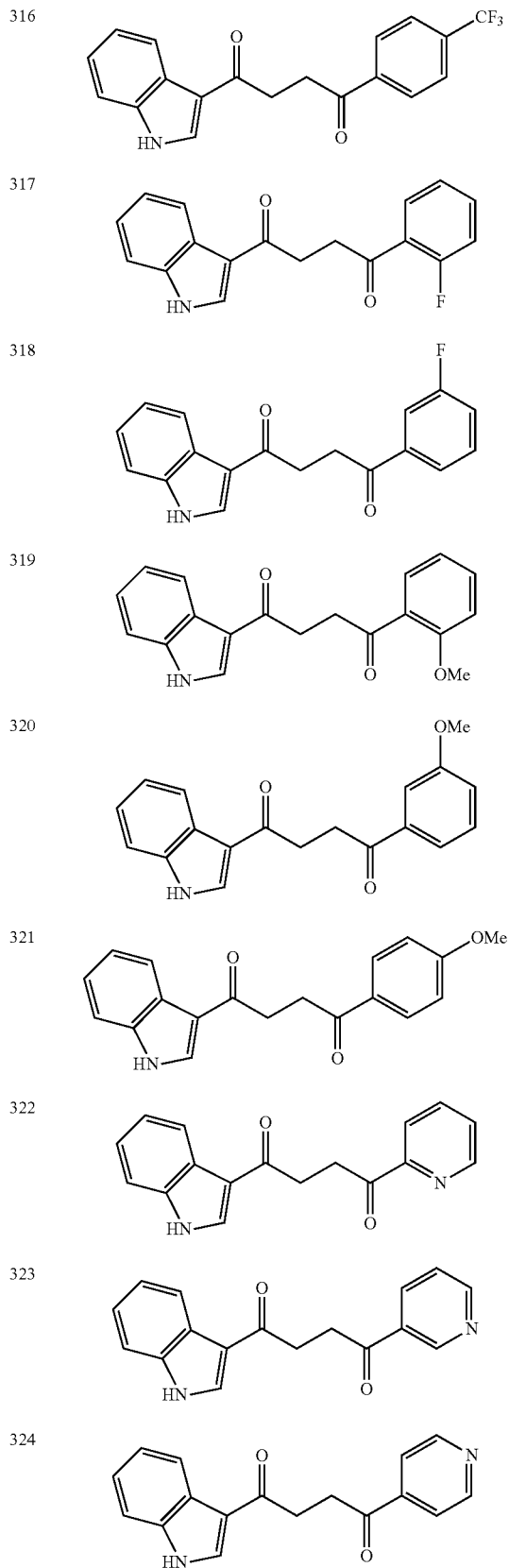
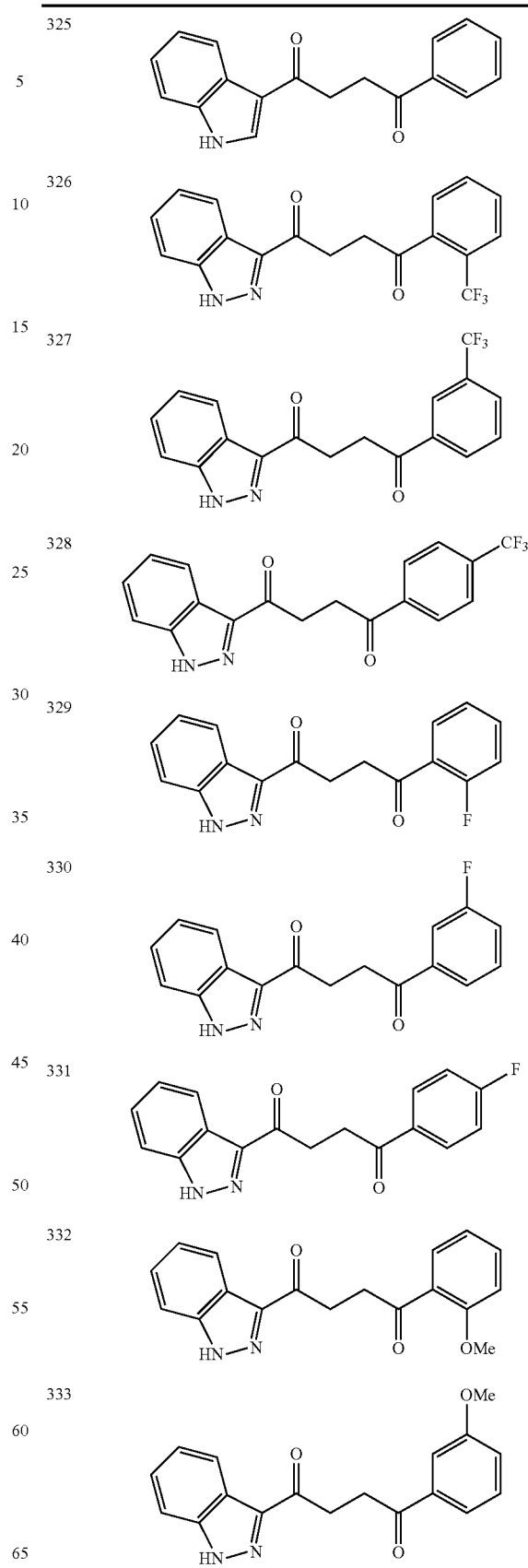

TABLE 1-continued
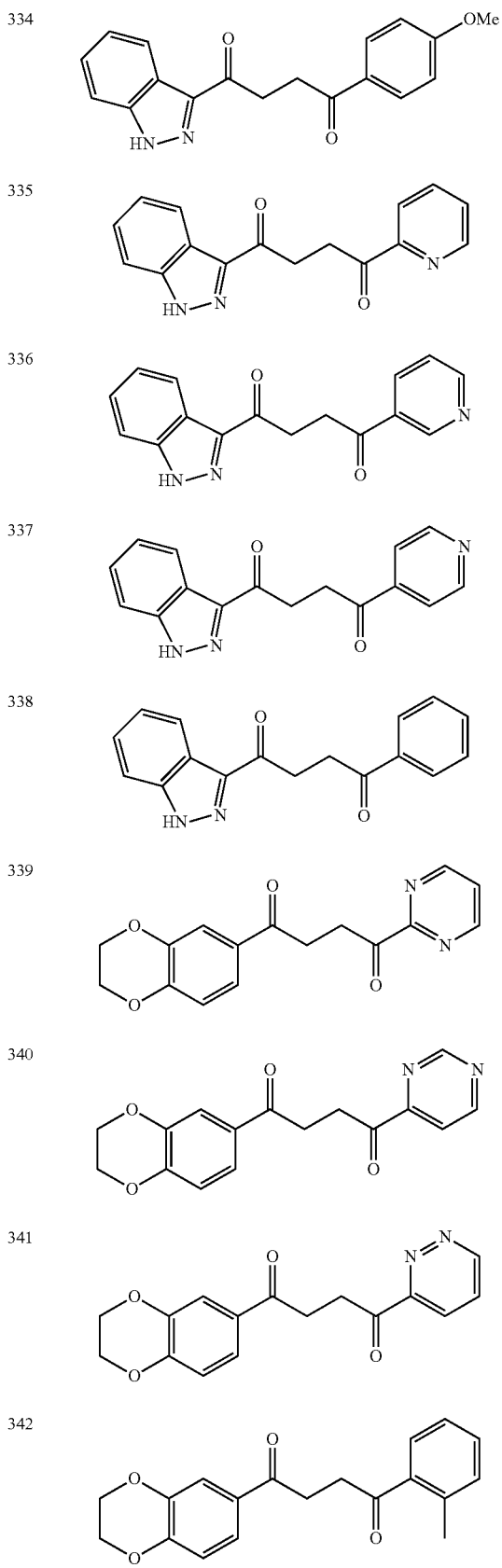
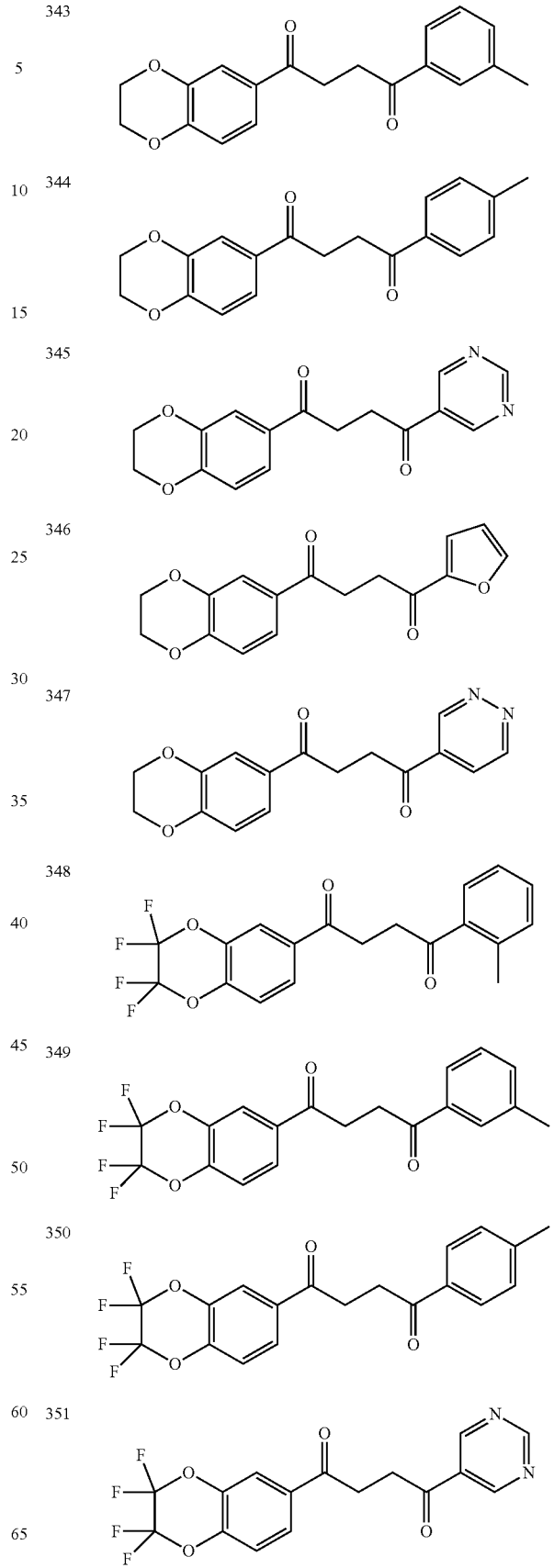

TABLE 1-continued
| | |
|---|---|
| 352 | 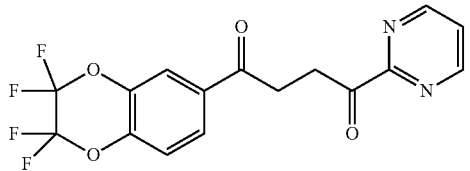 [SMILES: O=C(CCC(=O)c1ncccn1)c1ccc2c(c1)OC(F)(F)C(F)(F)O2] |
| 353 | 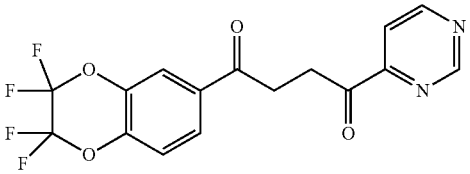 [SMILES: O=C(CCC(=O)c1ccncn1)c1ccc2c(c1)OC(F)(F)C(F)(F)O2] |
| 354 | 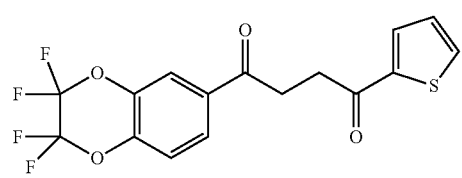 [SMILES: O=C(CCC(=O)c1cccs1)c1ccc2c(c1)OC(F)(F)C(F)(F)O2] |
| 355 | 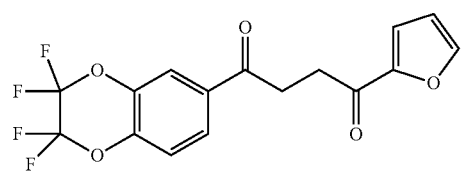 |
| 356 | 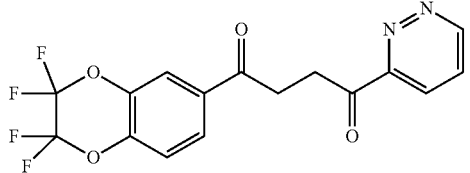 [SMILES: O=C(CCC(=O)c1cccnn1)c1ccc2c(c1)OC(F)(F)C(F)(F)O2] |
| 357 | 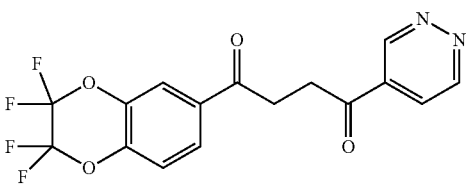 [SMILES: O=C(CCC(=O)c1ccc2c(c1)OC(F)(F)C(F)(F)O2)c1ccnnc1] |
| 358 | 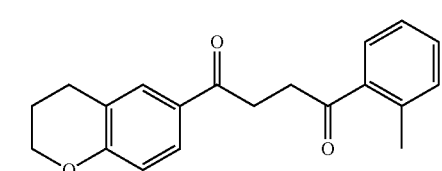 |
| 359 | 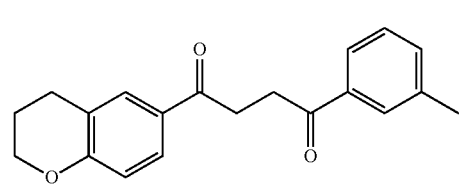 [SMILES: Cc1cccc(C(=O)CCC(=O)c2ccc3c(c2)CCCO3)c1] |
| 360 | 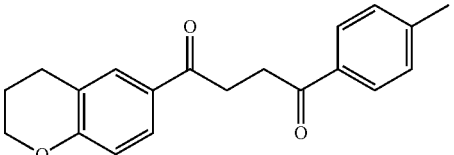 |
| 361 | 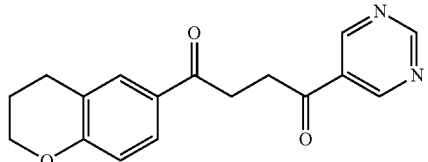 |
| 362 | 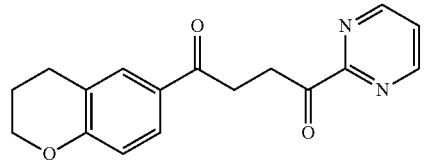 [SMILES: O=C(CCC(=O)c1ncccn1)c1ccc2c(c1)CCCO2] |
| 363 | 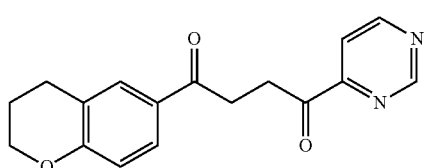 |
| 364 | 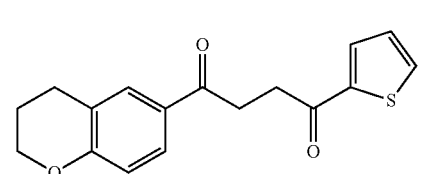 |
| 365 | 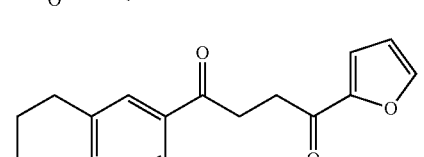 |
| 366 | 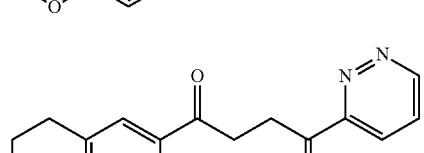 |
| 367 | 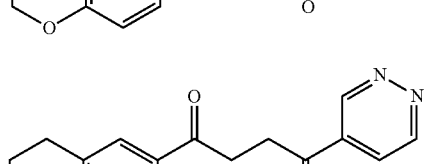 |
| 368 | 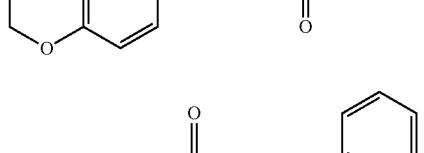 |

TABLE 1-continued
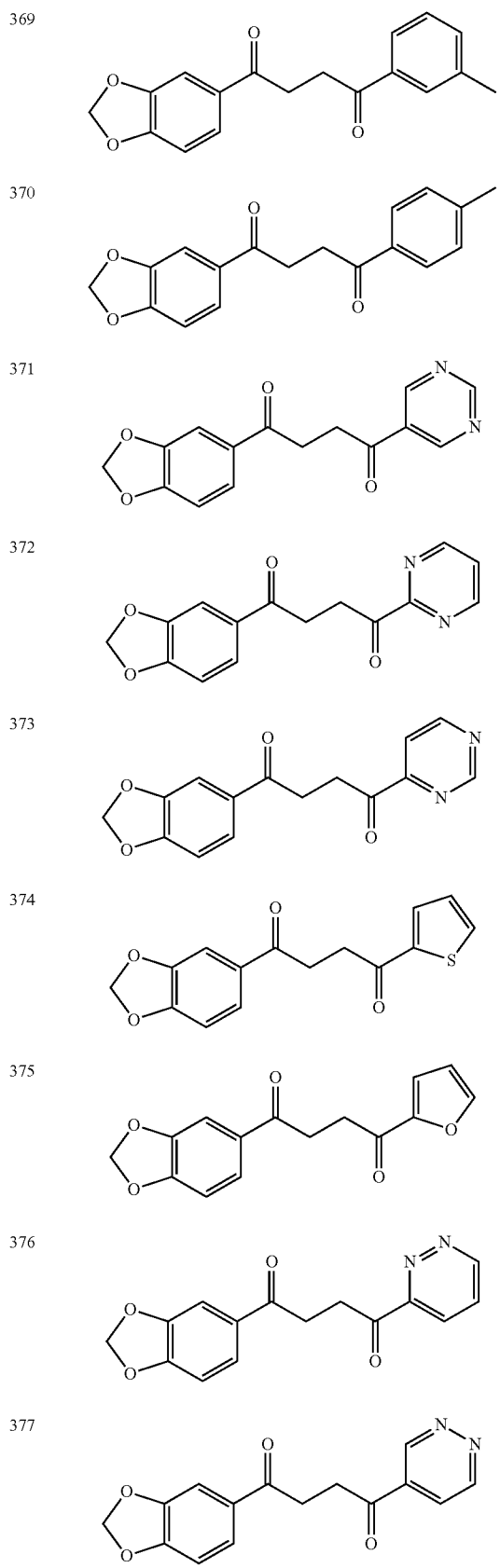
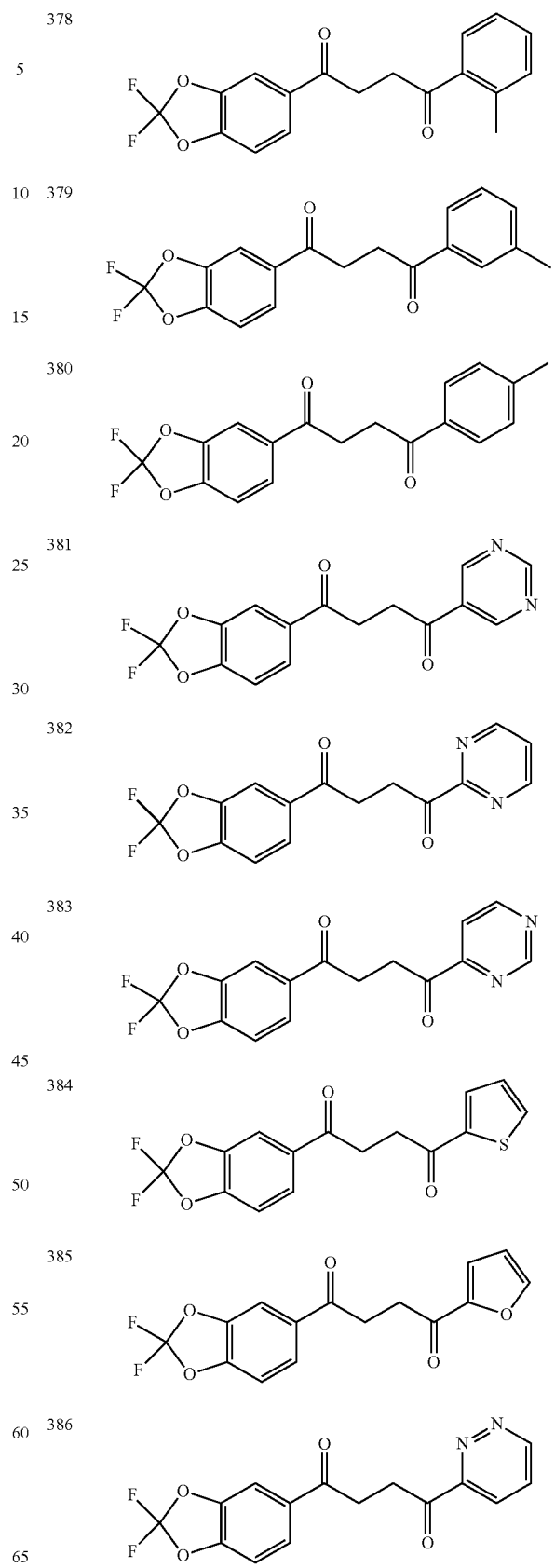

TABLE 1-continued
387 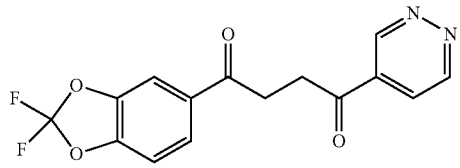 [SMILES: O=C(CCC(=O)c1ccc2c(c1)OC(F)(F)O2)c1ccnnc1]
388 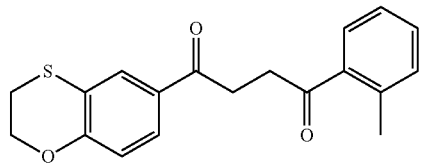
389 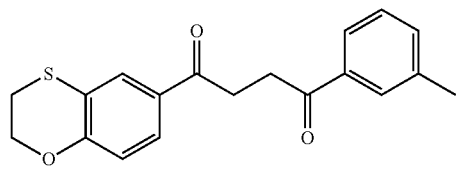 [SMILES: Cc1cccc(C(=O)CCC(=O)c2ccc3c(c2)SCCO3)c1]
390 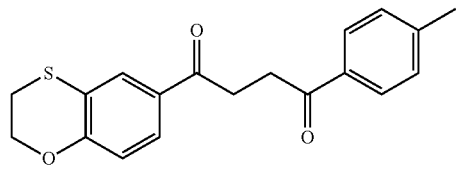 [SMILES: Cc1ccc(C(=O)CCC(=O)c2ccc3c(c2)SCCO3)cc1]
391 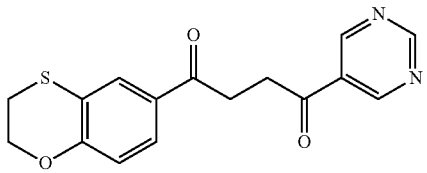
392 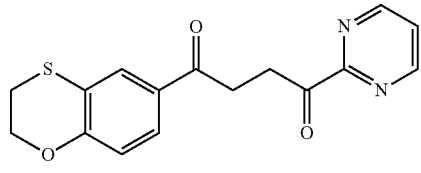
393 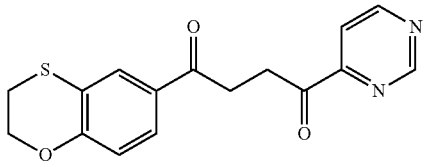 [SMILES: O=C(CCC(=O)c1ccncn1)c1ccc2c(c1)SCCO2]
394 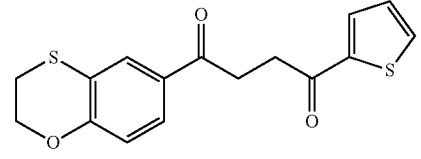 [SMILES: O=C(CCC(=O)c1cccs1)c1ccc2c(c1)SCCO2]
395 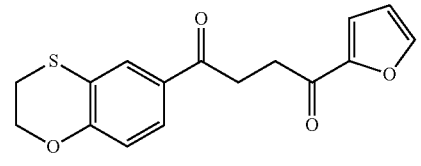 [SMILES: O=C(CCC(=O)c1ccco1)c1ccc2c(c1)SCCO2]
TABLE 1-continued
396 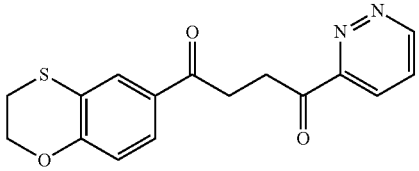
397 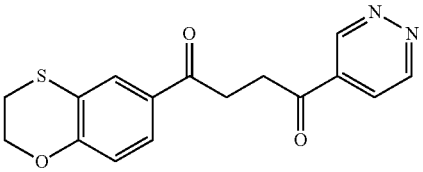
398 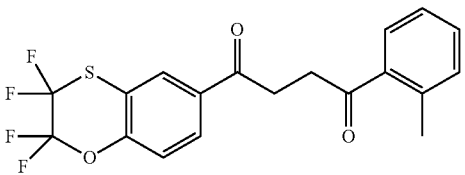 [SMILES: Cc1ccccc1C(=O)CCC(=O)c1ccc2c(c1)SC(F)(F)C(F)(F)O2]
399 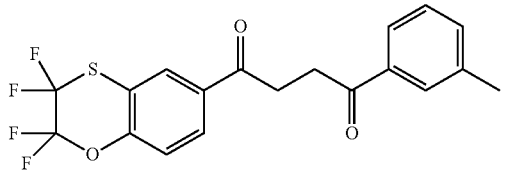 [SMILES: Cc1cccc(C(=O)CCC(=O)c2ccc3c(c2)SC(F)(F)C(F)(F)O3)c1]
400 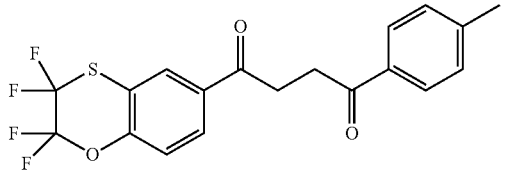 [SMILES: Cc1ccc(C(=O)CCC(=O)c2ccc3c(c2)SC(F)(F)C(F)(F)O3)cc1]
401 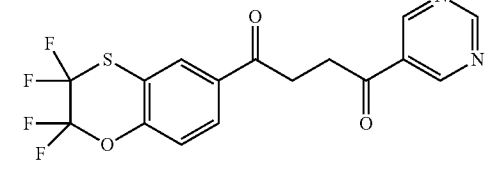
402 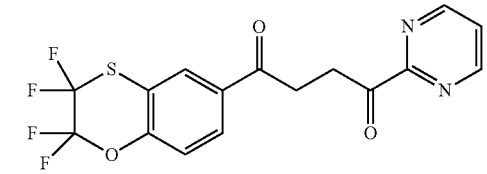 [SMILES: O=C(CCC(=O)c1ncccn1)c1ccc2c(c1)SC(F)(F)C(F)(F)O2]
403 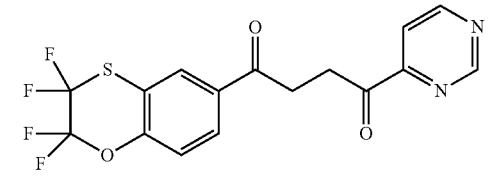 [SMILES: O=C(CCC(=O)c1ccncn1)c1ccc2c(c1)SC(F)(F)C(F)(F)O2]

TABLE 1-continued
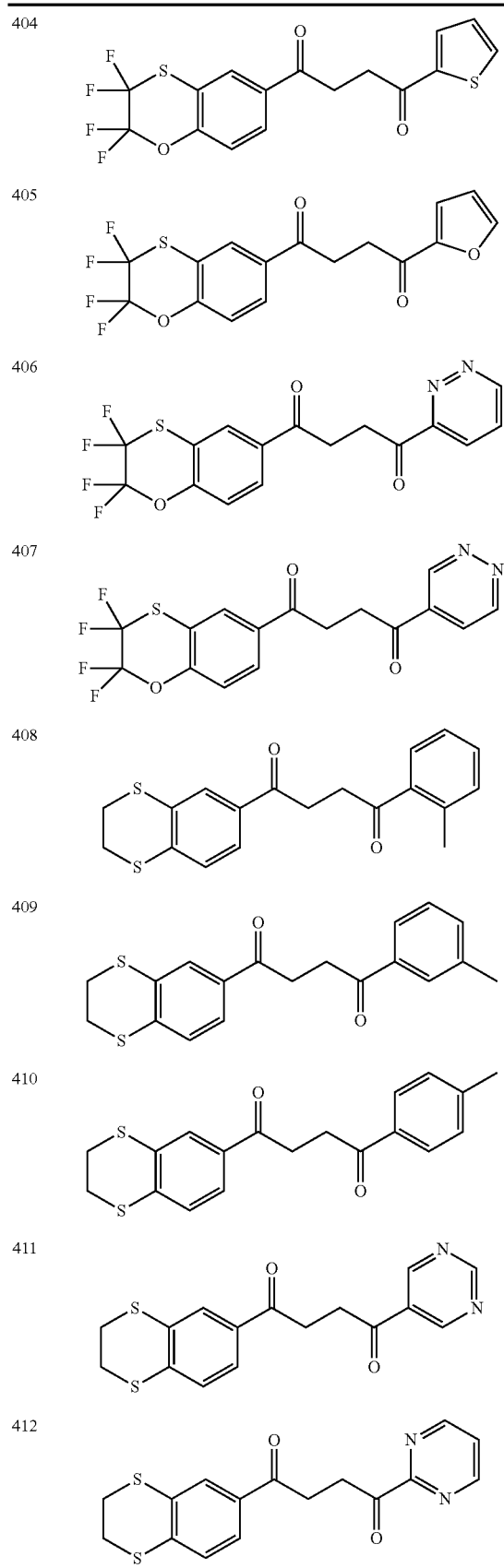
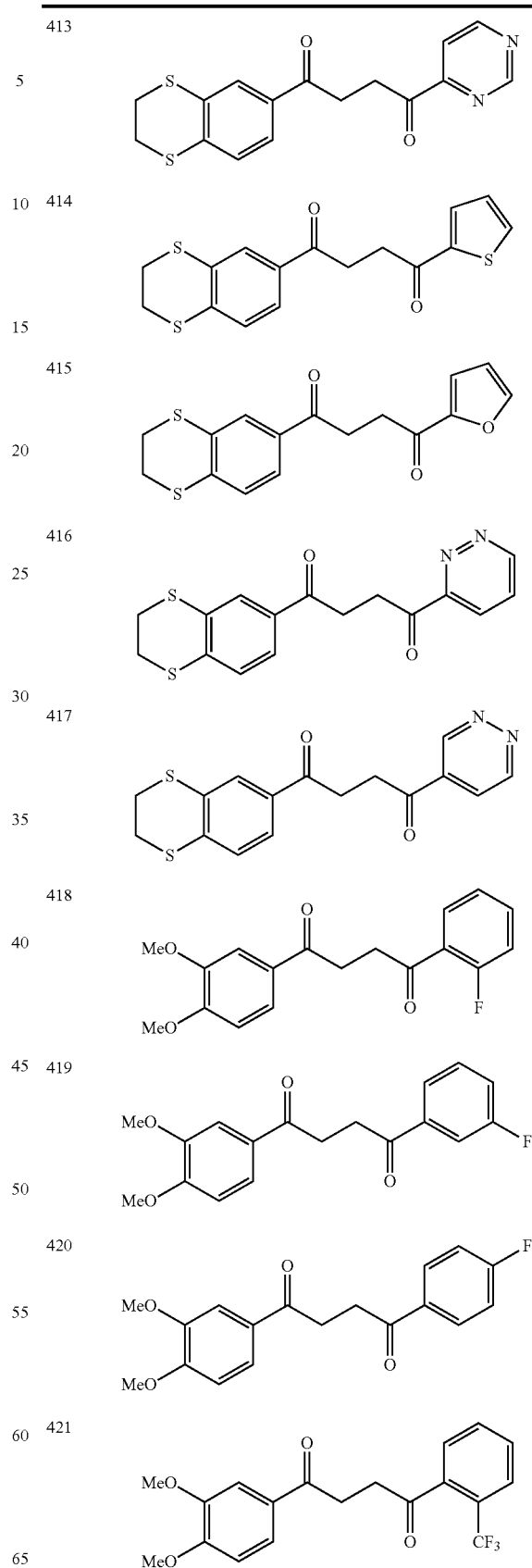

TABLE 1-continued
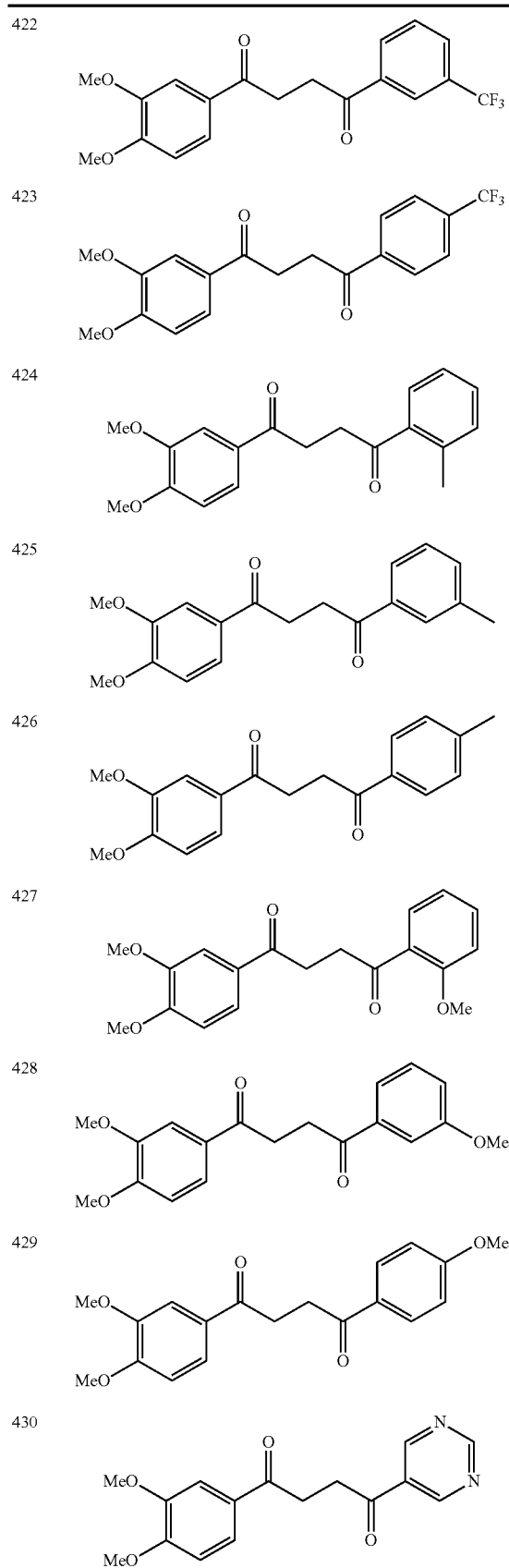
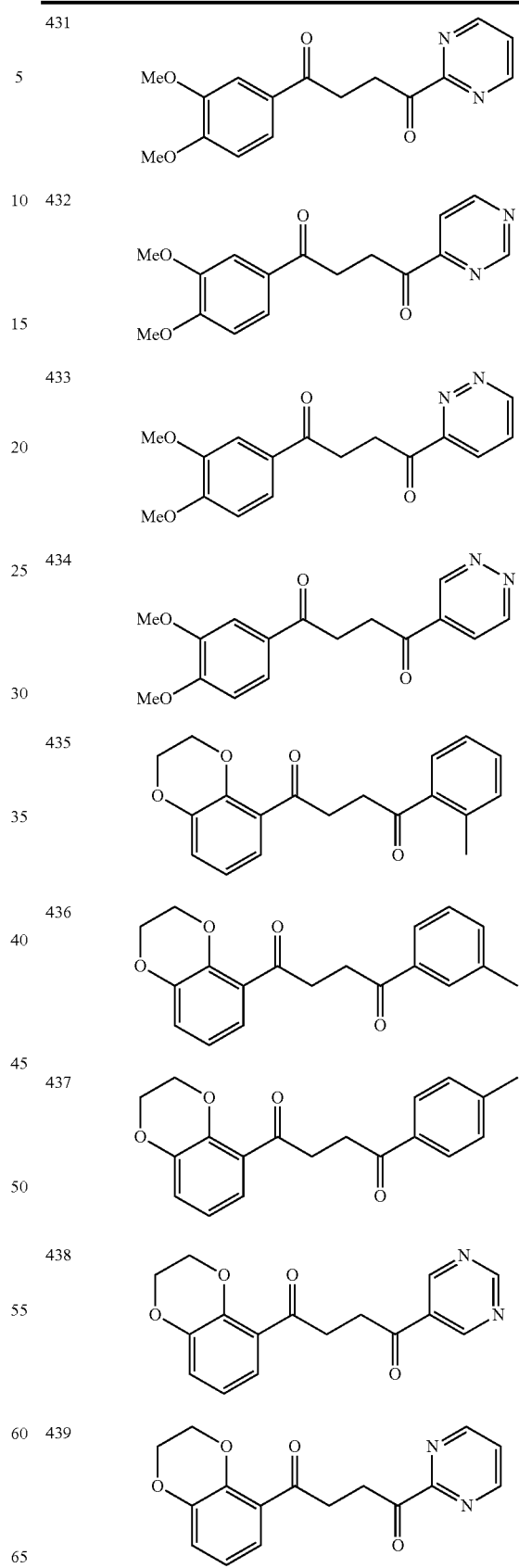

TABLE 1-continued
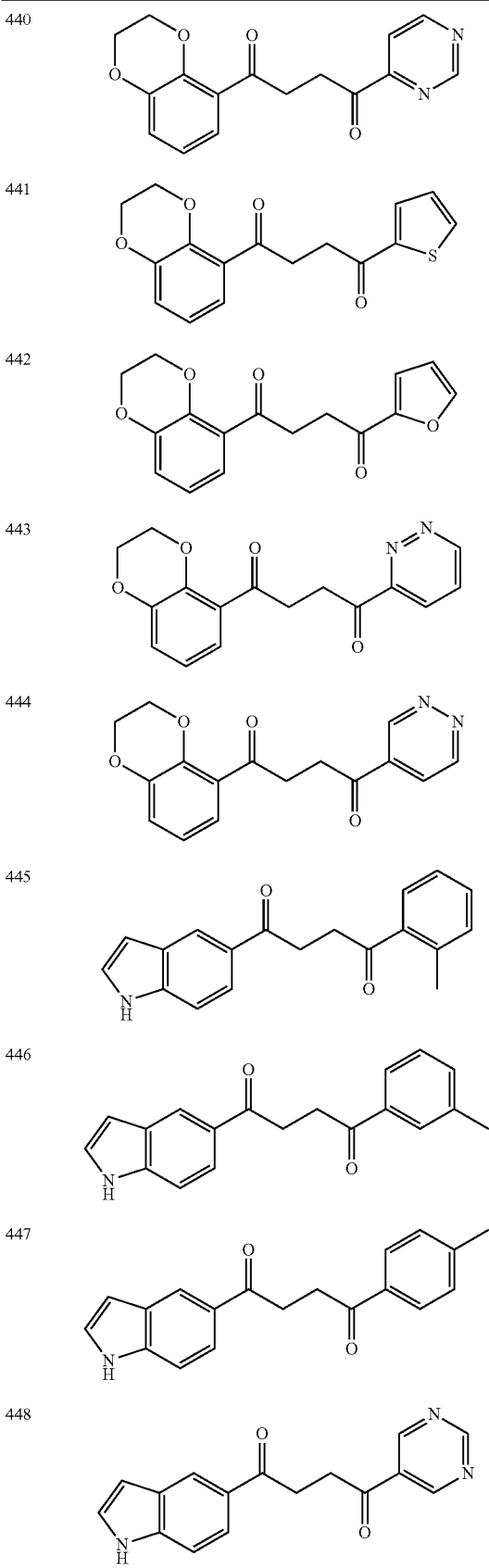
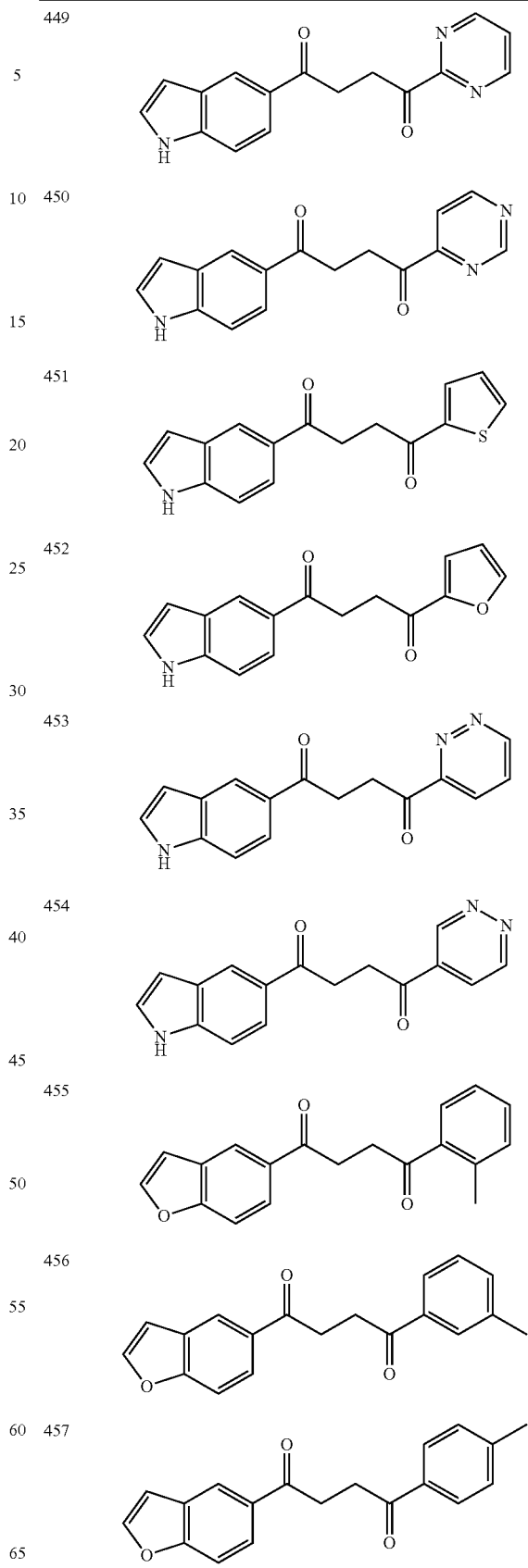

TABLE 1-continued
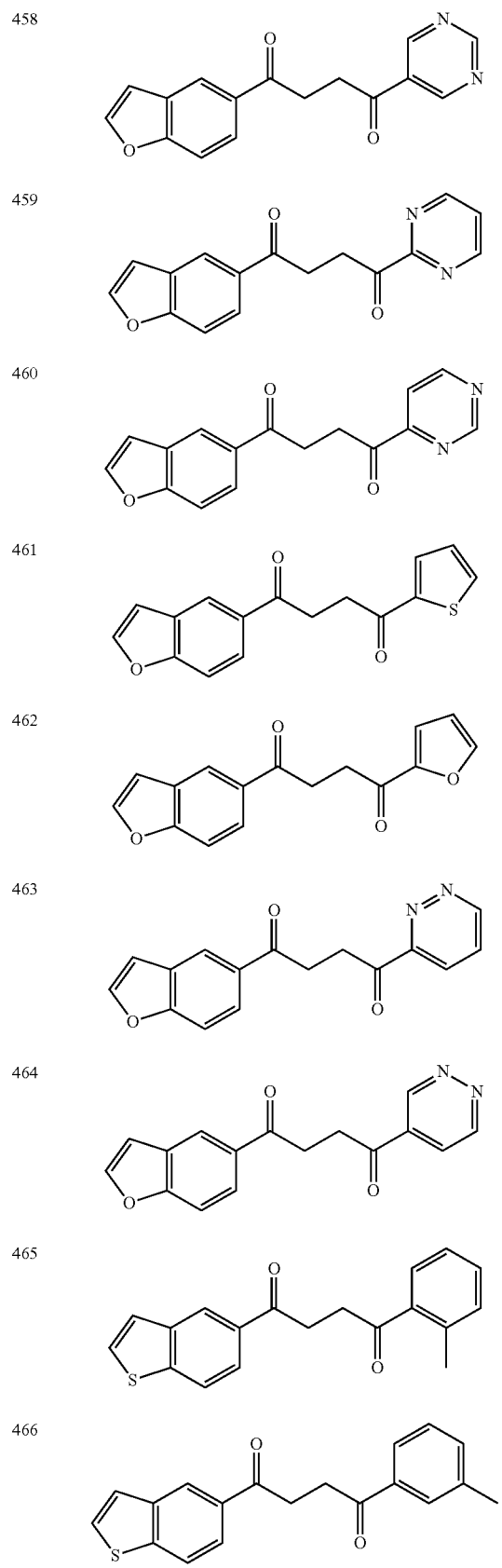
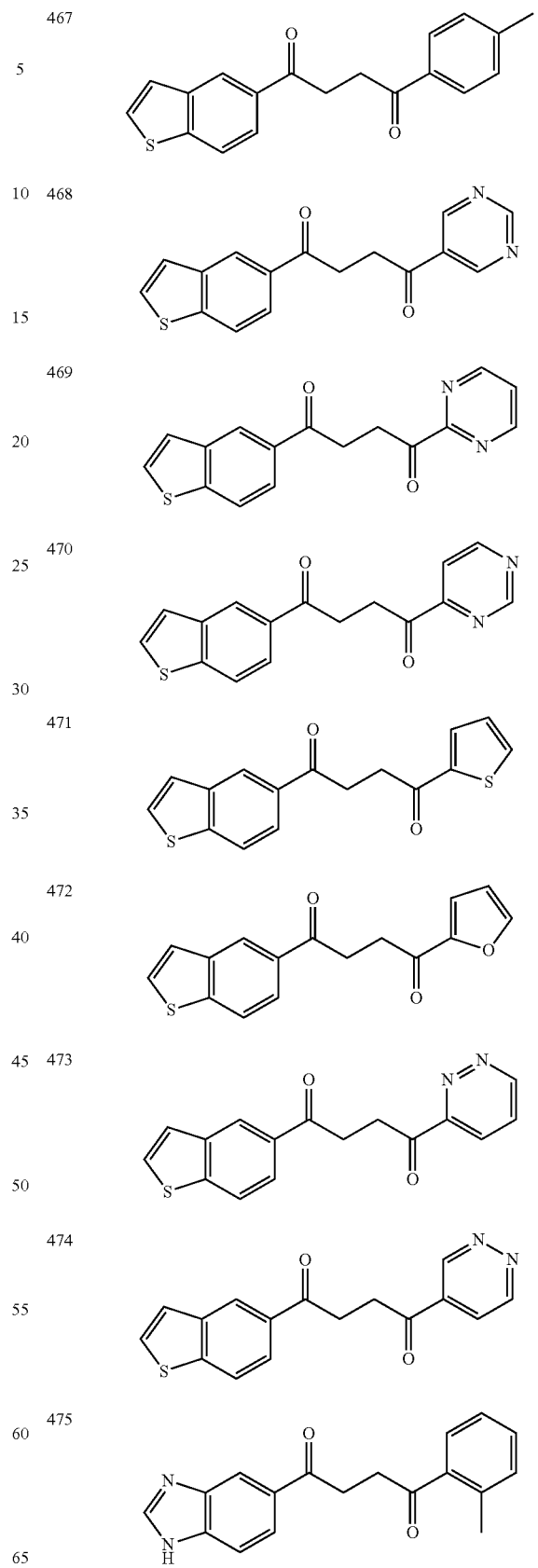

TABLE 1-continued
| | |
|---|---|
| 476 | 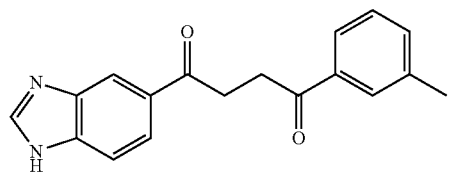 [SMILES: Cc1cccc(C(=O)CCC(=O)c2ccc3[nH]cnc3c2)c1] |
| 477 | 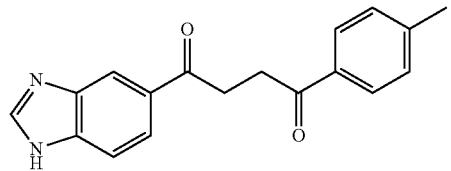 [SMILES: Cc1ccc(C(=O)CCC(=O)c2ccc3[nH]cnc3c2)cc1] |
| 478 | 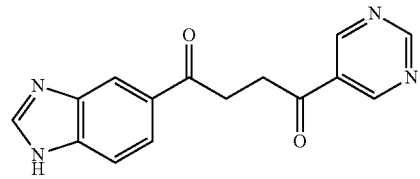 [SMILES: O=C(CCC(=O)c1ccc2[nH]cnc2c1)c1cncnc1] |
| 479 | 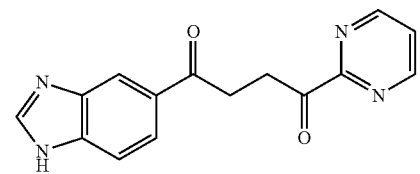 |
| 480 | 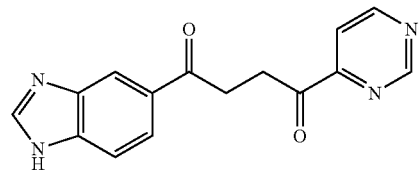 [SMILES: O=C(CCC(=O)c1ccncn1)c1ccc2[nH]cnc2c1] |
| 481 | 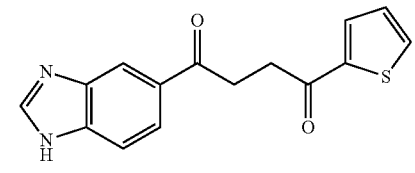 [SMILES: O=C(CCC(=O)c1cccs1)c1ccc2[nH]cnc2c1] |
| 482 | 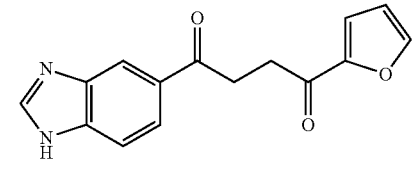 [SMILES: O=C(CCC(=O)c1ccco1)c1ccc2[nH]cnc2c1] |
| 483 | 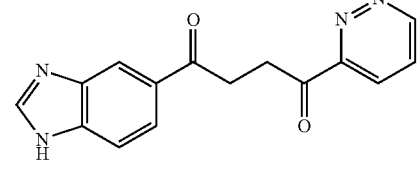 |
| 484 | 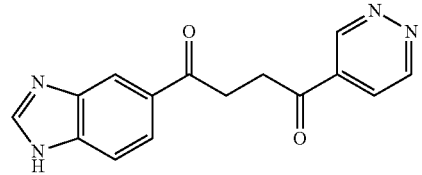 |
TABLE 1-continued
| | |
|---|---|
| 485 | 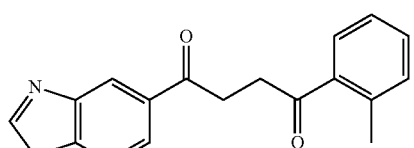 |
| 486 | 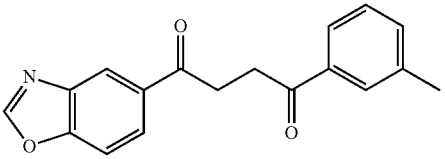 [SMILES: Cc1cccc(C(=O)CCC(=O)c2ccc3ocnc3c2)c1] |
| 487 | 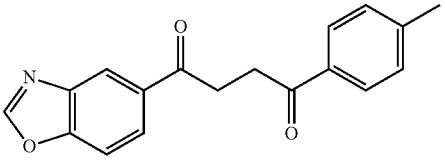 [SMILES: Cc1ccc(C(=O)CCC(=O)c2ccc3ocnc3c2)cc1] |
| 488 | 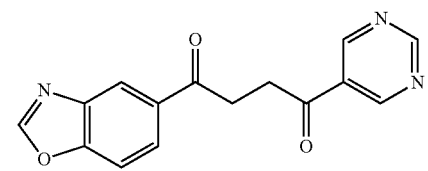 |
| 489 | 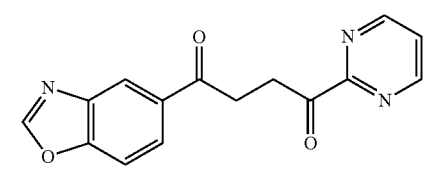 [SMILES: O=C(CCC(=O)c1ncccn1)c1ccc2ocnc2c1] |
| 490 | 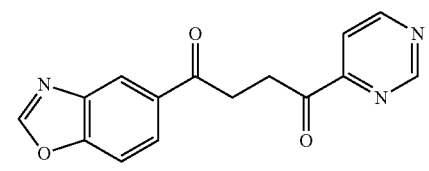 [SMILES: O=C(CCC(=O)c1ccncn1)c1ccc2ocnc2c1] |
| 491 | 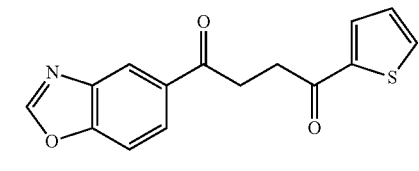 [SMILES: O=C(CCC(=O)c1cccs1)c1ccc2ocnc2c1] |
| 492 | 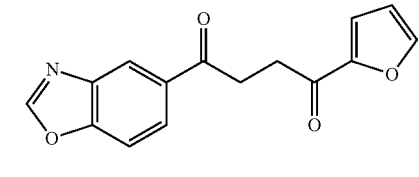 [SMILES: O=C(CCC(=O)c1ccco1)c1ccc2ocnc2c1] |
| 493 | 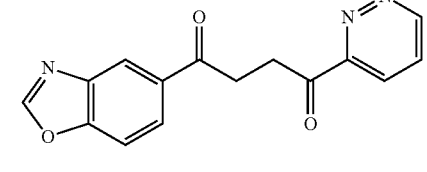 |

TABLE 1-continued
494 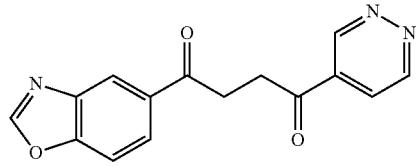
495 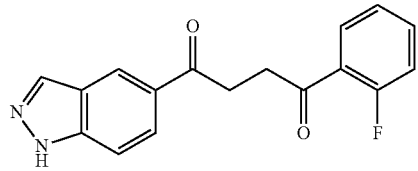
496 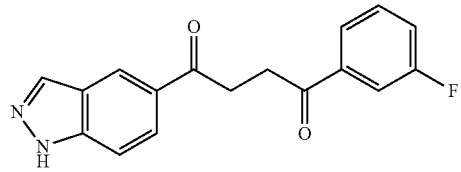 [SMILES: O=C(CCC(=O)c1ccc2[nH]ncc2c1)c1cccc(F)c1]
497 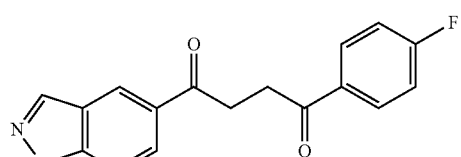
498 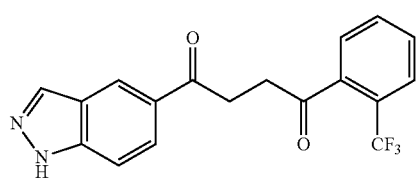
499 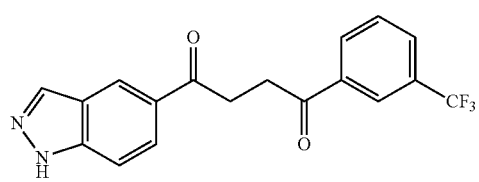 [SMILES: O=C(CCC(=O)c1ccc2[nH]ncc2c1)c1cccc(C(F)(F)F)c1]
500 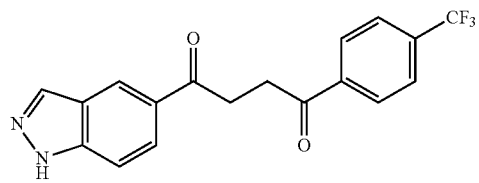 [SMILES: O=C(CCC(=O)c1ccc2[nH]ncc2c1)c1ccc(C(F)(F)F)cc1]
501 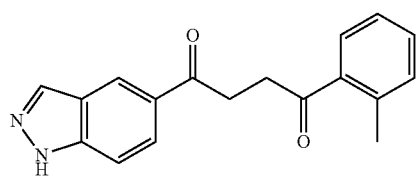
502 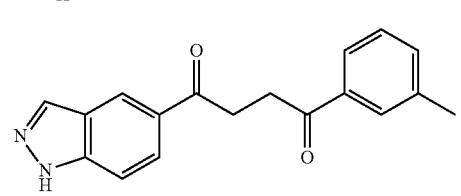 [SMILES: Cc1cccc(C(=O)CCC(=O)c2ccc3[nH]ncc3c2)c1]
TABLE 1-continued
503 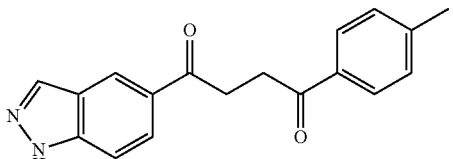
504 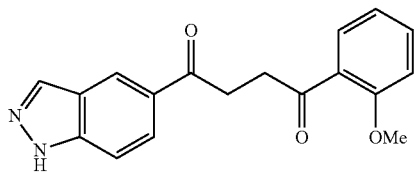 [SMILES: COc1ccccc1C(=O)CCC(=O)c1ccc2[nH]ncc2c1]
505 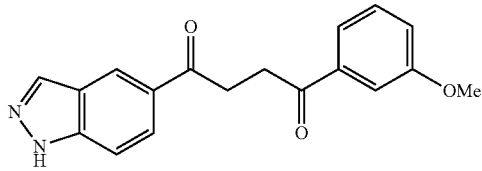 [SMILES: COc1cccc(C(=O)CCC(=O)c2ccc3[nH]ncc3c2)c1]
506 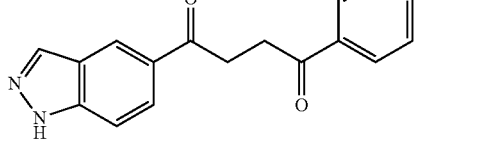
507 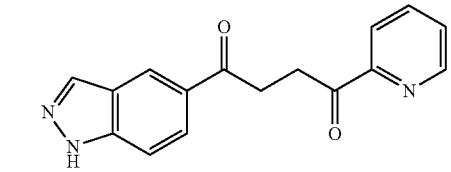 [SMILES: O=C(CCC(=O)c1ccccn1)c1ccc2[nH]ncc2c1]
508 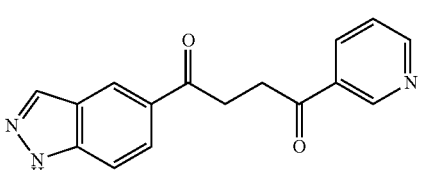
509 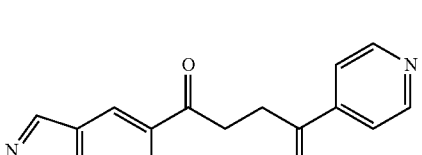
510 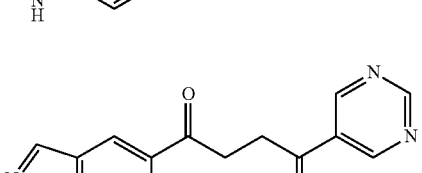

TABLE 1-continued
| | |
|---|---|
| 511 | 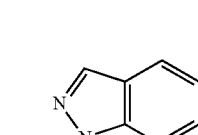 |
| 512 | 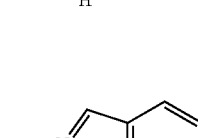 |
| 513 | 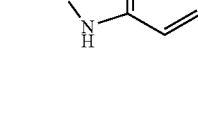 |
| 514 | 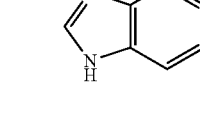 |
| 515 | 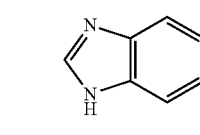 |
| 516 | 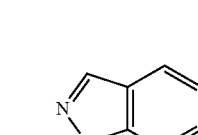 |
| 517 | 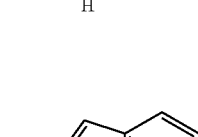 |
| 518 | 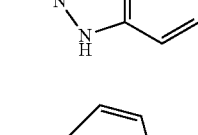 |
| 519 | 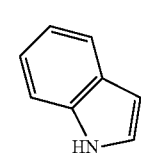 |
| 520 | 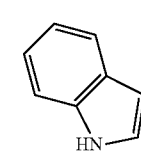 |
| 521 | 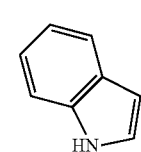 |
| 522 | 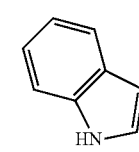 |
| 523 | 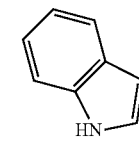 |
| 524 | 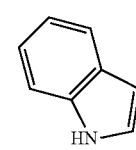 |
| 525 | 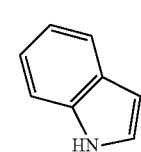 |
| 526 | 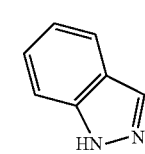 |
| 527 | 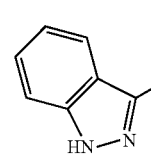 |
| 528 | |
| 529 | |

TABLE 1-continued
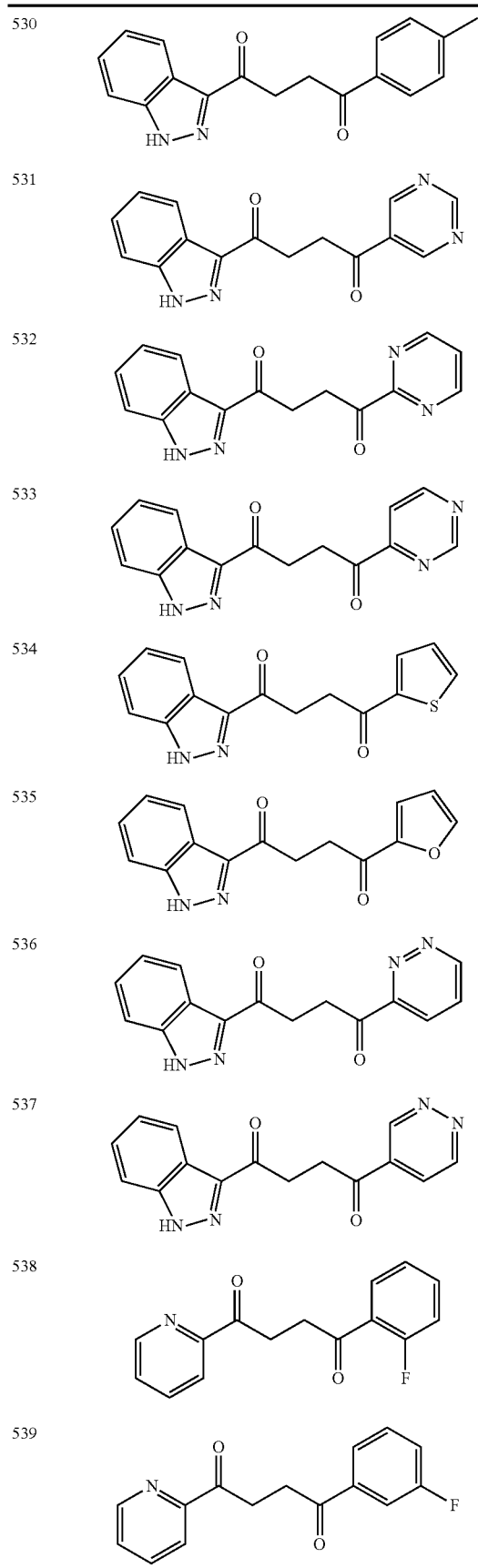
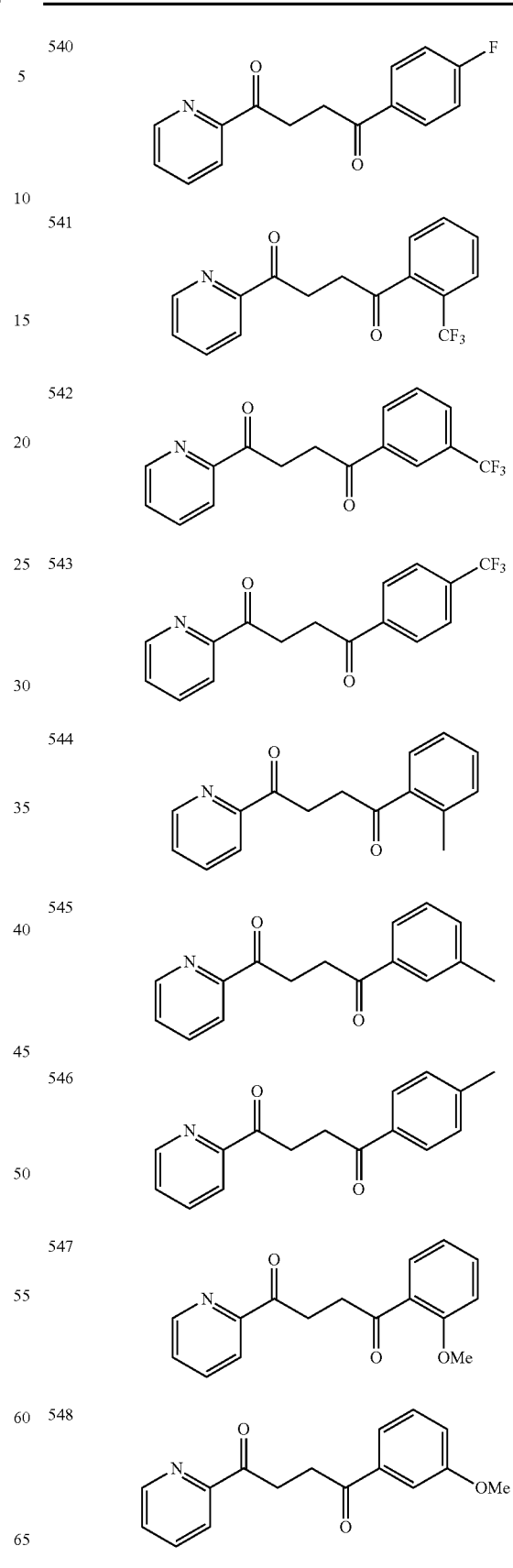

TABLE 1-continued
| 549 | 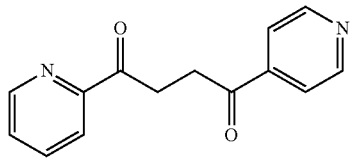 [SMILES: O=C(CCC(=O)c1ccccn1)c1ccncc1] |
| 550 | 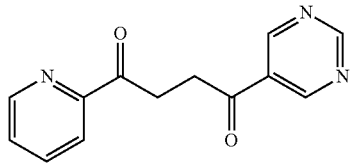 [SMILES: O=C(CCC(=O)c1ccccn1)c1cncnc1] |
| 551 | 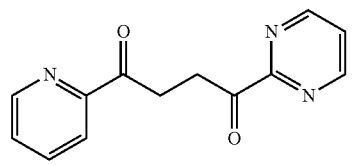 [SMILES: O=C(CCC(=O)c1ncccn1)c1ccccn1] |
| 552 | 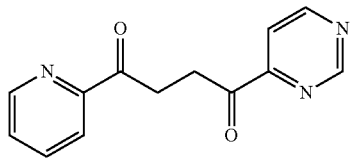 [SMILES: O=C(CCC(=O)c1ccncn1)c1ccccn1] |
| 553 | 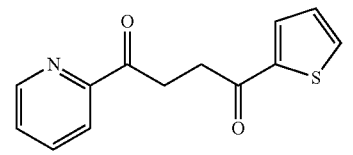 [SMILES: O=C(CCC(=O)c1cccs1)c1ccccn1] |
| 554 | 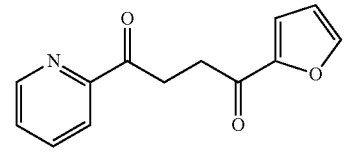 [SMILES: O=C(CCC(=O)c1ccco1)c1ccccn1] |
| 555 | 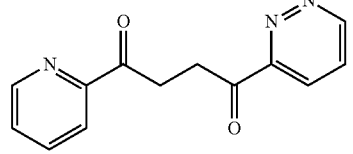 |
| 556 | 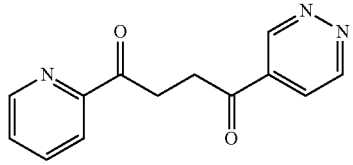 [SMILES: O=C(CCC(=O)c1ccccn1)c1ccnnc1] |
| 557 | 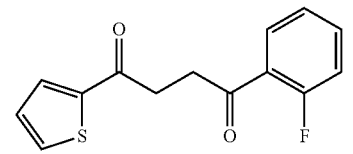 |
TABLE 1-continued
| 558 | 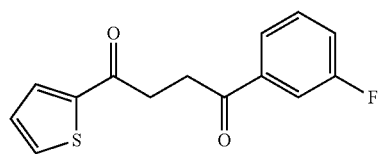 [SMILES: O=C(CCC(=O)c1cccs1)c1cccc(F)c1] |
| 559 | 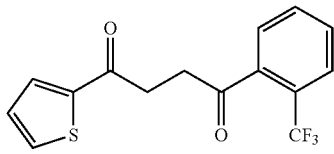 [SMILES: O=C(CCC(=O)c1ccccc1C(F)(F)F)c1cccs1] |
| 560 | 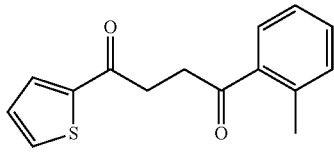 [SMILES: Cc1ccccc1C(=O)CCC(=O)c1cccs1] |
| 561 | 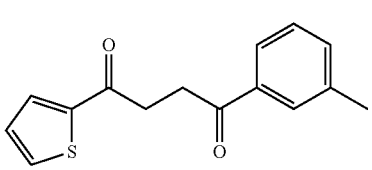 [SMILES: Cc1cccc(C(=O)CCC(=O)c2cccs2)c1] |
| 562 | 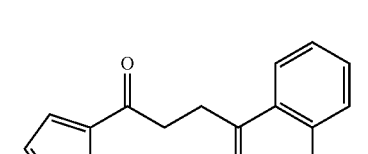 |
| 563 | 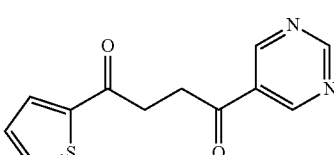 |
| 564 | 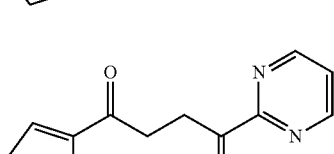 |
| 565 | 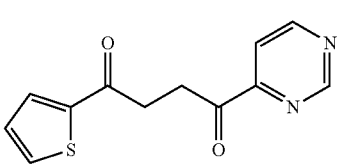 [SMILES: O=C(CCC(=O)c1cccs1)c1ccncn1] |
| 566 | 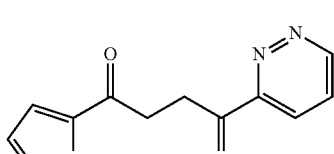 |

TABLE 1-continued
| | |
|---|---|
| 567 | 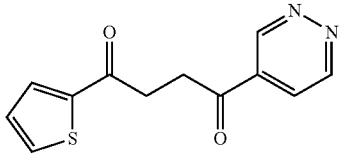 [SMILES: O=C(CCC(=O)c1cccs1)c1ccnnc1] |
| 568 | 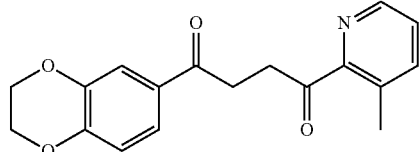 |
| 569 | 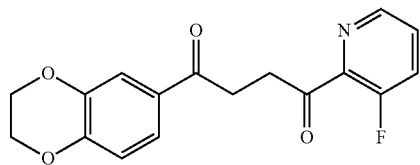 [SMILES: O=C(CCC(=O)c1ncccc1F)c1ccc2c(c1)OCCO2] |
| 570 | 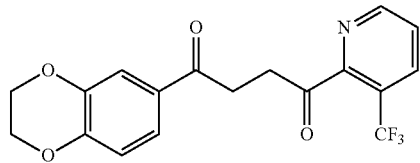 [SMILES: O=C(CCC(=O)c1ncccc1C(F)(F)F)c1ccc2c(c1)OCCO2] |
| 571 | 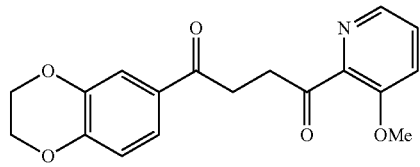 [SMILES: COc1cccnc1C(=O)CCC(=O)c1ccc2c(c1)OCCO2] |
| 572 | 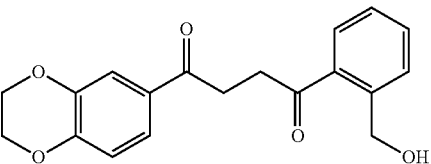 [SMILES: O=C(CCC(=O)c1ccccc1CO)c1ccc2c(c1)OCCO2] |
| 573 | 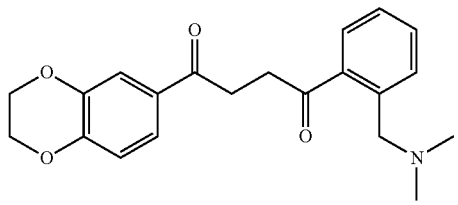 |
| 574 | 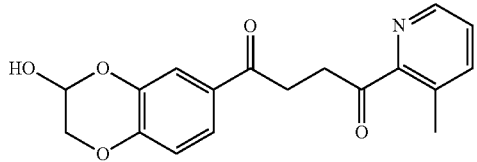 [SMILES: Cc1cccnc1C(=O)CCC(=O)c1ccc2c(c1)OC(O)CO2] |
| 575 | 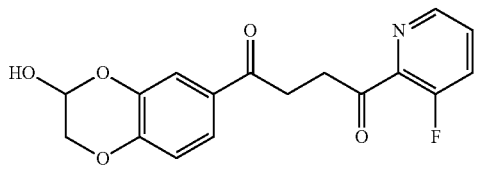 |
TABLE 1-continued
| | |
|---|---|
| 576 | 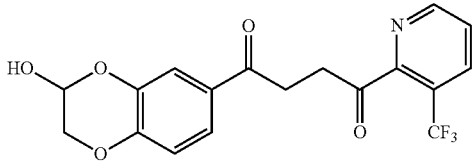 [SMILES: O=C(CCC(=O)c1ncccc1C(F)(F)F)c1ccc2c(c1)OC(O)CO2] |
| 577 | 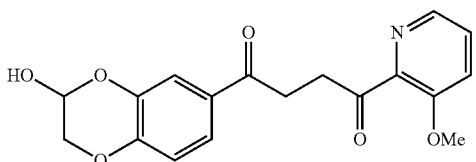 |
| 578 | 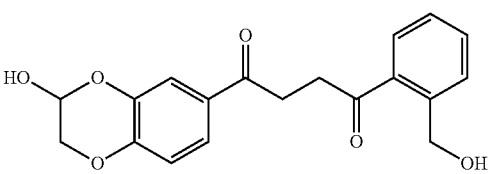 [SMILES: O=C(CCC(=O)c1ccccc1CO)c1ccc2c(c1)OC(O)CO2] |
| 579 | 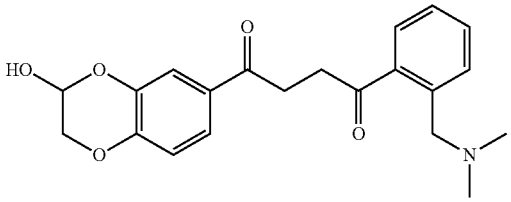 [SMILES: CN(C)Cc1ccccc1C(=O)CCC(=O)c1ccc2c(c1)OC(O)CO2] |
| 580 | 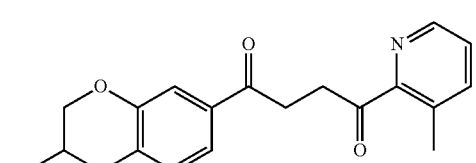 |
| 581 | 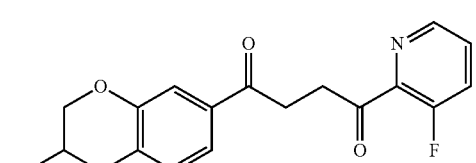 |
| 582 | 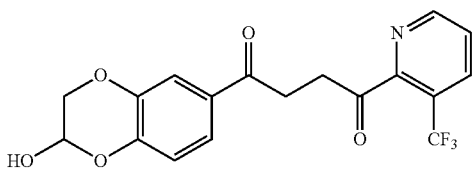 [SMILES: O=C(CCC(=O)c1ncccc1C(F)(F)F)c1ccc2c(c1)OCC(O)O2] |
| 583 | 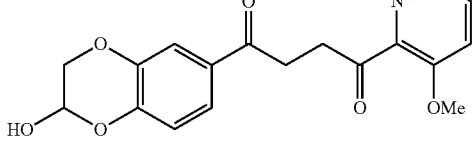 |
| 584 | 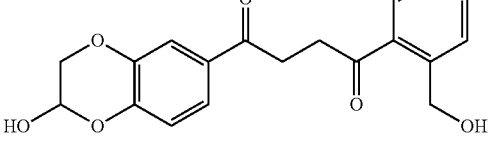 |

TABLE 1-continued
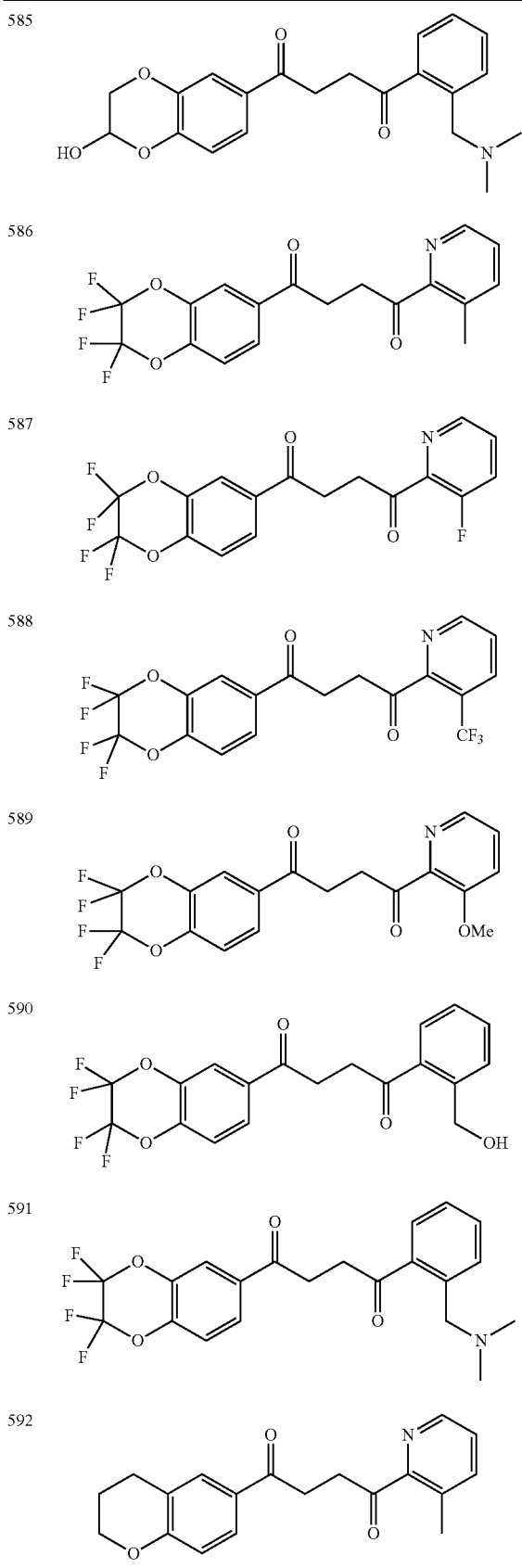
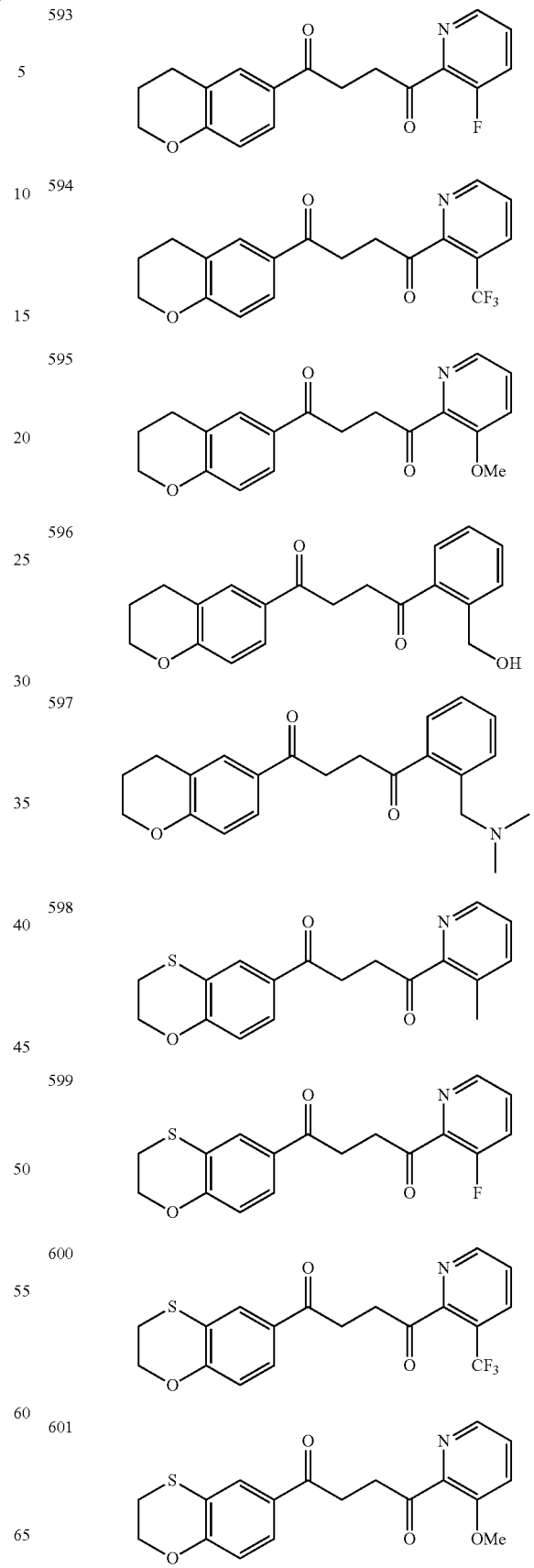

TABLE 1-continued
602 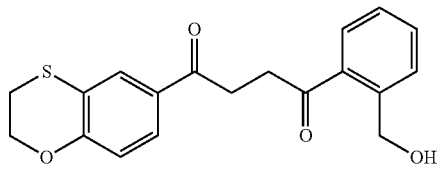 [SMILES: O=C(CCC(=O)c1ccccc1CO)c1ccc2c(c1)SCCO2]
603 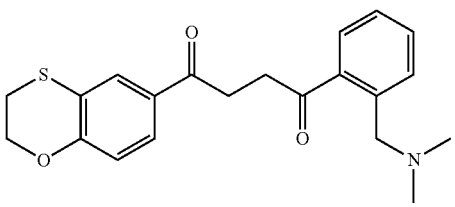 [SMILES: CN(C)Cc1ccccc1C(=O)CCC(=O)c1ccc2c(c1)SCCO2]
604 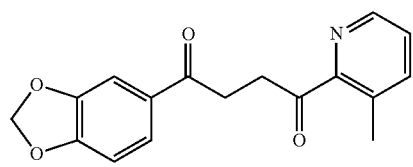
605 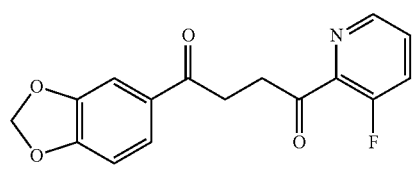 [SMILES: O=C(CCC(=O)c1ncccc1F)c1ccc2c(c1)OCO2]
606 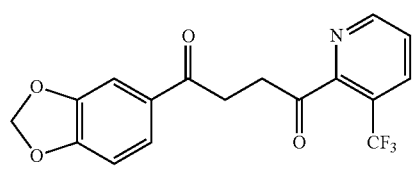
607 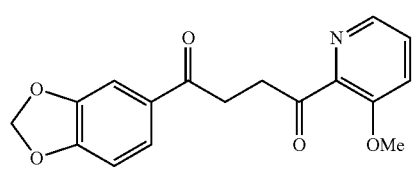
608 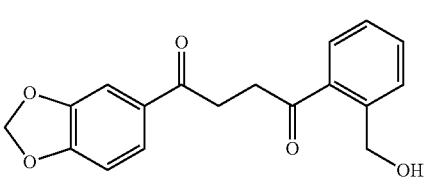 [SMILES: O=C(CCC(=O)c1ccccc1CO)c1ccc2c(c1)OCO2]
609 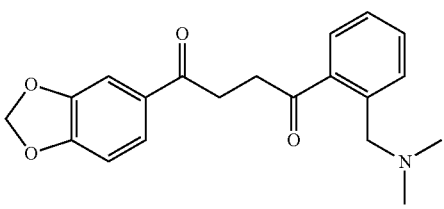
TABLE 1-continued
610 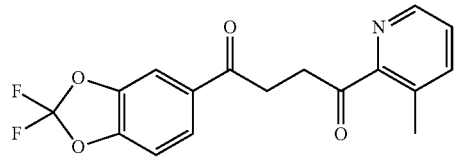 [SMILES: Cc1cccnc1C(=O)CCC(=O)c1ccc2c(c1)OC(F)(F)O2]
611 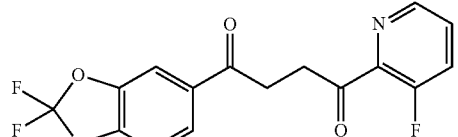
612 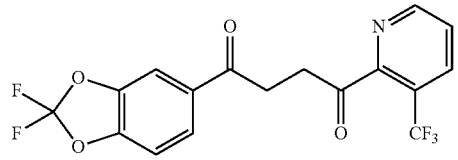 [SMILES: O=C(CCC(=O)c1ncccc1C(F)(F)F)c1ccc2c(c1)OC(F)(F)O2]
613 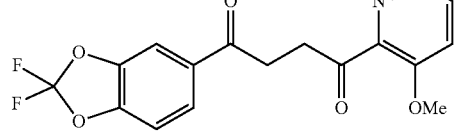
614 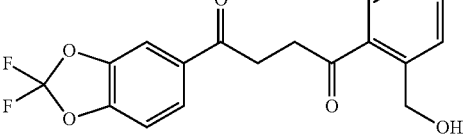
615 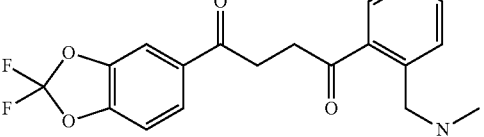
616 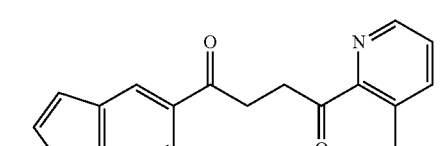
617 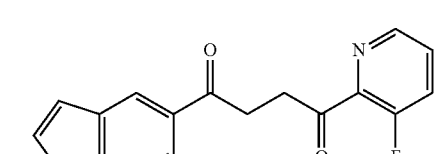
618 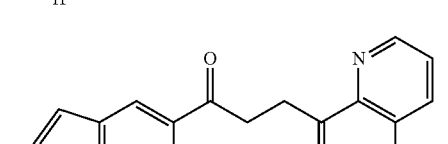

TABLE 1-continued
| | |
|---|---|
| 619 | 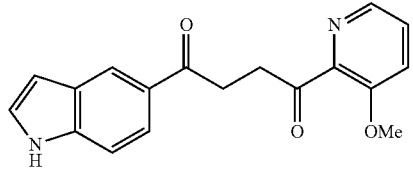 [SMILES: COc1cccnc1C(=O)CCC(=O)c1ccc2[nH]ccc2c1] |
| 620 | 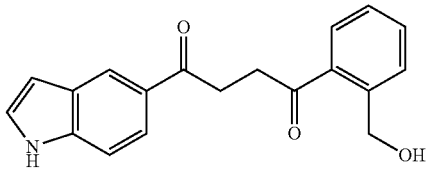 [SMILES: O=C(CCC(=O)c1ccccc1CO)c1ccc2[nH]ccc2c1] |
| 621 | 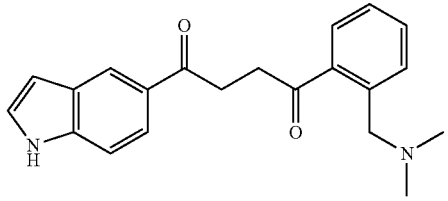 [SMILES: CN(C)Cc1ccccc1C(=O)CCC(=O)c1ccc2[nH]ccc2c1] |
| 622 | 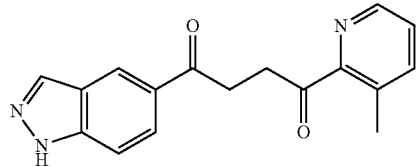 [SMILES: Cc1cccnc1C(=O)CCC(=O)c1ccc2[nH]ncc2c1] |
| 623 | 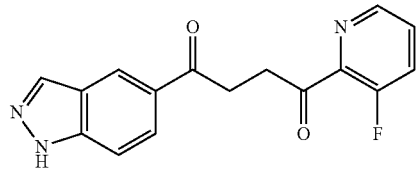 [SMILES: O=C(CCC(=O)c1ncccc1F)c1ccc2[nH]ncc2c1] |
| 624 | 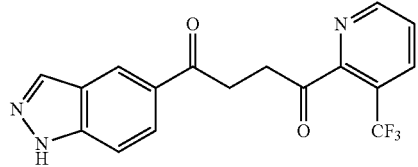 |
| 625 | 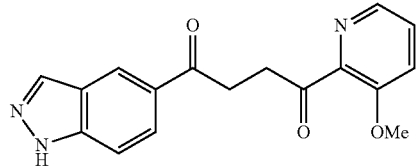 [SMILES: COc1cccnc1C(=O)CCC(=O)c1ccc2[nH]ncc2c1] |
| 626 | 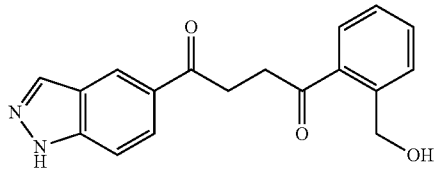 [SMILES: O=C(CCC(=O)c1ccccc1CO)c1ccc2[nH]ncc2c1] |
TABLE 1-continued
| | |
|---|---|
| 627 | 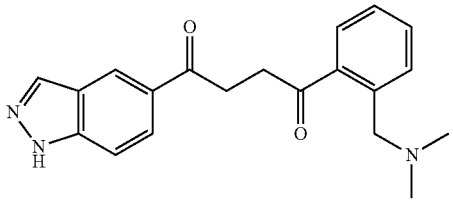 [SMILES: CN(C)Cc1ccccc1C(=O)CCC(=O)c1ccc2[nH]ncc2c1] |
| 628 | 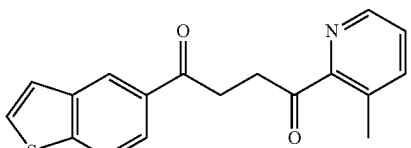 |
| 629 | 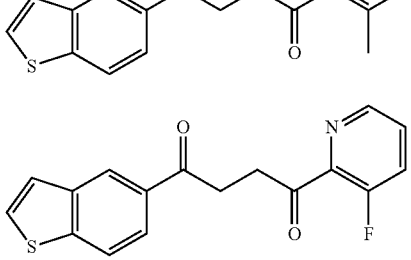 |
| 630 | 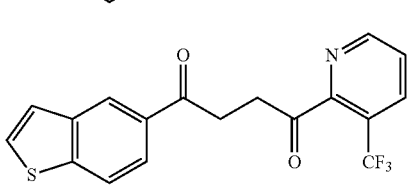 |
| 631 | 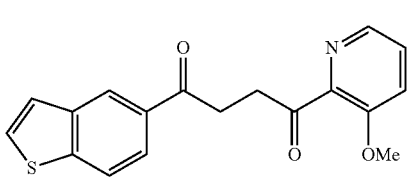 |
| 632 | 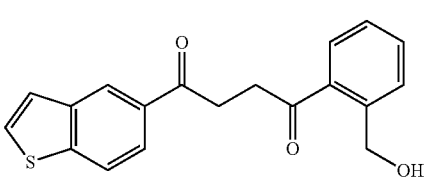 [SMILES: O=C(CCC(=O)c1ccccc1CO)c1ccc2sccc2c1] |
| 633 | 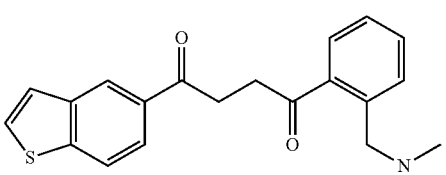 |
| 634 | 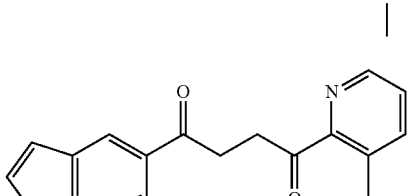 |
| 635 | 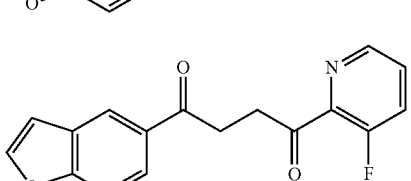 |

TABLE 1-continued
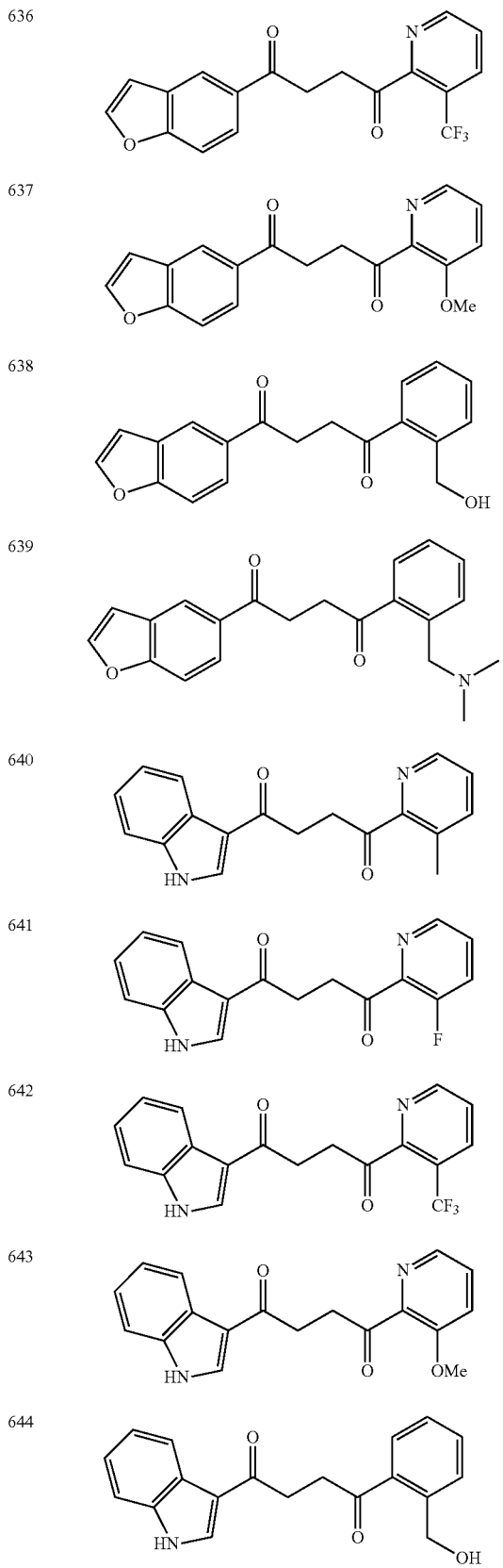
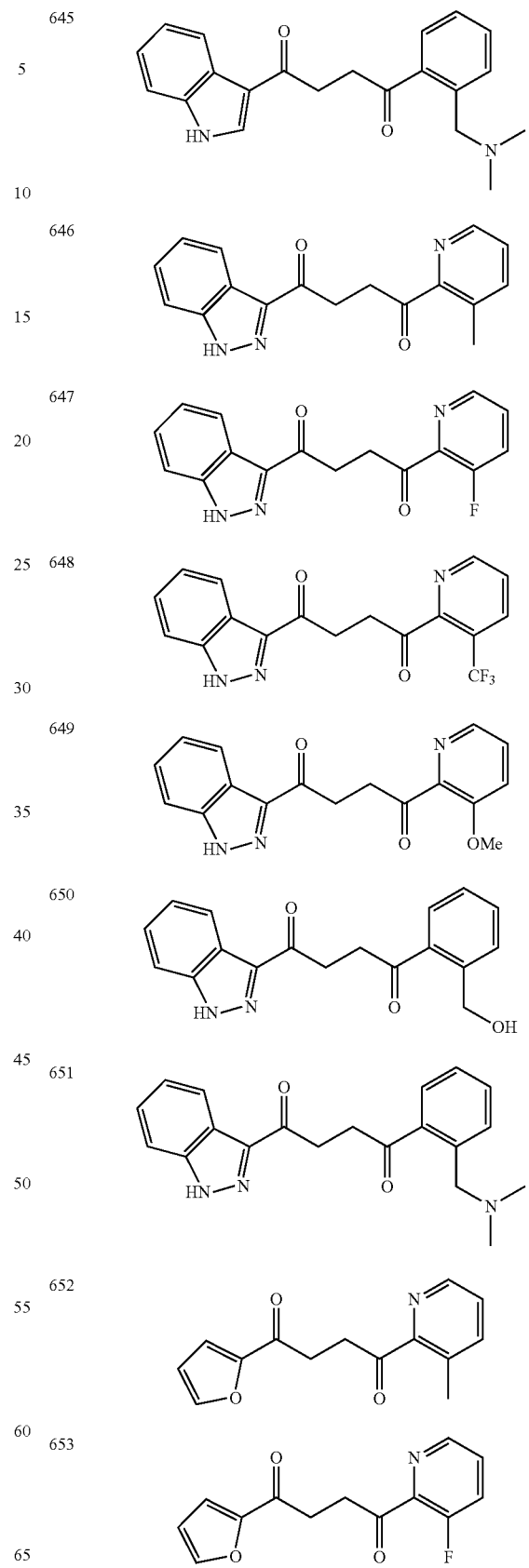

TABLE 1-continued
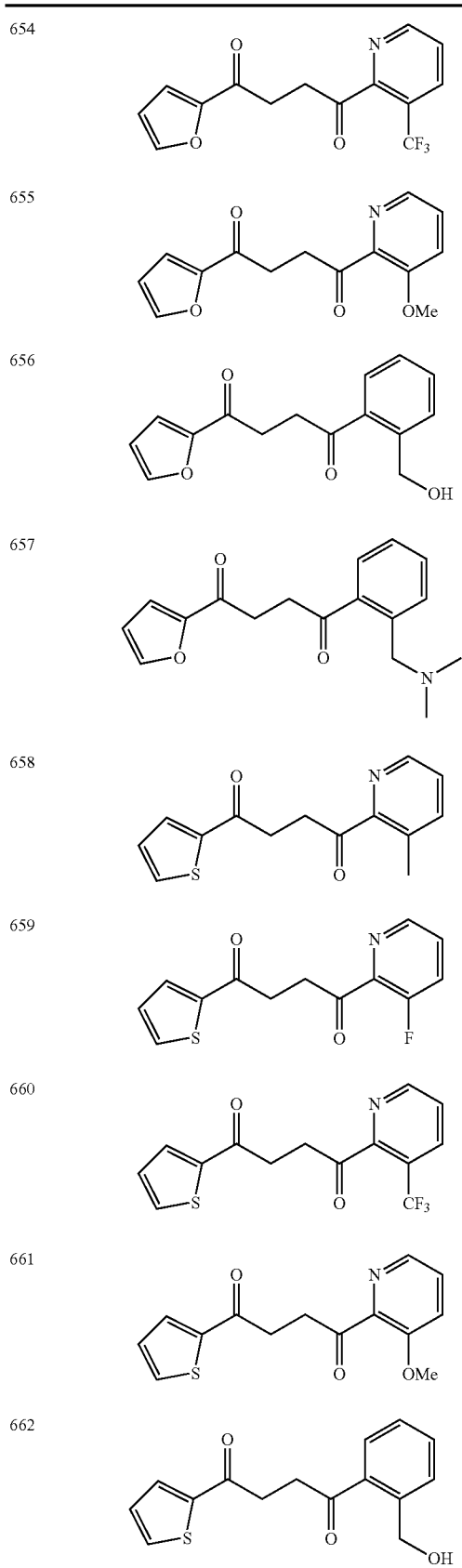
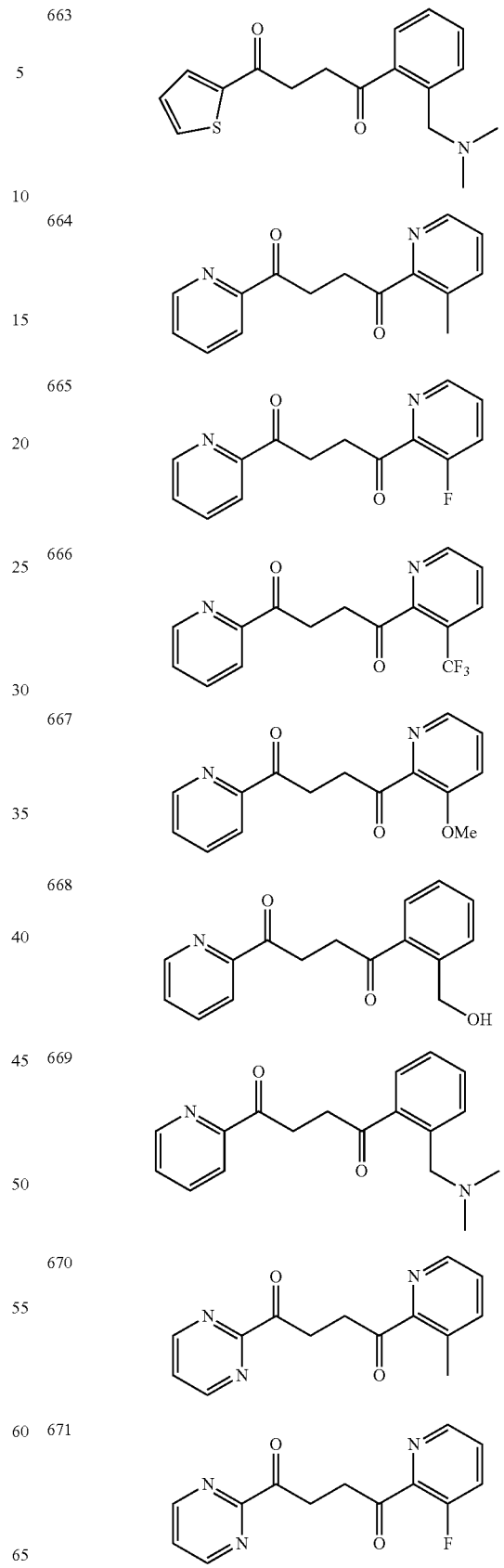

TABLE 1-continued
| | |
|---|---|
| 672 | 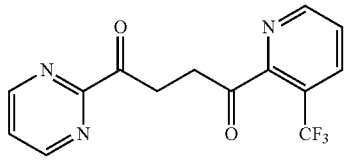 [SMILES: O=C(CCC(=O)c1ncccc1C(F)(F)F)c1ncccn1] |
| 673 | 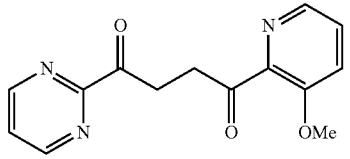 [SMILES: COc1cccnc1C(=O)CCC(=O)c1ncccn1] |
| 674 | 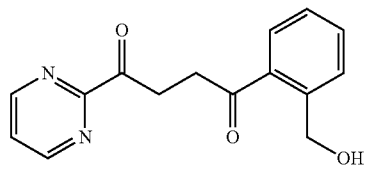 [SMILES: O=C(CCC(=O)c1ccccc1CO)c1ncccn1] |
| 675 | 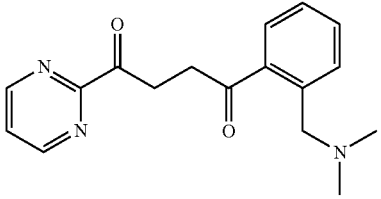 [SMILES: CN(C)Cc1ccccc1C(=O)CCC(=O)c1ncccn1] |
| 676 | 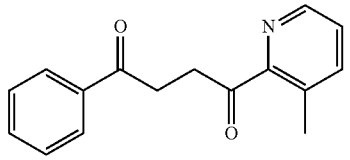 [SMILES: Cc1cccnc1C(=O)CCC(=O)c1ccccc1] |
| 677 | 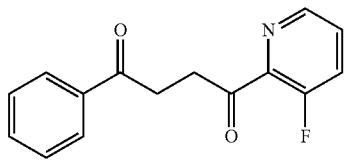 |
| 678 | 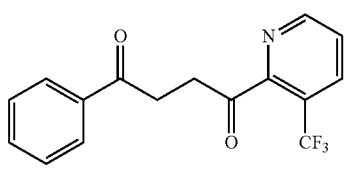 |
| 679 | 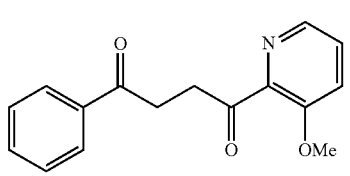 [SMILES: COc1cccnc1C(=O)CCC(=O)c1ccccc1] |
| 680 | 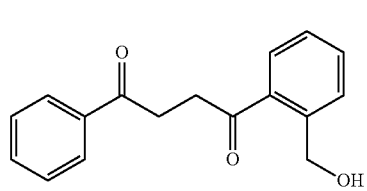 [SMILES: O=C(CCC(=O)c1ccccc1CO)c1ccccc1] |
| 681 | 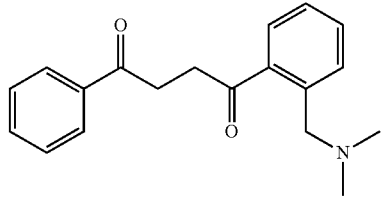 [SMILES: CN(C)Cc1ccccc1C(=O)CCC(=O)c1ccccc1] |
| 682 | 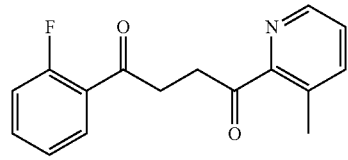 [SMILES: Cc1cccnc1C(=O)CCC(=O)c1ccccc1F] |
| 683 | 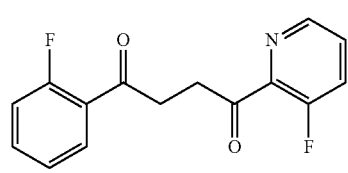 |
| 684 | 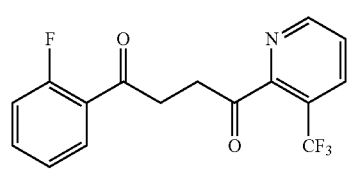 [SMILES: O=C(CCC(=O)c1ncccc1C(F)(F)F)c1ccccc1F] |
| 685 | 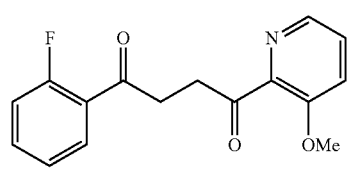 [SMILES: COc1cccnc1C(=O)CCC(=O)c1ccccc1F] |
| 686 | 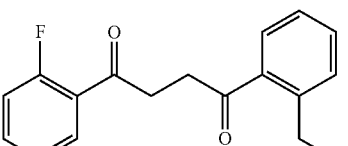 |
| 687 | 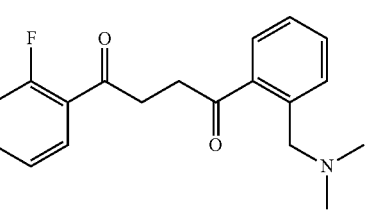 |
| 688 | 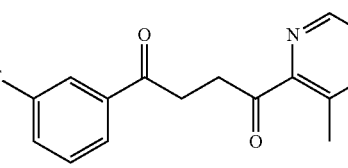 |
| 689 | 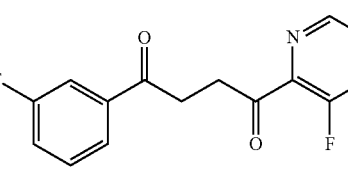 |

TABLE 1-continued
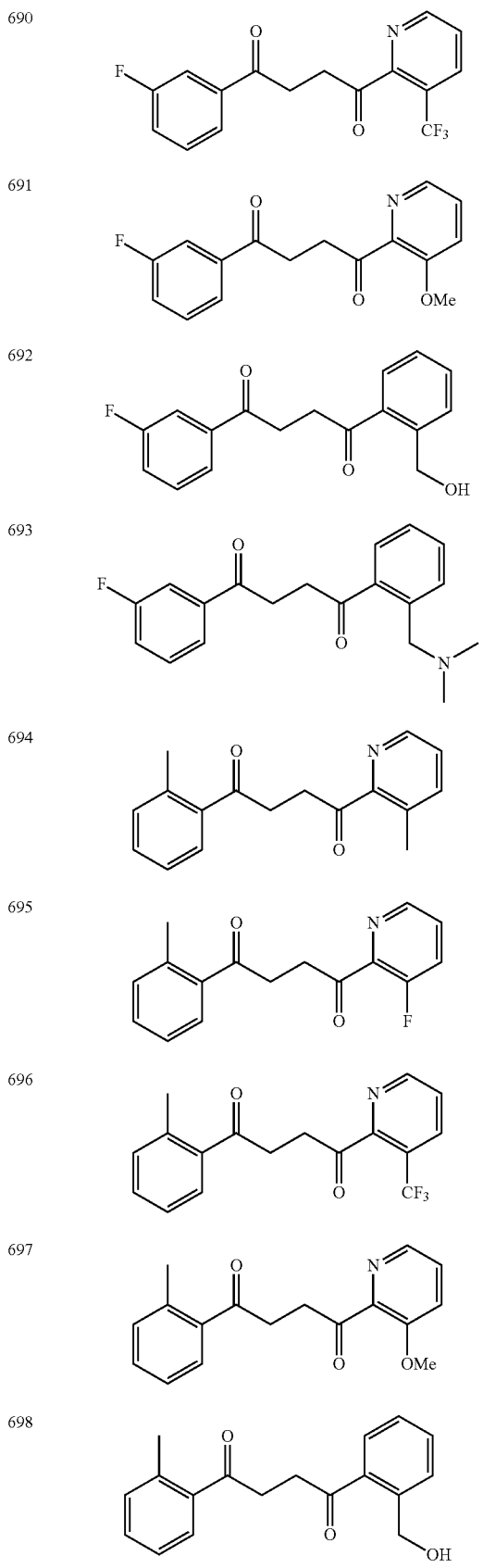
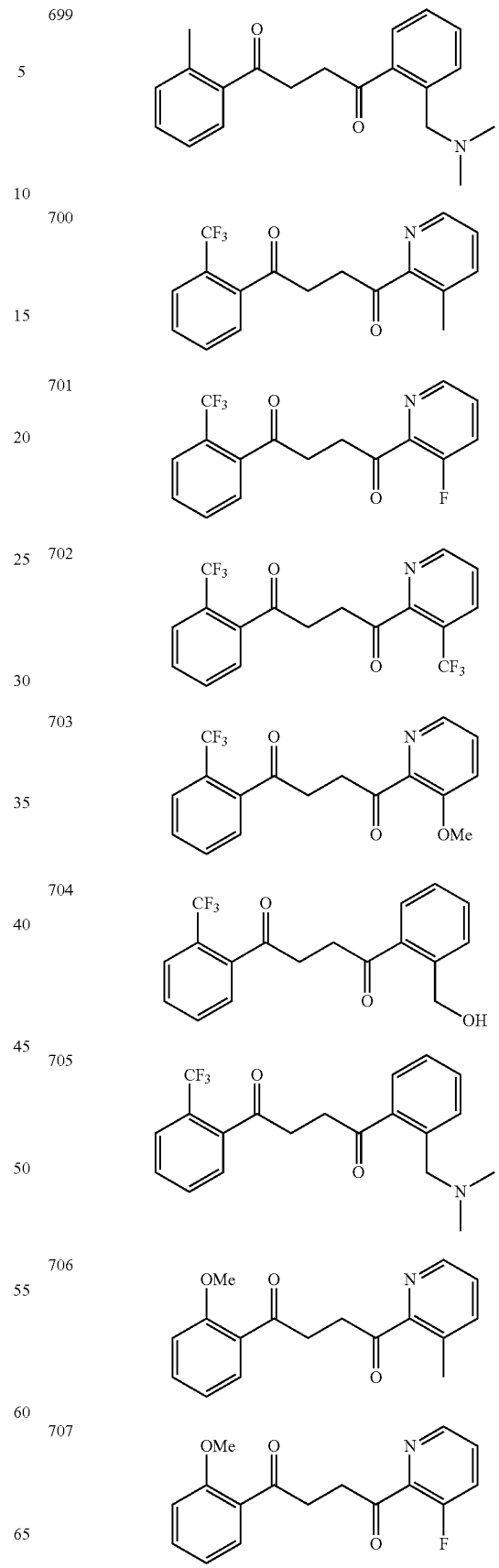

TABLE 1-continued
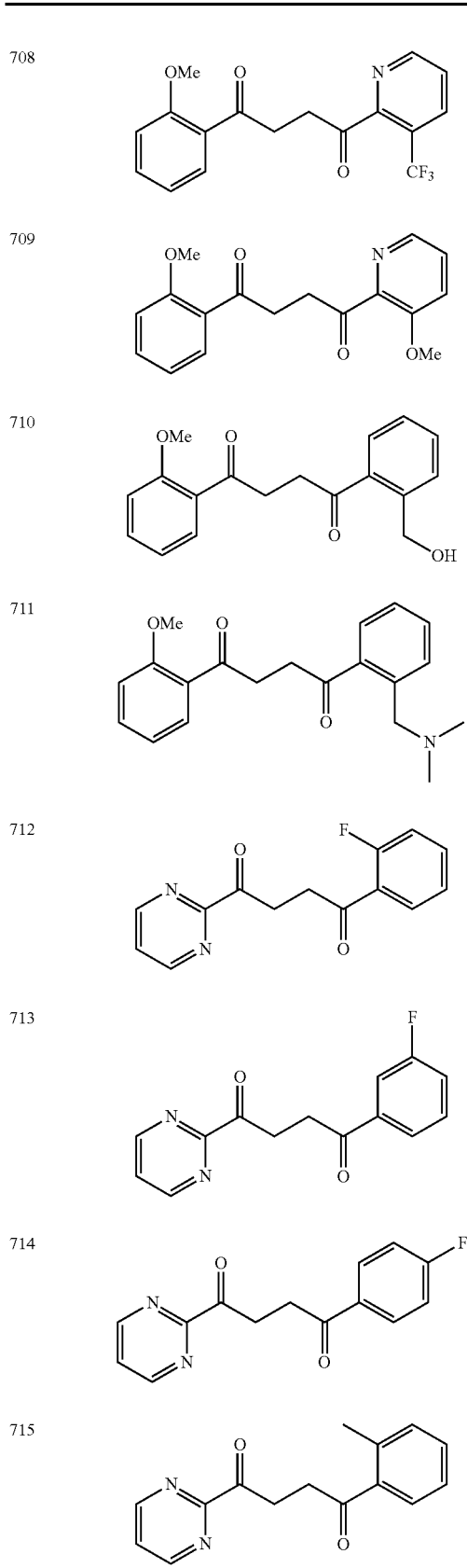
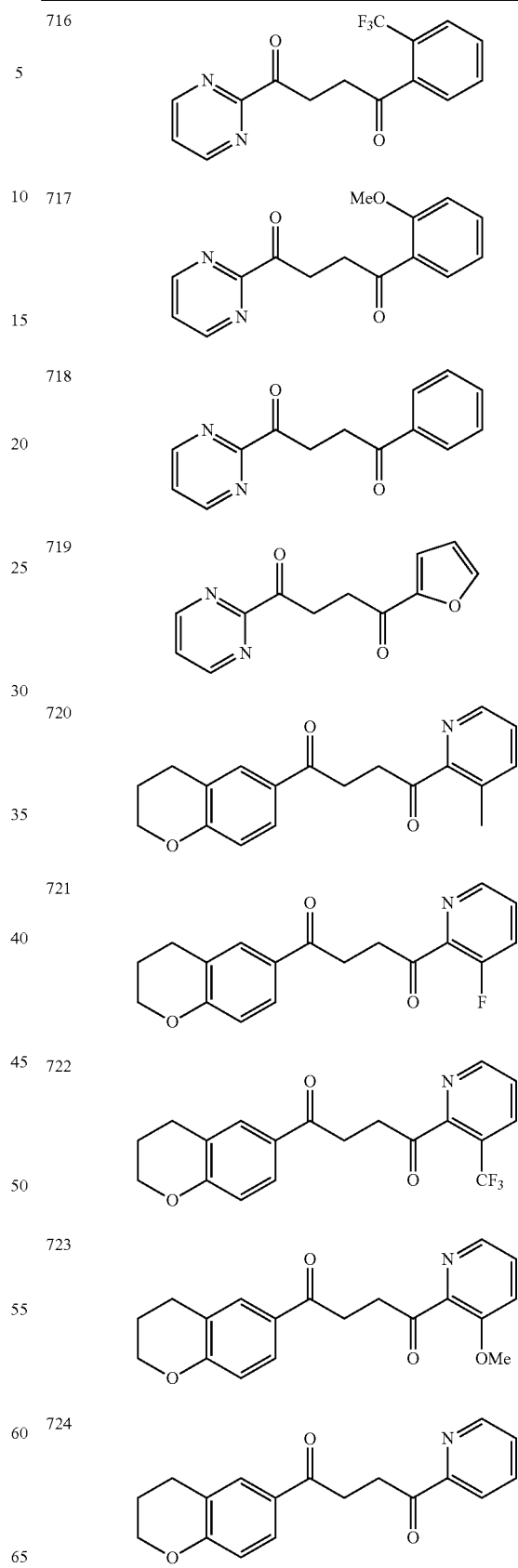

TABLE 1-continued
| | |
|---|---|
| 725 | 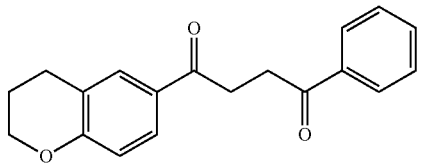 |
| 726 | 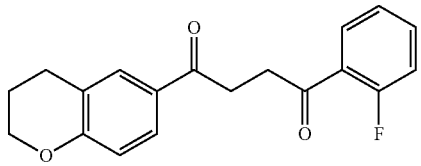 |
| 727 | 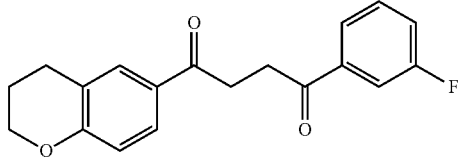 [SMILES: O=C(CCC(=O)c1ccc2c(c1)CCCO2)c1cccc(F)c1] |
| 728 | 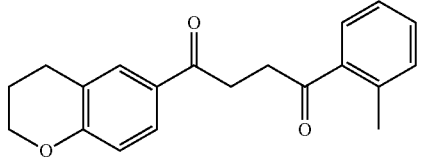 [SMILES: Cc1ccccc1C(=O)CCC(=O)c1ccc2c(c1)CCCO2] |
| 729 | 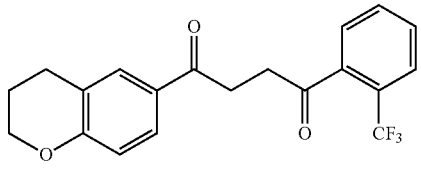 [SMILES: O=C(CCC(=O)c1ccccc1C(F)(F)F)c1ccc2c(c1)CCCO2] |
| 730 | 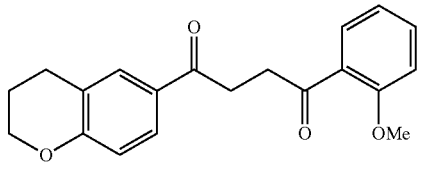 [SMILES: COc1ccccc1C(=O)CCC(=O)c1ccc2c(c1)CCCO2] |
| 731 | 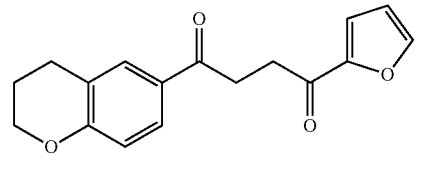 [SMILES: O=C(CCC(=O)c1ccco1)c1ccc2c(c1)CCCO2] |
| 732 | 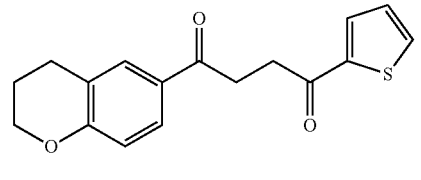 [SMILES: O=C(CCC(=O)c1cccs1)c1ccc2c(c1)CCCO2] |
| 733 | 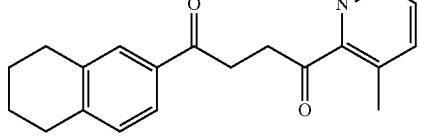 |
TABLE 1-continued
| | |
|---|---|
| 734 | 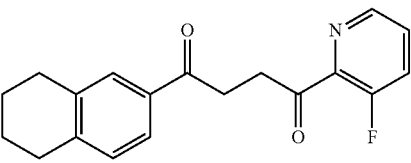 [SMILES: O=C(CCC(=O)c1ncccc1F)c1ccc2c(c1)CCCC2] |
| 735 | 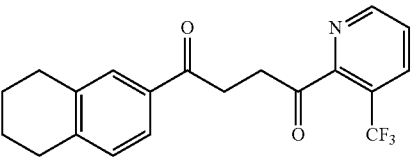 [SMILES: O=C(CCC(=O)c1ncccc1C(F)(F)F)c1ccc2c(c1)CCCC2] |
| 736 | 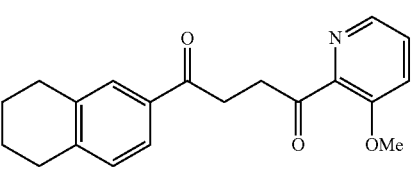 [SMILES: COc1cccnc1C(=O)CCC(=O)c1ccc2c(c1)CCCC2] |
| 737 | 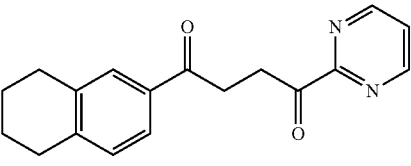 [SMILES: O=C(CCC(=O)c1ncccn1)c1ccc2c(c1)CCCC2] |
| 738 | 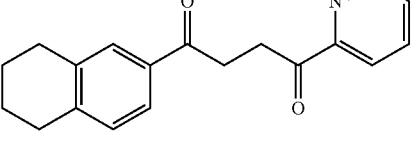 |
| 739 | 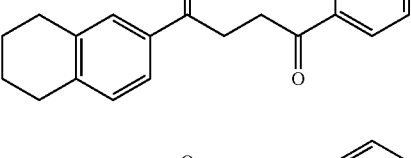 |
| 740 | 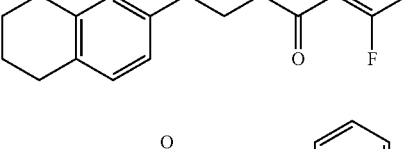 |
| 741 | 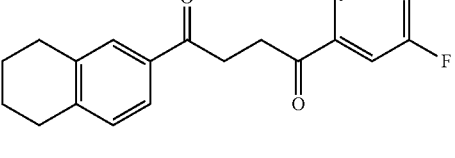 |
| 742 | 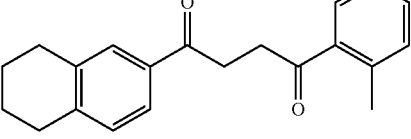 |

US 11,077,046 B2
TABLE 1-continued
| | |
|---|---|
| 743 | 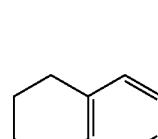 |
| 744 | 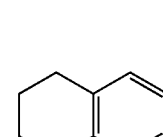 |
| 745 | 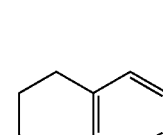 |
| 746 | 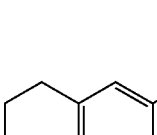 |
| 747 | 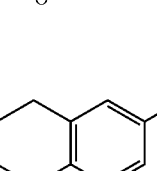 |
| 748 | 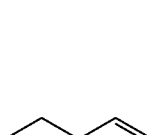 |
| 749 | 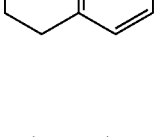 |
| 750 | 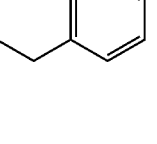 |
| 751 |  |
| 752 |  |
| 753 |  |
| 754 |  |
| 755 |  |
| 756 |  |
| 757 |  |
| 758 |  |
| 759 |  |
| 760 | |

TABLE 1-continued
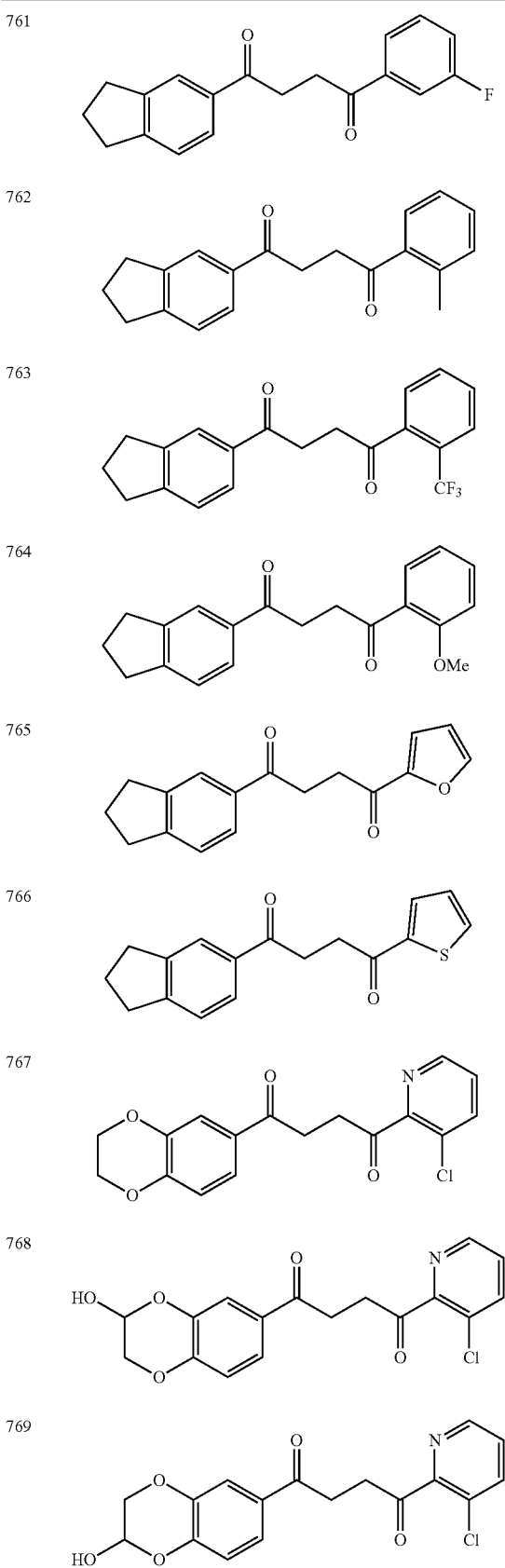
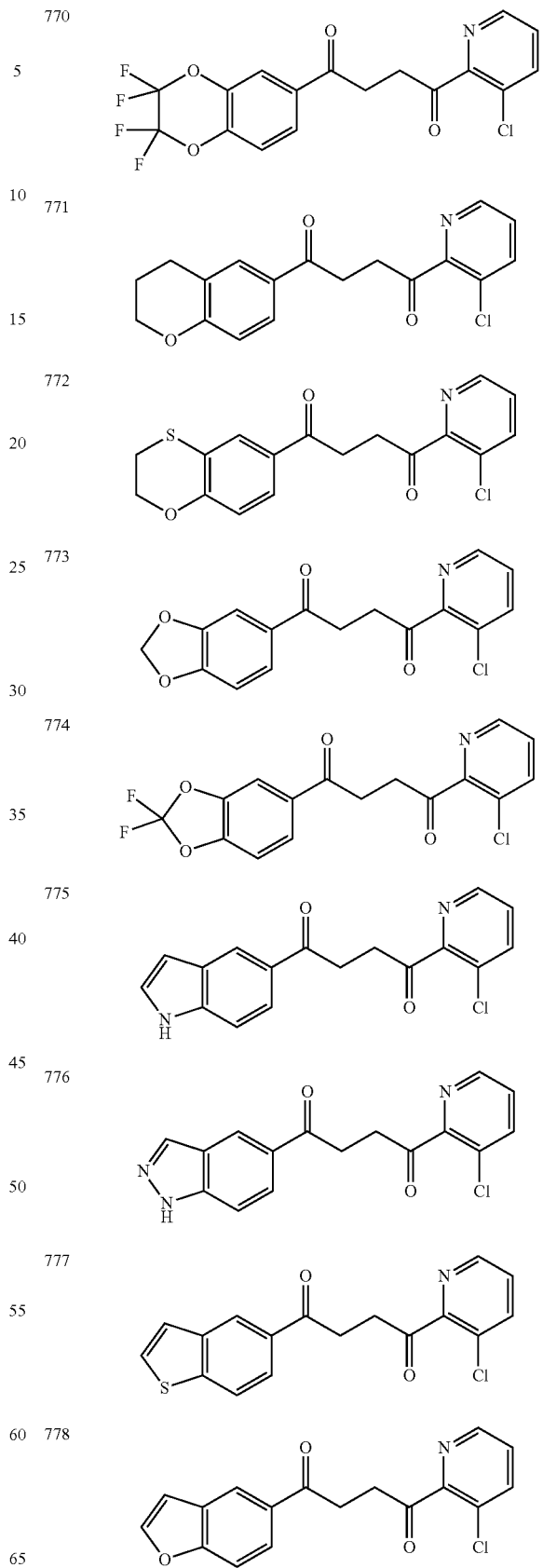

TABLE 1-continued
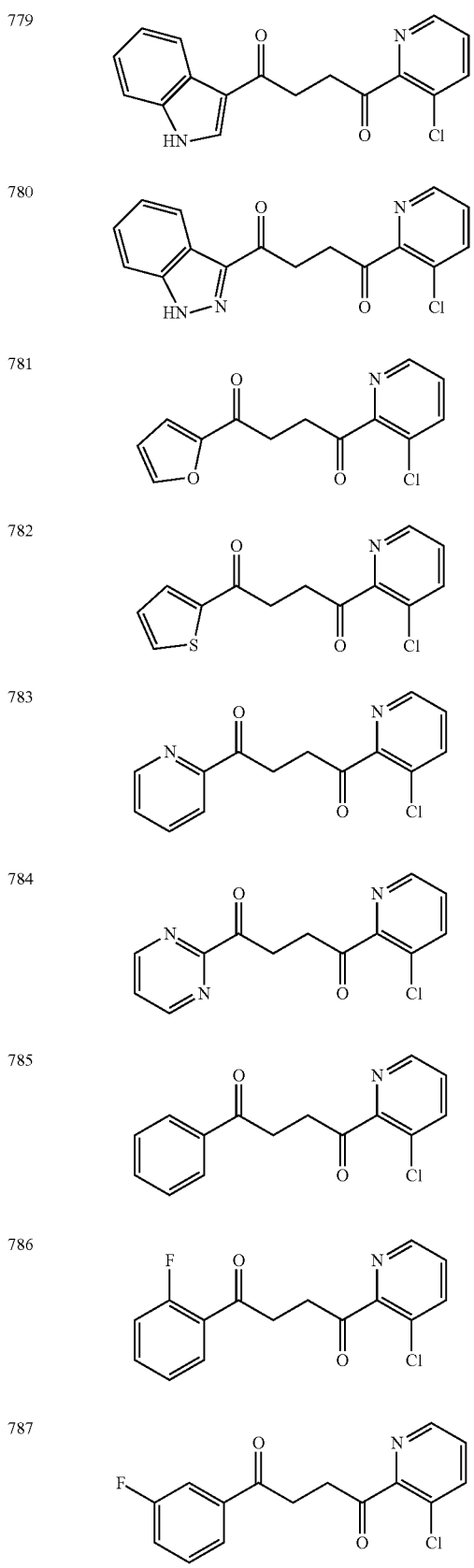
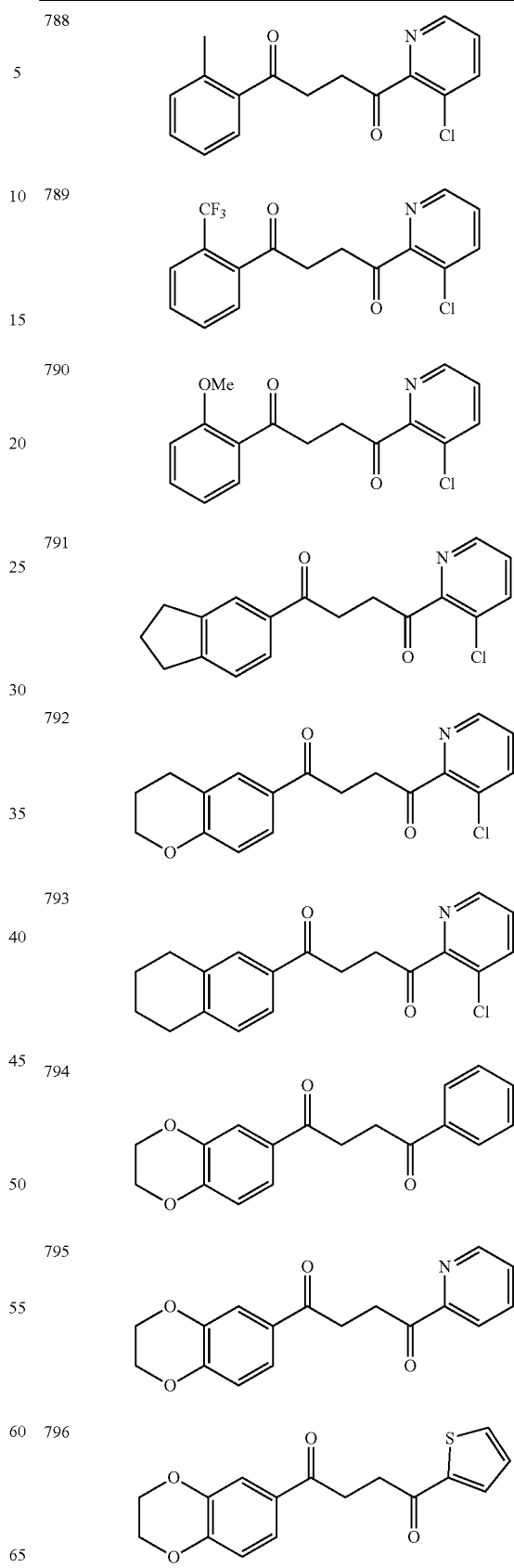

TABLE 1-continued
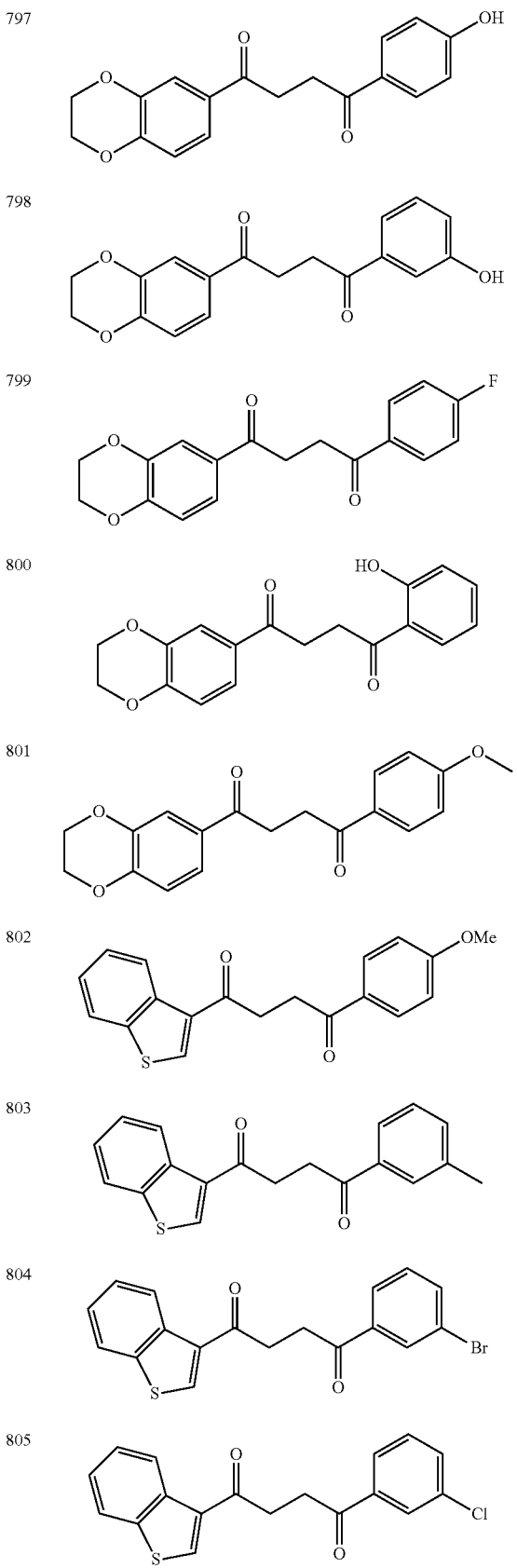
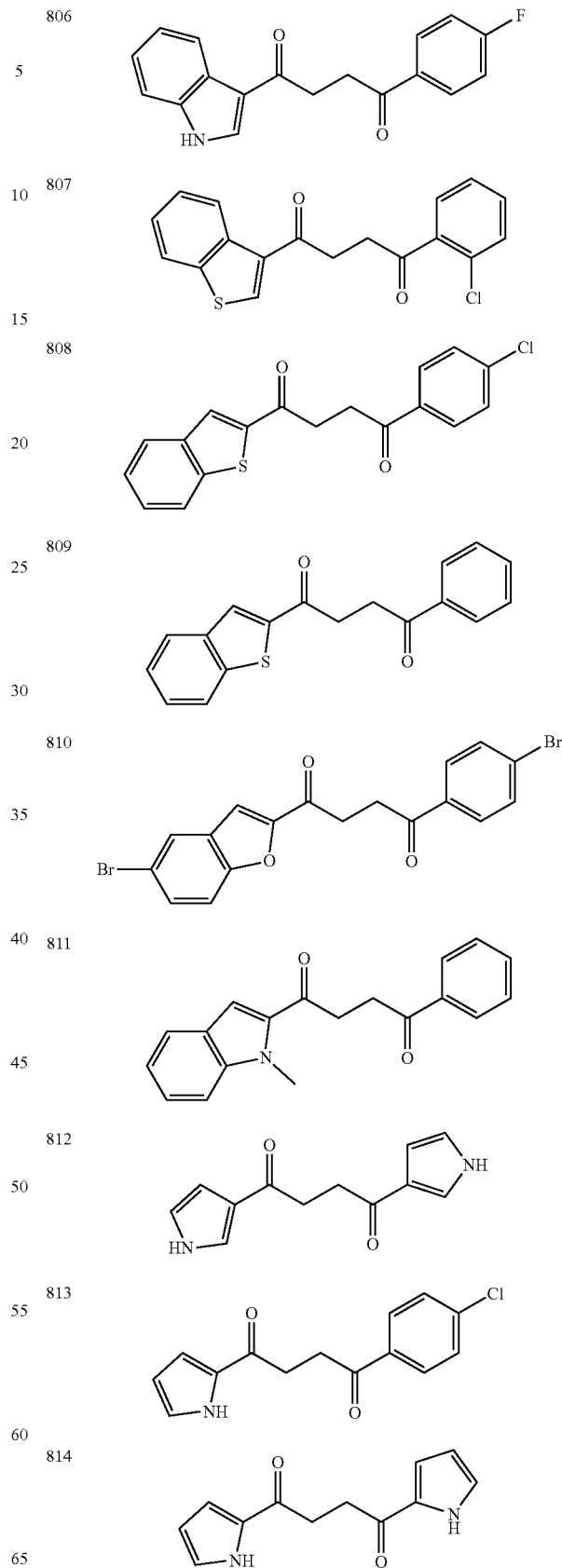

TABLE 1-continued
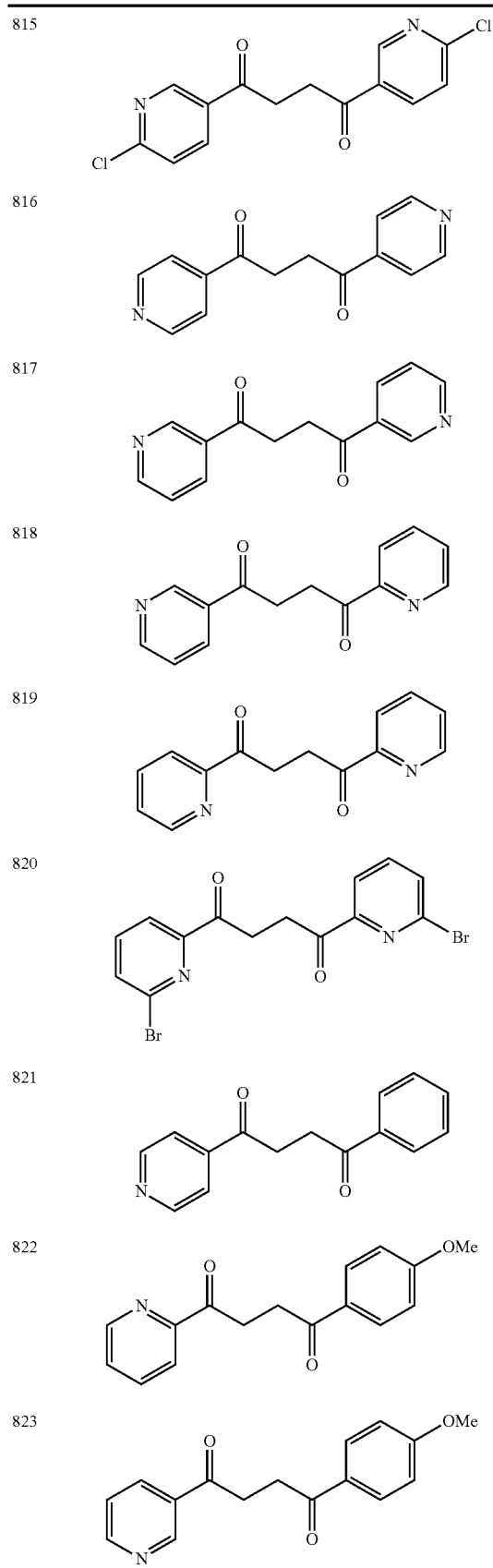
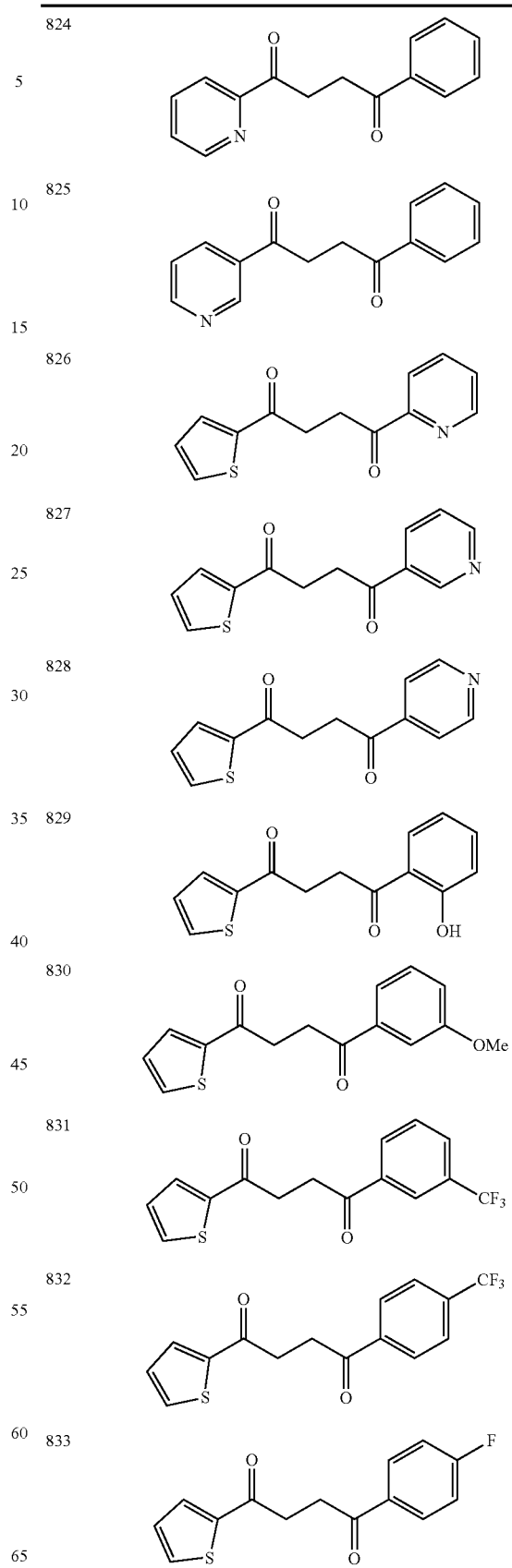

TABLE 1-continued
| | |
|---|---|
| 834 | 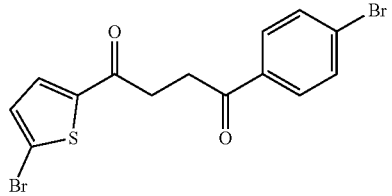 [SMILES: O=C(CCC(=O)c1ccc(Br)s1)c1ccc(Br)cc1] |
| 835 | 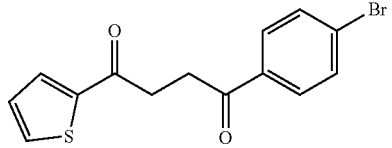 [SMILES: O=C(CCC(=O)c1cccs1)c1ccc(Br)cc1] |
| 836 | 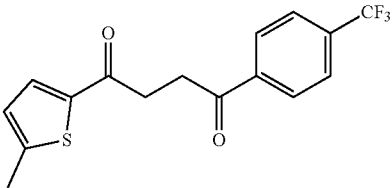 [SMILES: Cc1ccc(C(=O)CCC(=O)c2ccc(C(F)(F)F)cc2)s1] |
| 837 | 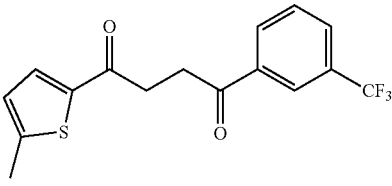 [SMILES: Cc1ccc(C(=O)CCC(=O)c2cccc(C(F)(F)F)c2)s1] |
| 838 | 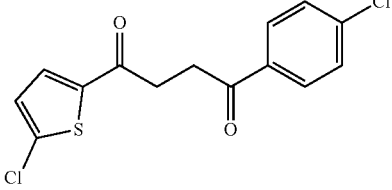 |
| 839 | 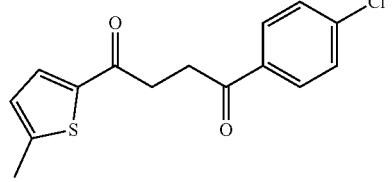 |
| 840 | 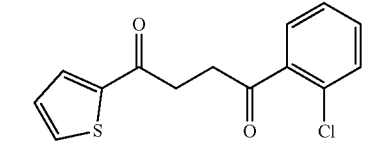 [SMILES: O=C(CCC(=O)c1ccccc1Cl)c1cccs1] |
| 841 | 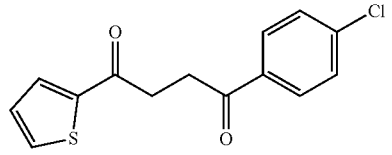 [SMILES: O=C(CCC(=O)c1cccs1)c1ccc(Cl)cc1] |
TABLE 1-continued
| | |
|---|---|
| 842 | 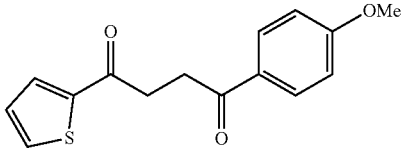 |
| 843 | 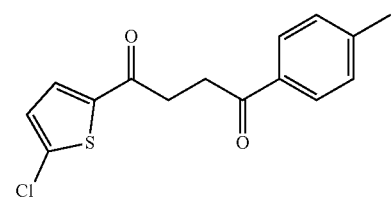 [SMILES: Cc1ccc(C(=O)CCC(=O)c2ccc(Cl)s2)cc1] |
| 844 | 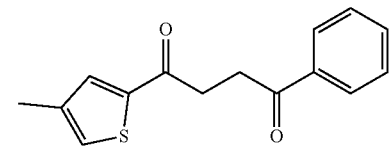 [SMILES: Cc1csc(C(=O)CCC(=O)c2ccccc2)c1] |
| 845 | 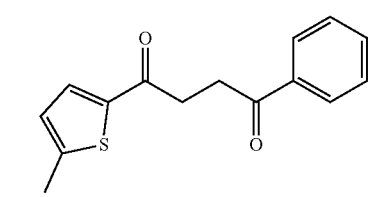 [SMILES: Cc1ccc(C(=O)CCC(=O)c2ccccc2)s1] |
| 846 | 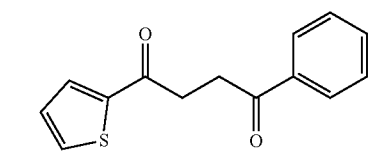 [SMILES: O=C(CCC(=O)c1cccs1)c1ccccc1] |
| 847 | 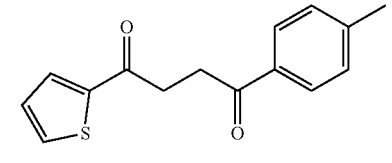 [SMILES: Cc1ccc(C(=O)CCC(=O)c2cccs2)cc1] |
| 848 | 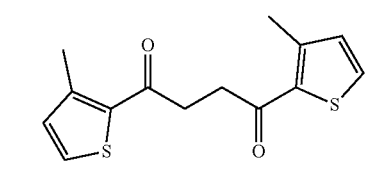 [SMILES: Cc1ccsc1C(=O)CCC(=O)c1sccc1C] |
| 849 | 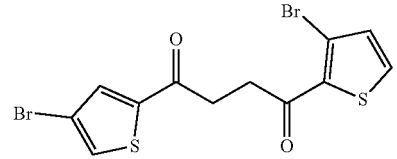 [SMILES: O=C(CCC(=O)c1sccc1Br)c1cc(Br)cs1] |
| 850 | 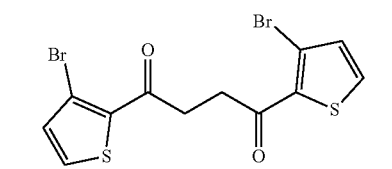 [SMILES: O=C(CCC(=O)c1sccc1Br)c1sccc1Br] |

TABLE 1-continued
| | |
|---|---|
| 851 | 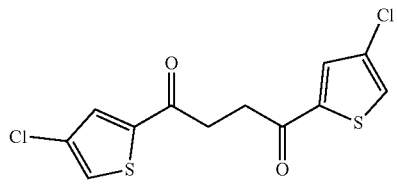 [SMILES: O=C(CCC(=O)c1cc(Cl)cs1)c1cc(Cl)cs1] |
| 852 | 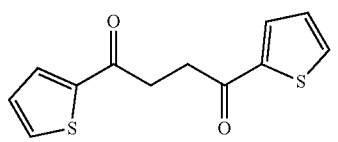 |
| 853 | 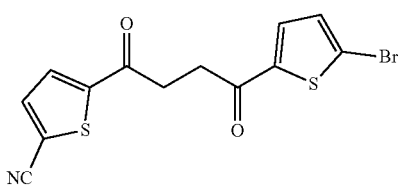 [SMILES: N#Cc1ccc(C(=O)CCC(=O)c2ccc(Br)s2)s1] |
| 854 | 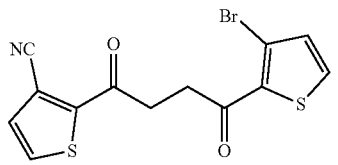 [SMILES: N#Cc1ccsc1C(=O)CCC(=O)c1sccc1Br] |
| 855 | 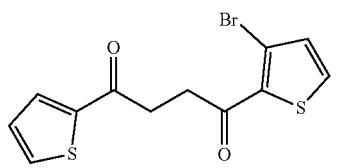 [SMILES: O=C(CCC(=O)c1sccc1Br)c1cccs1] |
| 856 | 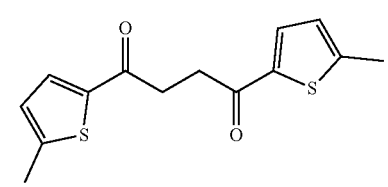 [SMILES: Cc1ccc(C(=O)CCC(=O)c2ccc(C)s2)s1] |
| 857 | 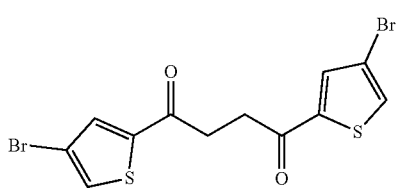 [SMILES: O=C(CCC(=O)c1cc(Br)cs1)c1cc(Br)cs1] |
| 858 | 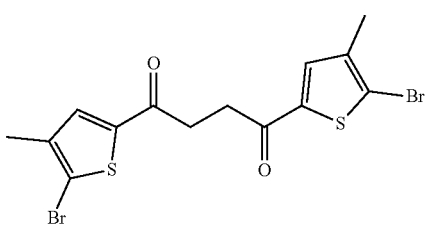 [SMILES: Cc1cc(C(=O)CCC(=O)c2cc(C)c(Br)s2)sc1Br] |
| 859 | 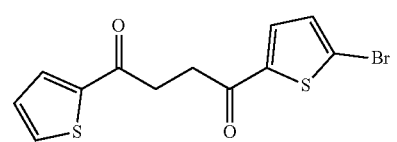 [SMILES: O=C(CCC(=O)c1ccc(Br)s1)c1cccs1] |
| 860 | 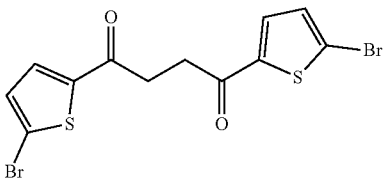 [SMILES: O=C(CCC(=O)c1ccc(Br)s1)c1ccc(Br)s1] |
| 861 | 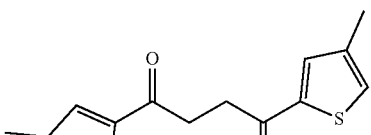 |
| 862 | 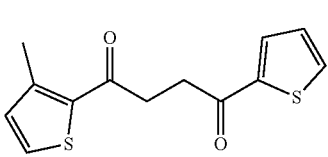 [SMILES: Cc1ccsc1C(=O)CCC(=O)c1cccs1] |
| 863 | 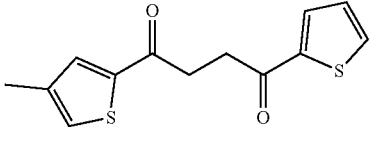 [SMILES: Cc1csc(C(=O)CCC(=O)c2cccs2)c1] |
| 864 | 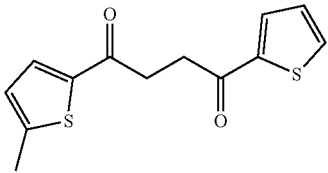 [SMILES: Cc1ccc(C(=O)CCC(=O)c2cccs2)s1] |
| 865 | 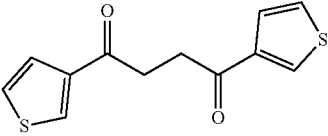 [SMILES: O=C(CCC(=O)c1ccsc1)c1ccsc1] |
| 866 | 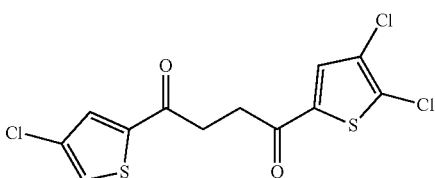 |
| 867 | 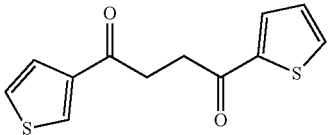 [SMILES: O=C(CCC(=O)c1cccs1)c1ccsc1] |
| 868 | 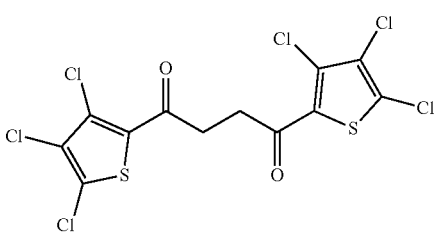 [SMILES: O=C(CCC(=O)c1sc(Cl)c(Cl)c1Cl)c1sc(Cl)c(Cl)c1Cl] |

TABLE 1-continued
| # | Structure |
|---|---|
| 869 | 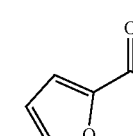 |
| 870 | 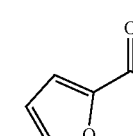 |
| 871 | 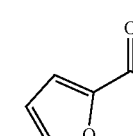 |
| 872 | 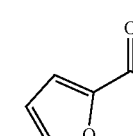 |
| 873 | 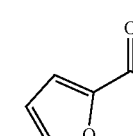 |
| 874 | 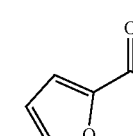 |
| 875 | 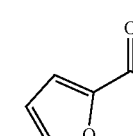 |
| 876 | 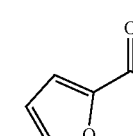 |
| 877 | 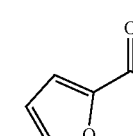 |
| 878 | 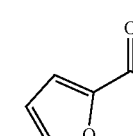 |
| 879 | 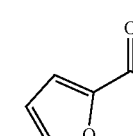 |
| 880 | 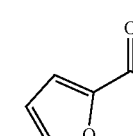 |
| 881 | |
| 882 | |
| 883 | |
| 884 | |
| 885 | |
| 886 | |

TABLE 1-continued
| | |
|---|---|
| 887 | 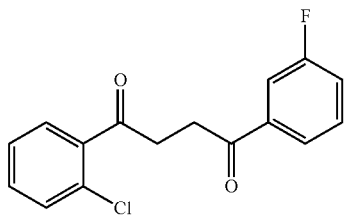 [SMILES: O=C(CCC(=O)c1ccccc1Cl)c1cccc(F)c1] |
| 888 | 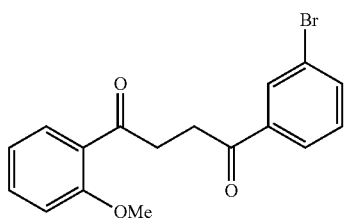 |
| 889 | 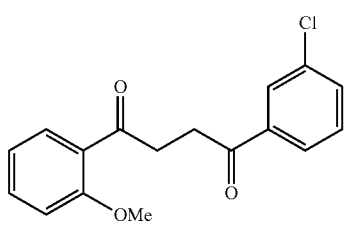 [SMILES: COc1ccccc1C(=O)CCC(=O)c1cccc(Cl)c1] |
| 890 | 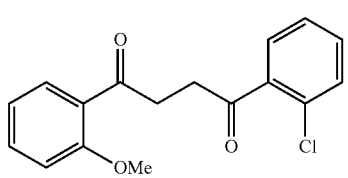 [SMILES: COc1ccccc1C(=O)CCC(=O)c1ccccc1Cl] |
| 891 | 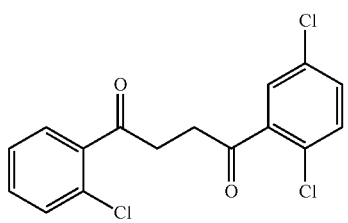 [SMILES: O=C(CCC(=O)c1cc(Cl)ccc1Cl)c1ccccc1Cl] |
| 892 | 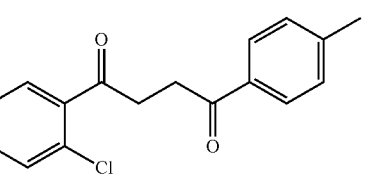 |
| 893 | 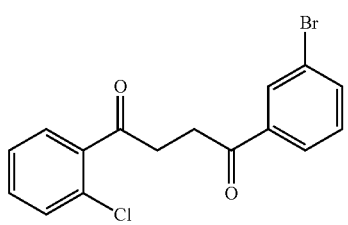 [SMILES: O=C(CCC(=O)c1ccccc1Cl)c1cccc(Br)c1] |
TABLE 1-continued
| | |
|---|---|
| 894 | 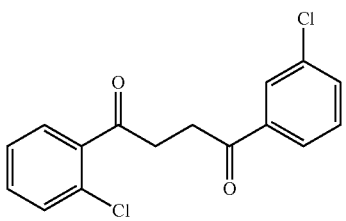 |
| 895 | 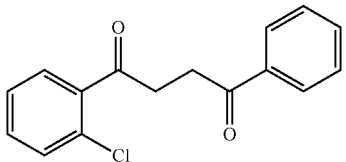 [SMILES: O=C(CCC(=O)c1ccccc1Cl)c1ccccc1] |
| 896 | 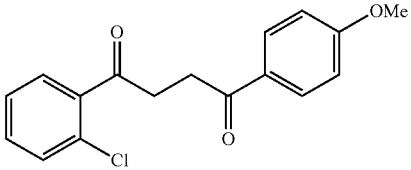 [SMILES: COc1ccc(C(=O)CCC(=O)c2ccccc2Cl)cc1] |
| 897 | 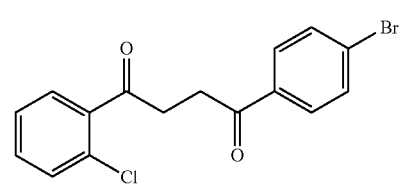 [SMILES: O=C(CCC(=O)c1ccccc1Cl)c1ccc(Br)cc1] |
| 898 | 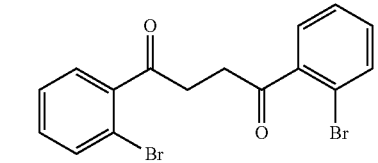 [SMILES: O=C(CCC(=O)c1ccccc1Br)c1ccccc1Br] |
| 899 | 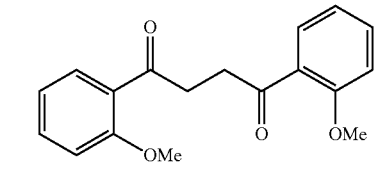 [SMILES: COc1ccccc1C(=O)CCC(=O)c1ccccc1OC] |
| 900 | 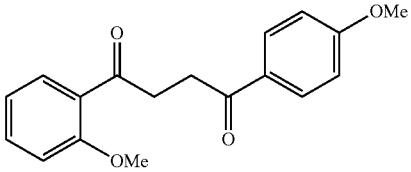 [SMILES: COc1ccc(C(=O)CCC(=O)c2ccccc2OC)cc1] |
| 901 | 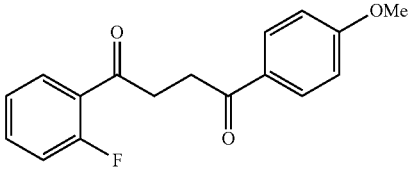 [SMILES: COc1ccc(C(=O)CCC(=O)c2ccccc2F)cc1] |

TABLE 1-continued

902
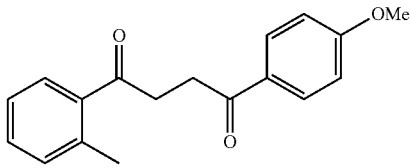 [SMILES: COc1ccc(C(=O)CCC(=O)c2ccccc2C)cc1]

903
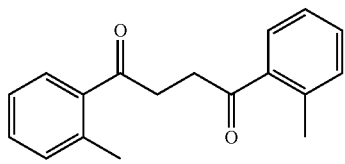 [SMILES: Cc1ccccc1C(=O)CCC(=O)c1ccccc1C]

904
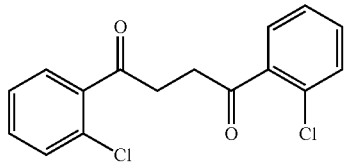 [SMILES: O=C(CCC(=O)c1ccccc1Cl)c1ccccc1Cl]

905
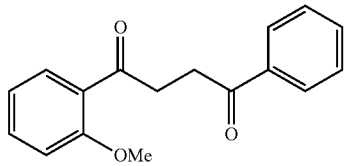 [SMILES: COc1ccccc1C(=O)CCC(=O)c1ccccc1]

The compounds provided herein can be prepared using methods known and understood by those of ordinary skill in the art. For example, synthetic methods such as those described in PCT/US2011/048086 and PCT/US2014/017794 can be used, and both applications are herein incorporated by reference in their entirety.

The skilled artisan will recognize that some structures described herein can be resonance forms or tautomers of compounds that can be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. Alkyl groups can be saturated or unsaturated (e.g., containing —C=C— or —C≡C— subunits), at one or several positions. Typically, alkyl groups will comprise 1 to 9 carbon atoms (for example, 1 to 6 carbon atoms, 1 to 4 carbon atoms, or 1 to 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. Typically, carbocyclyl groups will comprise 3 to 10 carbon atoms, for example, 3 to 6 carbon atoms.

As used herein, "lower alkyl" means a subset of alkyl having 1 to 3 carbon atoms, which is linear or branched. Examples of lower alkyls include methyl, ethyl, n-propyl and isopropyl. Likewise, radicals using the terminology "lower" refer to radicals having 1 to about 3 carbons in the alkyl portion of the radical.

As used herein, "aryl" means an aromatic ring system containing a single-ring (e.g., phenyl) or multiple condensed rings (e.g., naphthyl or anthryl) with only carbon atoms present in the ring backbone. Aryl groups can either be unsubstituted or substituted with one or more substituents. In some embodiments, the aryl is phenyl.

As used herein, "arylalkyl" means an aryl-alkyl-group in which the aryl and alkyl moieties are as previously described. In some embodiments, arylalkyl groups contain a $C_{1-4}$ alkyl moiety. Exemplary arylalkyl groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, 2,3-dihydrobenzo[b][1,4]oxathiine, and others.

As used herein, "heteroarylalkyl" means a heteroaryl-alkyl-group in which the heteroaryl and alkyl moieties are as previously described. In some embodiments, heteroarylalkyl groups contain a $C_{1-4}$ alkyl moiety. Exemplary heteroarylalkyl groups include pyridylmethyl.

As used herein, "acyl" means an H—CO— or alkyl-CO—, carbocyclyl-CO-aryl-CO—, heteroaryl-CO—, or heterocyclyl-CO— group wherein the alkyl, carbocyclyl, aryl or heterocyclyl group is as herein described. In some embodiments, acyls contain a lower alkyl. Exemplary alkyl acyl groups include formyl, acetyl, propanoyl, 2-methylpropanoyl, t-butylacetyl, butanoyl, and palmitoyl.

As used herein, "alkoxycarbonyl" means an alkyl-O—CO— group in which the alkyl group is as described herein. Exemplary alkoxycarbonyl groups include methoxy- and ethoxycarbonyl.

As used herein, "alkoxy" means an alkyl-O— group in which the alkyl group is as described herein. Exemplary alkoxy groups include difluoromethoxy, methoxy, trifluoromethoxy, ethoxy, n-propoxy, i-propoxy, n-butoxy, s-butoxy, t-butoxy, pentoxy, hexoxy and heptoxy, and also the linear or branched positional isomers thereof.

As used herein, the terms "halo", "halide" or "halogen" are used interchangeably and mean a chloro, bromo, fluoro, or iodo atom radical. In some embodiments, a halo is a chloro, bromo or fluoro. For example, a halo can be fluoro.

As used herein, "haloalkyl" means a hydrocarbon substituent, which is a linear or branched or cyclic alkyl, alkenyl or alkynyl substituted with one or more chloro, bromo, fluoro, or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls can be substituted or unsubstituted with one or more substituents. In some embodiments, heterocycles have 5-7 members. In six membered monocyclic heterocycles, the heteroatom(s) are selected from one up to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —NH($C_{1-3}$ alkyl), and —N($C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —NH($C_{1-3}$ alkyl), and —N($C_{1-3}$ alkyl)$_2$; —OPO(OH)$_2$; a phosphonate [such as —PO(OH)$_2$ and —PO(OR')$_2$]; —OPO(OR')R"; —NRR'; —C(O)NRR'; —C(NR)NR'R"; —C(NR')R"; a cyano; a nitro; an azido; —SH; —S—R; —OSO$_2$(OR); a sulfonate [such as —SO$_2$(OH) and —SO$_2$(OR)]; —SO$_2$NR'R"; and —SO$_2$R; in which each occurrence of R, R' and R" are independently selected from H; —($C_{1-9}$ alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

"Solvate" refers to the compound formed by the interaction of a solvent and a compound as provided herein or a salt thereof. Suitable solvates are pharmaceutically or dermatologically acceptable solvates including hydrates.

Methods of Use and/or Treatment

The compounds and compositions provided herein can be used in methods for treating, protecting and/or improving the condition and/or aesthetic appearance of skin. For example, the compounds and compositions provided herein can be used in methods for altering the aesthetic appearance of skin associated with or affected by, or for treating or preventing, fine lines and/or wrinkles of skin caused by, for example, cellular senescence, environmental damage or dermatoheliosis. The disclosure also relates to methods for stimulating skin cell renewal, increasing cell or tissue regeneration, promoting fibroblast proliferation and synthesizing elastin, collagen, proteoglycans, and/or new connective tissue, thereby reducing or improving the appearance of wrinkles, restoring elasticity, resiliency, and/or suppleness to the skin. Such methods include administering to a subject in need thereof an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a dermatologically acceptable salt thereof.

The compounds and compositions provided herein can be useful for improving the aesthetic appearance of skin. Such improvements can include, but are not limited to, all outward visibly and tactilely perceptible manifestations as well as any other macro or micro effects due to skin aging and damage. Such manifestations and effects can be induced or caused by intrinsic factors and/or extrinsic factors, e.g., chronological aging, environmental damage, climate, sun (UV) exposure, smoking, drugs, alcohol consumption, jetlag, night work, changes in circadian rhythm, pregnancy, menopause, genetic factors, nutritional factors and/or deficiencies, dehydration, stress, allergies (e.g., to plants, animals, medications, and other substances), exposure to industrial and/or household chemicals, indoor heating and cooling, various disorders and diseases such as arteriosclerosis, diabetes, heart disease, liver disease, and obesity, thinning of the outer layer of skin, decreases in the number of pigment-containing cells, increases in the size of pigment-containing cells, changes in the connective tissue, and reduction in the strength and elasticity of the skin.

The aesthetic appearance of skin can be improved, for example, by improving the appearance of skin associated with or affected by one or more of wrinkles, dry skin, sensitive skin; wrinkling and sagging; acne; vitiligo (skin condition in which there is a loss of brown color (pigment) from areas of skin); fine lines, wizened skin, thinning of the dermis, the degradation of collagen fibers, flaccid skin, thinned skin, and skin exposed to ultraviolet radiation. In some embodiments, a compound or composition can improve the aesthetic appearance of skin by decreasing the appearance of fine lines in the skin; creating a more youthful appearance of the skin; decreasing bags and/or rings around the eyes; increasing or restoring the elasticity, resiliency, and/or suppleness of the skin; increasing the apparent thickness, elasticity, flexibility, radiance, glow, and plumpness of the skin; improving the fineness of the skin texture; improving the appearance of wrinkles, lined, dry, flaky, aged, and/or photodamaged skin; treating or preventing photodamaged skin; reducing the signs of skin aging; reducing the appearance of hyperpigmentation; treating or preventing hyperpigmentation; treating or preventing pigment deposition in the skin (e.g., that caused by UV exposure); reducing the appearance of skin discolorations; and whitening, lightening, and/or bleaching the skin.

The compounds and compositions provided herein can also be used in methods of treating or preventing a skin condition or disorder. For example, a compound or composition can improve the aesthetic appearance of the skin by promoting proliferation and/or mobility of skin keratinocytes and/or dermis fibroblasts; improving epidermal cell repair activity; increasing fibroblast proliferation, keratinocyte proliferation, and/or expression of collagen; reducing collagenase activity; treating or preventing a wound healing disorder; increasing the thickness of the epidermis; and inhibiting melanin production.

In one embodiment, the present disclosure provides a method for improving the condition and aesthetic appearance of skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by skin aging. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by environmental damage to the skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by one or more of wrinkles, dry skin, sensitive skin, and dermatological symptoms caused by ineffective homeostatic regulation of healthy skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by, or treating or preventing, a skin condition/disorder (e.g., a skin condition/disorder accompanied with a loss of skin elasticity). The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for improving the barrier function and viability of the skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by wrinkling, sagging, and/or a loss of skin elasticity. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by, or treating or preventing, acne. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV. In some embodiments, the acne can be selected from one or more of simple acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne or medication-related acne.

In one embodiment, the present disclosure provides a method for altering the aesthetic appearance of skin associated with or affected by deteriorations in skin viscoelasticity. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In another embodiment, the disclosure relates to the use of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for altering the aesthetic appearance of skin associated with or affected by one or more of wrinkles and/or fine lines, wizened skin, a lack of elasticity and/or of tonus of the skin, thinning of the dermis, degradation of collagen fibers, flaccid skin, thinned skin, and the internal degradation of the skin following exposure to ultraviolet radiation.

In one embodiment, the present disclosure provides a method for decreasing the appearance of fine lines and/or wrinkles in the skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for creating a more youthful appearance of the skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for decreasing the appearance of bags and/or rings around the eyes. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for reducing the appearance of hyperpigmentation. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for increasing or restoring elasticity, resiliency, and/or suppleness of the skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for improving or increasing one or more of the thickness, elasticity, flexibility, radiance, glow, and plumpness of the skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for improving the fineness of skin texture. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for improving the appearance of wrinkled, lined, dry, flaky, aged or photodamaged skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by skin discolorations. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for whitening, lightening, and/or bleaching the skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by, or treating or preventing, hyperpigmentation. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for altering the aesthetic appearance of skin associated with or affected by, or treating or preventing, photodamaged skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for treating or preventing pigment deposition in the skin caused by UV exposure. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for treating or preventing vitiligo (skin condition in which there is a loss of brown color (pigment) from areas of skin). The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiments, the present disclosure provides a method for treating or preventing a wound healing disorder in a mammal. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV. For example, a compound or composition provided herein can be used as a medicament for preventing and/or treating a bedsore in a mammal.

In one embodiment, the present disclosure provides a method for promoting proliferation and/or mobility of skin keratinocyte and/or dermis fibroblasts (e.g., to increase skin regeneration). The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for improving the epidermal cell repair activity, for example, in a human. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for increasing fibroblast proliferation, keratinocyte proliferation, and/or expression of collagen. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for reducing collagenase activity. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for increasing or improving the thickness of the epidermis. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, the present disclosure provides a method for inhibiting melanin production. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

The various effects on the skin (e.g., skin conditions/disorders) described above can be caused by or be associated with various internal and external influences.

In some embodiments, the skin condition/disorder is caused by or associated with aging.

In some embodiments, the skin condition/disorder is caused by or associated with environmental factors.

In some embodiments, the skin condition/disorder is caused by or associated with genetic factors.

In some embodiments, the skin condition/disorder is caused by or associated with nutritional factors and/or deficiencies.

In some embodiments, the skin condition/disorder is caused by or associated with blood vessel diseases such as arteriosclerosis.

In some embodiments, the skin condition/disorder is caused by or associated with dehydration.

In some embodiments, the skin condition/disorder is caused by or associated with diabetes.

In some embodiments, the skin condition/disorder is caused by or associated with heart disease.

In some embodiments, the skin condition/disorder is caused by or associated with liver disease.

In some embodiments, the skin condition/disorder is caused by or associated with obesity.

In some embodiments, the skin condition/disorder is caused by or associated with stress.

In some embodiments, the skin condition/disorder is caused by or associated with allergies to plants and other substances.

In some embodiments, the skin condition/disorder is caused by or associated with climate.

In some embodiments, the skin condition/disorder is caused by clothing.

In some embodiments, the skin condition/disorder is caused by exposure to industrial and household chemicals.

In some embodiments, the skin condition/disorder is caused or associated with by indoor heating/cooling.

In some embodiments, the skin condition/disorder is caused by or associated with sunlight (UV exposure).

In some embodiments, the skin condition/disorder is caused by a reaction to a medication (e.g., an adverse reaction).

In some embodiments, the skin condition/disorder is related to thinning of the outer skin layer (epidermis).

In some embodiments, the skin condition/disorder is related to a decrease in the number of pigment-containing cells (melanocytes).

In some embodiments, the skin condition/disorder is related to an increase in the size of pigment-containing cells (melanocytes).

In some embodiments, the skin condition/disorder is related to enlarged pigmented spots (called age spots, liver spots, or lentigos).

In some embodiments, the skin condition/disorder is related to a change in the connective tissue.

In some embodiments, the skin condition/disorder is related to a reduction of the skin's strength and elasticity (elastosis).

In some embodiments, the skin condition/disorder is related to the blood vessels of the dermis becoming more fragile.

In some embodiments, the skin condition/disorder is related to a reduction in oil production (e.g., a reduction in the oil production of the sebaceous glands).

In some embodiments, the skin condition/disorder is related to a thinning of the subcutaneous fat layer.

In some embodiments, the skin condition/disorder is related to a reduction in sweat production by the sweat glands.

In some embodiments, the skin condition/disorder is related to a growth such as skin tags and/or warts.

The term "subject" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, a subject is a human.

The term "mammal" is used in its usual biological sense. Thus, it specifically includes humans, cattle, horses, monkeys, dogs, cats, mouse, rat, a cow, sheep, pig, goat, and non-human primate but also includes many other species.

The phrase an "effective amount" is used to mean a "therapeutically effective amount" or "cosmetically effective amount" depending on the intended use of the compound or composition to which it refers. An effective amount as used herein means an amount of a compound or composition sufficient for achieving a desirable result in response to one or more skin conditions/disorders, but low enough to avoid serious side effects. The effective amount of the compound or composition will vary with the particular condition being treated, the age and physical condition of the end user, the severity of the condition being treated/prevented, the duration of the treatment, the nature of other treatments, the specific compound or product/composition employed, the particular carrier utilized, and like factors. "Effective amount" is also intended to include one or more of the compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a dermatologically acceptable salt thereof, in combination with one or more other agents that have an intended cosmetic or dermopharmaceutical effect. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds.

"Treat," "treatment," or "treating," as used herein means reversing, alleviating (e.g., reducing or eliminating) one or more symptoms of, inhibiting the progress of, and/or delaying, either partially or completely, a disease or disorder of the skin including, for example, the skin conditions/disorders described herein.

The term "skin condition/disorder" includes, but is not limited to, one or more of aging skin, skin exposed to excessive sunlight (e.g. photoaged or photo damaged skin), age spots, unwanted wrinkles, fine lines, crevices, bumps, large pores (e.g. associated with adnexal structures such as sweat gland ducts, sebaceous glands, or hair follicles), unevenness or roughness of the skin, loss of skin elasticity (e.g., loss in activation of functional skin elastin), sagging (including puffiness in the eye area and j owls), loss of skin firmness, loss of skin tightness, loss of skin recoil from deformation, discoloration (including (black) under eye circles), blotching, sallowness, hyperpigmentation such as age spots and freckles, blemishes, stressed skin, rough skin, dry skin, cellulitis, irritated skin, scars, saggy lips, acne, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The term "wound" as used herein refers broadly to injuries to the skin and subcutaneous tissue initiated in any one of a variety of ways (e.g., pressure sores from extended bed rest, wounds induced by trauma, wounds received during or following a surgical procedure and the like) and with varying characteristics. Exemplary examples include, but are not limited to, bruises, scrapes, burn wounds, sunburn wounds, incisional wounds, excisional wounds, surgical wounds, necrotizing fasciitis, ulcers, venous stasis ulcers, diabetic ulcers, decubitus ulcers, aphthous ulcers, pressure ulcers, scars, alopecia areata, dermatitis, allergic contact dermatitis, atopic dermatitis, berloque dermatitis, diaper dermatitis, dyshidrotic dermatitis, psoriasis, eczema, erythema, warts, anal warts, angioma, cherry angioma, athlete's foot, atypical moles, basal cell carcinoma, Bateman's purpura, bullous pemphigoid, *candida*, chondrodermatitis helicis, Clark's nevus, cold sores, condylomata, cysts, Darier's disease, dermatofibroma, Discoid Lupus Erythematosus, nummular eczema, atopic eczema, dyshidrotic eczema, hand eczema, Multiforme Erythema Nodosum, Fordyce's Condition, Folliculitis Keloidalis Nuchae, Folliculitis, Granuloma Annulare, Grover's Disease, heat rash, herpes simplex, herpes zoster (shingles), Hidradenitis Suppurativa, Hives, Hyperhidrosis, Ichthyosis, Impetigo, Keratosis Pilaris, Keloids, Keratoacanthoma, Lichen Planus, Lichen Planus Like Keratosis, Lichen Simplex Chronicus, Lichen Sclerosus, Lymphomatoid Papulosis, Lupus of the Skin, Lyme Disease, Lichen Striatus, Myxoid Cysts, Mycosis Fungoides, Molluscum Contagiosum, Moles, Nail Fungus, Necrobiosis Lipoidica Diabeticorum, Nummular Dermatitis, Onychoschizia, Onychomycosis, Pityriasis Lichenoides, Pityriasis Rosea, Pityriasis Rubra Pilaris, Plantar Warts, Poison Ivy, Poison Oak, Pompholyx, Pseudofolliculitis Barbae, Pruritus Ani and Pityriasis Alba.

Evaluation of Biological Activity

The biological activity of the compounds and compositions described herein can be tested using any suitable in vivo or in vitro test. For example, the compounds and compositions can be evaluated using in vitro or in vivo assays, subjective evaluations of patients, and mechanical assays used to measure and evaluate physical parameters of the skin. Various factors can be used to determine the effectiveness of a compound or composition provided herein. Such factors include changes to the depth of wrinkles, changes in the frequency of wrinkles, changes in the frequency of acne, skin elasticity and firmness, and subject compliance and satisfaction.

Mechanical properties of the skin change not only with aging but also upon exposure to various environmental factors like UV irradiation and air pollution. This exposure can lead to decreases in the synthesis of collagen as well as damage due to processes like glycation or oxidative stress. Fibroblasts are major cell types present in the dermis, which are capable of producing collagen fibers—the main component of the extracellular matrix (ECM) of the dermal connective tissue. Fibroblasts are also thought to be connected with the collagen network and provide dermal support for the epidermis and give rise to elastic properties of a tissue.

A change in elastic properties of cells can be determined using atomic force microscopy to calculate the relative Young's modulus (a parameter describing the elastic properties of cells). This method is described in, for example, *International Journal of Peptide Research and Therapeutics* (2014), 20(1), 77-85. Another exemplary method uses infrared thermography in combination with a mechanical deformation system to measure skin elasticity and firmness (see, e.g., U.S. Patent Application No. 2013/0079643). Skin elasticity can also be measured using a Cutometer® (Courage+Khazaka electronic GmbH, Germany) by slightly pressing a testing probe on the skin resulting in a temporary vacuum. The skin is lifted, stretched and then released. These deflections can be optically recorded and evaluated as demonstrated in U.S. Patent Application No. 2005/0054578 (see, e.g., Example 13). Methods for determining skin moisturizing effects are shown in U.S. Patent Application No. 2013/0171274 (see. e.g., Example 5).

The effects of photo-aging on the skin can be determined by evaluating the ultraviolet light (UV)-induced photodimerization of thymine, the expression of the proinflammatory cytokine interleukin (IL)1-α, the free-radical scavenging properties of the skin by quantification of the biomarker of oxidative stress malondialdehyde (MDA), as well as the antiglycation activity (glycation reduces the ability of collagen fiber to regenerate, leading to skin wrinkling). Examples of related tests are shown in, for example, *Clinical, cosmetic and investigational dermatology* (2013), 7, 1-9. The expression of proinflammatory matrixmetalloproteinases (MMPs), production of reactive oxygen species (ROS) and NF-κB signaling (all indicators of UVB-induced photoaging) can be determined by methods described in, for example, *PLoS One* (2013), 8(9), e73877. Other non-limiting examples of such assays can be found in *American Journal of Chinese Medicine* (2010), *Journal of Dermatological Science, Supplement* (2006), 2(1), S65-S74, WO 2008/156345, and U.S. Pat. No. 8,741,357.

Wrinkle prevention can be evaluated using hairless mice exposed to chronic solar-simulating ultraviolet (UV) irradiation as demonstrated in *European journal of pharmacology* (2001), 411(1-2), 169-174, *International journal of dermatology* (2006), 45(4), 460-8, *BMB reports* (2013), 46(9), 465-70, U.S. Pat. No. 8,088,369 (e.g, Examples 1 and 2), and WO 2008/001921.

Mechanical and optical methods can also be used to measure wrinkles. Non-limiting examples of such instruments and methods include PRIMOS high resolution (GFMesstechnik, Germany) which can quantify periorbital wrinkles (crows feet), perioral wrinkles (around mouth and lips), nasiolabial wrinkles (cheek, forehead wrinkles, and/or frowning wrinkles), and glabella wrinkles (between the eye brows) by optical 3D measurement of the skin; and Antera 3D® (Miravex Limited, Ireland) which allows for a view of skin in 2 and 3 dimensions as well as multi-spectral analysis of epidermis and dermis. The scan can provide information on how rough the skin is, how deep the wrinkles are, and the degree of sun damage and redness. FOITS (Fast Optical in vivo Topometry of Human Skin) (Schrader Institute, Germany) is a non-contact method of 3D wrinkle analysis. This 3D wrinkle method methodology allows for quantification of the surface topography of the skin and excludes skin color tone and surface reflection artifacts. The in-vivo-3D Breuckmann scanner (AICON, Michigan, USA) uses an imaging metrology principle based on structured light projection, and a combination of GrayCode- and Phaseshift technology. The Visioscan® (Courage+Khazaka electronic GmbH, Germany) uses a UVA-light video camera with high resolution to study the skin surface directly. The images show the structure of the skin and the level of dryness of the skin. The software analyses the grey level distribution and allows for the calculation of four clinical parameters to quantitatively and qualitatively describe the skin surface as an index: skin smoothness, skin roughness, scaliness, and wrinkles.

Other non-limiting examples of devices include the Corneometer®, which can be used to determine the hydration level of the skin surface (Stratum corneum); the Mexameter®, which can be used to measure the two components mainly responsible for the color of the skin: melanin and hemoglobin (erythema) by reflectance; the Tewameter®, which evaluates the water barrier function of the skin; the CutiScan®, which measures the mechanical properties of the skin (viscoelasticity & anisotropy); and the Visiopor®, which uses a specific UV-light to visualize fluorescing acne lesions.

Administration and Cosmetic and Dermopharmaceutical Compositions

Also provided herein are cosmetic or dermopharmaceutical compositions comprising: (a) an effective amount of a compound provided herein, or its corresponding enantiomer, diastereoisomer or tautomer, or dermatologically acceptable salt thereof; and (b) a dermatologically acceptable carrier.

The compounds provided herein may also be useful in combination (administered together) with other known ingredients.

Based on the intended use, the compositions can be care, treatment, cleansing, and/or protective products for facial or body skin; anti-wrinkle or anti-aging compositions; skin firming compositions; skin lightening compositions; compositions for irritated skin; sunscreen compositions, artificial tanning (self-tanning) compositions or after-sun care compositions; scalp care compositions; shaving preparation compositions; depilatory compositions; or make-up products for the skin of the face or body.

The cosmetic and dermopharmaceutical compositions of the present disclosure can be prepared and used in the form of an aerosol spray, cream, emulsion, solid, liquid, dispersion, foam, oil, gel, lotion, mousse, ointment, powder, patch, pomade, solution, pump spray, stick, towelette, soap, or other forms commonly employed in the art of topical administration and/or cosmetic and skin care formulation. The compositions can be in an emulsion form. In addition, compounds provided herein used in the compositions provided herein can be used in color cosmetic compositions such as foundation makeups, blushes, eyeshadows, mascaras, concealers, eyeliners, lip colors, nail colors, and so on. Other cosmetic compositions can include perfumes, lipsticks, fingernail and toe nail polish, eye and facial makeup, towelettes, deodorants, hand sanitizer, baby products, bath oils, bubble baths, and butters. The cosmetic and dermopharmaceutical compositions of the present disclosure can be formulations for subcutaneous injection.

If desired, formulations of the disclosure can be incorporated into a gel formulation (e.g., U.S. Pat. Nos. 4,474,752 and 6,911,211).

The compounds provided herein are intended for cosmetic and/or dermopharmaceutical use and can be administered as crystalline or amorphous products. Cosmetic or dermopharmaceutical compositions as provided herein can include solid, semi-solid, liquid, solutions, colloidal, liposomes, emulsions, suspensions, complexes, coacervates and aerosols. Dosage forms, such as, e.g., powders, liquids, suspensions, suppositories, aerosols, controlled release or the like, are provided herein. The dosage forms can be obtained, for example, as solid plugs, powders, lipid nanoparticles, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may also be used.

Liquid cosmetic or dermopharmaceutical compositions can, for example, be prepared by dissolving, dispersing, etc. a compound as provided herein and optional cosmeceutical/cosmetic/dermatological adjuvants in a carrier (e.g., water, saline, aqueous dextrose, glycerol, glycols, ethanol or the like) to form a solution, colloid, liposome, emulsion, complexes (including inclusion complexes), coacervate, or suspension. If desired, the cosmetic and/or dermatological composition can also contain auxiliary substances such as wetting agents, emulsifying agents, co-solvents, solubilizing agents, pH buffering agents, and the like (e.g., sodium acetate, sodium citrate, cyclodextrins and derivatives, sorbitan monolaurate, triethanolamine acetate, triethanolamine oleate, hydroxyethylpiperazine and the like).

In some embodiments, the cosmetic or dermopharmaceutical composition comprises a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more additional ingredients, carriers, excipients, or diluents including, but not limited to, absorbents, anti-irritants, antibacterials, anti-acne agents, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Lists of ingredients, which are well known in the art, are disclosed, for example, in "Cosmetics: Science and Technology," edited by M. S. Balsam and E. Sagarin, 2nd Edition, 1972, Wiley Pub. Co.; "The Chemistry and Manufacture of Cosmetics" by M. G. DeNavasse; and "Harry's Cosmeticology," J. B. Wilkinson et al., 7th Edition, 1982, Chem. Pub. Co.; the disclosures of each of the above being incorporated herein by reference in their entirety.

In some embodiments, diluents, carriers, and excipients may include, but are not limited to, polyethylene glycols (such as PEG200, PEG300, PEG400, PEG540, PEG600, PEG1450 or mixtures thereof) and coconut oils (such as propylene glycol dicaprate, coco-caprylate/caprate, propylene glycol dicaprylate/dicaprate, caprylic/capric triglyceride, caprylic/capric/lauric triglyceride, caprylic/capric/linoleic triglyceride, tricaprin, tricaprylin, glyceryl trioleate, neopentyl glycol dicaprylate/dicaprate, caprylic/capric/palmitic/stearic triglceride, or mixtures thereof).

Absorbents are substances which are added to cosmetic/dermatological products to take up water and oil-soluble dissolved or finely dispersed substances. Cosmetic/dermatological chemical absorbents can also be used as cosmetic/dermatological thickeners in a wide variety of formulations including facial creams, lipsticks, shampoos and calamine lotions.

In some embodiments, absorbents may include, but are not limited to, alcohol (ethyl alcohol, methanol, isopropyl alcohol, SD alcohol [especially denatured alcohol] and benzyl alcohol), alumina (aluminum oxide), aluminum chlorohydrate, aluminum hydroxide, aluminum magnesium silicate, aluminum silicate, aluminum starch octenylsuccinate, aluminum sulfate, ammonium chloride, bentonite, bismuth oxychloride, boron nitride, calcium carbonate, carnauba wax, charcoal, China clay, clay, *Copernicia cerifera* wax, cornstarch, fuller's earth, hydrolyzed corn starch, iron powder, kaolin, lithium magnesium sodium silicate, magnesium, magnesium carbonate, magnesium hydroxide, montmorillonite, nylon-12, rice starch, silica, silicate, silk powder, silt, sodium carbonate, sodium polyacrylates, and zeolite.

Anti-Irritants are substances which are added to cosmetic/dermatological products to reduce certain signs of inflammation, such as swelling, tenderness, pain, itching, or redness. Many ingredients perform the function of anti-irritants or anti-inflammatories. Many antioxidants also function as anti-irritants because one of the skin's responses to free-radical damage is irritation and inflammation. These ingredients help the skin deal with sun exposure, pollution, skin-care routines (topical disinfectants, sunscreens, and exfoliants can be irritating to skin), and seasonal environmental extremes [*Exogenous Dermatology* (2004), 3(4), 154-160; and *Toxicology Letters* (2003), 146(1), 65-73].

In some embodiments, anti-irritants may include, but are not limited to, *Acacia senegal*, acetylsalicylic acid, *Achillea millefolium*, adenosine, adenosine triphosphate, *Aesculus hippocastanum*, allantoin, *Aloe barbadensis, aloe barbadensis* leaf juice extract, aloe extract, aloe juice, aloe vera, alpha bisabolol, *Althaea rosea, Althea officinalis*, aminobutyric acid, andiroba oil, *Anthemis nobilis* flower extract, *Arachis hypogaea* extract, *Arctium lappa*, adenosine triphosphate, *Avena sativa*, azulene, barberry, 3-hydroxy acids (BHA) (such as salicylic acid, β-hydroxybutyric acid, tropic acid and trethocanic acid), β-glucan, β-sitosterol, bisabolol, black tea, *Boerhavia diffusa* root extract, borage seed extract, borage seed oil, *Borago officinalis* extract, *Borago officinalis* seed oil, burdock root, butcher's broom extract, calcium gluconate, calendula extract, *Calluna vulgaris* flower extract, canola oil, *Centaurea cyanus*, chitosan, *chrysanthemum* extract, coenzyme Qio (ubiquinone), colloidal oatmeal, comfrey extract, coneflower, cornflower, *Cornus* extract, cranberry seed extract, curcumin, decarboxy carnosine HCL, dipotassium glycyrrhizate, dipotassium glycyrrhizinate, dogwood, epidermal growth factor (EGF), epigallocatechin gallate, *Epilobium angustifolium* extract, ergothioneine, evening primrose oil, 1 Evodia rutaecarpa extract, feverfew extract, *Filipendula rubra*, fireweed extract, Fu ling, genistein, *Gentiana lutea* (Gentian) root extract, ginger extract, ginger oil, glabridin, glycyrrhetic acid, *Glycyrrhiza glabra, Glycyrrhiza uralensis* root extract, green tea, gromwell, honey, honey extract, honeysuckle flower extract, horse chestnut extract, hydrocortisone, *Ilex paraguariensis*, Ju hua, jujube fruit extract, juniper berry, *Juniperus communis*, kava-kava extract, kawa extract, *Kigelia africana* extract, L-ascorbic acid, *Laminaria ochroleuca* extract, *Lamium album* flower extract, *lappa* extract, *Leontopodium alpinum* extract, licorice extract, licorice root, linoleic acid, *Lithospermum erythrorhizon, Lonicera caprifolium* flower extract, *Lonicera japonica, Lonicera japonica* flower extract, lotus seed extract, *Luffa cylindrica* seed oil or extract, mallow, *Malva sylvestris* extract, marigold, marshmallow, mate extract, *matricaria* flower extract, meadowsweet extract, *Morinda citrifolia*, nettle extract, niacinamide, noni juice, oat P3-glucan, oat bran extract, oatmeal, *Oenothera biennis* oil, oleanolic acid, opium poppy seed, *P. elisabethae*, pansy extract, *Perilla ocymoides*, petrolatum, *Phyllanthus emblica* fruit extract, *Picea excelsa* extract, *Poria cocos* extract, *Portulaca oleracea* extract, propolis, *Prunella vulgaris, Pseudopterogorgia elisabethae*, red clover, resveratrol, *Ruscus aculeatus*, salicin, salicylic acid, *Salix alba* extract, *Salix nigra* (willow) bark extract, *Sapindus mukurossi* peel extract, saponin, saw palmetto extract, *Scutellaria baicalensis* extract, sea whip extract, self-heal, *Serenoa serrulata* extract, silver tip white tea leaf extract, skullcap extract, slippery elm bark, soapberry extract, sodium ascorbyl phosphate, Sonojell, soy extract, soy isoflavones, soy oil, soy protein, *Spiraea ulmaria*, stearyl glycyrrhetinate, *Symphytum officinale* extract, tamanu oil, *Tanacetum parthenium*, Tazorac, *Terminalia sericea, Terminalia sericea* extract, tetrahydrobisdemethoxycurcumin, tetrahydrodemethoxycurcumin, tetrahydrodemethoxydiferuloylmethane, tetrahydrodiferuloylmethane, tetrahydromethoxycurcumin, *Trifolium pretense*, turmeric, *Ulmus fulva* bark extract, *Ulva lactuca* extract, *Urtica dioica, Vaccinium macrocarpon* fruit extract, *Vanilla planifolia* fruit extract, Viola tricolor extract, white nettle, white willow, wild ginger, willow bark, willow herb, witch hazel, Xi xin, yarrow extract, yerba mate extract, *yucca* extract, zinc, zinc oxide, *Zingiber officinale* roscoe, *Zingiber zerumbet*, Zingiberaceae, and *Zizyphus jujuba* fruit extract.

Antibacterial ingredients are substances which are added to cosmetic/dermatological products to destroy or inhibit the growth of bacteria; in the case of skin-care products, particularly the bacteria that cause blemishes.

Anti-acne ingredients are substances which are added to cosmetic/dermatological products to help to reduce and control acne, and acne related problems such as sebum production. Some agents work by increasing skin cell turnover promoting the extrusion of the plugged material in the follicle.

In some embodiments, antibacterial and/or anti-acne agents may include, but are not limited to, *Alchemilla vulgaris, Aleurites moluccana* seed oil, aluminum sulfate, amygdalic acid, anise, *Anthemis nobilis* flower extract, *Arctostaphylos uva ursi* leaf, Azadirachta indica, barberry, benzalkonium chloride, benzoin extract, benzoyl peroxide, *Berberis aristata*, β-hydroxy acids (BHA) (such as salicylic acid, β-hydroxybutyric acid, tropic acid and trethocanic acid), borate, boric acid, calendula extract, Centella *asiatica*, chamomile, *Chamomilla recutita* flower extract, chaparral extract, chaulmoogra oil, chitosan, chlorhexidine, chloroxylenol, *Cinnamomum*, cinnamon, colloidal silver, *Commiphora* myrrha extract, *Cymbopogon* citrates, *Epilobium angustifolium* extract, *eucalyptus* extract, *eucalyptus* oil, farnesol, farnesyl acetate, *Gentiana lutea* (Gentian) root extract, geranium oil, Geranium pretense, glucose oxidase, goldenseal, gotu kola, hoelen, hops, *Humulus lupulus* extract, *Hydnocarpus anthelmintica, Hydrastis canadenis*, hydrocotyl extract, hyssop, *Illicium vernum*, jujube fruit extract, lactoperoxidase, lady's mantle extract, *Larrea divaricata* extract, *Larrea tridentata*, lemon, lemongrass extract, *Lentinus edodes* extract, *Leptospermum scoparium* oil, magnesium, magnesium gluconate, magnesium hydroxide, manuka oil, marigold, *matricaria* oil, *Melaleuca alternifolia, Melia azadirachta, Mentha piperita*, menthol, menthone, *Mitracarpe scaber* extract, myrtle extract, *Myrtus communis* extract, *Nardostachys jatamansi*, neem extract or oil, oak root extract, oregano, *Origanum vulgare* flower extract, *P. elisabethae*, palmarosa oil, *Pelargonium graveolens* oil, peppermint, pine oil, pinecone extract, *Pinus sylvestris* extract, propolis, *Pseudopterogorgia elisabethae*, pyridoxine hydrochloride (HCL), *quercus, Quercus infectoria* extract, quillaja extract, *Ranunculus ficaria* extract, raspberry seed extract, raspberry seed oil, red raspberry extract, resorcinol, *Rubus idaeus, Saponaria officinalis* extract, silver, soapwort, sodium ascorbyl phosphate, sodium silicate, spikenard, star anise, sulfur, *Taraktogenos kurzii*, tea tree oil, *Terminalia sericea* extract, tretinoin, triclosan, Uva *ursi* extract, vetiver oil or extract, white oak bark extract, willow herb, zinc phenolsulfonate, and *Zizyphus jujuba* fruit extract.

Antioxidants ingredients are substances which are added to cosmetic/dermatological products to reduce free-radical damage and environmental stress on skin [*Clinics in Dermatology* (2008), 26(6), 614-626; *Skin Therapy Letter* (2008), 13(7), 5-9; and *Journal of Drugs in Dermatology* (2008), 7(2), S7-S12]. Antioxidants are useful in two ways: They prevent degradation of natural ingredients (proteins, sugars, lipids) in the cosmetic product. Antioxidants also protect the skin cells from being damaged and slow down the aging process. Antioxidants have been shown to boost the skin's radiance, minimize age spots, sun spots, and fine lines.

In some embodiments, antioxidants may include, but are not limited to, Acai, acetyl carnitine HCL, agar, *Agrimonia eupatoria* leaf extract, *Ahnfeltia concinna* extract, *ahnfeltia* extract, alanine, *Alaria esculenta*, alfalfa extract, algae, algae extract, algin, α-lipoic acid, α-tocopherol, *Anacystis nidulans* extract, *Angelica archangelica* root oil, *Angelica polymorpha sinensis* root extract, anise, *Anthemis nobilis* flower extract, anthocyanin, *Arctium lappa, Arctostaphylos uva ursi* leaf, argan oil, *Argania spinosa*, arginine, artemia extract, *Ascophyllum nodosum*, ascorbic acid, ascorbyl glucosamine, ascorbyl glucoside, ascorbyl methylsilanol pectinate, ascorbyl palmitate, asparagine, *Asparagopsis armata* extract, aspartic acid, astaxanthin, astaxanthin extract, *Astragalus membranaceus, Astragalus* sinicus, avocado oil, azulene, banana extract, bay leaf oil, beet root extract, *Bertholletia excelsa* extract, β-hydroxy acids (BHA) (such as salicylic acid, β-hydroxybutyric acid, tropic acid and trethocanic acid), β-vulgaris root extract, β-carotene, β-glucan, *Betula alba*, Butylated hydroxytoluene, bioflavonoids, birch bark extract, birch leaf extract, black elderberry, black locust extract, black raspberry, black tea, blackberry, bladderwrack extract, *Boerhavia diffusa* root extract, borage seed oil, *Borago officinalis* extract, *Borago officinalis* seed oil, boysenberry, *Brassica campestris*, Brazil nut extract, *Buddleja davidii* extract, burdock root, caffeic acid, caffeine, calcium ascorbate, calendula extract, *Calendula officinalis* flower extract, *Camellia japonica, Camellia oleifera, Camellia sinensis*, carnitine, carnosic acid, carnosine, carnosol acid, catalase, *Caulerpa taxifolia* extract, chamomile, *Chamomilla recutita* flower extract, chaparral extract, chlorella, cholecalciferol, *Chondrus crispus, Cichorium intybus, Cinnamomum*, cinnamon, *Citrus unshiu, Citrus unshiu* peel extract, cocoa extract, *Codium tomentosum* extract, coenzyme Q10, *Coffea arabica* (coffee) seed oil, *Coffea arabica* extract, collagen amino acids, copper gluconate, copper peptides, *Corallina officinalis* extract, *Cornus* extract, coumarin, cranberry seed extract, cranberry seed oil, cucumber extract, *Cucumis melo* (melon) fruit extract, *Cucumis sativus* extract, *Cucurbita pepo* seed extract, *Cucurbitea peponis*, curcumin, *Cymbopogon martini*, D-α-tocopherol, *Daucus carota*, diethylhexyl syringylidenemalonate, disodium rutinyl disulfate, dogwood, *Angelica polymorpha sinensis*, dulse, durian, *Durvillaea antarctica* extract, *Elaeis guineensis*, elderberry, ellagic acid, *Enteromorpha compressa* extract, epigallocatechin gallate, ergocalciferol, ergothioneine, *Eriobotrya japonica*, escin, ethyl vanillin, *Euterpe oleraca*, faex, *Fagus sylvatica* extract, farnesol, farnesyl acetate, fennel seed extract, *Ferula foetida*, ferulic acid, *Filipendula glaberrima*, flavonoid, flax, flaxseed oil, *Foeniculum vulgare* extract, folic acid, Fu ling, *Fucus vesiculosus* extract, galactoarabinan, γ-linolenic acid (GLA), *Ganoderma lucidum* extract, *Gardenia* florida extract, *Gellidiela acerosa* extract, genistein, geranium extract, Geranium pretense, *Ginkgo biloba* leaf extract, glutathione, *Glycine soja* oil, grape seed extract, grape seed oil, green tea, gromwell, *Haematococcus pluvialis* extract, *Hamamelis virginiana*, hamamelitannin, *Haslea ostrearia* extract, hawthorn extract, hesperidin, hesperidin methyl chalcone, hexylresorcinol, hibiscus, *Himanthalia* elongate extract, *Hippophae rhamnoides*, histidine, honey, honey extract, hops, *Hordeum vulgare* extract, horsetail extract, Huang qi, *Humulus lupulus* extract, hydrogenated olive oil, hydrogenated palm glycerides, hydrolyzed silk, hydroquinone, *Hypericum* extract, idebenone, *Ilex paraguariensis, Illicium vernum*, Irish moss extract, Isoflavone, isoleucine, jojoba butter, kelp extract, *Kigelia africana* extract, kiwi fruit extract, kojic acid, kojic dipalmitate, kudzu root, L-ascorbic acid, L-carnitine, L-cysteine, lady's thistle extract, *Laminaria digitata, Laminaria longicruris, Laminaria saccharine, Lamium album* flower extract, *lappa* extract, *Larrea divaricata* extract, *Larrea tridentate, Laurus nobilis*, lemon juice, *Leontopodium alpinum* extract, linden flower extract, linoleic acid, *Lithospermum erythrorhizon*, loquat extract, lotus seed extract, lupine, lupine oil, *Lupinus albus* extract, lutein, *Lycium* barbarum fruit extract, lycopene, lysine, magnesium ascorbyl palmitate, magnesium ascorbyl phosphate, *Malva sylvestris* extract, manganese gluconate, *Mangifera indica* root, marigold, marionberry, *Mastocarpus stellatus*, mate extract, *matricaria* flower extract, *matricaria* oil, *Medicago sativa*, methionine, methylsufonylsulfate, *Microcystis aeruginosa*, milk vetch root, *Morinda citrifolia*, N-acetyl-L tyrosine, *Nasturtium officinale* extract, natto gum, noni juice, nordihydroguaiaretic acid, *Nymphaea tetragona*, oat 3-glucan, oat bran extract, *Olea europaea* fruit oil, *Olea europaea* oil unsaponifiables, oleanolic acid, olive oil/olive fruit oil, oryzanol, oxidoreductase, *Padina pavonica* extract, *Paeonia suffruticosa* extract, palm oil, *Palmaria palmata* extract, *Panax ginseng* root extract, pansy extract, *Passiflora edulis* seed oil, peony root extract, *Perilla ocymoides, Persea gratissima* oil, *Persicaria* hydropiper, phenylalanine, phenylethyl resorcinol, phloretin, *Phyllanthus emblica* fruit extract, phytic acid, pinecone extract, *Pinus sylvestris* extract, *Pisum sativum*, plum extract, *Polygonum cuspidatum* root extract, polysaccharide, pomegranate extract, *Poria cocos* extract, potassium ascorby tocopheryl phosphate, proline, *Prunella vulgaris, Prunus Americana, Prunus domestica* seed extract, *Pueraria lobata*, pullulan, pumpkin, pumpkin seed extract, *Punica granatum* extract, Pycnogenol, pyridoxine hydrochloride (HCL), quercetin, rapeseed oil, raspberry seed extract, raspberry seed oil, red algae, red clover, red raspberry extract, resveratrol, retinol, retinyl palmitate, *Robinia pseudacacia* extract, *Rosa canina, Rosa centifolia, Rosa centifolia* flower, *Rosa eglanteria, Rosa mosqueta, Rosa roxburghii* extract, *Rosa rubiginosa*, rose hip, rose hip oil, rosemary extract, rosemary oil, *Rosmarinus officinalis* extract, *Rubus idaeus, Rubus occidentalis, Rubus ursinus, Rubus ursinus×idaeus, Rubus* villoscus, rutin, *Saccharomyces* copper ferment, *Saccharomyces* iron ferment, *Saccharomyces* lysate, *Saccharomyces* magnesium ferment, *Saccharomyces* manganese ferment, *Saccharomyces* potassium ferment, *saccharomyces* selenium ferment, *Saccharomyces* silicon ferment, safflower seed oil, *Sambucus Canadensis, Sambucus* cerulean, *Sambucus nigra, Sapindus mukurossi* peel extract, saponin, *Sargassum filipendula* extract, *Scutellaria baicalensis* extract, sea buckthorn, Sea-mollient, seaweed, selenium, self-heal, sericin, serine, Shao-yao, silk, silk protein, silver tip white tea leaf extract, skullcap extract, soapberry extract, sodium ascorbate, sodium ascorbyl phosphate, sodium citrate, sodium metabisulfite, *Solanum lycopersicum* extract, soy extract, soy isoflavones, soy oil, soy protein, *spirulina*, squalane, squalene, St. John's wort, star anise, superoxide dismutase, *Tamarindus indica* seed extract, tannic acid, *Terminalia catappa*, tetradibutyl pentaerithrityl hydroxyhydrocinnamate, tetrahexyldecyl ascorbate, tetrahydrobisdemethoxycurcumin, tetrahydrobisdemethoxydiferuloylmethane, tetrahydrodemethoxycurcumin, tetrahydrodemethoxydiferuloylmethane, tetrahydrodiferuloylmethane, tetrahydromethoxycurcumin, thioctic acid, thiodipropionic acid, thiotaurine, threonine, thyme extract, thyme oil, *Thymus serpillum* extract, *Thymus vulgaris, Thymus vulgaris* oil, *Tilia cordata*, tocopherol, tocopherol acetate, tocopheryl acetate, tocopheryl lineolate, tocotrienols, tomato extract, *Trifolium* pretense, tryptophan, turmeric, *Ulva lactuca* extract, *Undaria pinnatifida, Vaccinium macrocarpon* fruit extract, valine, *Vanilla planifolia* fruit extract, Viola tricolor extract, vitamin A, vitamin C, vitamin D, vitamin E, vitamin F, *Vitis vinifera*, walnut extract, watercress extract, whey, white tea leaf extract, witch hazel, yeast, yerba mate extract, *yucca* extract, zinc, and zinc oxide.

Coloring Agents/Pigments are any dye, pigment, or substance that imparts color when added or applied to a food, drug, cosmetic/dermatological, or to the human body and which are deemed to be safe and FDA-approved for use in foods, drugs, and cosmetics. Most organic colorants are synthetic and are available as either water soluble, oil soluble or insoluble (=Lakes) agents in all kinds of shades. Inorganic colorants are composed of insoluble metallic compounds which are either derived from natural sources (e.g. china clay, carbon deposits) or synthesized.

In some embodiments, coloring agents/pigments may include, but are not limited to, aluminum powder, barium sulfate, beet root extract, 3-vulgaris root extract, blue 1, blue 1 lake, bronze powder, caramel, carmine, chromium hydroxide green, chromium oxide green, D&C (drugs & cosmetics) colors, Ext. D&C (external drugs and cosmetics) colors, FD&C (food, drug and cosmetic) colors, ferric ammonium ferrocyanide, ferric ferrocyanide, iron oxides, manganese violet, mica, red 27 lake, red 33, red 6 lake, titanium dioxide, ultramarines, yellow 5, yellow 6 lake, zinc oxide, and zinc stearate.

Emollients are supple, waxlike, lubricating, thickening substances which are added to cosmetic/dermatological products to prevent water loss and have a softening and soothing effect on the skin.

In some embodiments, emollients may include, but are not limited to, 10-hydroxydecanoic acid, acetyl glyceryl ricinoleate, acetylated castor oil, acetylated hydrogenated cottonseed glyceride, acetylated lanolin, acetylated lanolin alcohol, acetylated palm kernel glycerides, agar, *Ahnfeltia concinna* extract, *ahnfeltia* extract, *Alaria esculenta*, algae extract, algin, almond oil, α-glucan oligosaccharide, amodimethicone, *Anacystis nidulans* extract, apricot kernel oil, arachidic acid, arachidonic acid, arachidyl alcohol, arachidyl propionate, *Arachis hypogaea* extract, argan oil, artemia extract, *Ascophyllum nodosum, Asparagopsis armata* extract, Astrocaryum murumuru seed butter, avocado oil, babassu oil, batyl alcohol, beeswax, behentrimonium chloride, bis-diglyceryl polyacyladipate, bis-PEG-18 methyl ether dimethyl silane, borage seed oil, *Borago officinalis* extract, *Borago officinalis* seed oil, *Brassica campestris, Butyrospermum* fruit, *Butyrospermum parkii, Buxus chinensis*, $C_{10-30}$ cholesterol/lanosterol esters, $C_{12-15}$ alkyl benzoate, $C_{12-18}$ acid triglyceride, $C_{18-36}$ acid triglyceride, candelilla wax, *Cannabis sativa* L. oil, caprylic/capric triglyceride, caprylyl methicone, carrot oil, *Carthamus tinctorius* oil, *Carya illinoensis* oil, castor isostearate succinate, castor oil, *Caulerpa taxifolia* extract, cephalin, cera microcristallina, cetearyl alcohol, cetearyl ethylhexanoate, cetearyl octanoate, cetyl acetate, cetyl alcohol, cetyl dimethicone copolyol, cetyl esters, cetyl hydroxyethylcellulose, cetyl palmitate, *chlorella*, cholesterol, *Chondrus crispus*, cocoa butter, cocoglycerides, coconut oil, *Cocus nucifera, Codium tomentosum* extract, *Corallina officinalis* extract, corn oil, *Corylus Americana, Corylus avellana*, cyclohexasiloxane, cyclomethicone, cyclopentasiloxane, cyclotetrasiloxane, decyl oleate, dicaprylyl carbonate, diethylhexyl carbonate, diethylhexyl malate, diisopropyl adipate, diisopropyl dimer dilinoleate, diisostearoyl trimethylolpropane siloxy silicate, diisostearyl dimer dilinoleate, diisostearyl malate, dimer dilinoleyl dimer dilinoleate, dimethicone, dimethicone copolyol, dimethicone crosspolymer, dimethicone/PEG-10/ 15 crosspolymer, Dimethiconol, dipentaerythrityl hexacaprylate/hexacaprate, disodium diglyceryl phosphate, disodium glyceryl phosphate, docosahexaenoic acid, Dromiceius oil, dulse, *Durvillaea antarctica* extract, egg yolk, eicosapentaenoic acid, *Elaeis guineensis*, emu oil, *Enteromorpha compressa* extract, ethyl macadamiate, ethylhexyl palmitate, ethylhexyl stearate, *Euphorbia* cerifera wax, evening primrose oil, γ-linolenic acid (GLA), *Gellidiela acerosa* extract, glycereth-26, glycereth-26 phosphate, glycereth-6 laurate, glycerol monostearate, glycerol triacetate, glycerol trioleate, glyceryl behanate, glyceryl cocoate, glyceryl dibehanate, glyceryl dipalmitate, glyceryl distearate, glyceryl ester, glyceryl isopalmitate, glyceryl isostearate, glyceryl myristate, glyceryl oleate, glyceryl palmitate, glyceryl stearate, glyceryl stearate SE, *Glycine soja* oil, *Glycine soja* seed extract, *Glycine soja* sterols, glycol stearate, glycolipid, grape seed oil, *Haslea ostrearia* extract, hazelnut oil, *Helianhtus annuus* seed oil, *Helianthus* oil, hemp seed oil, hexyl laurate, hexyldecanol, *Himanthalia elongate* extract, hydrogenated coco-glyceride, hydrogenated lecithin, hydrogenated olive oil, hydrogenated palm glycerides, hydrogenated polydecene, hydrogenated polyisobutene, hydrogenated vegetable glycerides citrate, hydrolyzed jojoba esters, hydrolyzed jojoba protein, hydroxylated lecithin, Irish moss extract, isononyl isononanoate, isopropyl isostearate, isopropyl lanolate, isopropyl myristate, isopropyl palmitate, Japan wax, jojoba butter, jojoba esters, jojoba oil, jojoba wax, kelp extract, kukui nut oil, *Laminaria longicruris, Laminaria saccharine*, lanolin, lanolin alcohol, lauryl lactate, lecithin, linoleic acid, lupine, lupine oil, *Lupinus albus* extract, macadamia nut oil, *Mangifera indica* (mango) seed butter, *Mastocarpus stellatus*, meadowfoam seed oil, methicone, methyl glucose sesquistearate, methyl trimethicone, methylsilanol mannuronate, methylsilanol PEG-7 glyceryl cocoate, *Microcystis aeruginosa*, mineral oil, murumuru seed butter, myristyl myristate, neopentyl glycol dicaprylate/dicaprate, octyl palmitate, octyl stearate, octyldodecanol, octyldodecyl myristate, octyldodecyl neopentanoate, *Oenothera biennis* oil, *Olea europaea* fruit oil, *Olea europaea* oil unsaponifiables, olive oil/olive fruit oil, *Orbignya martiana, Orbignya oleifera, Oryza sativa* oil, *Padina pavonica* extract, palm kernel acid, palm oil, *Palmaria palmata* extract, palmitic acid, *Paraffinum liquidum*, peanut oil, pecan oil, pectin, PEG 90M, PEG-10 dimethicone, PEG-10 dimethicone/vinyl dimethicone crosspolymer, PEG-10 rapeseed sterol, PEG-100 stearate, PEG-12 dimethicone, PEG-20 methyl glucose sesquistearate, PEG-40 hydrogenated castor oil, PEG-60 almond glycerides, PEG-60 hydrogenated castor oil, PEG-7 glyceryl cocoate, PEG-8, PEG/PPG-17/6 copolymer, PEG/PPG-18/18 dimethicone, PEG/PPG-20/15 dimethicone, pentaerythrityl tetraoctanoate, *Persea gratissima* oil, petrolatum, phenyl trimethicone, phosphatidylcholine, phosphatidylethanolamine, phytosterol, pistachio seed oil, *Pistacia vera* seed oil, polyethylene, polyglycerol monostearate, polyglyceryl 2 triisostearate, polyglyceryl-3 methylglucose distearate, polyglyceryl-4 isostearate, polyglyceryl-6 isostearate, polymethylsilsesquioxane, PPG-3 benzyl ether myristate, propylene glycol isostearate, propylene glycol laurate, *Prunus amygdalus dulcis, Prunus dulcis*, pumpkin seed extract, *quinoa* oil, rapeseed oil, red algae, rice bran oil, rice oil, *Ricinus communis, Rosa canina, Rosa centifolia, Rosa centifolia* flower, *Rosa eglanteria, Rosa mosqueta, Rosa rubiginosa*, rose hip, rose hip oil, rutin, saccharide isomerate, safflower seed oil, *Sargassum filipendula* extract, Seamollient, sesame oil, *Sesamum indicum*, sesquioleate, shea butter, silicone, siloxane, *Simmondsia chinensis*, sodium PEG-7 olive oil carboxylate, sodium polyacrylate, Sonojell, soy oil, soya sterol, *spirulina*, squalane, squalene, stearates, stearic acid, stearyl alcohol, stearyl methicone, sunflower seed oil, sweet almond, sweet almond oil, synthetic beeswax, *Theobroma cacao* seed butter, tribehenin, tribehenin PEG-20 esters, tricaprylin, tridecyl stearate, triethoxycaprylylsilane, triethoxysilylethyl polydimethylsiloxyethyl hexyl dimethicone, triglyceride, trihydroxystearin, triisocetyl citrate, trilaurin, trimethylsiloxysilicate, trioctanoin, trioctyldodecyl citrate, *Triticum vulgare* oil, *Undaria pinnatifida*, vitamin F, *Vitis vinifera*, walnut oil, wheat germ glycerides, wheat germ oil, and *Ximenia americana* oil.

Film-Forming/Holding agents are substances which are added to cosmetic/dermatological products to help leave a pliable, cohesive, and continuous covering over the skin. This film has water-binding properties and leaves a smooth feel on skin.

In some embodiments, film-forming/holding agents may include, but are not limited to, acrylate, acrylates copolymer, acrylates/$C_{10-30}$ alkyl acrylate crosspolymer, acrylates/dimethicone copolymer, adipic acid/neopentyl glycol/trimellitic anhydride copolymer, allyl methacrylates crosspolymer, carnauba wax, cellulose gum, *Copernicia cerifera* wax, dextrin, diisopropyl adipate, glyceryl polymethacrylate, hydrolyzed wheat protein, hydroxyethylcellulose, locust bean, neopentyl glycol diheptanoate, PEG-40 hydrogenated castor oil, polyacrylamide, polyacrylate-17, polyglucuronic acid, polyglyceryl methacrylate, polyisobutene, polymethyl methacrylate, polyquaternium-10, polyquaterniums, polyvinyl alcohol, polyvinylpyrrolidone, propylene carbonate, PVM/MA (polyvinyl methyl ether/maleic acid) decadiene crosspolymer, PVP [poly(vinylpyrrolidone)] copolymer, PVP/dimethylaminoethyl-methacrylate, sodium carbomer, sodium polyacrylate, styrene/acrylates copolymer, triethoxycaprylylsilane crosspolymer, VA (vinyl acetate)/crotonates, VA/crotonates copolymer, VP (vinylpyrrolidone)/eicosene copolymer, and VP/hexadecene copolymer.

Fragrance ingredients are a single or a blend of volatile and/or fragrant plant oils (or synthetically derived oils) that impart aroma and odor to cosmetic/dermatological products. The level of fragrance to use varies according to the product type. In some embodiments, a face cream may contain about 0.01% fragrance by weight.

In some embodiments, fragrances (e.g, synthetic and fragrant plant extracts) may include, but are not limited to, *Acacia farnesiana* extract, *Aerocarpus santalinus*, amyl cinnamate, amyl salicylate, amyris oil, *Anethum graveolens*, *Angelica archangelica* root oil, anisaldehyde, anise, balm mint extract, balsam peru, bay leaf oil, bergamot oil, bitter orange flower, bois de rose oil, bois oil, *Boswellia carterii*, butylphenyl methylpropional, *cananga* extract, *Cananga odorata*, cardamom, cedarwood, cherry extract, *Citrus aurantifolia, Citrus aurantium, Citrus aurantium* extract, *Citrus medica limonium*, clary oil, *Commiphora myrrha* extract, coriander, *Cucurbitea peponis*, cyclamen aldehyde, dill extract, ethyl vanillin, eugenol, farnesol, farnesyl acetate, *Ferula galbaniflua*, fir needle oil, floralozone, *Foeniculum vulgare* extract, frankencense extract, *galbanum*, *Gardenia* florida extract, grapefruit oil, guaiac wood, *Guaiacum officinale*, hedione, hexyl cinnamal, hyssop, *Illicium vernum*, Iris florentina extract, jasmine oil, *Jasminium grandiflorum*, jonquil extract, *Laurus nobilis*, lauryl lactate, lavandin oil, *Lavandula angustifolia, Lavandula officinalis*, lavender extract and oil, lemon, lemon balm, lemongrass oil, *Levisticum officinale* root extract, lime oil and extract, limonene, linalool, *Litsea cubeba*, mandarin orange oil or extract, marjoram, *Melissa officinalis, Mentha piperita, Mentha spicata, Mentha viridis*, menthol, menthone, menthoxypropanediol, menthyl lactate, methyldihydrojasmonate, *mimosa* oil or extract, mint, *Narcissus poeticus* wax, neroli, neroli oil, olibanum extract, orange blossom, orchid, *Origanum majorana*, orris root, patchouli, pentadecalactone, petitgrain mandarin, Pogostemon cablin, *Rosa damascena* oil, *Rosa gallica* flower extract, rose flower, rose flower oil, rose oil, rosemary extract, rosemary oil, rosewood oil, sandalwood oil, Santalum album seed extract, sausurrea oil, sclareolide, spearmint oil, star anise, tangerine oil, *Thymus vulgaris* oil, *Vanilla planifolia* fruit extract, *verbena* extract, vetiver oil or extract, and ylang ylang.

Exfoliation involves the removal of the oldest dead skin cells on the skin's outermost surface and can be achieved through mechanical or chemical means. Mechanical exfoliation involves the use of scrub agents or body polishers which are solid materials from natural origins (fine powder of seeds or shells of different vegetables), or are obtained by chemical synthesis (tiny beads of styrene or polyethylene). Scrub agent containing cosmetic/dermatological products are used to remove superficial skin stratum corneum (horny layer) by mechanical abrasion, leaving behind a fresh, smooth skin surface. Scrub agents are selected based on the body part to be treated. Chemical exfoliants are often referred to as leave-on exfoliants. Leave-On Exfoliant ingredients are substances which are added to cosmetic/dermatological products to give a subject a low concentration of acid on a daily basis. They are usually applied after cleansing and are for oily, acne-prone and sun-damaged skin. They may also help with lightening discoloration areas and with scarring.

In some embodiments, leave-on exfoliants may include, but are not limited to, α-hydroxy acids (AHA) (such as glycolic acid, lactic acid, malic acid, citric acid, hydroxycaprylic acid, hydroxycapric acid and tartaric acid), ammonium glycolate, amygdalic acid, *Ananas sativus* fruit extract, β-hydroxy acids (BHA) (such as salicylic acid, β-hydroxybutyric acid, tropic acid and trethocanic acid), bromelain, mandelic acid, papain, *papaya* extract, pawpaw extract, pineapple extract, polyhydroxy acid (PHA) such as gluconolactone and lactobionic acid, and urea.

In some embodiments, prescription drugs may include, but are not limited to, adapalene (Differin®, Teva, Pimpal®, Gallet, Adaclene, Adapen™, Adeferin™), all-trans retinoic acid (Tretinoin, Aberela®, Airol®, A-Ret™, Atralin®, Avita®, Retacnyl$^{MR}$, Refissa®, Renova®, Retin-A®, Retino-A*, ReTrieve®, or Stieva-A™), aminophylline (Aminophyl, Procellix, Phyllocontin®, Celluthin, Cellulean®), azelaic acid (AzClear Action, Azelex®, SynCare, Finacea®, Finevin®, Skinoren®, Melazepam, Azelex®, Azaclear®, Aziderm®), bimatoprost (Lumigan®, Latisse®), hydroquinone (Lustra-AF®, Unblemish, Lustra®, Sunvanish™, PCA Pigment Gel®, Sledgehammer™), isotretinoin (Accutane®, Roaccutane®, Amnesteem®, Claravis™, Absorica™, Isotroin, Epuris™, Sotret®), and Tazarotene (Tazorac®, Avage®, Zorac®, and Fabior™).

Preservatives are substances which prevent bacterial, microbial or fungal contamination of cosmetic/dermatological products thereby increasing the product's shelf life and consumer safety. Some of these agents also have stabilizing effects able to preserve the function of various active ingredients including anti-oxidants (vitamins), emulsifiers and surfactants.

In some embodiments, preservatives may include, but are not limited to, 1,2-hexanediol, benzoic acid, benzothonium chloride, borax, bronopol, butylparaben, caprylyl glycol, chlorophene, chloroxylenol, chlorphenesin, dehydroacetic acid, diazolidinyl urea, DMDM hydantoin, ethylhexylglycerin, ethylparaben, formaldehyde-releasing preservative, Germaben II, hoelen, imidazolidinyl urea, iodopropynyl butylcarbamate, isobutylparaben, methylchloroisothiazolinone, methyldibromo glutaronitrile, Methylisothiazolinone, methylparaben, o-cymen-5-ol, phenoxyethanol, phenoxyisopropanol, phytosphingosine, polyaminopropyl biguanide, potassium sorbate, propylparaben, quaternium-15, sodium benzoate, sodium citrate, sodium dehydroacetate, sodium hexametaphosphate, sodium hydroxymethylglycinate, sodium lactobionate, sodium metabisulfite, sodium sulfite, sorbic acid, and *styrax benzoin*.

In some embodiments, scrub agents may include, but are not limited to, alumina, aluminum silicate, apricot kernel, azuki beans, diatomaceous earth, polyethylene, polyethylene glycol (PEG), sea salt, sodium chloride, and walnut-shell powder.

Silicone ingredients are substances which are added to cosmetic/dermatological products to create a silky-like feel on the skin, impart emolliency, and be a water-binding agent that holds up well, even when skin becomes wet. Silicones also act as skin protectant, conditioner, pearlizer, film-former, moisturizer, thickener, and emulsifier. As silicones are very mild, they are often used to reduce irritation of harsh surfactants. Some cosmetic/dermatological compositions can be used for wound healing and for improving the appearance of scars [*Journal of Wound Care* (2000), 9(7), 319-324].

In some embodiments, silicones may include, but are not limited to, acrylates/dimethicone copolymer, amodimethicone, bis-PEG-18 methyl ether dimethyl silane, bis-phenylpropyl dimethicone, caprylyl methicone, cetyl dimethicone, cetyl dimethicone copolyol, cetyl PEG/PPG-10/1-dimethicone, diisostearoyl trimethylolpropane siloxy silicate, dimethicone, dimethicone copolyol, dimethicone crosspolymer, dimethicone/PEG-10/15 crosspolymer, dimethicone/vinyl dimethicone crosspolymer, dimethiconol, isopropyl titanium triisostearte/triethoxycaprylylsilane crosspolymer, methicone, methyl trimethicone, methylsilanol mannuronate, methylsilanol PEG-7 glyceryl cocoate, PEG-10 dimethicone, PEG-10 dimethicone/vinyl dimethicone crosspolymer, PEG-12 dimethicone, PEG/PPG-18/18 dimethicone, PEG/PPG-20/15 dimethicone, phenyl trimethicone, polymethylsilsesquioxane, polysilicone-11, silica dimethyl silylate, silicone, siloxane, simethicone, stearyl dimethicone, stearyl methicone, triethoxycaprylylsilane, triethoxycaprylylsilane crosspolymer, trimethylsiloxysilicate, and vinyl dimethicone/methicone silsesquioxane crosspolymer.

The term "skin-identical agents" or "skin-repairing agents" refers to the substances between skin cells (technically referred to as the intercellular matrix) that keep skin cells connected and help maintain skin's fundamental external structure. They can be added to the compositions provided herein to help keep the skin moisturized and hydrated without causing unnecessary inflammation or irritation.

In some embodiments, skin-identical/repairing agents may include, but are not limited to, acetyl hexapeptide-3, acetyl octapeptide-3, adenine, aquaporins, aspartic acid, β-sitosterol, *Butyrospermum parkii, Buxus chinensis*, canola oil, carrot oil, ceramide 1, ceramide 2, ceramide 3, ceramide 6-II, cetearyl octanoate, cholesterol, chondroitin sulfate, creatine, cysteine, cysteine, decylene glycol, dextran, dimethylaminoethanol (DMAE), elastin, fibronectin, fructose, glucose, glutamine, glycerin, glycerine, glycerol, glycine, glycogen, glycolipid, glycosaminoglycans, glycosphingolipid, hyaluronic acid, hydrogenated palm glycerides, hydrolyzed glycosaminoglycans, hydroxyproline, inositol, isoleucine, jojoba oil, jojoba wax, lactobionate, lanolin, lanolin alcohol, lecithin, leucine, lysine, *Mangifera indica* (mango) seed butter, melibiose, methionine, milk protein, mucopolysaccharide, N-acetyl-L tyrosine, natural moisturizing factor (NMF), *Olea europaea* fruit oil, *Olea europaea* oil unsaponifiables, olive oil/olive fruit oil, palm oil, palmitic acid, palmitoyl oligopeptide, phenylalanine, phosphatidylcholine, phosphatidylethanolamine, phospholipid, phytosphingosine, polysaccharide, proline, pumpkin seed extract, RNA, saccharide isomerate, saccharides, *Saccharomyces cerevisiae*, serine, *Simmondsia chinensis*, sodium chondroitin sulfate, sodium dilauramidoglutamide lysine, sodium hyaluronate, sodium pyrrolidone carboxylic acid (PCA), sphingolipids, squalane, squalene, stearates, stearic acid, sucrose, thiotaurine, threonine, tribehenin, trihydroxystearin, tryptophan, urea, valine, and wheat protein.

The term "slip agent" is used to describe a range of ingredients which can help other ingredients spread over the skin and penetrate into the skin. Slip agents can also have humectant (hygroscopic) properties.

In some embodiments, slip agents may include, but are not limited to, amodimethicone, bis-PEG-18 methyl ether dimethyl silane, bis-phenylpropyl dimethicone, butylene glycol, cetyl dimethicone, cetyl dimethicone copolyol, cetyl PEG/PPG-10/1-dimethicone, cyclohexasiloxane, cyclomethicone, cyclopentasiloxane, cyclotetrasiloxane, decylene glycol, diisostearoyl trimethylolpropane siloxy silicate, dimethicone, dimethicone copolyol, dimethicone crosspolymer, dimethiconol, dipropylene glycol, hexylene glycol, hydrolyzed silk, isododecane, methicone, methyl trimethicone, methylsilanol mannuronate, methylsilanol PEG-7 glyceryl cocoate, Good, PEG-10 dimethicone, PEG-10 dimethicone/vinyl dimethicone crosspolymer, PEG-12 dimethicone, PEG/PPG-18/18 dimethicone, PEG/PPG-20/15 dimethicone, pentylene glycol, phenyl trimethicone, polymethylsilsesquioxane, PPG-3 benzyl ether myristate, silica dimethyl silylate, silk powder, siloxane, simethicone, sorbitol, stearyl dimethicone, stearyl methicone, triethoxycaprylylsilane, trimethylsiloxysilicate, xylitol, and zinc stearate.

Sunscreen actives are substances which are added to cosmetic/dermatological products to protect the skin against UV rays. They can be organic molecules which absorb high-energy ultraviolet rays and release the energy as lower-energy rays, thereby preventing the skin-damaging ultraviolet rays from reaching the skin. They can be inorganic particulates that reflect, scatter, and absorb UV light. They can also be organic particulates that mostly absorb light like organic chemical compounds, but contain multiple chromophores, may reflect and scatter a fraction of light like inorganic particulates, and behave differently in formulations than organic chemical compounds.

In some embodiments, sunscreen actives may include, but are not limited to, avobenzone, benzophenone-3, benzophenones, bumetrizole, butyl methoxydibenzoylmethane, ecamsule, ensulizole, ethylhexyl methoxycinnamate, homosalate, menthyl anthranilate, meradmiate, Mexoryl SX, octinoxate, octisalate, octocrylene, octyl methoxycinnamate, octyl salicylate, oxybenzone, padimate O, para-aminobenzoic acid (PABA), Parsol 1789, terephthalylidine dicamphor sulfonic acid, Tinosorb M, Tinosorb S, and titanium dioxide.

Emulsifiers are substances which are added to cosmetic/dermatological products to help keep unlike ingredients (such as oil and water) from separating in an emulsion. There are 2 types of emulsifiers. Oil-in-water (o/w) emulsifiers keep oil drops packed in water, while water-in-oil (w/o) emulsifiers keep water drops packed in oil. W/O emulsifiers are used for a fatty feel (e.g. night & sun protection creams). O/W emulsifiers are used more in moisturizing products (e.g. body lotions, day creams).

Surfactants are substances which are added to cosmetic/dermatological products to degrease and emulsify oils and fats and suspend soil, allowing them to be washed away, as laundry products do. They are sometimes refer to as "detergent cleansing agents." Based on their cleansing power surfactants are classified into primary and secondary or co-surfactants. Based on the chemical structure there are anionic, amphoteric, non-ionic, and quaternary agents. Surfactants form the base of all personal cleansing products and can also have wetting, conditioning, defatting, emulsifying, & thickening effects.

In some embodiments, emulsifiers, surfactants, and detergents may include, but are not limited to, ammonium laureth sulfate, ammonium lauryl sulfate, arachidyl glucoside, behenic acid, bis-PEG-18 methyl ether dimethyl silane, $C_{20-40}$ pareth-40, cocamidopropyl betaine, cocamidopropyl dimethylamine, cocamidopropyl hydroxysultaine, coco-glucoside, coconut oil, decyl glucoside, dicetyl phosphate, dihydrocholeth-30, disodium cocoamphodiacetate, disodium cocoyl glutamate, disodium lauraminopropionate, glyceryl behanate, hydrogenated vegetable glycerides citrate, isohexadecane, isostearamide DEA, lauramphocarboxyglycinate, laureth-23, laureth-4, laureth-7, lauryl PEG-9 polydimethylsiloxyethyl dimethicone, lauryl alcohol, lauryl glucoside, magnesium laureth sulfate, magnesium oleth sulfate, myristic acid, nonoxynols, oleic acid, oleth 10, palm kernel acid, palmitic acid, PEG-60 almond glycerides, PEG-75 shea butter glycerides, PEG 90M, PEG-10 dimethicone, PEG-10 dimethicone/vinyl dimethicone crosspolymer, PEG-10 rapeseed sterol, PEG-100 stearate, PEG-12 dimethicone, PEG-120 methyl glucose dioleate, PEG-20 methyl glucose sesquistearate, PEG-40 stearate, PEG-60 hydrogenated castor oil, PEG-7 glyceryl cocoate, PEG-8, PEG-80 sorbitan laurate, PEG/PPG-17/6 copolymer (polyethylene glycol/polypropylene glycol-17/6 copolymer), PEG/PPG-18/18 dimethicone, PEG/PPG-20/15 dimethicone, poloxamer 184, Poloxamer 407, poloxamers, polyglyceryl-3 beeswax, polyglyceryl-4 isostearate, polyglyceryl-6 isostearate, polysorbate 20, polysorbate 60, polysorbate 80, potassium cetyl phosphate, potassium hydroxide, potassium myristate, PPG-12 buteth-16, PPG-26-Buteth-26, *Salvia officinalis, Saponaria officinalis* extract, soapwort, sodium $C_{14-16}$ olefin sulfonate, sodium cetearyl sulfate, sodium cocoamphoacetate, sodium cocoate, sodium cocoyl glutamate, sodium cocoyl isethionate, sodium dilauramidoglutamide lysine, sodium hexametaphosphate, sodium hydroxide, sodium laureth sulfate, sodium laureth-13 carboxylate, sodium lauroamphoacetate, sodium lauroyl lactylate, sodium lauroyl sarcosinate, sodium lauryl glucose carboxylate, sodium lauryl sulfate, sodium methyl cocoyl taurate, sodium methyl taurate, sodium myreth sulfate, sodium palm kernelate, sodium palmate, sodium PEG-7 olive oil carboxylate, sodium trideceth sulfate, steareth-20, TEA-lauryl sulfate (triethanolamine-lauryl sulfate), and tribehenin PEG-20 esters.

Thickeners are substances which are added to cosmetic/dermatological products to enhance the consistency, volume and viscosity of cosmetic products, thereby providing more stability and better performance. While some thickeners have also emulsifying or gelling properties, the majority of thickeners have the ability to retain water on the skin and act therefore as moisturizers. Thickeners can be completely natural like waxes but also synthetic or semi-synthetic.

In some embodiments, thickeners may include, but are not limited to, *Acacia* senegal, acetyl glyceryl ricinoleate, acetylated castor oil, acetylated hydrogenated cottonseed glyceride, acetylated palm kernel glycerides, acrylates/steareth-20 methacrylate copolymer, agar, *Ahnfeltia concinna* extract, *ahnfeltia* extract, *Alaria esculenta*, algae, algae extract, algin, alkyloamides, *Althaea rosea, Althea officinalis*, alumina, aluminum hydroxide, aluminum stearate, ammonium acryloyldimethyltaurate/VP copolymer, *Anacystis nidulans* extract, arachidic acid, arachidonic acid, arachidyl alcohol, arachidyl propionate, arrowroot, artemia extract, *Ascophyllum nodosum*, ascorbyl methylsilanol pectinate, *Asparagopsis armata* extract, beeswax, behenic acid, behentrimonium chloride, behenyl alcohol, bis-diglyceryl polyacyladipate, bismuth oxychloride, $C_{12-15}$ alkyl benzoate, $C_{12-18}$ acid triglyceride, $C_{13-14}$ isoparaffin, $C_{18-36}$ acid triglyceride, candelilla wax, caprylic/capric triglyceride, carbomer, carbopol, carnauba wax, carrageenan, *Caulerpa taxifolia* extract, cellulose, Cellulose gum, cephalin, Cera alba, ceresin, ceteareth-20, cetearyl alcohol, cetearyl ethylhexanoate, cetearyl glucoside, cetearyl octanoate, cetyl alcohol, cetyl dimethicone copolyol, cetyl hydroxyethylcellulose, cetyl palmitate, cetyl PEG/PPG-10/1-dimethicone, *chlorella, Chondrus crispus*, cocamide DEA and MEA, cocoglycerides, *Codium tomentosum* extract, *Copernicia cerifera* wax, *Corallina officinalis* extract, *Cyamopsis tetragonoloba*, DEA oleth-10 phosphate, diethanolamine (DEA), di-PPG-3 myristyl ether adipate, dimethicone crosspolymer, dimethicone/vinyl dimethicone crosspolymer, dimer dilinoleyl dimer dilinoleate, dipentaerythrityl hexacaprylate/hexacaprate, disodium diglyceryl phosphate, disodium glyceryl phosphate, docosahexaenoic acid, dulse, *Durvillaea antarctica* extract, eicosapentaenoic acid, *Enteromorpha compressa* extract, erythropoietin (Epo), ethyl macadamiate, ethylhexyl stearate, *Euphorbia* cerifera wax, fuller's earth, gelatin, *Gellidiela acerosa* extract, glycereth-26, glycereth-26 phosphate, glycereth-6 laurate, glycerol monostearate, glycerol triacetate, glycerol trioleate, glyceryl behanate, glyceryl cocoate, glyceryl dipalmitate, glyceryl distearate, glyceryl isopalmitate, glyceryl isostearate, glyceryl myristate, glyceryl oleate, glyceryl palmitate, glyceryl polymethacrylate, glyceryl stearate, glyceryl stearate SE, glycol stearate, glycolipid, guar gum, guar hydroxypropyltrimonium chloride, gums, *Haslea ostrearia* extract, hepatocyte growth factor (HGF), *Himanthalia* elongate extract, hydrogenated coco-glyceride, hydrogenated didecene, hydroxyethyl acrylate/sodium acryloyldimethyl taurate copolymer, hydroxyethylcellulose, hydroxypropyl guar, hydroxypropyl starch phosphate, interleukin (IL), Irish moss extract, isohexadecane, isoparaffin, isopropyl lanolate, isopropyl myristate, isopropyl palmitate, isopropyl titanium triisostearte/triethoxycaprylylsilane crosspolymer, isostearamide DEA, isostearic acid, Japan wax, kelp extract, *Laminaria digitata, Laminaria longicruris, Laminaria* saccharine, laureth-23, laureth-4, laureth-7, lauryl PEG-9 polydimethylsiloxyethyl dimethicone, lithium magnesium sodium silicate, locust bean, magnesium aluminum silicate, magnesium stearate, magnesium sulfate, mallow, marshmallow, *Mastocarpus stellatus*, monoethanolamine (MEA), microcrystalline wax, Microcystis *aeruginosa*, montan wax, myristyl myristate, neopentyl glycol dicaprylate/dicaprate, neopentyl glycol diheptanoate, nylon-12, octyl palmitate, octyl stearate, octyldodecanol, octyldodecyl myristate, oleic acid, oleth 10, ozokerite, *Padina pavonica* extract, *Palmaria palmata* extract, palmitoyl hexapeptide-12, palmitoyl oligopeptide, palmitoyl pentapeptide-3, palmitoyl tetrapeptide-7, palmitoyl tripeptide-5, paraffin, pectin, PEG-100 stearate, PEG-150 distearate, PEG-32, PEG-40 hydrogenated castor oil, pentaerythrityl tetraisostearate, pentaerythrityl tetraoctanoate, polybutene, polyethylene, polyethylene glycol, polyglycerol monostearate, polyglyceryl 2 triisostearate, polyglyceryl-3 beeswax, polyglyceryl-3 methylglucose distearate, polyisobutene, polysorbate 20, polysorbate 60, polysorbate 80, polysorbates, PPG-12 buteth-16, PPG-2 myristyl ether propionate, propylene glycol isostearate, propylene glycol stearate, pullulan, pumpkin seed extract, PVM/MA decadiene crosspolymer, *Pyrus cydonia, Pyrus malus*, quaternium-18 hectorite, quince seed, red algae, ricinoleate, *Salvia officinalis, Sargassum filipendula* extract, *sclerotium* gum, Seamollient, seaweed, sesquioleate, silent information regulator two proteins (sirtuins), silica, silicate, sodium acrylate/acryloydimethyl taurate copolymer, sodium carboxymethyl 3-glucan, sodium hexametaphosphate, sodium lauroyl lactylate, sodium lauryl sulfate, sodium polyacrylate, *Solanum tuberosum* extract, sorbitan oleate, sorbitan sesquioleate, sorbitan stearate, sorbitol, *spirulina*, stearic acid, stearyl alcohol, subtilisin, synthetic beeswax, TEA-lauryl sulfate, titanium dioxide, tragacanth, transforming growth factor (TGF), tribehenin, tridecyl stearate, tridecyl trimellitate, triglyceride, *trigonella* foenum-graecum seed extract, trihydroxystearin, trilaurin, tripeptide-32, trioctanoin, *Undaria pinnatifida*, vascular endothelial growth factor (VEGF), vinyl dimethicone/methicone silsesquioxane crosspolymer, wheat germ glycerides, xanthan gum, xylitol, zinc oxide, and zinc stearate.

In some embodiments, penetration enhancers can be used to aid the compounds or compositions provided herein in passing through the out later (epidermis) of the skin and into the dermis and/or hypodermis of the skin. Penetration enhancers may selected from one of the following classes of compounds:

1. Fatty alcohols, fatty acids and related compounds.
2. Biologics such as lecithins, phospholipids.
3. Amines and amides.
4. Complexing agents such as cyclodextrins.
5. Surfactants including Brij, tweens, spans, and pluronics.
6. N-methyl pyrrolidone and related compounds.
7. Ionic compounds such as ascorbate and sodium hyaluronate.
8. Dimethyl sulfoxide and related compounds.
9. Solvents such as ethanol, acetone, glycols, glycerols, squalene, tween 20, etc.
10. Azone and related compounds.

The cosmetic or dermopharmaceutical compositions provided herein can include cleansers, facial masks, toners, moisturizers, sunscreen, tanning oils and lotions, skin lighteners, serums, and exfoliants.

In addition, various adjuvants such as are commonly used in the art can be included. These and other such compounds are described in the literature, e.g., Rowe, R. C.; Sheskey, P. J. & Quinn, M. E. (Eds.). (2009). Handbook of Pharmaceutical Excipients. London Chicago: Pharmaceutical Press; Hoepfner E., et al. (2002). Fiedler Encyclopedia of Excipients for Pharmaceuticals, Cosmetics and Related Areas, Aulendorf, Germany: Cantor; Kemper, F. H., et al. (2000). Blue List Cosmetic Ingredients, Aulendorf, Germany: Cantor; and Smolinske, S. C. (1992). Handbook of Food, Drug and Cosmetic Excipients, Boca Raton, Fla.: CRC Press.

Ingredients, additives, products or materials, and adjuvants, which can be employed in the compositions discussed herein are referred to by their commonly used chemical names or by the international nomenclature, (recognized by the European Union), commonly referred to as INCI name given them in any edition of the International Cosmetic Ingredient Dictionary and Handbook, (hereafter INCI Dictionary), or in any edition of the International Buyers' Guide, all published by the Personal Care Products Council (PCPC), Washington D.C. Numerous commercial suppliers of materials listed by INCI name, trade name, or both, can be found in any edition of the INCI Dictionary and in numerous commercial trade publications.

Cosmetic or dermopharmaceutical compositions provided herein can be administrated to any skin type including normal skin, dry skin, oily skin, combination skin (a combination of both oily and dry or normal skin, e.g. certain areas of the face are oily and the others dry), sensitive skin, and acne prone skin.

The term "administration" or "administering" refers to a method of providing a dosage of a compound or cosmetic or dermopharmaceutical composition to a subject, where the method is epicutaneous (topical) or subcutaneous. Modes of administration, dosing schedules disclosed compounds and compositions can be determined according to the criteria generally taken into account in the establishment of a cosmetic and/or dermatological treatment adapted to, for example, a patient's type of skin. The compositions can be administered such that they cover the entire area to be treated.

As used herein, "topical use" and "topically applying" means directly laying on or spreading on the skin, hair, or nail, e.g., by use of the hands or an applicator such as a wipe.

The term "topical composition" as used herein refers to any composition suitable for the topical application to mammalian keratinous tissue such as in particular to human skin. In particular, the topical compositions according to the present disclosure are cosmetic compositions that can be topically applied to mammalian keratinous tissue, particularly to human skin.

The term "dermatologically acceptable" is used to refer to compounds and compositions that retain biological effectiveness and which are suitable for use in contact with the skin or hair of humans and lower animals without undue toxicity, incompatibility, instability, irritation, allergic response, and the like.

The term "dermatologically acceptable carrier", "dermatologically acceptable diluent" or "dermatologically acceptable excipient" are well known in the art and are selected based on the end use application and refer to a non-toxic, inert, and/or physiologically compatible composition component. Except insofar as any conventional media or agent is incompatible with the active ingredient, its use in the cosmetic and demorpharmaceutical compositions is contemplated.

The term "dermatologically acceptable salt" refers to salts that retain the biological effectiveness and properties of the compounds provided herein and, which are suitable for use in contact with the skin or hair of humans and lower animals without undue toxicity, incompatibility, instability, irritation, allergic response, and the like. Non-limiting examples include, but are not limited to, acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Cosmetically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this disclosure or of their dermatologically acceptable salts. Organic or inorganic acids also include, but are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic, and trifluoroacetic acid.

Administration of the compounds disclosed herein or the dermatologically acceptable salts thereof can be via any of the accepted modes of administration for agents that serve similar utilities including, but are not limited to, topically, intravaginally, rectally, intranasally, intralesionally, auricularly, conjunctivaly, by irrigation, and oropharyngeally.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for topical delivery is about 1.0 µg/cm$^2$ to about 100 µg/cm$^2$.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for topical delivery is about 1.5 µg/cm$^2$ to about 95 µg/cm$^2$.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for topical delivery is about 2.0 µg/cm$^2$ to about 85 µg/cm$^2$.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for topical delivery is about 2.5 µg/cm$^2$ to about 75 µg/cm$^2$.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for topical delivery is about 5 µg/cm$^2$ to about 50 µg/cm$^2$.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for topical delivery is about 10 µg/cm$^2$ to about 25 µg/cm$^2$.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

The present disclosure is also directed to a composition comprising up to 75% by weight of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a combination thereof.

In some embodiments, a composition can comprise about 0.01 to about 10% of the compound in solution.

In some embodiments, the composition will comprise about 0.01 to about 5% of the compound in solution.

In some embodiments, the composition will comprise about 0.01 to about 1% of the compound in solution.

In some embodiments, the composition will comprise about 0.05 to about 0.5% of the compound in solution.

In some embodiments, the composition will comprise about 0.05 to about 0.2% of the compound in solution.

In some embodiments, the composition will comprise about 0.05 to about 0.15% of the compound in solution.

In some embodiments, the composition will comprise about 0.1 to about 0.45% of the compound in solution.

In some embodiments, the composition will comprise about 0.1 to about 0.25% of the compound in solution.

In some embodiments, the composition will comprise about 0.1 to about 0.2% of the compound in solution.

In some embodiments, the composition will comprise about 0.15 to about 0.40% of the compound in solution.

In some embodiments, the composition will comprise about 0.15 to about 0.25% of the compound in solution.

In some embodiments, the composition will comprise about 0.15 to about 0.20% of the compound in solution.

In some embodiments, the composition will comprise about 0.2 to about 0.35% of the compound in solution.

In some embodiments, the composition will comprise about 0.25 to about 0.3% of the compound in solution.

It is to be noted that concentrations and dosage values may also vary depending on the specific compound and the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Provided herein are compositions comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV that can be used to improve the condition and aesthetic appearance of skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by skin aging.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by environmental damage to the skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by one or more of wrinkles, dry skin, sensitive skin, or dermatological symptoms caused by ineffective homeostatic regulation of healthy skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to altler the aesthetic appearance of skin associated with or affected by, or treating or preventing, a skin condition/disorder (e.g., a skin condition/disorder accompanied with a loss of skin elasticity).

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to improve the barrier function and viability of the skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by wrinkling, sagging, and/or a loss of skin elasticity.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by, or treating or preventing, acne. For example, the acne can be selected from one or more of simple acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne or medication-related acne.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by deteriorations in skin viscoelasticity.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by one or more of wrinkles and/or fine lines, wizened skin, a lack of elasticity and/or of tonus of the skin, thinning of the dermis, degradation of collagen fibers, flaccid skin, thinned skin, and the internal degradation of the skin following exposure to ultraviolet radiation.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to decrease the appearance of fine lines and/or wrinkles in the skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to create a more youthful appearance of the skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to decrease the appearance of bags and/or rings around the eyes.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to reduce the appearance of hyperpigmentation.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to increase or restore elasticity, resiliency, and/or suppleness of the skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to improve or increase one or more of the thickness, elasticity, flexibility, radiance, glow, and plumpness of the skin. The method comprising administering to a subject an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to improve the fineness of skin texture.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to improve the appearance of wrinkled, lined, dry, flaky, aged or photodamaged skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by skin discolorations.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to whiten, lighten, and/or bleach the skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by, or treat or prevent, hyperpigmentation.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to alter the aesthetic appearance of skin associated with or affected by, or treat or prevent, photodamaged skin.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to treat or prevent pigment deposition in the skin caused by UV exposure.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to treat or prevent vitiligo (skin condition in which there is a loss of brown color (pigment) from areas of skin).

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to treat or prevent a wound healing disorder in a mammal. For example, a compound or composition provided herein can be used as a medicament for preventing and/or treating a bedsore in a mammal.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to promote proliferation and/or mobility of skin keratinocyte and/or dermis fibroblasts (e.g., to increase skin regeneration).

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to improve epidermal cell repair activity, for example, in a human.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to increase fibroblast proliferation, keratinocyte proliferation, and/or expression of collagen.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to reduce collagenase activity.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to improve the thickness of the epidermis.

In one embodiment, a composition comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to inhibit melanin production.

In some embodiments, the compositions are cosmetic compositions.

In some embodiments, the compositions are dermopharmaceutical compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient).

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety.

The term "comprising" as used herein is synonymous with "including," "containing," or "characterized by," and is inclusive or open-ended and does not exclude additional, unrecited elements or method steps.

EXAMPLES

Example 1

This example demonstrates the anti-aging benefits of compounds of the current disclosure on human female subjects.

Three groups of women were recruited to evaluate and compare the efficacy of three anti-aging test products (targeting the periorbital eye area) intended to reduce the appearance of fine lines, wrinkles in the outer canthus of the eyes (crow's feet area) over a 12 week period. Wrinkle assessment was conducted instrumentally using a Visioscan image analysis system. Effectiveness of the test product was evaluated using panelist self-assessment via questionnaire responses comprised of 3-4 questions (Q1, Q2, Q3 & Q4). Each stage in the progression of treatments was photographically documented using a High Resolution Scientifically Matched Photography technique. Image analysis was utilized to quantify changes in fine lines and crow's feet condition observed in the Scientifically Matched Photographs.

Subject Selection:
Number: Six subjects (two per group) to complete the study.
Sex: Females
Race: Caucasian/Asian/Hispanic
Age Range: 40 through 60 years old
Test Samples:
Topical 0.15% of Compound #222 in Oil (a 50/50 mixture of Propylene Glycol Dicaprylate/Dicaprate and Caprylic/Capric Triglyceride) (Cohort 1)
Topical 0.15% of Compound #222 in PEG400 (Cohort 2)
Topical 0.05% of Compound #222 in PEG400 (Cohort 3)

Prior to baseline measurements being taken, areas of involvement were marked on the facial surface using a standard template, to ensure that instruments were repositioned in the same location at each visit. The biophysical measurements (Surface Evaluation of Living Skin via Visioscan) were conducted by a trained technician. Pre-treatment High Resolution Scientifically Matched Photographs were taken.

All subjects were instructed to use the test material once a day, as part of their daily skin care routine. Immediately following baseline evaluations, the subjects were issued the product with the following instructions:

GROUP 1—Compound #222 Topical 0.15% in oil (Cohort 1): The subjects were instructed to hold the bottle at an angle such that the roller-ball was at bottom and apply the roller-ball to the periorbital area, including the crow's feet area, 2-3 times, starting from the area under the eye (and above the cheekbone) and moving up towards the outer tip of the eye-brow. After 2-3 rolls, they were able to see wetness on the treated area. This procedure was repeated for the other eye.

GROUPS 2 & 3—Compound #222 Topical 0.15% in PEG (Cohort 2) & Compound #222 Topical 0.05% in PEG (Cohort 3): The subjects were instructed to hold the dispenser upright with one hand and with the tip of the index finger on the pump (similar to holding a spray container), pour a small amount of the product into the palm of their other hand by pumping once or twice. The product was then applied on to the periorbital area, including the crow's feet area, of both eyes with their index finger.

After 2, 4, 8 and 12 weeks of daily use of the test products, the test subjects returned to the study site with the test product applied. After acclimating to ambient conditions, High Resolution Scientifically Matched Photographs were be taken and biophysical measurements (Surface Evaluation of Living Skin via Visioscan) were repeated using the standard template to identify test sites on the face. In addition (during the acclimation period) all participants were be asked to fill out a self-assessment questionnaire.

Surface Evaluation of Living Skin—Visioscan: The Visioscan (Courage and Khazaka) took a direct image of the living skin using a measuring head containing a CCD-camera and two metal halogen lamps positioned opposite each other in order to ensure even illumination of the measuring field on the skin (*Skin Pharmacol Appl Skin Physiol* (1999), 12(1-2), 1-11 and *Cosmetic & Toiletries magazine* (2009), 124(6), 51-54). The grey level distribution of the pixels in the image correspond to different phenomena (white pixels represent desquamation on the skin, dark pixels represent lines and wrinkles). The software with the Visioscan automatically calculates skin smoothness, skin roughness, scaliness and wrinkle parameters. Visioscan images were taken at the following time points: Baseline Day 0 (beginning of the study), Week 2, Week 4, Week 8, and Week 12 (end of the test).

High Resolution Scientifically Matched Photography with PhotoGrammetrix™ Image Analysis: Exclusively detailed, high resolution before and after digital photographs are taken, with fixed camera background, angles, settings, lighting, panelist positioning, color bars, white balance, standardized and digitally certified unretouched. Each stage in the progression of the product treatment was photographically documented. This set of photographs provided a visual record of the efficacy of the products. Full face, frontal, left 45° and right 45° view photographs were taken at the following time points: Baseline Day 0 (beginning of the study), Week 2, Week 4, Week 8, and Week 12 (end of the test).

The source data was Visioscan and PhotoGrammetrix Image Analysis readings along with subjective assessments, which were totaled and reported as average scores. Photographs were placed side by side as to compare the photographs of before and after application of the test product in the eye area. Wrinkle reduction analysis source data consisted of crow's feet area quantification in relative units (px), collected at baseline and, the week 2, 4, 8 and 12 evaluations. The data obtained via Visioscan and from PhotoGrammetrix Image Analysis was quoted as % differences from baseline at each of the previously described time points. A paired t-test analysis was conducted in order to compare the results of post test product application measurements to baseline measurements where applicable. Statistical significance was established if $p \leq (\alpha = 0.05)$ was calculated.

TABLE 2

Self-assessment questionnaire - Compound #222 Topical 0.15% in Oil (Cohort 1)

1. My wrinkles in the eye area have improved since the beginning of the study. Q1

| | | | Answer: | | |
|---|---|---|---|---|---|
| | Strongly agree | Agree | Neither agree or disagree | Disagree | Strongly disagree |
| | | | Score: | | |
| | 1 | 2 | 3 | 4 | 5 |
| Panelist ID Nos.: | | Day 7 | | Day 14 | |
| Subject #1 | | | 5 | | 4 |
| Subject #2 | | | 2 | | 2 |
| Average Score: | | | 3.50 | | 3.00 |
| Score vs. % | 1 | | 0% | | 0% |
| Responders: | 2 | | 50% | | 50% |
| | 3 | | 0% | | 0% |
| | 4 | | 0% | | 50% |
| | 5 | | 50% | | 0% |

2. Compared to the beginning of the study, the appearance of my skin around either of my eyes is . . . Q2

| | | | Answer: | | |
|---|---|---|---|---|---|
| | Better | Little better | Same | Little worse | Worse |
| | | | Score: | | |
| | 1 | 2 | 3 | 4 | 5 |
| Panelist ID Nos.: | | Day 7 | | Day 14 | |
| Subject #1 | | | 3 | | 3 |
| Subject #2 | | | 2 | | 2 |
| Average Score: | | | 2.50 | | 2.50 |
| Score vs. % | 1 | | 0% | | 0% |
| Responders: | 2 | | 50% | | 50% |
| | 3 | | 50% | | 50% |
| | 4 | | 0% | | 0% |
| | 5 | | 0% | | 0% |

3. Compared to the beginning of the study, how do you feel about the treated area surrounding your eyes and the appearance of wrinkles? Q3

| | | | Answer: | | |
|---|---|---|---|---|---|
| | Very Satisfied | Satisfied | Neither satisfied or dissatisfied | Dissatisfied | Very Dissatisfied |
| | | | Score: | | |
| | 1 | 2 | 3 | 4 | 5 |
| Panelist ID Nos.: | | Day 7 | | Day 14 | |
| Subject #1 | | | 3 | | 3 |
| Subject #2 | | | 2 | | 1 |
| Average Score: | | | 2.50 | | 2.00 |
| Score vs. % | 1 | | 0% | | 50% |
| Responders: | 2 | | 50% | | 0% |
| | 3 | | 50% | | 50% |
| | 4 | | 0% | | 0% |
| | 5 | | 0% | | 0% |

4. Compared to the beginning of the study, have you felt any discomfort, other than slight tingling, in the treated area during the study? Q4

| | | | Answer: | | |
|---|---|---|---|---|---|
| | No | Yes, occasional discomfort lasting less than an hour | Yes, occasional discomfort lasting more than one hour | Yes, every day lasting less than an hour | Yes, everyday lasting more than an hour |
| | | | Score: | | |
| | 1 | 2 | 3 | 4 | 5 |
| Panelist ID Nos.: | | Day 7 | | Day 14 | |
| Subject #1 | | 1 | | | 1 |
| Subject #2 | | 2 | | | 2 |
| Average Score: | | 1.50 | | | 1.50 |

TABLE 2-continued

Self-assessment questionnaire - Compound #222 Topical 0.15% in Oil (Cohort 1)

| Score vs. % Responders: | | | |
|---|---|---|---|
| | 1 | 50% | 50% |
| | 2 | 50% | 50% |
| | 3 | 0% | 0% |
| | 4 | 0% | 0% |
| | 5 | 0% | 0% |

TABLE 3

Self-assessment questionnaire - Compound #222 Topical 0.15% in PEG (Cohort 2)

1. My wrinkles in the eye area have improved since the beginning of the study. Q1

| | Answer: | | | | |
|---|---|---|---|---|---|
| | Strongly agree | Agree | Neither agree or disagree | Disagree | Strongly disagree |
| | | | Score: | | |
| | 1 | 2 | 3 | 4 | 5 |
| Panelist ID Nos.: | | Day 7 | | Day 14 | |
| Subject #3 | | | 3 | | 2 |
| Subject #4 | | | 4 | | 4 |
| Average Score: | | | 3.50 | | 3.00 |
| Score vs. % Responders: | 1 | | 0% | | 0% |
| | 2 | | 0% | | 50% |
| | 3 | | 50% | | 0% |
| | 4 | | 50% | | 50% |
| | 5 | | 0% | | 0% |

2. Compared to the beginning of the study, the appearance of my skin around either of my eyes is . . . Q2

| | Answer: | | | | |
|---|---|---|---|---|---|
| | Better | Little better | Same | Little worse | Worse |
| | | | Score: | | |
| | 1 | 2 | 3 | 4 | 5 |
| Panelist ID Nos.: | | Day 7 | | Day 14 | |
| Subject #3 | | 2 | | 2 | |
| Subject #4 | | 3 | | 3 | |
| Average Score: | | 2.50 | | 2.50 | |
| Score vs. % Responders: | 1 | 0% | | 0% | |
| | 2 | 50% | | 50% | |
| | 3 | 50% | | 50% | |
| | 4 | 0% | | 0% | |
| | 5 | 0% | | 0% | |

3. Compared to the beginning of the study, how do you feel about the treated area surrounding your eyes and the appearance of wrinkles? Q3

| | Answer: | | | | |
|---|---|---|---|---|---|
| | Very Satisfied | Satisfied | Neither satisfied or dissatisfied | Dissatisfied | Very Dissatisfied |
| | | | Score: | | |
| | 1 | 2 | 3 | 4 | 5 |
| Panelist ID Nos.: | | Day 7 | | Day 14 | |
| Subject #3 | | 2 | | 2 | |
| Subject #4 | | 3 | | 4 | |
| Average Score: | | 2.50 | | 3.00 | |
| Score vs. % Responders: | 1 | 0% | | 0% | |
| | 2 | 50% | | 50% | |
| | 3 | 50% | | 0% | |
| | 4 | 0% | | 50% | |
| | 5 | 0% | | 0% | |

TABLE 3-continued

Self-assessment questionnaire - Compound #222 Topical 0.15% in PEG (Cohort 2)

4. Compared to the beginning of the study, have you felt any discomfort, other than slight tingling, in the treated area during the study? Q4

| | | Answer: | | | |
|---|---|---|---|---|---|
| | No | Yes, occasional discomfort lasting less than an hour | Yes, occasional discomfort lasting more than one hour | Yes, every day lasting less than an hour | Yes, everyday lasting more than an hour |
| | | | Score: | | |
| Panelist ID Nos.: | 1 | 2 | 3 | 4 | 5 |
| | | Day 7 | | Day 14 | |
| Subject #3 | | 2 | | 4 | |
| Subject #4 | | 1 | | 1 | |
| Average Score: | | 1.50 | | 2.50 | |
| Score vs. % Responders: | 1 | 50% | | 50% | |
| | 2 | 50% | | 0% | |
| | 3 | 0% | | 0% | |
| | 4 | 0% | | 50% | |
| | 5 | 0% | | 0% | |

TABLE 4

Self-assessment questionnaire - Compound #222 Topical 0.05% in PEG (Cohort 3)

1. My wrinkles in the eye area have improved since the beginning of the study. Q1

| | | Answer: | | | |
|---|---|---|---|---|---|
| | Strongly agree | Agree | Neither agree or disagree | Disagree | Strongly disagree |
| | | | Score: | | |
| Panelist ID Nos.: | 1 | 2 | 3 | 4 | 5 |
| | | Day 7 | | Day 14 | |
| Subject #5 | | 2 | | 1 | |
| Subject #6 | | 2 | | 2 | |
| Average Score: | | 2.00 | | 1.50 | |
| Score vs. % Responders: | 1 | 0% | | 50% | |
| | 2 | 100% | | 50% | |
| | 3 | 0% | | 0% | |
| | 4 | 0% | | 0% | |
| | 5 | 0% | | 0% | |

2. Compared to the beginning of the study, the appearance of my skin around either of my eyes is . . . Q2

| | | Answer: | | | |
|---|---|---|---|---|---|
| | Better | Little better | Same | Little worse | Worse |
| | | | Score: | | |
| Panelist ID Nos.: | 1 | 2 | 3 | 4 | 5 |
| | | Day 7 | | Day 14 | |
| Subject #5 | | 1 | | 1 | |
| Subject #6 | | 2 | | 2 | |
| Average Score: | | 1.50 | | 1.50 | |
| Score vs. % Responders: | 1 | 50% | | 50% | |
| | 2 | 50% | | 50% | |
| | 3 | 0% | | 0% | |
| | 4 | 0% | | 0% | |
| | 5 | 0% | | 0% | |

TABLE 4-continued

Self-assessment questionnaire - Compound #222 Topical 0.05% in PEG (Cohort 3)

3. Compared to the beginning of the study, how do you feel about the treated area surrounding your eyes and the appearance of wrinkles? Q3

| | Answer: | | | | |
|---|---|---|---|---|---|
| | Very Satisfied | Satisfied | Neither satisfied or dissatisfied | Dissatisfied | Very Dissatisfied |
| Score: | 1 | 2 | 3 | 4 | 5 |
| Panelist ID Nos.: | | Day 7 | | Day 14 | |
| Subject #5 | | 1 | | 1 | |
| Subject #6 | | 3 | | 2 | |
| Average Score: | | 2.00 | | 1.50 | |
| Score vs. % Responders: | 1 | 50% | | 50% | |
| | 2 | 0% | | 50% | |
| | 3 | 50% | | 0% | |
| | 4 | 0% | | 0% | |
| | 5 | 0% | | 0% | |

4. Compared to the beginning of the study, have you felt any discomfort, other than slight tingling, in the treated area during the study? Q4

| | Answer: | | | | |
|---|---|---|---|---|---|
| | No | Yes, occasional discomfort lasting less than an hour | Yes, occasional discomfort lasting more than one hour | Yes, every day lasting less than an hour | Yes, everyday lasting more than an hour |
| Score: | 1 | 2 | 3 | 4 | 5 |
| Panelist ID Nos.: | | Day 7 | | Day 14 | |
| Subject #5 | | 1 | | 1 | |
| Subject #6 | | 1 | | 1 | |
| Average Score: | | 1.00 | | 1.00 | |
| Score vs. % Responders: | 1 | 100% | | 100% | |
| | 2 | 0% | | 0% | |
| | 3 | 0% | | 0% | |
| | 4 | 0% | | 0% | |
| | 5 | 0% | | 0% | |

TABLE 5

Roughness reduction [SEr] via Visioscan - Compound #222 Topical 0.15% in Oil (Cohort 1)

| Panelist ID No.: | Baseline | Day 7 | Individual % Difference | Day 14 | Individual % Difference |
|---|---|---|---|---|---|
| Subject #1 | 2.50 | 2.46 | −1.60% | 2.25 | −9.82% |
| Subject #2 | 1.90 | 1.48 | −21.90% | 1.29 | −31.93% |
| Mean: | 2.20 | 1.97 | | 1.77 | |
| % Difference | | −10.36% | | −19.36% | |

TABLE 6

Roughness reduction [SEr] via Visioscan - Compound #222 Topical 0.15% in PEG (Cohort 2)

| Panelist ID No.: | Baseline | Day 7 | Individual % Difference | Day 14 | Individual % Difference |
|---|---|---|---|---|---|
| Subject #3 | 2.21 | 1.95 | −11.79% | 1.90 | −13.83% |
| Subject #4 | 1.51 | 1.39 | −7.84% | 1.35 | −10.63% |
| Mean: | 1.86 | 1.67 | | 1.62 | |
| % Difference | | −10.19% | | −12.53% | |

TABLE 7

Roughness reduction [SEr] via Visioscan - Compound #222 Topical 0.05% in PEG (Cohort 3)

| Panelist ID No.: | Baseline | Day 7 | Individual % Difference | Day 14 | Individual % Difference |
|---|---|---|---|---|---|
| Subject #5 | 2.58 | 1.83 | −29.07% | 1.77 | −31.40% |
| Subject #6 | 1.52 | 1.44 | −5.26% | 1.24 | −18.42% |
| Mean: | 2.05 | 1.64 | | 1.51 | |
| % Difference | | −20.24% | | −26.59% | |

Example 2

Four groups of women were recruited to evaluate and compare the efficacy of four anti-aging test products (targeting the periorbital eye area) intended to reduce the appearance of fine lines, wrinkles in the outer canthus of the eyes (crow's feet area) over a 12 week period. Wrinkle assessment was conducted instrumentally using a Visioscan image analysis system. Effectiveness of the test product was evaluated using panelist self-assessment via questionnaire responses. Each stage in the progression of treatments was photographically documented using High Resolution Scientifically Matched Photography technique. Image analysis was utilized to quantify changes in fine lines and crow's feet condition observed in the Scientifically Matched Photographs.

Subject Selection:
Number: Eighty three subjects (twenty or twenty one per group) to complete the study.
Sex: Females
Race: Caucasian/Asian/Hispanic
Age Range: 40 through 60 years old
Test Samples:
Topical 0.15% of Compound #222 in Oil (a 50/50 mixture of Propylene Glycol Dicaprylate/Dicaprate and Caprylic/Capric Triglyceride) (Cohort 1)
Topical 0.05% of Compound #222 in Oil (a 50/50 mixture of Propylene Glycol Dicaprylate/Dicaprate and Caprylic/Capric Triglyceride) (Cohort 2)
Topical 0.15% of Compound #222 in PEG400 (Cohort 3)
Topical 0.05% of Compound #222 in PEG400 (Cohort 4)
The testing protocol and evaluation was the same as in Example 1.

FIGS. 1 and 2 show the average change in roughness from baseline and percent wrinkle reduction of test subjects skin after topical treatment of the periorbital areas by compound #222 in all 4 cohorts.

Table 8 below shows more detail of Cohort 1 at week 8 and week 12 as compared to baseline.

TABLE 8

Change in Roughness and Change in Wrinkle Depth via Visioscan - Compound #222 Topical 0.05% in Oil (Cohort 2) at week 8 and week 12.

|  | Week 8 | Week 12 |
|---|---|---|
| Number of test subjects | 21 | 21 |
| Change in Roughness | | |
| Mean (SD) | −0.85 (0.59) | −1.01 (0.59) |
| Median [Min, Max] | −0.67 [−2.00, −0.02] | −0.79 [−1.79, −0.21] |
| % Change in Roughness | | |
| Mean (SD) | −32.9% (15.8) | −39.3% (14.6) |
| Median [Min, Max] | −33.9% [−57.7, −0.9] | −40.9% [−59.8, −10.3] |
| Change in Wrinkle Depth (×10$^4$) | | |
| Mean (SD) | −0.89 (0.63) | −0.92 (0.76) |
| Median [Min, Max] | −0.79 [−2.10, 0.05] | −0.85 [−2.47, 0.49] |
| % Change in Wrinkle Depth | | |
| Mean (SD) | −58.0% (24.2) | −54.1% (35.5) |
| Median [Min, Max] | −59.3% [−86.8, 4.1] | −63.5% [−88.2, 38.9] |

What is claimed is:

1. A method for improving the aesthetic appearance of a subject's skin, the method comprising administering to the subject an effective amount of a compound of Formula IIIa, or a dermatologically acceptable salt thereof:

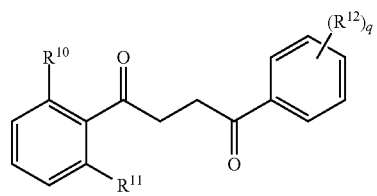

IIIa wherein:

$R^{10}$ is selected from the group consisting of H, unsubstituted —$C_{1-6}$ alkyl, —$C_{1-3}$ haloalkyl, halide, —$OR^{13}$, and CN;

$R^{11}$ is selected from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN;

$R^{12}$ is a substituent attached to the phenyl ring and is independently selected at each occurrence from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN;

each $R^{13}$ is independently selected from the group consisting of unsubstituted —$C_{1-6}$ alkyl, and —$C_{1-3}$ haloalkyl;

each $R^{13b}$ is independently selected from the group consisting of H and unsubstituted —$C_{1-3}$ alkyl; and each q is 0 to 5.

2. The method of claim 1, wherein the compound of Formula IIIa is selected from the group consisting of:

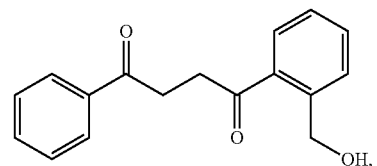

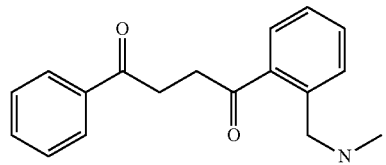

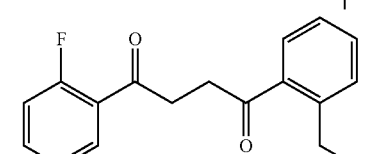

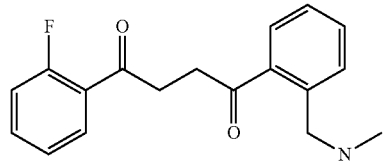

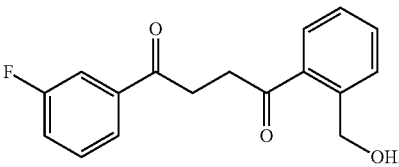

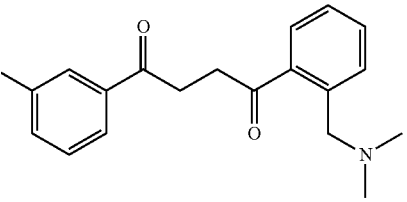

245
-continued
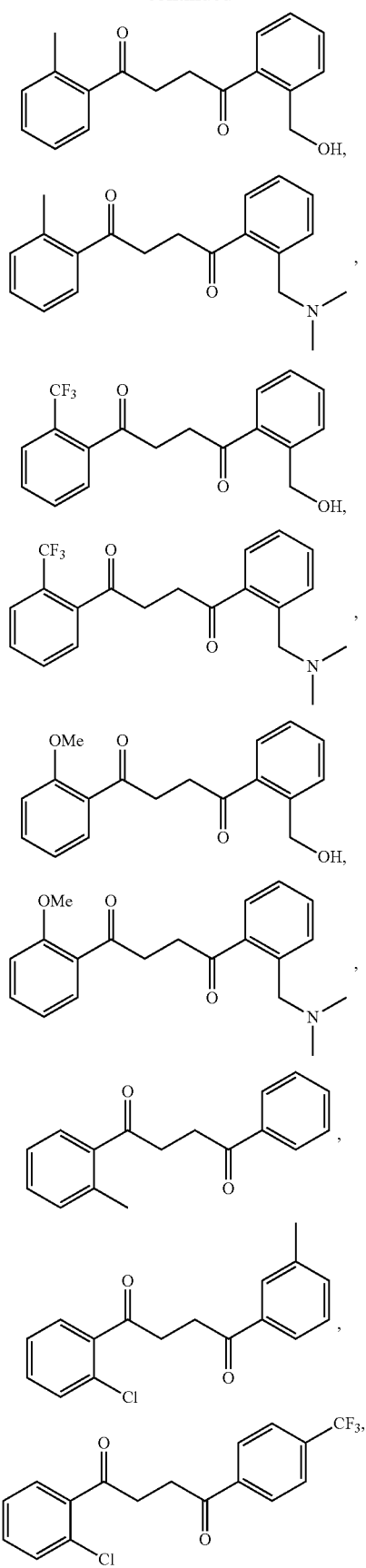
246
-continued
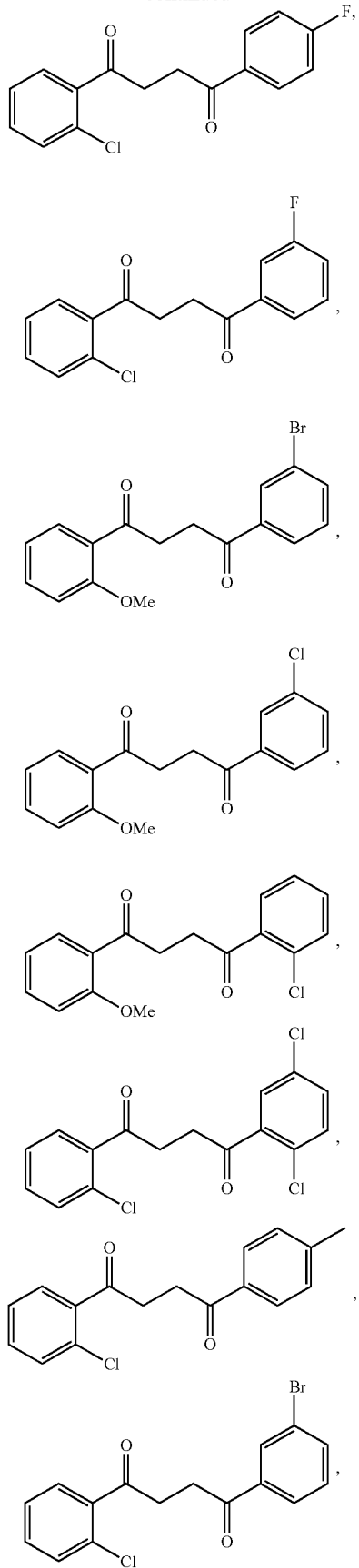

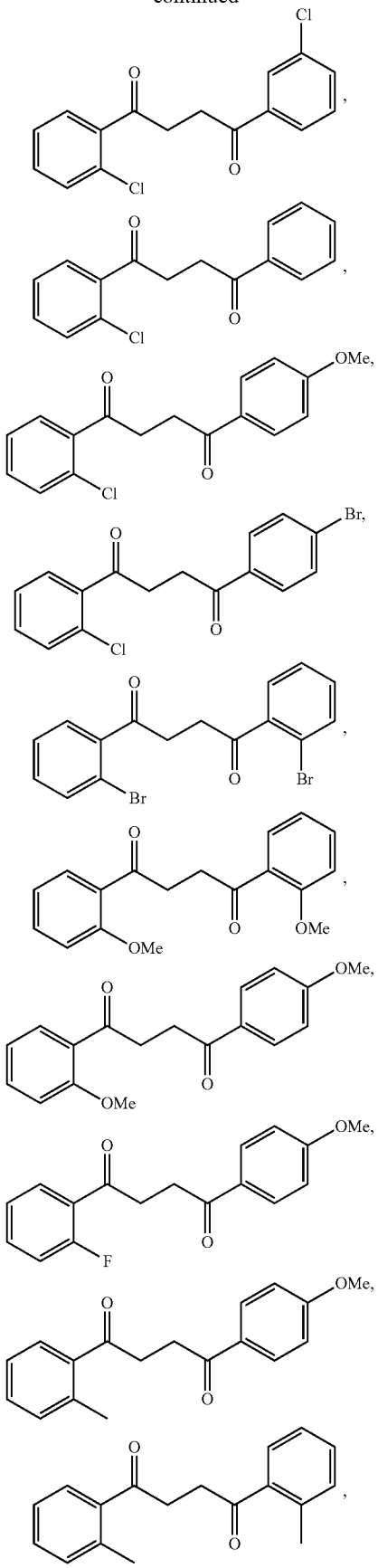

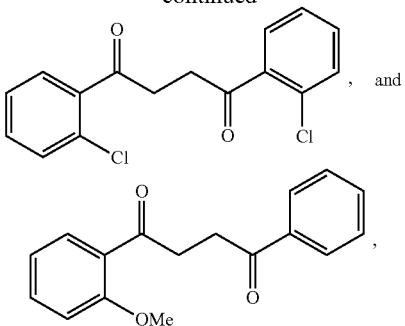

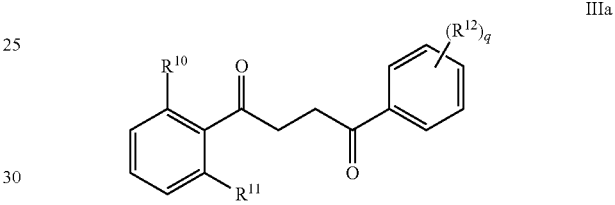

or a dermatologically acceptable salt thereof.

3. A method for improving the aesthetic appearance of a subject's skin, the method comprising administering to skin an effective amount of a cosmetic or dermopharmaceutical composition comprising a compound according to Formula IIIa, or a dermatologically acceptable salt thereof:

$$\text{IIIa}$$

wherein:

$R^{10}$ is selected from the group consisting of H, unsubstituted —$C_{1-6}$ alkyl, —$C_{1-3}$ haloalkyl, halide, —$OR^{13}$, and CN;

$R^{11}$ is selected from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN;

$R^{12}$ is a substituent attached to the phenyl ring and is independently selected at each occurrence from the group consisting of unsubstituted —$C_{1-6}$ alkyl, —$CH_2OH$, —$CH_2N(R^{13b})_2$, —$C_{1-3}$ haloalkyl, halide, —$OR^{13}$, and CN;

each $R^{13}$ is independently selected from the group consisting of unsubstituted —$C_{1-6}$ alkyl, and —$C_{1-3}$ haloalkyl;

each $R^{13b}$ is independently selected from the group consisting of H and unsubstituted —$C_{1-3}$ alkyl; and each q is 0 to 5.

4. The method of claim 1, wherein the improvement in aesthetic appearance is improvement in one or more of skin tone, radiance, clarity, tautness, skin firmness, plumpness, suppleness, softness, skin texture, skin texturization and moisturization, appearance of skin contours, appearance of hollow cheeks, appearance of sunken, baggy, or dark circles under eyes, skin luster, brightness, skin thickness, and skin elasticity and/or resiliency.

5. The method of claim 1, wherein the improvement in aesthetic appearance is the reduction and/or prevention of fine lines or wrinkles.

6. The method of claim 1, wherein the improvement in aesthetic appearance is the improvement in procollagen and/or collagen production.

7. The method of claim 1, wherein the compound is administered as a cosmetic or dermopharmaceutical composition.

8. The method according to claim 7, wherein the cosmetic or dermopharmaceutical composition is a topical composition.

9. The method according to claim 7, wherein the cosmetic composition is intended for use as a non-therapeutic treatment.

10. The method according to claim 1, wherein the subject is human.

11. The method according to claim 3, wherein the subject is human.

* * * * *